United States Patent
Zhang et al.

(10) Patent No.: US 12,202,835 B2
(45) Date of Patent: Jan. 21, 2025

(54) SUBSTITUTED AROMATIC RING-LINKED DIOXINOQUINAZOLINES AND DIOXINOQUINOLINES AS KINASE INHIBITORS

(71) Applicant: BEIJING SCITECH-MQ PHARMACEUTICALS LIMITED, Beijing (CN)

(72) Inventors: Qiang Zhang, Beijing (CN); Shannan Yu, Beijing (CN); Yueming Sun, Beijing (CN); Leifu Yang, Beijing (CN); Nanqiao Zheng, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 824 days.

(21) Appl. No.: 17/293,416

(22) PCT Filed: Nov. 15, 2019

(86) PCT No.: PCT/CN2019/118776
§ 371 (c)(1),
(2) Date: May 12, 2021

(87) PCT Pub. No.: WO2020/103769
PCT Pub. Date: May 28, 2020

(65) Prior Publication Data
US 2022/0002308 A1 Jan. 6, 2022

(30) Foreign Application Priority Data

Nov. 19, 2018 (CN) .......................... 201811375832.6
Nov. 1, 2019 (CN) .......................... 201911058051.9

(51) Int. Cl.
*A61K 31/357* (2006.01)
*C07D 319/10* (2006.01)
*C07D 491/056* (2006.01)

(52) U.S. Cl.
CPC ................................ *C07D 491/056* (2013.01)

(58) Field of Classification Search
CPC ........................... A61K 31/357; C07D 319/40
USPC .......................................... 514/454; 549/387
See application file for complete search history.

(56) References Cited

U.S. PATENT DOCUMENTS 10,106,508 B2   10/2018   Sheng et al.

FOREIGN PATENT DOCUMENTS

| CN | 104530063 A | 4/2015 | | |
|---|---|---|---|---|
| EP | 3865487 A1 * | 8/2021 | ................ | A61P 1/00 |
| JP | 2014-533287 A | 12/2014 | | |
| JP | 2017-537154 A | 12/2017 | | |
| WO | 2013/074633 A1 | 5/2013 | | |
| WO | 2016/112847 A1 | 7/2016 | | |
| WO | 2018/153293 A1 | 8/2018 | | |
| WO | 2018/157730 A1 | 9/2018 | | |

OTHER PUBLICATIONS

Jordan, V. C. Nature Reviews: Drug Discovery, 2, 2003, 205.*
Vippagunta, et al. Advanced Drug Delivery Reviews, 48, 2001, 18.*
Wolff, Manfred E., Ed. Burger's Medicinal Chemistry and Drug Discovery—Fifth Edition, vol. 1: Principles and Practice, New York: John Wiley & Sons, 1994, 975-977.*
International Search Report and Written Opinion for Application No. PCT/CN2019/118776, dated Feb. 18, 2020, 6 pages.
Graham et al., Ectopic Expression of the Proto-oncogene Mer in Pediatric T-Cell Acute Lymphoblastic Leukemia. Clin Cancer Res. May 2006;12(9):2662-9.
Schlegal et al., MERTK receptor tyrosine kinase is a therapeutic target in melanoma. J Clin Invest. May 1, 2013;123(5):2257-67.
Sutherland et al., Synthesis and structure-activity relationships of antitubercular 2-nitroimidazooxazines bearing heterocyclic side chains. J Med Chem. 2010;53(2):855-66.
Wang et al., Mer receptor tyrosine kinase promotes invasion and survival in glioblastoma multiforme. Oncogene. 2013;32:872-82.

* cited by examiner

*Primary Examiner* — Douglas M Willis
(74) *Attorney, Agent, or Firm* — McCarter & English, LLP; Xin Zhang

(57) ABSTRACT

Disclosed are a class of compounds as inhibitors of kinases such as TRK, c-MET, AXL, MER and/or VEGFR2, compositions and use thereof. In particular, disclosed are a class of compounds (as shown in formula (1)) or isomers, solvates, hydrates, pharmaceutically acceptable salts, and prodrugs thereof having strong inhibition activities for kinases such as TRK, c-MET, AXL, MER and/or VEGFR2, and pharmaceutical compositions comprising said compounds. Also disclosed is use of the compounds or pharmaceutical compositions in the preparation of a medicament for treating autoimmune diseases or cancers.

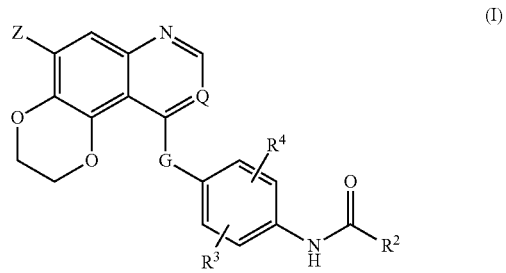

17 Claims, No Drawings

SUBSTITUTED AROMATIC RING-LINKED DIOXINOQUINAZOLINES AND DIOXINOQUINOLINES AS KINASE INHIBITORS

CROSS REFERENCE TO RELATED APPLICATIONS

The present application is a national application of PCT/CN2019/118776 filed on Nov. 15, 2019, which claims the priority of the Chinese Patent Application No. 201811375832.6 filed on Nov. 19, 2018 and the Chinese Patent Application No. 201911058051.9 filed on Nov. 1, 2019. The Chinese Patent Application No. 201811375832.6 and Chinese Patent Application No. 201911058051.9 are incorporated herein by reference as part of the disclosure of the present application.

FIELD OF THE INVENTION

The present disclosure belongs to the field of medicinal chemistry, and specifically relates to a class of aromatic ring-linked dioxino-quinazoline or dioxino-quinoline compounds, or isomers, hydrates, solvates, pharmaceutically acceptable salts or prodrugs thereof, and pharmaceutical compositions and uses thereof in the manufacture of medicaments for treating diseases related to tyrosine kinase TRK, c-MET, AXL, MER and/or VEGFR2.

BACKGROUND OF THE INVENTION

Receptor tyrosine kinases (RTKs) cross cell membranes and affect the trans-cellular membrane transmission of biochemical signals. They are consisted of three parts: an extracellular domain containing a ligand binding site, a single transmembrane region, and an intracellular domain containing the activity of tyrosine protein kinase. The binding of a ligand to a receptor stimulates the activity of the relevant receptor tyrosine kinase, which leads to the phosphorylation of tyrosine residues on the receptor and other intracellular molecules, which in turn triggers cascade signals that cause various cellular responses. The overexpression of tyrosine receptor activates downstream signal transduction pathways, which ultimately leads to abnormal transformation and proliferation of cells, and promotes the occurrence and development of tumors.

A hepatocyte growth factor receptor (c-MET) is a kind of tyrosine kinase receptors, the abnormal activation of which plays an important role in the occurrence and development of various malignant tumors including lung cancer. A hepatocyte growth factor (HGF) is a specific ligand for c-MET, and c-MET binds to HGF to play a biological role through HGF/c-MET signaling pathway. The HGF/c-MET signaling pathway can induce a series of biological effects such as cell proliferation, dispersion, migration, organ morphogenesis, and angiogenesis. Abnormal activation of c-MET can manifest as receptor overexpression, gene mutation, amplification, translocation, rearrangement, etc. These changes can lead to dysregulation of downstream signaling pathways, such as serine/threonine protein kinase (AKT), extracellular signaling kinase (ERK), phosphatidylinositol-3-hydroxykinase, and retinoblastoma inhibitory protein (Rb), thereby mediating processes such as tumorigenesis, invasion and metastasis, angiogenesis, and epithelial-mesenchymal transition. c-MET plays an important role in cell proliferation, metabolism, tumor generation, metastasis, and angiogenesis, and has become an important target for the anti-tumor therapy. Targeted therapy with c-MET as the target has shown great significance in the treatment of various malignant tumors including lung cancer.

MER is one of the three members of the TAM subfamily of RTK kinases, and the other two members are Tyro-3 and Axl, respectively. Each member of the TAM family contains an extracellular domain, a transmembrane domain and a conserved intracellular kinase domain. Overexpression or abnormal expression of TAM receptors have been found in a variety of cancers, wherein Axl and MER are overexpressed in various types of leukemia and most solid tumors, and have certain contribution on the drug resistance and metastasis of cancer cells.

Studies have shown that the expression of MER is related to the disease process. It has been found that MER is highly expressed in metastatic melanoma (Jennifer et al., "MERTK receptor tyrosine kinase is a therapeutic target inmelanoma" J. Clin. Invest., 2013, 123(5), 2257-2267). According to a report by Wang et al., activation of MER can promote the invasion and survival of glioblastoma multiforme ("Mer receptor tyrosine kinase promotes invasion and survival in glioblastoma multiforme" oncogene, 2013, 32, 872-882). At the same time, the study by Graham et al. also showed that MER plays a role in acute lymphoblastic leukemia (ALL), i.e., there is ectopic expression of MER in at least 50% of pediatric T-cell acute lymphoblastic leukemia samples and pre-B acute lymphoblastic leukemia ("Ectopic expression of the proto-oncogene Mer in pediatric T-cell acute lymphoblastic leukemia", Clin. Cancer Res., 2006, 12(9), 2662-2669). Therefore, MER receptor tyrosine kinase is considered to be a therapeutic target for various solid tumors or hematological malignancies, and the development of its inhibitors is expected to be used in the treatment of various solid tumors.

During the treatment with anti-tumor drugs, the interaction of multiple signaling pathways will affect the effect of anti-tumor drugs. For example, the interaction of the HFG/c-MET signaling pathway with other pathways affects the therapeutic effect of anti-tumor drugs and produces drug resistance. Therefore, drug combination against multiple kinase targets has become a new anti-tumor therapy. Moreover, the successful marketing of Crizotinib and Cabozantinib shows that the development of inhibitors for multiple kinase targets has good potential and application value.

Inhibitors like Cabozantinib that act on multiple targets have many advantages, and thus there are many researches on this type of inhibitor. At present, there are few such drugs on the market, the drug availability is limited, and the drugs that have been marketed encounter problems such as drug resistance and side effects during use. Therefore, compared with marketed inhibitors against single target, small molecular inhibitors for multiple targets will have better therapeutic effects and application prospects.

SUMMARY OF THE INVENTION

In view of the above discussion, the present disclosure aims to provide a class of aromatic ring-linked dioxino-quinazoline or dioxino-quinoline compounds, or isomers, hydrates, solvates, pharmaceutically acceptable salts or prodrugs thereof, and pharmaceutical compositions and uses thereof in the manufacture of medicaments for treating diseases related to tyrosine kinase TRK, c-MET, AXL, MER and/or VEGFR2.

One aspect of the present disclosure provides a compound of structural formula (I), or an isomer, a hydrate, a solvate, a pharmaceutically acceptable salt, or a prodrug thereof,

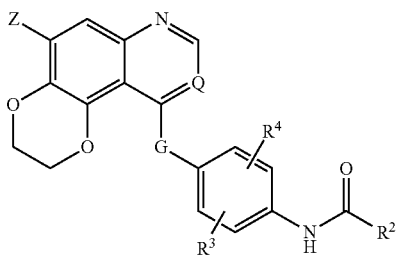

(I)

wherein
Q is N or CH;
G is O, S or NH;
Z is H or —OR$^1$;
R$^1$ is —H, C$_3$-C$_8$ cycloalkyl, C$_1$-C$_{10}$ alkyl, or —(CH$_2$)$_n$—R$^8$, wherein the C$_3$-C$_8$ cycloalkyl is unsubstituted or substituted with 1 to 3 substituents selected from the group consisting of C$_1$-C$_6$ alkoxy, C$_1$-C$_6$ alkylthio, C$_1$-C$_3$ acyl, hydroxyl, halogen, trifluoromethyl, cyano, —CONH$_2$, oxo (=O) and —NR$^a$R$^b$; the C$_1$-C$_{10}$ alkyl is unsubstituted or substituted with 1 to 3 substituents selected from the group consisting of C$_1$-C$_6$ alkoxy, C$_1$-C$_6$ alkylthio, C$_1$-C$_3$ acyl, hydroxyl, halogen, trifluoromethyl, cyano, —CONH$_2$, C$_3$-C$_7$ cycloalkyl, and —NR$^a$R$^b$; and R$^8$ is a substituted or unsubstituted 4- to 8-membered heteroalicyclic group containing 1 to 2 atoms selected from the group consisting of N, O, and S as a ring atom, and the substituted 4- to 8-membered heteroalicyclic group is substituted with 1 to 3 substituents selected from the group consisting of halogen, C$_1$-C$_3$ alkyl, C$_1$-C$_3$ alkoxy, C$_1$-C$_3$ alkylthio, hydroxyl, —NR$^a$R$^b$, C$_1$-C$_3$ acyl, trifluoromethyl, cyano, and oxo, and n is an integer from 0 to 10,
R$^a$ and R$^b$ are each independently —H, C$_1$-C$_6$ alkyl, C$_3$-C$_6$ cycloalkyl, C$_1$-C$_6$ alkyl substituted with C$_1$-C$_3$ alkoxy, C$_1$-C$_6$ alkyl substituted with C$_1$-C$_3$ alkylthio, or C$_1$-C$_6$ alkyl substituted with unsubstituted or mono- or di-C$_1$-C$_3$ alkyl-substituted amino;
R$^3$ and R$^4$ are each independently —H, —CF$_3$, halogen, C$_1$-C$_3$ alkyl, or C$_1$-C$_3$ alkoxy;
R$^2$ is

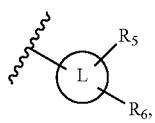

wherein L is an aryl group, a 5- to 6-membered unsaturated heterocyclyl or heteroaryl group containing 1 to 3 heteroatoms selected from the group consisting of N, O, and S,

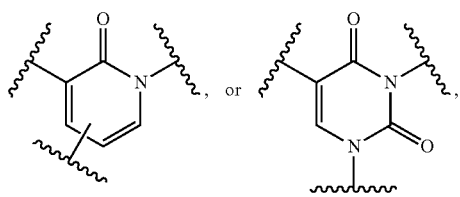

R$_5$ is —H, C$_1$-C$_6$ alkyl, C$_1$-C$_3$ alkoxy, or C$_1$-C$_3$ alkyl, wherein the C$_1$-C$_3$ alkyl is substituted with 1 to 3 substituents selected from the group consisting of C$_3$-C$_6$ cycloalkyl, hydroxyl, C$_1$-C$_3$ alkoxy, halogen, carboxyl, tert-butoxycarbonyl, alkenyl, morpholinyl, piperazinyl, 4-methylpiperazinyl, pyrrolyl, piperidinyl, 4,4-dimethylpiperidinyl, 4-methyl-4-hydroxy-piperidinyl, and 4-methyl-4-aminopiperidinyl,
R$_6$ is —(CH$_2$)—R$^7$, where t is an integer from 0 to 3, and R$^7$ is an aryl or heteroaryl group or C$_3$-C$_6$ cycloalkyl, wherein the aryl or heteroaryl group is unsubstituted or substituted with one or more of trifluoromethyl, halogen, C$_1$-C$_3$ alkyl, and C$_1$-C$_3$ alkoxy, and the C$_3$-C$_6$ cycloalkyl is unsubstituted or substituted with one or more of trifluoromethyl, halogen, C$_1$-C$_3$ alkyl, and C$_1$-C$_3$ alkoxy.
Alternatively, R$^1$ is —H, unsubstituted C$_3$-C$_8$ cycloalkyl, C$_1$-C$_5$ alkyl, or —(CH$_2$)$_n$—R$^8$, wherein the C$_1$-C$_8$ alkyl is unsubstituted or substituted with 1 to 3 substituents selected from the group consisting of C$_1$-C$_6$ alkoxy, C$_1$-C$_6$ alkylthio, C$_1$-C$_3$ acyl, hydroxyl, —F, trifluoromethyl, cyano, —CONH$_2$, C$_3$-C$_6$ cycloalkyl, and —NR$^a$R$^b$, R$^8$ is a substituted or unsubstituted 4- to 8-membered heteroalicyclic group containing 1 to 2 atoms selected from the group consisting of N, O, and S as a ring atom, and the substituted 4- to 8-membered heteroalicyclic group is substituted with 1 to 3 substituents selected from the group consisting of —F, C$_1$-C$_3$ alkyl, C$_1$-C$_3$ alkoxy, hydroxy, —NR$^a$R$^b$, C$_1$-C$_3$ acyl, trifluoromethyl, cyano, and oxo, and n is an integer from 0 to 8,
R$^a$ and R$^b$ are each independently —H, C$_1$-C$_6$ alkyl, C$_3$-C$_6$ cycloalkyl, or C$_1$-C$_6$ alkyl substituted with C$_1$-C$_3$ alkoxy.
Yet alternatively, R$^1$ is —H, unsubstituted C$_3$-C$_6$ cycloalkyl, C$_1$-C$_6$ alkyl, or —(CH$_2$)$_n$—R$^8$, wherein the C$_1$-C$_6$ alkyl is unsubstituted or substituted with 1 to 3 substituents selected from the group consisting of C$_1$-C$_3$ alkoxy, C$_1$-C$_3$ alkylthio, C$_1$-C$_3$ acyl, hydroxyl, —F, trifluoromethyl, cyano, —CONH$_2$, C$_3$-C$_5$ cycloalkyl, and —NR$^a$R$^b$, R$^8$ is a substituted or unsubstituted 4- to 6-membered heteroalicyclic group containing 1-2 atoms selected from the group consisting of N, O, and S as a ring atom, and the substituted 4- to 6-membered heteroalicyclic group is substituted with 1 to 3 substituents selected from the group consisting of —F, C$_1$-C$_3$ alkyl, C$_1$-C$_3$ alkoxy, hydroxyl, —NR$^a$R$^b$, C$_1$-C$_3$ acyl, trifluoromethyl, cyano, and oxo, and n is an integer from 0 to 6,
R$^a$ and R$^b$ are each independently —H, C$_1$-C$_3$ alkyl, C$_3$-C$_6$ cycloalkyl, or C$_1$-C$_3$ alkyl substituted with C$_1$-C$_3$ alkoxy.
Furthermore, R$^1$ can be —H, cyclopropyl, cyclobutyl, cyclopentyl, cyclohexyl, C$_1$-C$_6$ alkyl or —(CH$_2$)$_n$—R$^8$, wherein the C$_1$-C$_6$ alkyl is unsubstituted or substituted with 1 to 3 substituents selected from the group consisting of methoxy, ethoxy, propoxy, isopropoxy, methylthio, ethylthio, formyl, acetyl, hydroxyl, —F, trifluoromethyl, cyano, —CONH$_2$, cyclopropyl, cyclobutyl, cyclopentyl, and —NR$^a$R$^b$; R$^8$ is a substituted or unsubstituted 4- to 6-membered heteroalicyclic group containing 1 to 2 atoms selected from the group consisting of N, O, and S as a ring atom, and the substituted 4- to 6-membered heteroalicyclic group is substituted with 1 to 3 substituents selected from the group consisting of —F, methyl, ethyl, hydroxy, amino, acetyl, formyl, trifluoromethyl, cyano, and oxo, and n is an integer from 0 to 6,
The 4- to 6-membered heteroalicyclic group is selected from the group consisting of a 4- to 6-membered oxacycloalkyl group, a 4- to 6-membered azacycloalkyl group, a 4- to 6-membered thiacycloalkyl group, and the following groups:

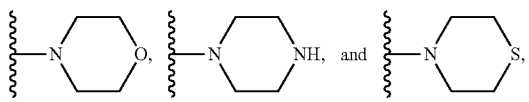

$R^a$ and $R^b$ are each independently —H, methyl, ethyl, methoxymethyl, methoxyethyl, methoxypropyl, cyclopropyl, or cyclobutyl.

Still alternatively, $R^1$ is $C_1$-$C_4$ alkyl, oxetan-3-yl, tetrahydrofuran-3-yl, tetrahydropyran-4-yl, tetrahydropyran-3-yl, hydroxyethyl, hydroxypropyl, methoxyethyl, methoxypropyl, ethoxyethyl, ethoxypropyl, cyanomethyl, cyanoethyl, cyanopropyl, cyclopropylmethyl,

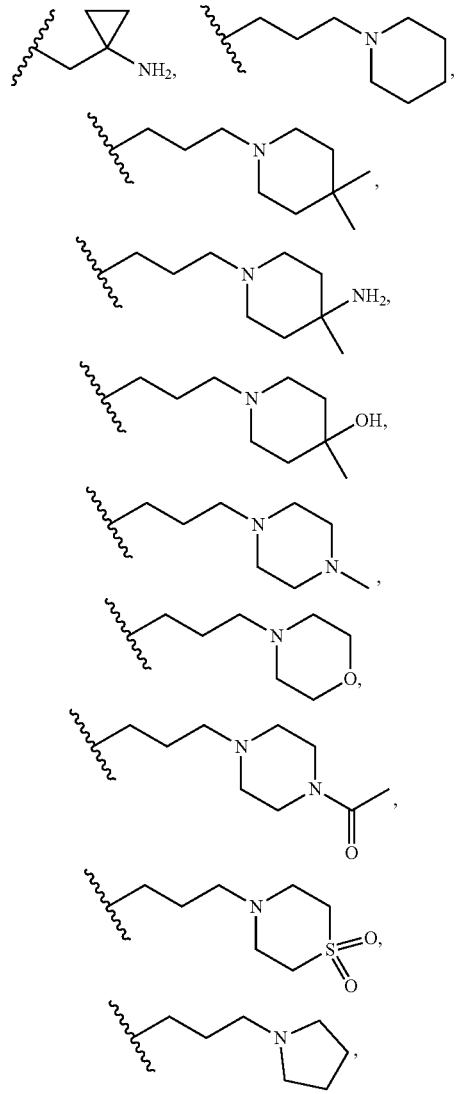

or —$(CH_2)_n$—$NR^aR^b$, wherein $R^a$ and $R^b$ are each independently H, methyl, ethyl, hydroxy, methoxymethyl, methoxyethyl, cyclopropyl, or cyclobutyl, and n is an integer of 1 to 6.

$R^3$ and $R^4$ are each independently —H, —$CF_3$, halogen, $C_1$-$C_3$ alkyl, or $C_1$-$C_3$ alkoxy;

Alternatively, $R^3$ and $R^4$ are each independently —H, —$CF_3$, —F, —Cl, methyl, ethyl, propyl, or isopropyl;

Alternatively, in the above-mentioned $R^2$, L is phenyl, pyridyl, pyrimidinyl, naphthyl, imidazolyl, pyrazolyl, thiazolyl, oxazolyl, pyrrolyl, pyridyl, pyranyl,

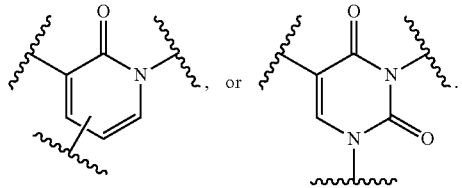

Yet alternatively, $R^2$ is $R^1$ is

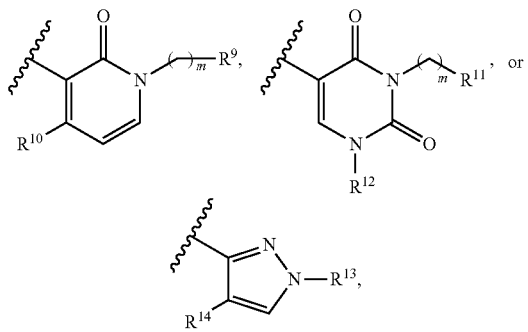

wherein $R^{10}$ and $R^{14}$ are each independently H, $C_1$-$C_3$ alkyl, or $C_1$-$C_3$ alkoxy, $R^9$ and $R^{11}$ are each independently a phenyl, pyridyl, or pyrimidinyl group or a $C_3$-$C_6$ cycloalkyl, wherein the phenyl, pyridyl, or pyrimidinyl group is unsubstituted or substituted with one or more of trifluoromethyl, halogen, $C_1$-$C_3$ alkyl, and $C_1$-$C_3$ alkoxy, and the $C_3$-$C_6$ cycloalkyl group is unsubstituted or substituted with one or more of trifluoromethyl, halogen, $C_1$-$C_3$ alkyl, and $C_1$-$C_3$ alkoxy, $R^{12}$ is H, $C_1$-$C_6$ alkyl, or $C_1$-$C_3$ alkyl, wherein the $C_1$-$C_3$ alkyl is substituted with 1 to 3 substituents selected from the group consisting of $C_3$-$C_6$ cycloalkyl, hydroxyl, $C_1$-$C_3$ alkoxy, halogen, carboxy, tert-butoxycarbonyl, alkenyl, and morpholinyl, $R^{13}$ is a phenyl, pyridyl, or pyrimidinyl group, wherein the phenyl, pyridyl, or pyrimidinyl group is unsubstituted or substituted with one or more of trifluoromethyl, halogen, $C_1$-$C_3$ alkyl, and $C_1$-$C_3$ alkoxy.

Still alternatively, $R^{10}$ and $R^{14}$ are each independently H, methoxy, or ethoxy, $R^9$ and $R^{11}$ are each independently $C_3$-$C_6$ cycloalkyl, or a phenyl, pyridyl, or pyrimidinyl group, wherein the phenyl, pyridyl, or pyrimidinyl group is substituted with at least one substituent selected from the group consisting of methyl, ethyl, —F, and —Cl, $R^{12}$ is methyl, ethyl, propyl, isopropyl, isobutyl, cyclopropylmethyl, hydroxyethyl, hydroxypropyl, methoxyethyl, methoxypropyl, ethoxyethyl, ethoxypropyl, fluoroethyl, morpholinopropyl, a hydroxylcarbonylmethyl group, tert-butoxycarbonylmethyl, or allyl, $R^{13}$ is a methylphenyl, pyridyl, or pyrimidinyl group, wherein the methylphenyl, pyridyl, or pyrimidinyl group is substituted with at least one substituent selected from the group consisting of —F and —Cl.

According to some embodiments of the present disclosure, in formula (I), Q is CH;

G is O;

Z is —OR¹;

R¹ is $C_1$-$C_6$ alkyl, or —$(CH_2)_n$—R⁸, wherein the $C_1$-$C_6$ alkyl is unsubstituted or substituted with 1 to 3 substituents selected from the group consisting of methoxy, ethoxy, propoxy, isopropoxy, methylthio, ethylthio, formyl, acetyl, hydroxyl, —F, trifluoromethyl, cyano, —$CONH_2$, cyclopropyl, cyclobutyl, cyclopentyl, and —$NR^aR^b$, and wherein R⁸ is substituted or unsubstituted 4- to 6-membered heteroalicyclic group containing 1 to 2 atoms selected from the group consisting of N, O, and S as a ring atom, and the substituted 4- to 6-membered heteroalicyclic group is substituted with 1 to 3 substituents selected from the group consisting of —F, methyl, ethyl, hydroxyl, amino, acetyl, formyl, trifluoromethyl, cyano, and oxo, and n is 0 to 6, the 4- to 6-membered heteroalicyclic group is selected from the group consisting of a 4- to 6-membered oxacycloalkyl group, a 4- to 6-membered azacycloalkyl group, a 4- to 6-membered thiacycloalkyl group, and the following groups:

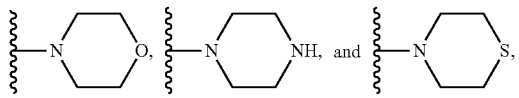

$R^a$ and $R^b$ are each independently —H, methyl, ethyl, methoxymethyl, methoxyethyl, methoxypropyl, cyclopropyl, or cyclobutyl;

R³ and R⁴ are each independently —H, —F, —Cl, methyl, or ethyl;

R² is

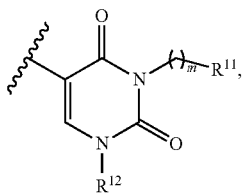

R¹¹ is phenyl unsubstituted or substituted with one or more of trifluoromethyl, F, Cl, methyl, ethyl, methoxy, and ethoxy, R¹² is H, methyl, ethyl, propyl, or isopropyl.

The disclosure also provides a method for preparing the compound of formula (I), or a pharmaceutically acceptable salt, an isomer, a hydrate, a solvate, or a prodrug thereof, which is characterized in that the method comprises the step of reacting the compound represented by formula (III) with the compound represented by formula (II) to afford the compound of formula (I), wherein Q, Q Z, R¹, R², R³ and R⁴ are as defined above, and X is hydroxy, or halogen,

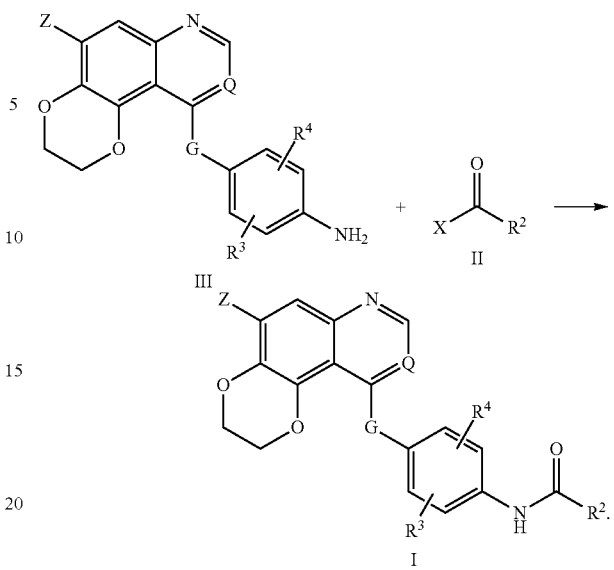

Alternatively, X is hydroxyl or Cl. Yet alternatively, X is Cl.

According to some embodiments of the present disclosure, the pharmaceutically acceptable salt of the compound is selected from the group consisting of one or more of the following salts: hydrochloride, hydrobromide, hydroiodide, perchlorate, sulfate, nitrate, phosphate, formate, acetate, propionate, glycolate, lactate, succinate, maleate, tartrate, malate, citrate, fumarate, gluconate, benzoate, mandelate, methanesulfonate, isethionate, benzenesulfonate, oxalate, palmitate, 2-naphthalenesulfonate, p-toluenesulfonate, cyclohexylsulfamate, salicylate, hexonate, trifluoroacetate, aluminum salt, calcium salt, chloroprocaine salt, choline salt, diethanolamine salt, ethylenediamine salt, lithium salt, magnesium salt, potassium salt, sodium salt and zinc salt.

Another aspect of the present disclosure relates to use of the aromatic ring-linked dioxino-quinazoline or dioxino-quinoline compound of formula (I), or an isomer, a hydrate, a solvate, a pharmaceutically acceptable salt, or a prodrug thereof, in the manufacture of a medicament for treating diseases related to tyrosine kinase TRK, c-MET, AXL, MER and/or VEGFR2, wherein the diseases related to tyrosine kinase TRK, c-MET, AXL, MER and/or VEGFR2 include fundus oculi disease, xerophthalmia, psoriasis, vitiligo, dermatitis, alopecia areata, rheumatoid arthritis, colitis, multiple sclerosis, systemic lupus erythematosus, Crohn's disease, atherosclerosis, pulmonary fibrosis, liver fibrosis, bone marrow fibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myelocytic leukemia, non-Hodgkin's lymphoma, nasopharyngeal cancer, esophageal cancer, brain tumor, B-cell and T-cell lymphoma, lymphoma, multiple myeloma, biliary tract cancerous sarcoma, and bile duct cancer.

Another aspect of the present disclosure provides a pharmaceutical composition comprising the compound represented by formula (I) or an isomer, a hydrate, a solvate, a pharmaceutically acceptable salt, or a prodrug thereof of the present disclosure, and one or more pharmaceutically acceptable carriers or excipients.

According to some embodiments of the present disclosure, the pharmaceutical composition may also include one or more other therapeutic agents.

The present disclosure also relates to a method for treating diseases or conditions mediated by tyrosine kinase TRK, c-MET, AXL, MER and/or VEGFR2, which comprises administering a therapeutically effective amount of a compound of formula (I) or a salt thereof to a patient (human or other mammals, especially human) in need thereof, wherein the diseases or conditions mediated by tyrosine kinase TRK, c-MET, AXL, MER and/or VEGFR2 include those mentioned above.

DETAILED DESCRIPTION OF THE INVENTION

Unless otherwise stated, the following terms used in this application (including the specification and claims) have the definitions given below. In this application, the use of "or" or "and" means "and/or" unless stated otherwise. In addition, the use of the term "comprising" and other forms such as "including", "containing" and "having" is not limiting. The chapter headings used herein are for organizational purposes only and should not be interpreted as limitations on the topics described.

"Alkyl" refers to an aliphatic hydrocarbon group. An alkyl group is saturated or unsaturated. An alkyl moiety, whether saturated or unsaturated, can be branched or linear. "Alkyl" can have 1 to 10 carbon atoms, preferably 1 to 6 carbon atoms. In one aspect, the alkyl group is selected from methyl, ethyl, propyl, isopropyl, n-butyl, isobutyl, sec-butyl and tert-butyl. Typical alkyl groups include, but are not limited to, methyl, ethyl, propyl, isopropyl, butyl, isobutyl, sec-butyl, tert-butyl, pentyl, neopentyl, hexyl, allyl, vinyl, ethynyl, but-2-enyl, but-3-enyl, etc.

The term "cycloalkyl" refers to a monocyclic or polycyclic aliphatic non-aromatic group in which each atom that makes up the ring (i.e., the backbone atom) is a carbon atom. A cycloalkyl group can be saturated or partially unsaturated. A cycloalkyl group can be fused with an aromatic ring and the point of attachment is on a carbon that is not an carbon atom in the aromatic ring. A cycloalkyl group includes a group having 3-10 ring atoms. In some embodiments, a cycloalkyl group is selected from cyclopropyl, cyclobutyl, cyclopentyl, cyclopentenyl, cyclohexyl, cyclohexenyl, cycloheptyl, and cyclooctyl. A cycloalkyl group can be substituted or unsubstituted. Depending on the structure, a cycloalkyl group can be a monovalent group or a divalent group (i.e., a cycloalkylene group, such as, but not limited to, cyclopropan-1,1-diyl, cyclobutan-1,1-diyl, cyclopentan-1,1-diyl, cyclohexan-1,1-diyl, cyclohexan-1,4-diyl, cycloheptan-1,1-diyl, etc.). In one aspect, a cycloalkyl group is $C_3$-$C_6$ cycloalkyl.

"Alkoxyalkyl" refers to a (alkyl)O(alkyl)- group, and "alkylthioalkyl" refers to a (alkyl)S(alkyl)- group, wherein the alkyl group is as defined herein. Preferably, the alkoxyalkyl group is $C_1$-$C_3$ alkoxyalkyl, more preferably $C_1$-$C_3$ alkoxy-$C_1$-$C_3$ alkyl, more preferably $C_1$-$C_3$ alkoxyethyl or $C_1$-$C_3$ alkoxypropyl. Preferably, the alkylthioalkyl group is $C_1$-$C_3$ alkylthioalkyl, more preferably $C_1$-$C_3$ alkylthio-$C_1$-$C_3$ alkyl, more preferably $C_1$-$C_3$ alkylthioethyl, or $C_1$-$C_3$ alkylthiopropyl.

"Heterocyclyl" in the term "5- to 6-membered heterocyclyl" refers to an aromatic heterocyclic ring (also referred to as heteroaryl) and a heterocycloalkyl ring (also referred to as an aliphatic heterocyclic group) containing one or more heteroatoms in the ring, wherein each heteroatom in the ring is selected from O, S, and N, wherein each heterocyclyl group contains 5-6 atoms in its ring system. Moreover, the 5- to 6-membered heterocyclyl may be a heterocyclyl containing 1 to 2 heteroatoms selected from N, O, and S, which is unsubstituted or substituted with 1 to 2 substituents selected from hydroxy, $C_1$-$C_3$ alkyl, and $C_1$-$C_3$ acyl.

In this disclosure, the term "isomer" refers to different compounds having the same molecular formula, and may include various isomeric forms such as stereoisomers and tautomers. "Stereoisomers" are isomers that differ only in the arrangement of their atoms in space. Certain compounds described herein contain one or more asymmetric centers and thus can give rise to enantiomers, diastereomers, and other stereoisomeric forms which can be defined as (R)- or (S)-based on absolute stereochemistry. The chemical entities, pharmaceutical compositions, and methods disclosed herein are intended to include all of these possible isomers, including racemic mixtures, optically pure forms, and intermediate mixtures. Optically active (R)- and (S)-isomers can be prepared using chiral synthons or chiral reagents or resolved using conventional techniques. The optical activity of a compound can be analyzed by any suitable method, including but not limited to chiral chromatography and polarimetry, and the degree of dominance of one stereoisomer over other isomers can be determined.

"Tautomers" are structurally different isomers that can be converted to each other through tautomerization. "Tautomerization" is a form of isomerization and includes a proton transfer tautomerization, which can be considered as a subset of acid-base chemistry. "Proton transfer tautomerization" involves the migration of a proton accompanied by a bond-level transformation, which is often exchange of a single bond with an adjacent double bond. When tautomerization is possible (for example, in solution), a chemical equilibrium of tautomers can be reached. An example of tautomerization is keto-enol tautomerization.

In this disclosure, a compound of formula (I), or an isomer, a crystal, a prodrug or a pharmaceutically acceptable salt thereof may exist in solvated and unsolvated forms. For example, the solvated form may be a water-soluble form. The present disclosure includes all of these solvated and unsolvated forms.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into the compound of the present disclosure in vivo. Such transformation is affected by hydrolysis of the prodrug in the blood or enzymatic conversion to the parent compound in the blood or tissue.

Pharmaceutical compositions of this disclosure comprise the compound described herein or a pharmaceutically acceptable salt thereof; an additional agent selected from a kinase inhibitory agent (small molecule, polypeptide, antibody, etc.), an immunosuppressant, an anticancer agent, an anti-viral agent, anti-inflammatory agent, antifungal agent, antibiotic, or an anti-vascular hyper proliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, comprising a method for administering to the subject a therapeutically effective amount of a composition containing the compound of the present disclosure. The method of the present disclosure also comprises the treatment of a cancer that is resistant to one or more other treatment methods. The compound of the present disclosure can be used as monotherapy or in combination therapy, and can be used in combination with multiple compounds of the present disclosure or in combination with other drugs other than the compounds of the present disclosure.

The present disclosure also includes the use of the compound of the present disclosure, or a pharmaceutically acceptable derivative thereof, in the manufacture of a medicament for treating cancers and autoimmune diseases related to tyrosine kinase TRKA, c-MET, AXL, MER, or VEGFR2. The cancers (including non-solid tumors, solid tumors, primary or metastatic cancer, as indicated elsewhere herein and including one or more of other therapies to which the cancer is resistant or refractory), as well as other diseases (including, but not limited to, ocular fundus diseases, psoriasis, atheroma, pulmonary fibrosis, liver fibrosis, myelofibrosis, and the like). The cancer includes, but is not limited to any one of non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, and cholangiocarcinoma. The autoimmune diseases include, but are not limited to: psoriasis, vitiligo, dermatitis, alopecia areata, rheumatoid arthritis, colitis, multiple sclerosis, systemic lupus erythematosus, and Crohn's disease.

The present disclosure also provides a method for preparing the corresponding compounds. A variety of synthetic methods can be used to prepare the compounds described herein, including the method involved in the following examples. The compounds of the present disclosure, or pharmaceutically acceptable salts, isomers or hydrates thereof, can be synthesized using the following methods, synthetic methods known in the field of organic chemical synthesis, or variations of these methods understood by those skilled in the art. Preferred methods include but are not limited to the following methods.

In order to make the objectives, technical solutions and advantages of the present disclosure more clear, the present disclosure will be further described in detail below in conjunction with specific examples. It should be understood that the specific examples described here are only used to explain the present disclosure and are not intended to limit the present invention. If no specific technology or conditions are indicated in examples, the technology or conditions described in the literature in the art or the product specification shall be followed. If reagents or instruments used do not indicate manufacturers, they are all conventional products that are commercially available. The term "and/or" as used herein includes any and all combinations of one or more related listed items. The names of some compounds in this disclosure are generated by Chemdraw and translated into Chinese.

Synthesis of Intermediates

Preparation of 10-chloro-5-methoxy-2,3-dihydro-[1,4]dioxino[2,3-f]quinoline

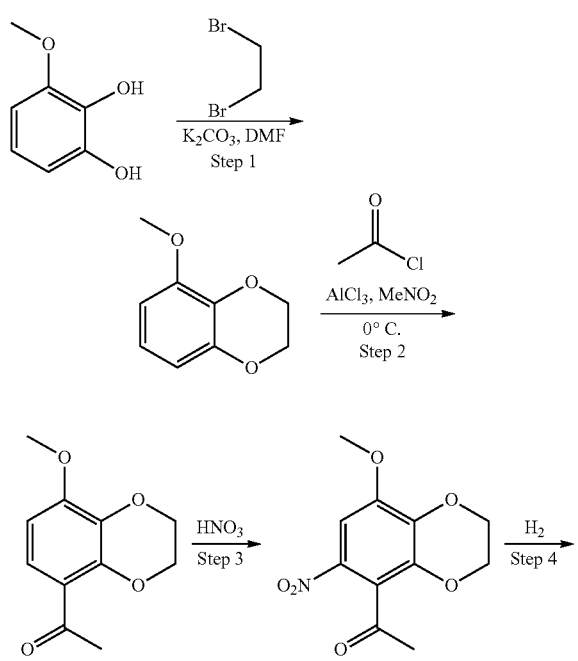

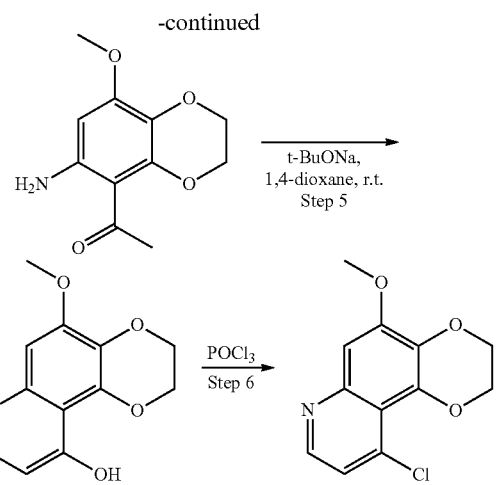

Step 1): A solution of 3-methoxycatechol (25.3 g, 180 mmol), potassium carbonate (104.5 g, 756 mmol), and 1,2-dibromoethane (74.4 g, 396 mmol) in DMF (100 mL) was heated and reacted at 60° C. under nitrogen atmosphere for 6 hours. The reaction solution was quenched with water and extracted with ethyl acetate. The organic phase was washed with saturated sodium bicarbonate solution, dried over magnesium sulfate, filtered, and concentrated to afford 5-methoxy-2,3-dihydrobenzo[b][1,4]dioxine as a dark gray oil (25.4 g, 153 mmol, yield: 85%);

Step 2): Acetyl chloride (5.57 mL, 78 mmol) was slowly added dropwise to nitromethane (200 mL) containing AlCl₃ (12.0 g, 90 mmol) in an ice-water bath under nitrogen atmosphere. A solution of the product (10.0 g, 60 mmol) obtained in step 1) in nitromethane (100 mL) was then slowly added dropwise. The reaction solution was reacted with stirring at room temperature for 5 hours, and then quenched with 1N hydrogen chloride solution. The organic phase was washed with saturated sodium chloride solution, dried over magnesium sulfate, filtered and concentrated. The residue was heated under reflux in isopropanol (25 mL), cooled and allowed to stand, and filtered to afford 5-acetyl-2,3-dihydro-8-methoxy-1,4-benzodioxine as a gray solid (10.1 g, 49 mmol, 81%);

Step 3): Concentrated nitric acid (62%, 20 mL) was added dropwise to a solution of 5-acetyl-2,3-dihydro-8-methoxy-1,4-benzodioxine (10.1 g, 49 mmol) in acetic acid (60 mL) under an ice-water bath, and stirred at room temperature for 3 hours. The reaction solution was slurried with water, and filtered. The filter cake was dried to afford 1-(8-methoxy-6-nitro-2,3-dihydrobenzo[b][1,4]dioxin-5-yl)ethyl-1-one as a yellow solid (10.5 g, yield: 85%);

Step 4): Wet palladium on carbon (10%, 0.5 g) was added to a solution of the product (10.1 g, 40 mmol) obtained in step 3) in methanol (100 mL), purged with hydrogen gas, and then reacted with stirring for 10 hours. The reaction solution was filtered and concentrated to afford 1-(6-amino-8-methoxy-2,3-dihydrobenzo[b][1,4]dioxin-5-yl)ethyl-1-one as a purple oil (8.8 g, yield: 95%), MS: 224 [M+H]⁺;

Step 5): Sodium tert-butoxide (4.4 g, 46 mmol) was added to a solution of the product (4.5 g, 20 mmol) obtained in step 4) in dioxane (80 mL), and stirred at room temperature for half an hour. A solution of methyl formate (10.8 mL, 132 mmol) in dioxane (10 mL) was added, and stirred at room temperature for 15 hours. The reaction solution was added to ice water and adjusted to a pH of 7 with 2 N dilute hydrochloric acid. The reaction solution was slurried, and filtered. The filter cake was dried to afford 5-methoxy-2,3-dihydro-[1,4]dioxino[2,3-f]quinolin-10-ol as a gray solid (3.8 g, yield: 82%) MS: 234 [M+H]+;

Step 6): Triethylamine (3 mL) was added to a solution of the product (2.4 g, 10 mmol) obtained in step 5) in phosphorous oxychloride (30 mL) under an ice-water bath, heated to reflux and reacted for 5 hours. The reaction solution was cooled and concentrated. The residue was dissolved with water and adjusted to a pH of 9 with potassium bicarbonate. The reaction solution was slurried, and filtered. The filter cake was dried to afford 2.2 g of 10-chloro-5-methoxy-2,3-dihydro-[1,4]dioxino[2,3-f]quinoline as an ochre solid (yield: 88%), MS: 252 [M+H]+.

Class A Intermediates

Intermediate A-1. Preparation of 1-(4-fluorophenyl)-2-oxo-1,2-dihydropyridine-3-carbonyl chloride

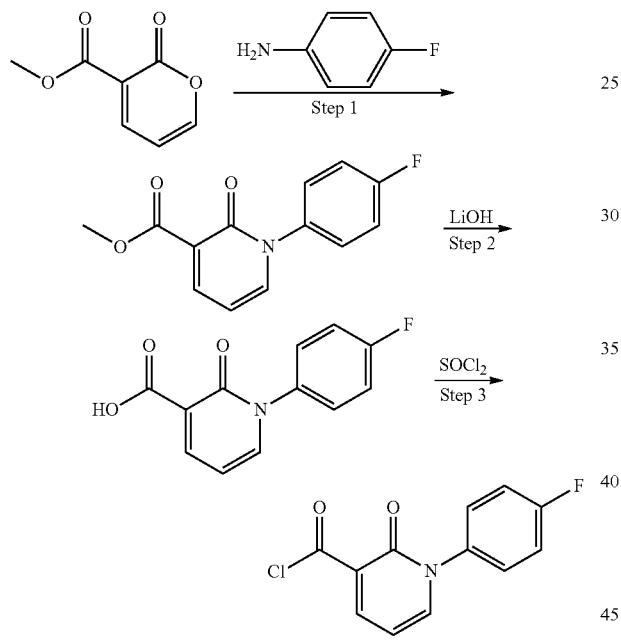

Step 1): Methyl 2-oxo-2H-pyran-3-carboxylate (0.72 g, 6.5 mmol) and 4-fluoroaniline (1 g, 6.5 mmol) were added to DMF (6 mL) under an ice-water bath. The reaction solution was reacted with stirring at room temperature for 5 hours. EDC (1-(3-dimethylaminopropyl)-3-ethylcarbodiimide hydrochloride) (1.62 g, 8.5 mmol) and DMAP (4-dimethylaminopyridine) (0.2 g, 1.6 mmol) were added and reacted with stirring at room temperature for 15 hours. The reaction solution was concentrated, extracted with ethyl acetate, and washed with saturated sodium chloride. The organic phase was dried, concentrated and purified by column chromatography to afford 0.88 g of methyl 1-(4-fluorophenyl)-2-oxo-1,2-dihydropyridine-3-carboxylate as a yellow solid (yield: 55%) MS: 248 [M+H]+;

Step 2): The yellow solid (0.88 g, 3.6 mmol) obtained in step 1 was added to a mixed solution of methanol (5 mL), tetrahydrofuran (5 mL) and water (1 mL). Hydrated lithium hydroxide (0.15 g, 3.6 mmol) was then added, and reacted with stirring at room temperature for 10 hours. The reaction solution was extracted with ethyl acetate. The aqueous phase was adjusted to a pH of 4 with dilute hydrochloric acid. A white solid was precipitated out. The solid was filtered and dried to afford 0.7 g of 1-(4-fluorophenyl)-2-oxo-1,2-dihydropyridine-3-carboxylic acid as a white solid, MS: 234 [M+H]+;

Step 3): The product (230 mg, 1 mmol) obtained in step 2 was dissolved in thionyl chloride (2 mL), and heated under reflux for 1 hour. The reaction solution was cooled and concentrated to afford 1-(4-fluorophenyl)-2-oxo-1,2-dihydropyridine-3-carbonyl chloride as a yellowish solid (250 mg, yield: 100%).

Intermediate A-2. Preparation of 1-(4-fluorophenyl)-4-ethoxy-2-oxo-1,2-dihydropyridine-3-carbonyl chloride

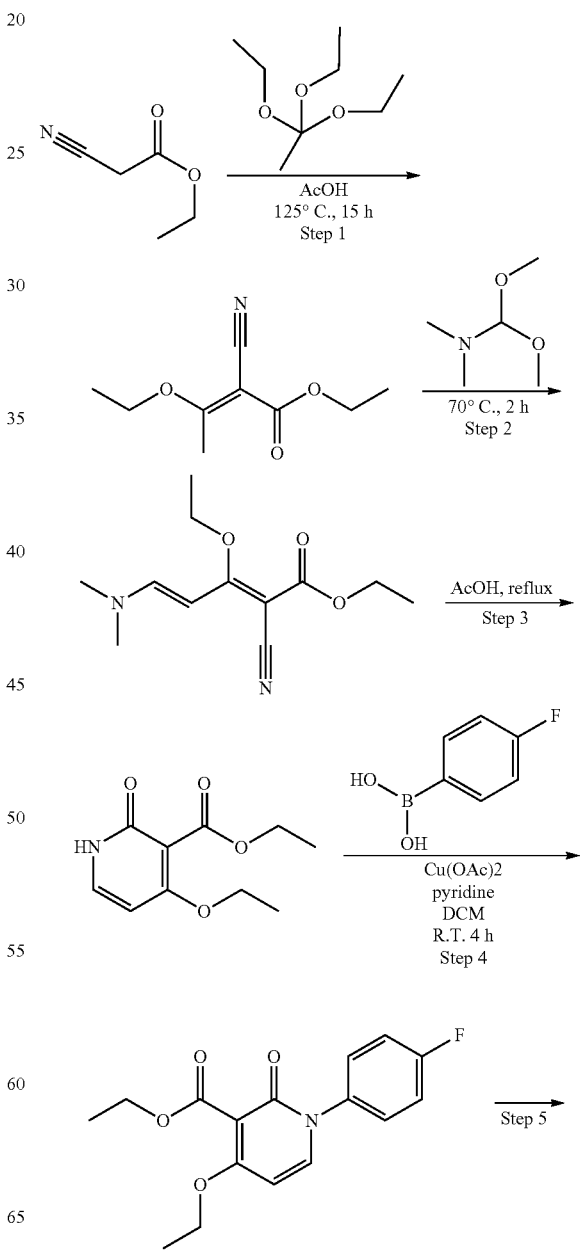

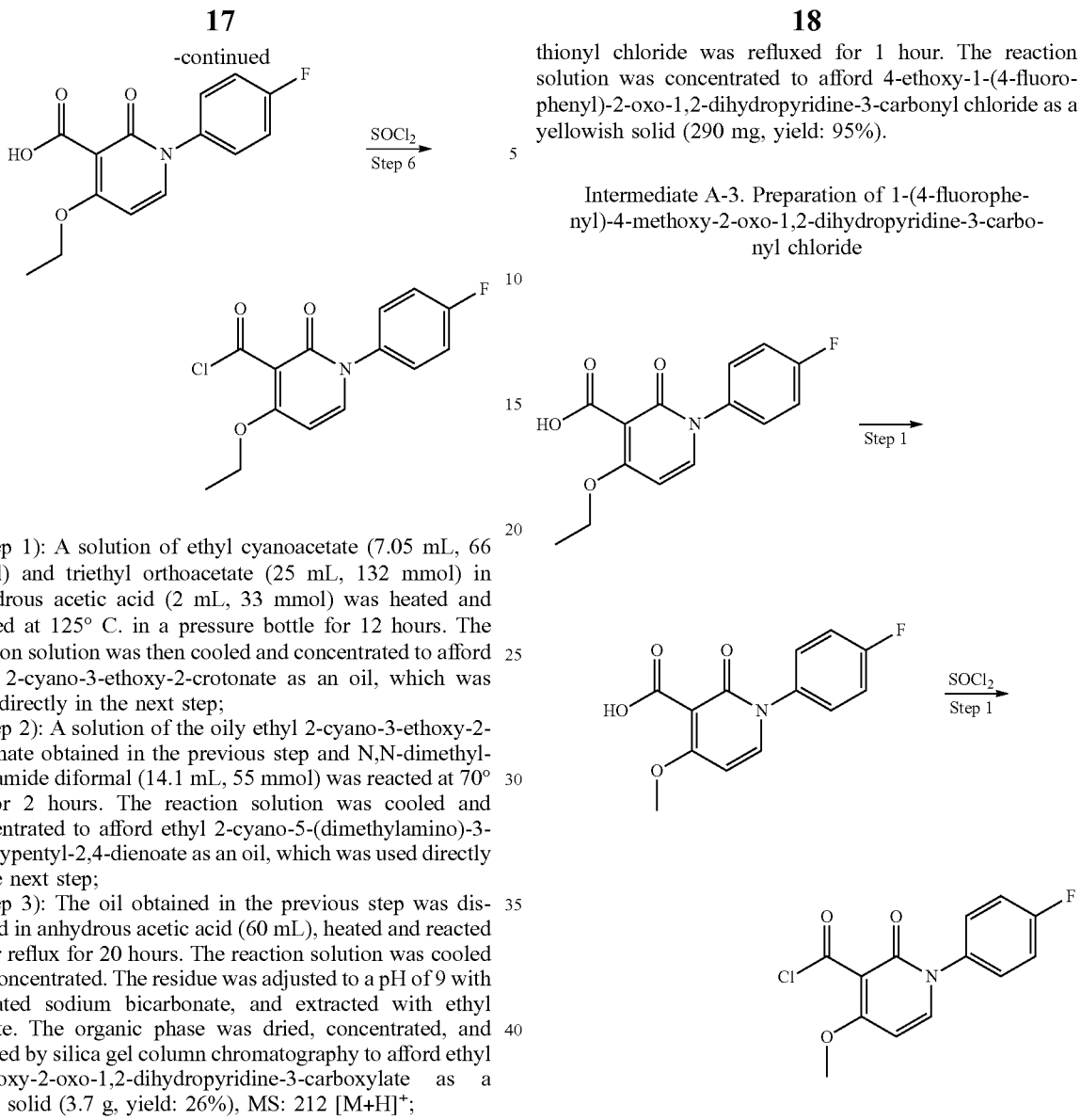

Step 1): A solution of ethyl cyanoacetate (7.05 mL, 66 mmol) and triethyl orthoacetate (25 mL, 132 mmol) in anhydrous acetic acid (2 mL, 33 mmol) was heated and reacted at 125° C. in a pressure bottle for 12 hours. The reaction solution was then cooled and concentrated to afford ethyl 2-cyano-3-ethoxy-2-crotonate as an oil, which was used directly in the next step;

Step 2): A solution of the oily ethyl 2-cyano-3-ethoxy-2-crotonate obtained in the previous step and N,N-dimethyl-formamide diformal (14.1 mL, 55 mmol) was reacted at 70° C. for 2 hours. The reaction solution was cooled and concentrated to afford ethyl 2-cyano-5-(dimethylamino)-3-ethoxypentyl-2,4-dienoate as an oil, which was used directly in the next step;

Step 3): The oil obtained in the previous step was dissolved in anhydrous acetic acid (60 mL), heated and reacted under reflux for 20 hours. The reaction solution was cooled and concentrated. The residue was adjusted to a pH of 9 with saturated sodium bicarbonate, and extracted with ethyl acetate. The organic phase was dried, concentrated, and purified by silica gel column chromatography to afford ethyl 4-ethoxy-2-oxo-1,2-dihydropyridine-3-carboxylate as a white solid (3.7 g, yield: 26%), MS: 212 [M+H]$^+$;

Step 4): Ethyl 4-ethoxy-2-oxo-1,2-dihydropyridine-3-carboxylate (3 g, 14.2 mmol), 4-fluorophenylboronic acid (4 g, 42.6 mmol), copper acetate (5.7 g, 28.4 mmol) and pyridine (4.4 g, 57 mmol) in dichloromethane (30 mL) were exposed to the air and stirred at room temperature for 5 hours. The reaction solution was filtered, and the filter residue was washed three times with dichloromethane. The organic phase was concentrated and purified by column chromatography to afford ethyl 4-ethoxy-1-(4-fluorophenyl)-2-oxo-1,2-dihydropyridine-3-carboxylate as a white solid (3.2 g, yield: 80%), MS: 306 [M+H]$^+$;

Step 5): Ethyl 4-ethoxy-1-(4-fluorophenyl)-2-oxo-1,2-dihydropyridine-3-carboxylate (3 g, 10 mmol) and LiOH·H$_2$O (1.26 g, 30 mmol) were added to a mixed solution of ethanol (10 mL) and water (5 mL), and reacted with stirring at room temperature for 12 hours. The reaction solution was concentrated to remove ethanol, and extracted with ethyl acetate. The aqueous phase was adjusted to a pH of 2 with dilute hydrochloric acid, and then extracted with ethyl acetate. The organic phase was dried and concentrated to afford 4-ethoxy-1-(4-fluorophenyl)-2-oxo-1,2-dihydropyridine-3-carboxylic acid as a white solid (2.2 g, yield: 82%);

Step 6): A solution of 4-ethoxy-1-(4-fluorophenyl)-2-oxo-1,2-dihydropyridine-3-carboxylic acid (280 mg, 1 mmol) in thionyl chloride was refluxed for 1 hour. The reaction solution was concentrated to afford 4-ethoxy-1-(4-fluorophenyl)-2-oxo-1,2-dihydropyridine-3-carbonyl chloride as a yellowish solid (290 mg, yield: 95%).

Intermediate A-3. Preparation of 1-(4-fluorophenyl)-4-methoxy-2-oxo-1,2-dihydropyridine-3-carbonyl chloride Step 1): 4-Ethoxy-1-(4-fluorophenyl)-2-oxo-1,2-dihydropyridine-3-carboxylic acid (370 mg, 1.2 mmol) was added to a solution of sodium methoxide (28%) in methanol, and stirred at room temperature for 2 hours. The reaction solution was concentrated to remove methanol, and extracted with ethyl acetate. The aqueous phase was adjusted to a pH of 2 with dilute hydrochloric acid, and then extracted with ethyl acetate. The organic phase was dried and concentrated to afford 1-(4-fluorophenyl)-4-methoxy-2-oxo-1,2-dihydropyridine-3-carboxylic acid as a white solid (0.25 g, MS: 264 [M+H]$^+$;

Step 2): 1-(4-Fluorophenyl)-4-methoxy-2-oxo-1,2-dihydropyridine-3-carboxylic acid (130 mg, 0.5 mmol) was heated in thionyl chloride (1 mL) under reflux for 1 hour. The reaction solution was cooled and concentrated to afford 1-(4-fluorophenyl)-4-methoxy-2-oxo-1,2-dihydropyridine-3-carbonyl chloride as a yellowish solid (150 mg, yield: 95%).

Intermediate A-4 to A-9 can be prepared with the same method as above by using phenylboronic acid with different substituents, and the structural formulae thereof are as shown in Table 1 below:

TABLE 1

Structures and names of intermediates A-4 to A-9

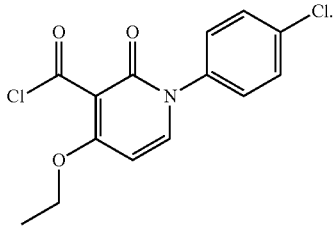

A-4
1-(4-chlorophenyl)-4-ethoxy-
2-oxo-1,2-dihydropyridine-
3-carbonyl chloride

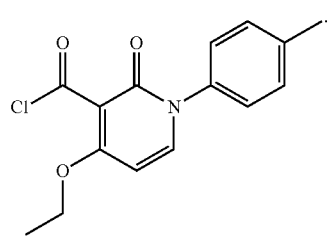

A-5
1-(4-methylphenyl)-4-
ethoxy-2-oxo-1,2-
dihydropyridine-3-carbonyl
chloride

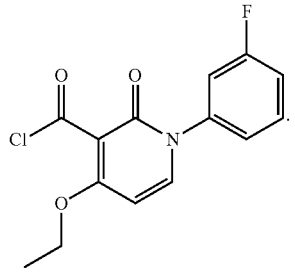

A-6
1-(3-fluorophenyl)-4-ethoxy-
2-oxo-1,2-dihdyropyridine-
3-carbonyl chloride

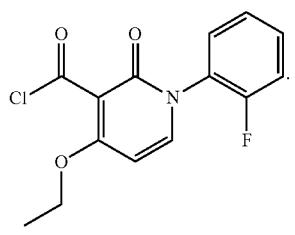

A-7
1-(2-fluorophenyl)-4-ethoxy-
2-oxo-1,2-dihydropyridine-
3-carbonyl chloride

TABLE 1-continued

Structures and names of intermediates A-4 to A-9

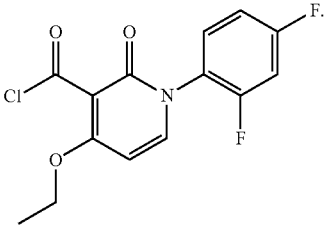

A-8
1-(2,4-difluorophenyl)-4-
ethoxy-2-oxo-1,2-dihydro
pyridine-3-carbonyl
chloride

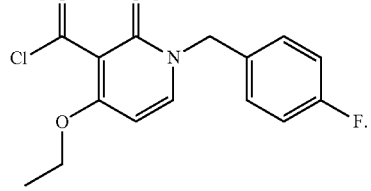

A-9
1-(4-fluorobenzyl)-4-ethoxy-
2-oxo-1,2-dihydropyridine-
3-carbonyl chloride

Class B Intermediates

Intermediate B-1. Preparation of ethyl 1-(4-fluoro-
2-methylphenyl)-1H-pyrazole-3-carboxylate

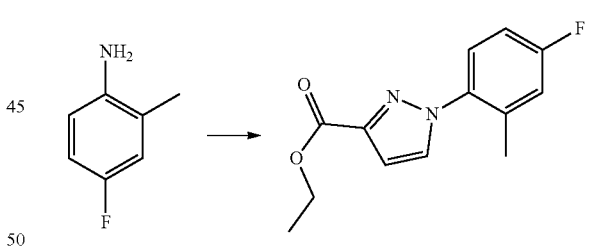

For the synthetic method, see Journal of Medicinal Chemistry, 53(2), 855-866; 2010.

Intermediate B-2

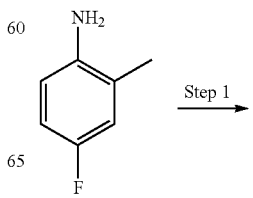

Step 1

-continued

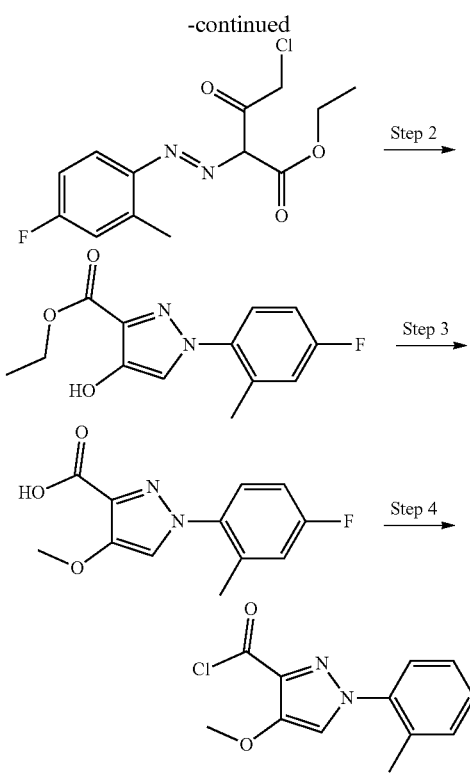

Step 1): A pre-cooled solution of sodium nitrite (9.02 g, 108 mmol, 1.2 eq.) in concentrated sulfuric acid (40 mL) was slowly added dropwise to a mixed solution of dichloromethane/acetic acid (1:1, 180 mL) containing 2-methyl-4-fluoroaniline (10 g, 90.0 mmol, 1.0 eq.) under an ice-water bath. The reaction solution was reacted with stirring in an ice-water bath for 1 hour, and then a solution of ethyl 4-chloroacetoacetate (14.6 mL, 17.8 g, 108 mmol, 1.2 eq.) in acetic acid (60 mL) and water (120 mL) was added. The reaction solution was further reacted with stirring at 0° C. for half an hour, and then an aqueous solution (210 mL) of sodium carbonate (100 g, 1.219 mol, 13.5 eq.) was slowly added. The reaction solution was stirred at 0° C. for half an hour, and then stirred at room temperature for 1 hour. The mixture was extracted with dichloromethane (200 mL) to afford an organic phase. The aqueous phase was further extracted three times with dichloromethane (100 mL). The organic phases were combined, washed with saturated sodium chloride solution, dried over anhydrous magnesium sulfate, filtered, and concentrated to afford ethyl 4-chloro-2-(2-methyl-4-fluorophenyl)azo-3-oxobutanoate as a yellow oil;

Step 2): Potassium acetate (12.4 g, 126 mmol, 1.4 eq.) was added to a solution of the above-mentioned oil in absolute ethanol (180 mL), and then reacted under reflux for 1 h. The reaction solution was slurried with ethyl acetate and then washed with water. The aqueous phase was extracted with ethyl acetate. The organic phase was washed with saturated aqueous sodium chloride solution, dried over anhydrous sodium sulfate, and concentrated. The crude product was recrystallized from ethyl acetate to afford 18.21 g of ethyl 1-(4-fluoro-2-methylphenyl)-4-hydroxy-1H-pyrazole-3-carboxylate as a brown solid. MS: 265 [M+H]$^+$, 287 [M+Na]$^+$;

Step 3): Ethyl 1-(4-fluoro-2-methylphenyl)-4-hydroxy-1H-pyrazole-3-carboxylate (265 mg, 1 mmol), potassium carbonate (210 mg, 1.5 mmol) and methyl iodide (0.1 mL) were added to DMF (5 mL), heated and reacted at 60° C. for 2 hours. Water was added, and the mixture was extracted with ethyl acetate. The organic phase was washed with saturated sodium chloride solution, dried and concentrated to afford 280 mg of a brown solid. This solid was added to a solution of lithium hydroxide (50 mg, 2 mmol) in the mixture of water (0.5 mL), tetrahydrofuran (2.5 mL), and methanol (2.5 mL), and reacted with stirring at room temperature for two hours. The reaction solution was extracted with ethyl acetate, and the aqueous phase was adjusted to a pH of 3. A white solid was precipitated out. The solid was filtered and dried to afford 160 mg of 1-(4-fluoro-2-methylphenyl)-4-methoxy-1H-pyrazol-3-carboxylic acid as a white solid, MS: 251 [M+H]$^+$;

Step 4): 1-(4-Fluoro-2-methylphenyl)-4-methoxy-1H-pyrazol-3-carboxylic acid (125 mg, 0.5 mmol) was dissolved in thionyl chloride (2 mL), and heated under reflux for 2 hours. The reaction solution was cooled and concentrated to afford 130 mg of 1-(4-fluoro-2-methylphenyl)-4-methoxy-1H-pyrazol-3-carbonyl chloride as a yellow solid.

Intermediate B-3. It was prepared using the synthesis of Intermediate B-2, except that methyl iodide in step 3) was replaced with bromoethane.

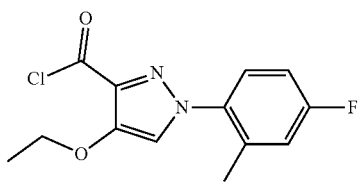 [SMILES: CCOc1cn(-c2ccc(F)cc2C)nc1C(=O)Cl]

Intermediate C

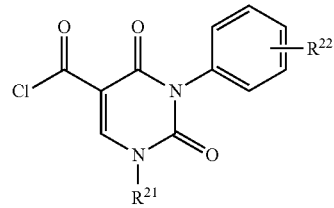

Synthesis of Intermediate C-1

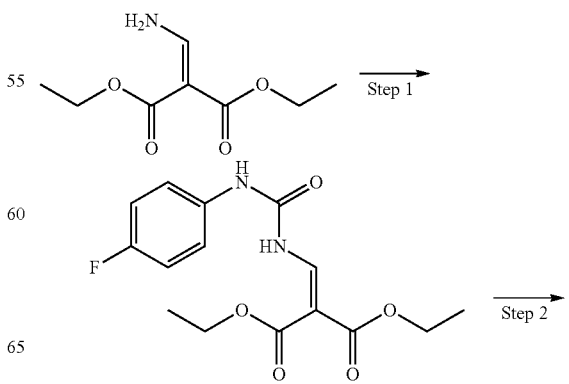

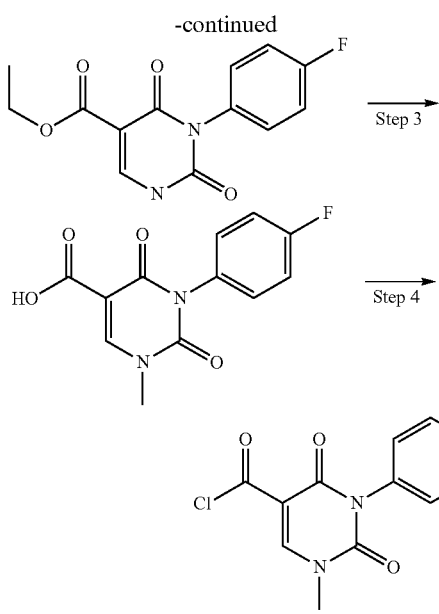

cooled and concentrated to afford 3-(4-fluorophenyl)-1-methyl-2,4-dioxo-1,2,3,4-tetrahydropyrimidine-5-carbonyl chloride as a white solid (270 mg, yield: 95%).

Intermediates C-2 to C-13 with different $R^{21}$ and $R^{22}$ were prepared by the same method as that for C-1 above, except that different $R^{22}$ was obtained by reacting with phenyl isocyanates substituted with different $R^{22}$ in step 1 and different $R^{21}$ was obtained by reacting with halides with different $R^{21}$ in step 3. The structures of the C-2 to C-13 intermediates were shown in Table 2 below:

TABLE 2

Structures and names of intermediates C-2 to C-13

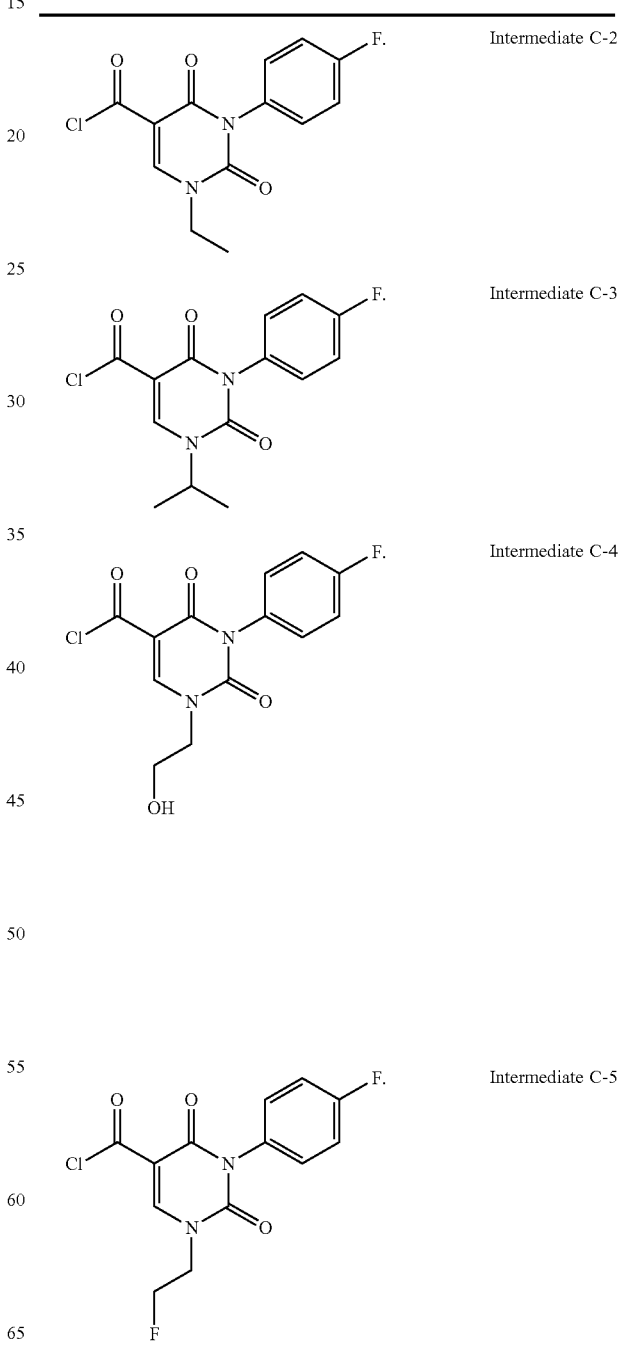

Step 1): N,N-diisopropylethylamine DIEA (17.1 mL, 98.1 mmol) was added to a solution of diethyl 2-(aminomethylene)malonate (16.7 g, 89.2 mmol) and 4-fluorophenyl isocyanate (10.6 mL, 93.7 mmol) in 1,2-dichloroethane (25 mL, 320 mmol), and reacted at 100° C. for 6 h. The reaction solution was cooled and a solid was precipitated out, which was washed with diethyl ether to afford diethyl 2-[3-(4-fluorophenyl)ureidomethylene]malonate as a yellow solid (24.5 g, yield: 85%), MS: 347 $[M+Na]^+$;

Step 2): Diethyl 2-[3-(4-fluorophenyl)ureidomethylene] malonate (24 g, 70 mmol) was uniformly dispersed in ethanol (100 mL), and then a 21% solution of NaOEt in ethanol (41.7 mL, 112 mmol) was added dropwise carefully. The mixture was stirred at room temperature for 4 hours. The reaction solution was concentrated, adjusted to a pH of 2 with dilute hydrochloric acid, and then filtered to afford a solid. The solid was washed with diethyl ether to afford ethyl 3-(4-fluorophenyl)-2,4-dioxo-1,2,3,4-tetrahydropyrimidine-5-carboxylate as a white solid, MS: 279 $[M+H]^+$;

Step 3): A solution of ethyl 3-(4-fluorophenyl)-2,4-dioxo-1,2,3,4-tetrahydropyrimidine-5-carboxylate (3.50 g, 11.6 mmol), potassium carbonate (3.22 g, 23.3 mmol) and methyl iodide (2.16 mL, 35.0 mmol) in DMF (10 mL) was heated to 65° C. and reacted for 12 hours. The reaction solution was cooled to room temperature, and extracted with ethyl acetate. The organic phase was washed with saturated sodium chloride solution, dried with anhydrous sodium sulfate, filtered, and concentrated to afford a yellow oil. The afforded oil was dissolved in a mixture of methanol (10 mL), tetrahydrofuran (10 mL) and an aqueous solution of lithium hydroxide (1M, 10.6 mL), and stirred at room temperature for 6 hours. The reaction solution was extracted with ethyl acetate. The aqueous phase was adjusted to a pH of 4 with dilute hydrochloric acid, and a white solid was precipitated out. The precipitated solid was filtered and dried to afford 3-(4-fluorophenyl)-1-methyl-2,4-dioxo-1,2,3,4-tetrahydro-pyrimidine-5-carboxylic acid as a white solid, MS: 265 $[M+H]^+$;

Step 4): A solution of 3-(4-fluorophenyl)-1-methyl-2,4-dioxo-1,2,3,4-tetrahydropyrimidine-5-carboxylic acid (260 mg, 1 mmol) in thionyl chloride (2 mL) was heated and reacted under reflux for 2 hours. The reaction solution was TABLE 2-continued
Structures and names of intermediates C-2 to C-13
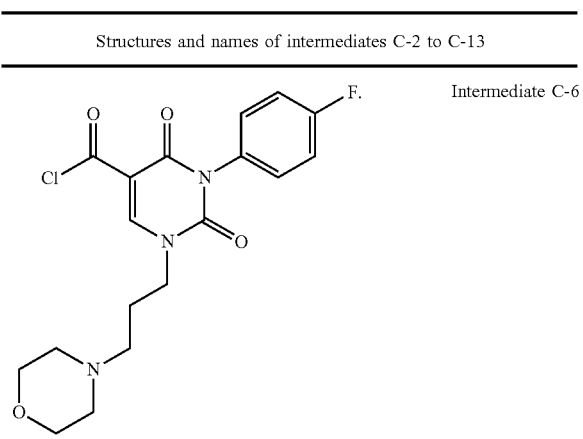
Intermediate C-6
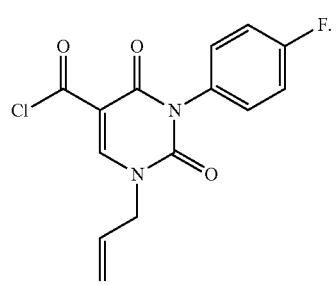 [SMILES: C=CCn1cc(C(=O)Cl)c(=O)n(-c2ccc(F)cc2)c1=O]
Intermediate C-7
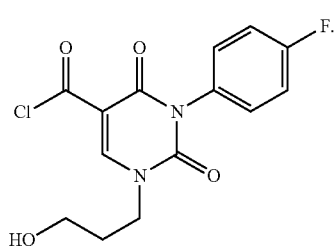 [SMILES: O=C(Cl)c1cn(CCCO)c(=O)n(-c2ccc(F)cc2)c1=O]
Intermediate C-8
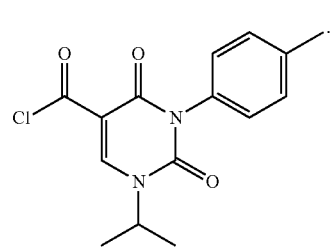 [SMILES: Cc1ccc(-n2c(=O)c(C(=O)Cl)cn(C(C)C)c2=O)cc1]
Intermediate C-9
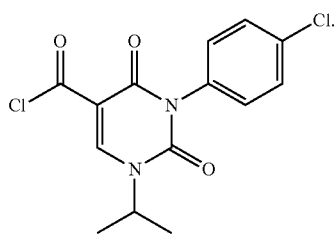 [SMILES: CC(C)n1cc(C(=O)Cl)c(=O)n(-c2ccc(Cl)cc2)c1=O]
Intermediate C-10
TABLE 2-continued
Structures and names of intermediates C-2 to C-13
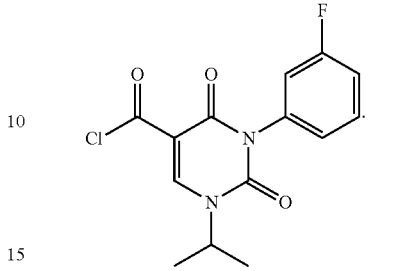
Intermediate C-11
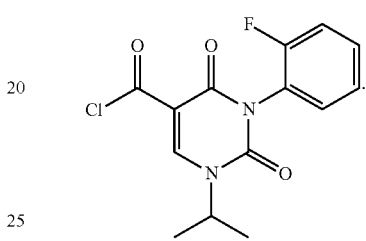
Intermediate C-12
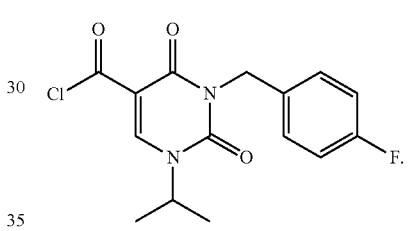
Intermediate C-13
Intermediate D.
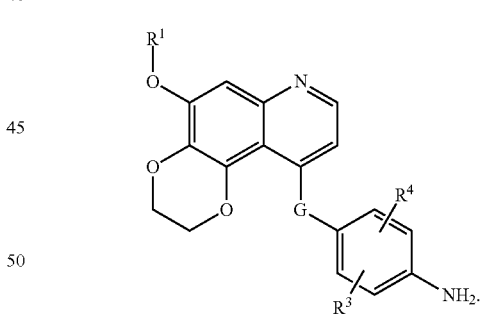
D-1
Intermediate D-1. 3-fluoro-4-((5-methoxy-2,3-dihydro-[1,4]dioxino[2,3-f]quinolin-10-yl)oxy)aniline
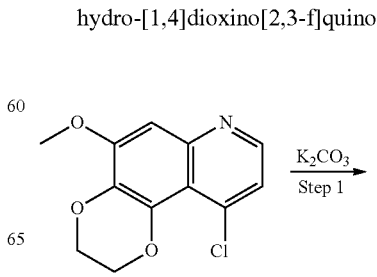

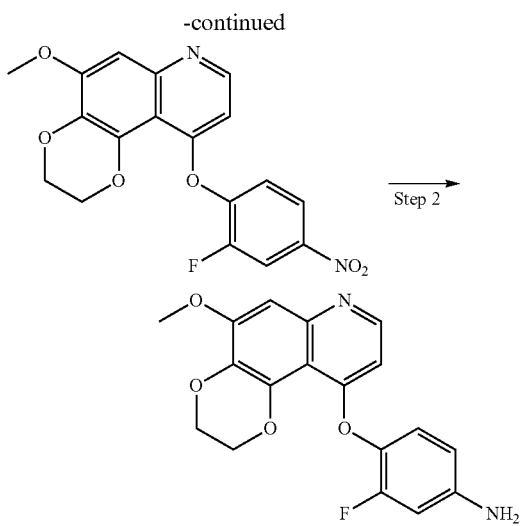

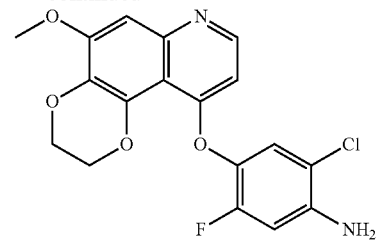

Step 1): A solution of 10-chloro-5-methoxy-2,3-dihydro-[1,4]dioxino[2,3-f]quinoline (2.5 g, 10 mmol), 5-chloro-2-fluoro-4-nitrophenol (1.9 g, 10 mmol) and potassium carbonate (2.1 g, 15 mmol) in DMF (20 mL) was heated and reacted at 80° C. for 3 hours. The reaction solution was cooled, slurried with water, and filtered. The filter cake was dried to afford 10-(5-chloro-2-fluoro-4-nitrophenoxy)-5-methoxy-2,3-dihydro-[1,4]dioxino[2,3-f]quinoline as an off-white solid (3.8 g, yield: 94%);

Step 2): Zinc powder (650 mg, 10 mmol) was added to a solution of 10-(5-chloro-2-fluoro-4-nitrophenoxy)-5-methoxy-2,3-dihydro-[1,4]dioxino[2,3-f]quinoline (410 mg, 1 mmol) in ethanol (30 mL) and ammonium chloride (550 mg, 10 mmol) under an ice-water bath, and reacted with stirring at room temperature for 10 hours. The reaction solution was washed with water, and extracted with ethyl acetate. The organic phase was washed with saturated sodium chloride solution, concentrated, and dried to afford 2-chloro-5-fluoro-4-((5-methoxy-2,3-dihydro-[1,4]dioxino[2,3-f]quinolin-10-yl)oxy)aniline as a purple solid (310 mg, yield: 82%), MS: 377 [M+H]$^+$.

Step 1): A solution of 10-chloro-5-methoxy-2,3-dihydro-[1,4]dioxino[2,3-f]quinoline (2.5 g, 10 mmol), 2-fluoro-4-nitrophenol (1.6 g, 10 mmol) and potassium carbonate (2.1 g, 15 mmol) in DMF (20 mL) was heated and reacted at 80° C. for 3 hours. The reaction solution was cooled, slurried with water, and filtered. The filter cake was dried to afford 10-(2-fluoro-4-nitrophenoxy)-5-methoxy-2,3-dihydro-[1,4]dioxino[2,3-f]quinoline as a white solid (3.5 g, yield: 94%);

Step 2): Raney nickel was added to a solution of 10-(2-fluoro-4-nitrophenoxy)-5-methoxy-2,3-dihydro-[1,4]dioxino[2,3-f]quinoline (370 mg, 1 mmol) in methanol (30 mL), and reacted with stirring under hydrogen atmosphere at room temperature for 5 hours. The reaction solution was filtered, washed, and concentrated to afford 3-fluoro-4-((5-methoxy-2,3-dihydro-[1,4]dioxino[2,3-f]quinolin-10-yl)oxy)aniline as a purple solid (330 mg, yield: 96%), MS: 343 [M+H]$^+$.

Intermediate D-3. 3-fluoro-4-((5-(3-morpholinopropoxy)-2,3-dihydro-[1,4]dioxino[2,3-f]quinolin-10-yl)oxy)aniline Intermediate D-2. 2-chloro-5-fluoro-4-((5-methoxy-2,3-dihydro-[1,4]dioxino[2,3-f]quinolin-10-yl)oxy)aniline

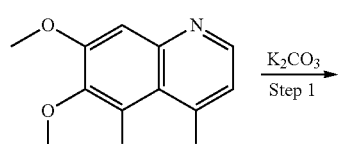

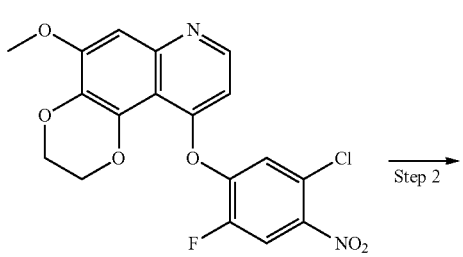

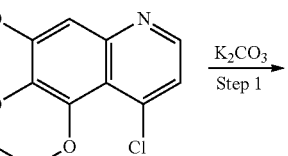

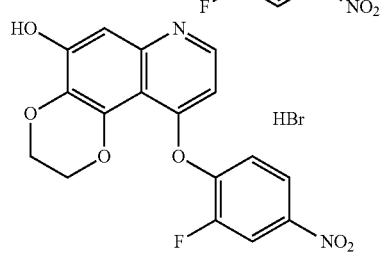

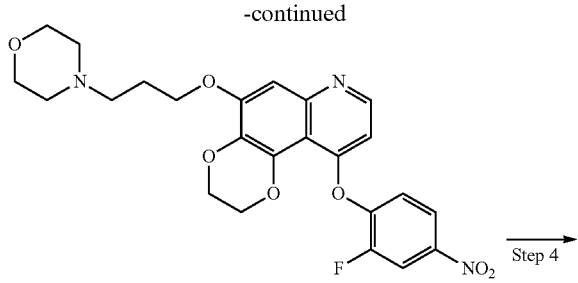

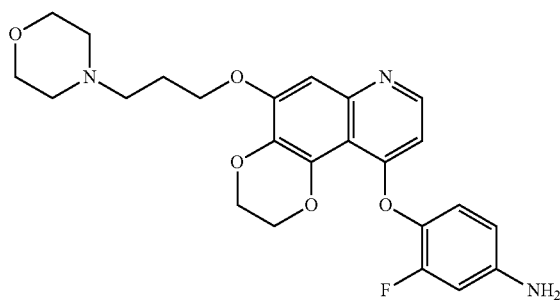

Step 1): A solution of 10-chloro-5-methoxy-2,3-dihydro-[1,4]dioxino[2,3-f]quinoline (2.5 g, 10 mmol), 2-fluoro-4-nitrophenol (1.6 g, 10 mmol) and potassium carbonate (2.1 g, 15 mmol) in DMF (20 mL) was heated and reacted at 80° C. for 3 hours. The reaction solution was cooled, slurried with water, and filtered. The filter cake was dried to afford 10-(2-fluoro-4-nitrophenoxy)-5-methoxy-2,3-dihydro-[1,4]dioxino[2,3-f]quinoline as an off-white solid (3.5 g, yield: 94%);

Step 2): 10-(2-Fluoro-4-nitrophenoxy)-5-methoxy-2,3-dihydro-[1,4]dioxino[2,3-f]quinoline (350 mg, 1 mmol) was added to a solution of hydrogen bromide in acetic acid (33%, 5 mL), heated and reacted at 90° C. for 15 hours. The reaction solution was cooled, slurried with ethyl acetate (15 mL), and filtered. The filter cake was dried to afford 10-(2-fluoro-4-nitrophenoxy)-2,3-dihydro-[1,4]dioxino[2,3-f]quinolin-5-ol as a light green solid (3.8 g, yield: 87%), MS: 359 [M+H]$^+$;

Step 3): 4-(3-Chloropropyl)morpholine (250 mg, 1.5 mmol) and potassium carbonate (280 mg, 2 mmol) were added to a solution of 10-(2-fluoro-4-nitrophenoxy)-2,3-dihydro-[1,4]dioxino[2,3-f]quinolin-5-ol (440 mg, 1 mmol) in DMF (5 mL), heated and reacted at 80° C. for 10 hours. The reaction solution was cooled, and water was added. The mixture was extracted with ethyl acetate. The organic phase was washed with saturated sodium chloride solution, dried, concentrated, and purified by column chromatography to afford 10-(2-fluoro-4-nitrophenoxy)-5-(3-morpholinopropoxy)-2,3-dihydro-[1,4]dioxino[2,3-f]quin oline as a light-yellow solid (390 mg, yield: 80%), MS: 486 [M+H]$^+$;

Step 4): Raney nickel was added to a solution of 10-(2-fluoro-4-nitrophenoxy)-5-(3-morpholinopropoxy)-2,3-dihydro-[1,4]dioxino[2,3-f]quin oline (390 mg) in methanol (30 mL), and reacted with stirring under hydrogen atmosphere at room temperature for 3 hours. The reaction solution was filtered and washed. The filtrate was concentrated to afford 3-fluoro-4-((5-(3-morpholinopropoxy)-2,3-dihydro-[1,4]dioxino[2,3-f]quinolin-10-yl)oxy)aniline as a purple solid (290 mg, yield: 79%), MS: 456 [M+H]$^+$.

The synthesis of intermediates D-4 to D-48 was carried out using the same method as that for the synthesis of the above-mentioned D-3 intermediate, except that corresponding nitro compounds (step 1) and halides with R$^1$ or p-toluene sulfonate esters of R$^1$ (step 3) were used. The structural formula of each intermediate was shown in Table 3 below:

TABLE 3

Structures and names of intermediates D-4 to D-48

Intermediate D-4

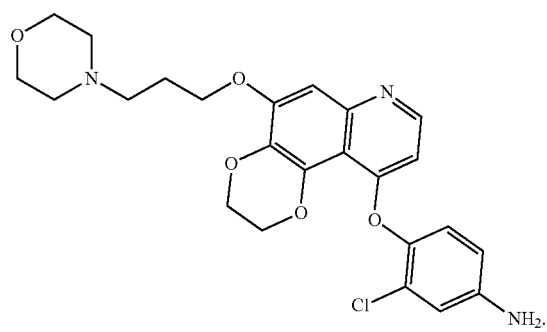

3-chloro-4-((5-(3-morpholino-propoxy)-2,3-dihydro-[1,4]dioxino[2,3-f]quinolin-10-yl)oxy)aniline TABLE 3-continued Structures and names of intermediates D-4 to D-48

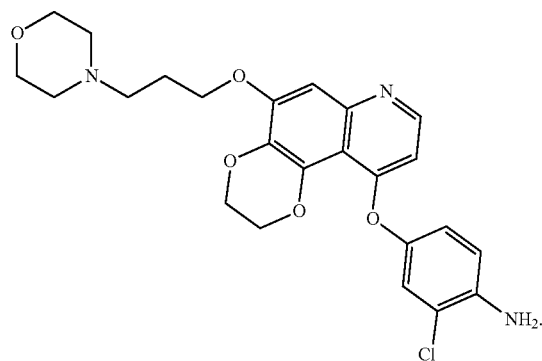

2-chloro-4-((5-(3-morpholino-
propoxy)-2,3-dihydro-[1,4]
dioxino[2,3-f]quinolin-10-yl)
oxy)aniline Intermediate D-5

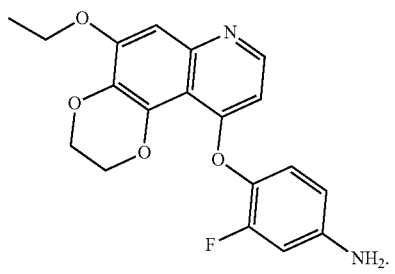

3-fluoro-4-((5-ethoxy-2,3-dihydro-
[1,4]dioxino[2,3-f]quinolin-10-yl)
oxy)aniline Intermediate D-6

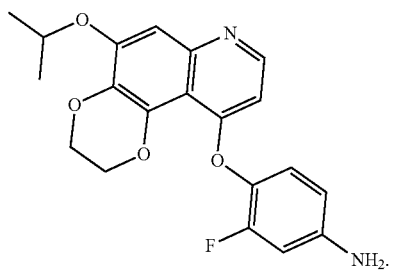

3-fluoro-4-((5-isopropoxy-2,3-
dihydro-[1,4]dioxino[2,3-f]
quinolin-10-yl)oxy)aniline Intermediate D-7

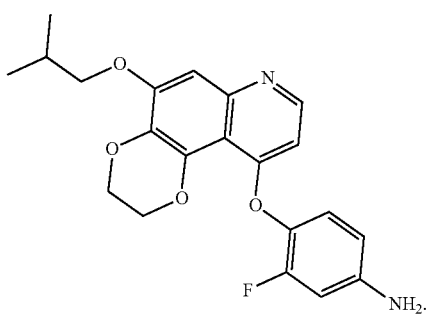

3-fluoro-4-((5-isobutoxy-2,3-
dihydro-[1,4]dioxino[2,3-f]
quinolin-10-yl)oxy)aniline Intermediate D-8

TABLE 3-continued

Structures and names of intermediates D-4 to D-48

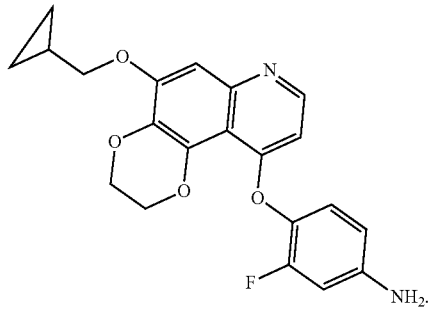

Intermediate D-9

3-fluoro-4-((5-(cyclopropylmethoxy)-
2,3-dihydro-[1,4]dioxino[2,3-f]
quinolin-10-yl)oxy)aniline

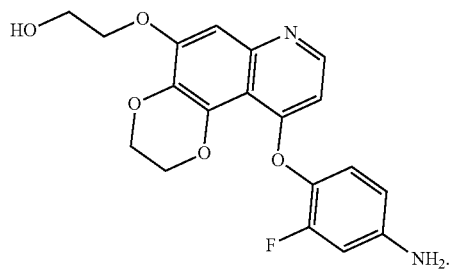

Intermediate D-10

3-fluoro-4-((5-(2-hydroxyethoxy)-
2,3-dihydro-[1,4]dioxino[2,3-f]
quinolin-10-yl)oxy)aniline

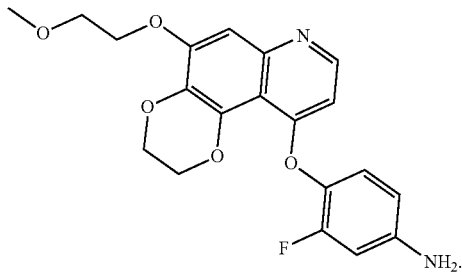

Intermediate D-11

3-fluoro-4-((5-(2-methoxyethoxy)-2,3-
dihydro-[1,4]dioxino[2,3-f]quinolin-10-
yl)oxy)aniline

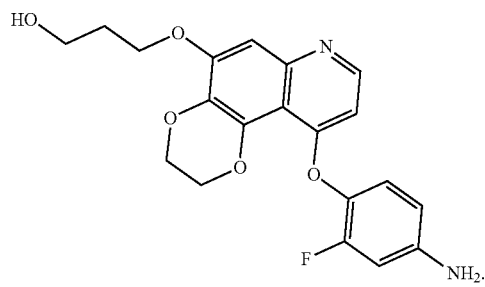

Intermediate D-12

3-fluoro-4-((5-(3-hydroxypropoxy)-2,3-
dihydro-[1,4]dioxino[2,3-f]quinolin-10-yl)
oxy)aniline TABLE 3-continued Structures and names of intermediates D-4 to D-48

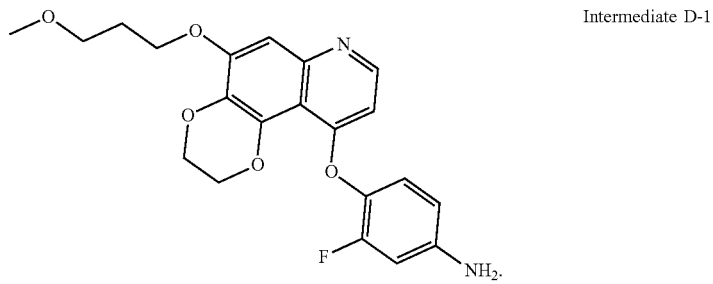

Intermediate D-13

3-fluoro-4-((5-(3-methoxypropoxy)-2,3-
dihydro-[1,4]dioxino[2,3-f]quinolin-10-yl)
oxy)aniline

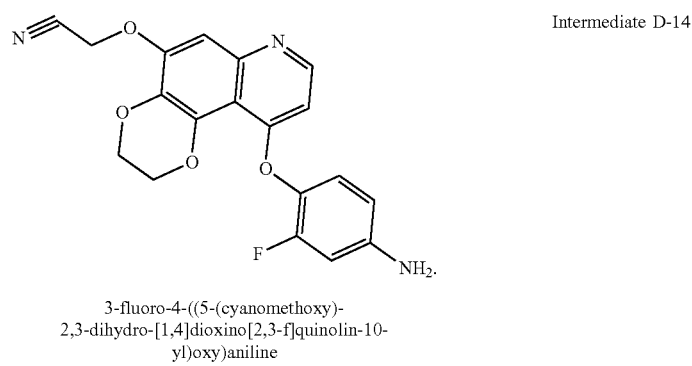

Intermediate D-14

3-fluoro-4-((5-(cyanomethoxy)-
2,3-dihydro-[1,4]dioxino[2,3-f]quinolin-10-
yl)oxy)aniline

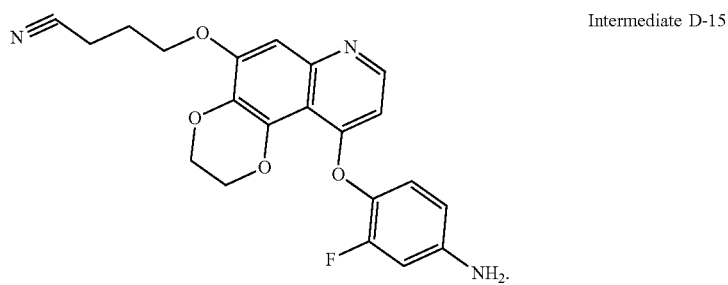

Intermediate D-15

3-fluoro-4-((5-(3-cyanopropoxy)-
2,3-dihydro-[1,4]dioxino[2,3-f]
quinolin-10-yl)oxy)aniline

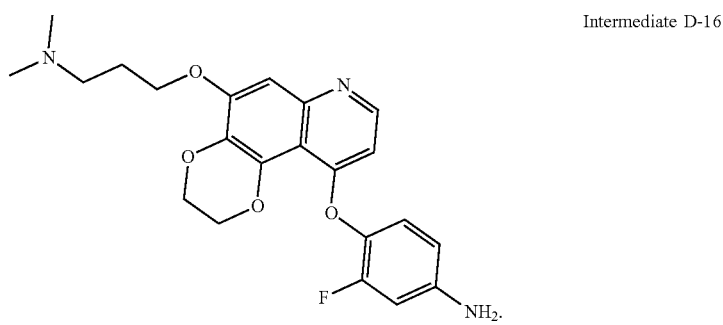

Intermediate D-16

3-fluoro-4-((5-((3-dimethylamino)
propoxy)-2,3-dihydro-[1,4]dioxino[2,3-f]
quinolin-10-yl)oxy)aniline TABLE 3-continued
Structures and names of intermediates D-4 to D-48
Intermediate D-17
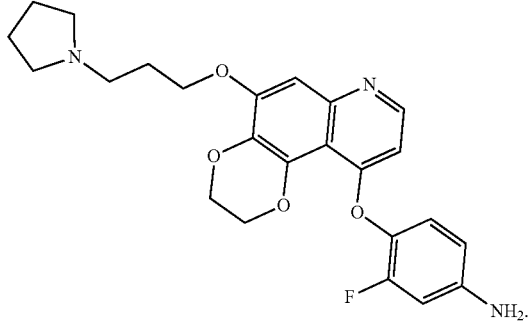
3-fluoro-4-((5-(3-(pyrrolidin-1-
yl)propoxy)-2,3-dihydro-
[1,4]dioxino[2,3-f]quinolin-
10-yl)oxy)aniline
Intermediate D-18
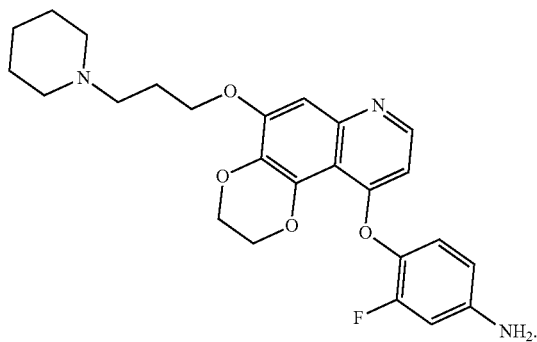
3-fluoro-4-((5-(3-(piperidin-1-yl)
propoxy)-2,3-dihydro-[1,4]dioxino
[2,3-f]quinolin-10-yl)oxy)aniline
Intermediate D-19
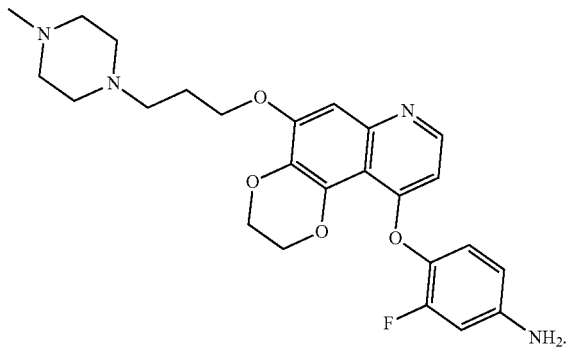
3-fluoro-4-((5-(3-(4-methylpiperazin-
1-yl)propoxy)-2,3-dihydro[1,4]
dioxino[2,3-f]quinolin-10-yl)oxy)aniline TABLE 3-continued
Structures and names of intermediates D-4 to D-48
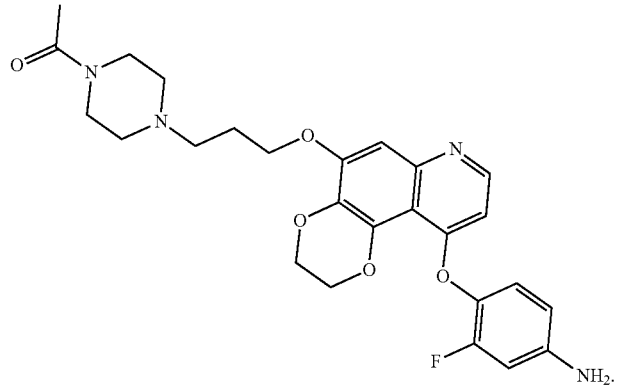
Intermediate D-20
3-fluoro-4-((5-(3-(4-acetylpiperazin-
1-yl)propoxy)-2,3-dihydro-[1,4]
dioxino[2,3-f]quinolin-10-yl)oxy)aniline
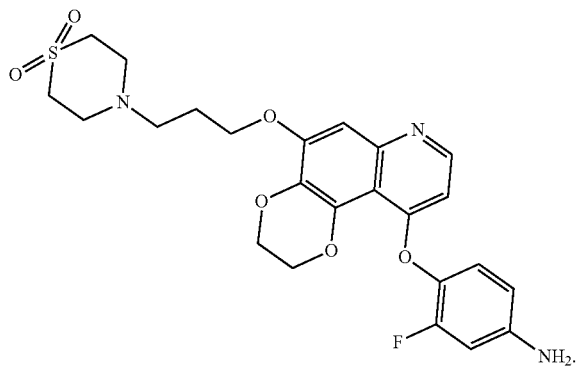
Intermediate D-21
3-fluoro-4-((5-(3-(1,1-dioxidothio-
morpholino)propoxy)-2,3-dihydro-
[1,4]dioxino[2,3-f]quinolin-10-yl)
oxy)aniline
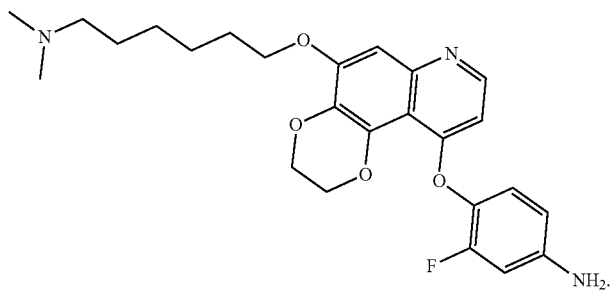
Intermediate D-22
3-fluoro-4-((5-(6-(dimethylamino)
hexyloxy)-2,3-dihydro-[1,4]
dioxino[2,3-f]quinolin-10-yl)oxy)aniline TABLE 3-continued Structures and names of intermediates D-4 to D-48

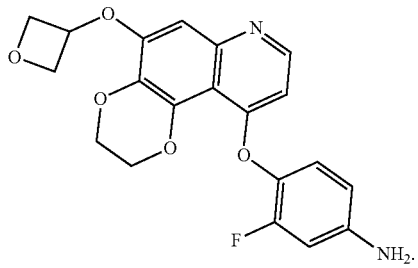

Intermediate D-23

3-fluoro-4-((5-((oxetan-3-yl)
oxy)-2,3-dihydro-[1,4]dioxino
[2,3-f]quinolin-10-yl)oxy)aniline

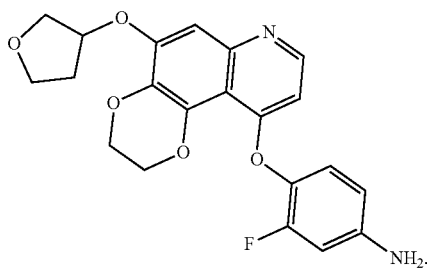

Intermediate D-24

3-fluoro-4-((5-((tetrahydrofuran-3-
yl)oxy)-2,3-dihydro-[1,4]dioxino
[2,3-f]quinolin-10-yl)oxy)aniline

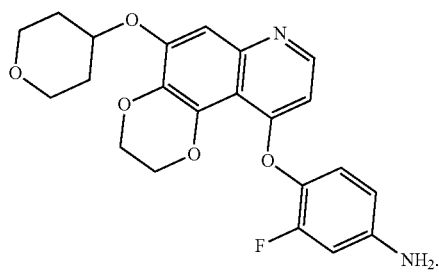

Intermediate D-25

3-fluoro-4-((5-((tetrahydropyran-
4-yl)oxy)-2,3-dihydro-[1,4]
dioxino[2,3-f]quinolin-10-
yl)oxy)aniline

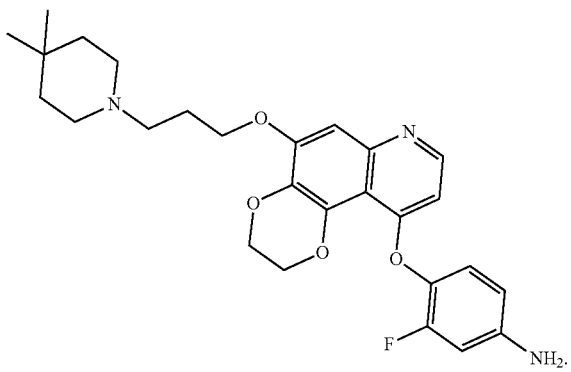

Intermediate D-26

3-fluoro-4-((5-(3-(4,4-dimethylpiperidin-1-yl)
propoxy)-2,3-dihydro-[1,4]dioxino[2,3-f]
quinolin-10-yl)oxy)anilinne TABLE 3-continued Structures and names of intermediates D-4 to D-48

Intermediate D-27

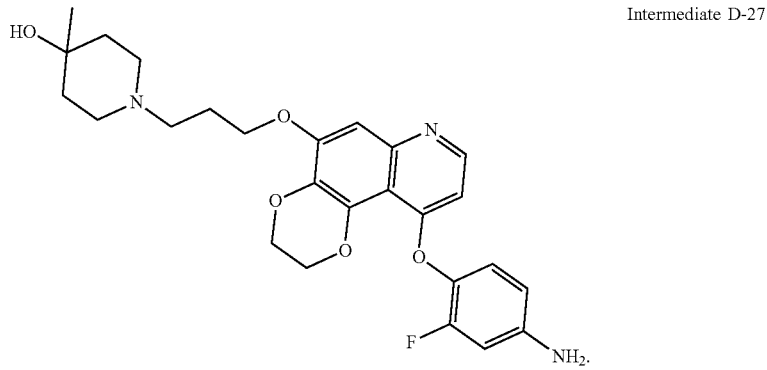

3-fluoro-4-((5-(3-(4-hydroxy-4-
methylpiperidin-1-yl)propoxy)-2,3-
dihydro-[1,4]dioxino[2,3-f]quinolin-
10-yl)oxy)aniline Intermediate D-28

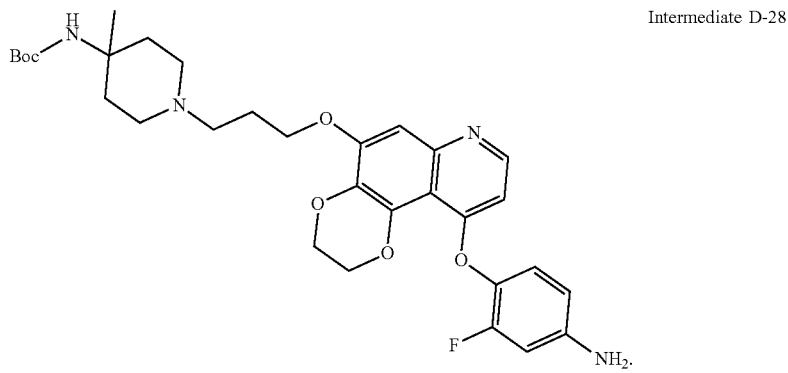

tert-butyl (1-(3-((10-(4-amino-2-fluoro
phenoxy)-2,3-dihydro-[1,4]
dioxino[2,3-f]quinolin-5-yl)
oxy)propyl)-4-methylpiperidin-
4-yl)carbamate Intermediate D-29

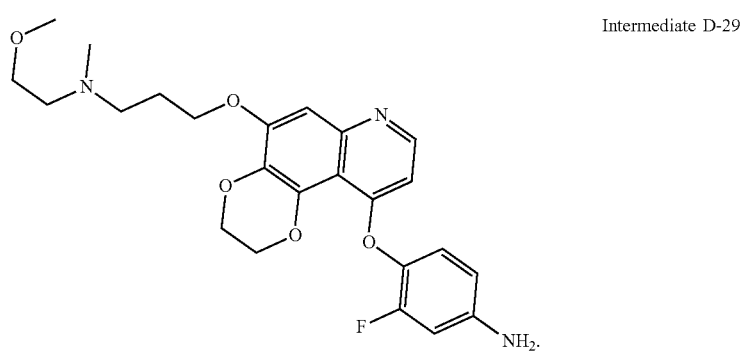

3-fluoro-4-((5-(3-((N-2-
methoxyethyl)(N-methyl)amino)
propoxy)-2,3-dihydro-[1,4]
dioxino[2,3-f]quinolin-10-yl)
oxy)aniline TABLE 3-continued Structures and names of intermediates D-4 to D-48

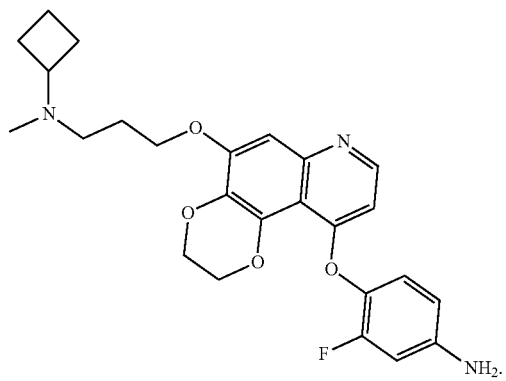

Intermediate D-30

4-((5-(3-(cyclobutyl(methyl)amino)
propoxy)-2,3-dihydro-[1,4]dioxino
[2,3-f]quinolin-10-yl)oxy)-3-
fluoroaniline

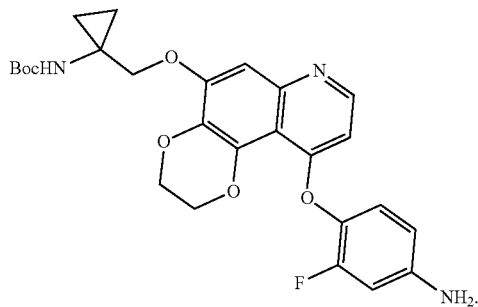

Intermediate D-31 tert-butyl
(1-(((10-(4-amino-2-fluorophenoxy)-2,3-dihydro-
[1,4]dioxino[2,3-f]quinolin-5-yl)oxy)methyl)
cyclopropyl)carbamate

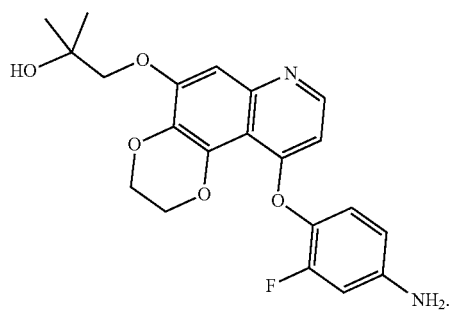

Intermediate D-32

1-((10-(4-amino-2-fluorophenyoxy)-2,3-
dihydro-[1,4]dioxino[2,3-f]quinolin-5-yl)oxy)-
2-methylpropyl-2-ol TABLE 3-continued
Structures and names of intermediates D-4 to D-48
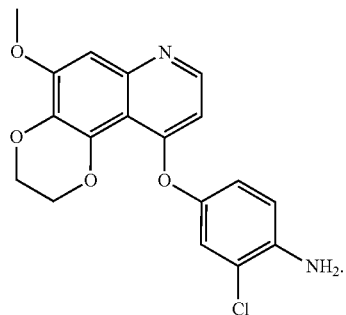
Intermediate D-33
2-chloro-4-((5-methoxy-2,3-dihydro-[1,4]dioxino[2,3-f]quinolin-10-yl)oxy)aniline
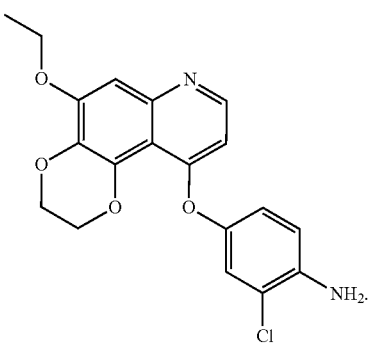
Intermediate D-34
2-chloro-4-((5-ethoxy-2,3-dihydro-[1,4]dioxino[2,3-f]quinolin-10-yl)oxy)aniline
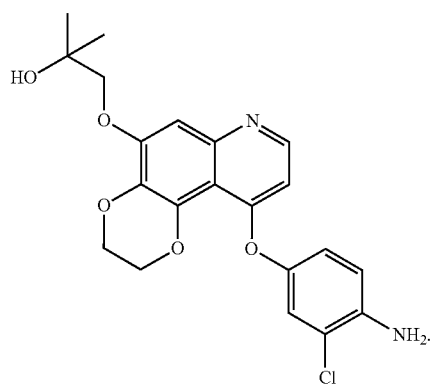
Intermediate D-35
2-chloro-4-((5-(2-hydroxy-2-methylpropoxy)-2,3-dihydro-[1,4]dioxino[2,3-f]quinolin-10-yl)oxy)aniline TABLE 3-continued
Structures and names of intermediates D-4 to D-48
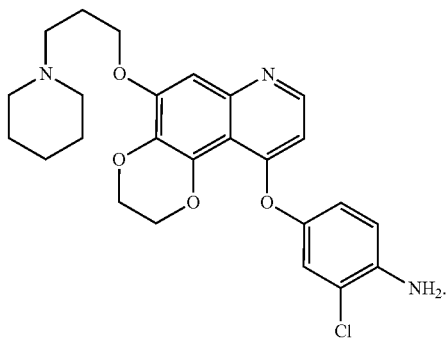
Intermediate D-36
2-chloro-4-((5-(3-(piperidin-1-yl)
propoxy)-2,3-dihydro-[1,4]dioxino
[2,3-f]quinolin-10-yl)oxy)aniline
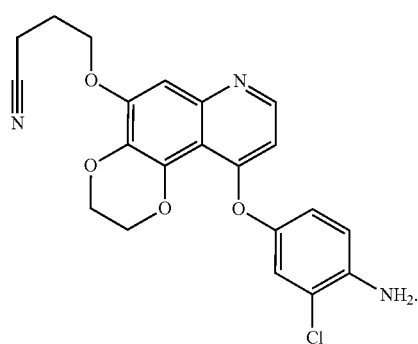
Intermediate D-37
4-((10-(4-amino-3-chlorophenoxy)-2,3-
dihydro-[1,4]dioxino[2,3-f]quinolin-5-yl)oxy)
butyronitile
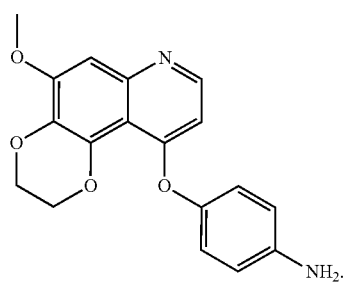
Intermediate D-38
4-((5-methoxy-2,3-dihydro-
[1,4]dioxino[2,3-f]quinolin-10-
yl)oxy)aniline TABLE 3-continued
Structures and names of intermediates D-4 to D-48
Intermediate D-39
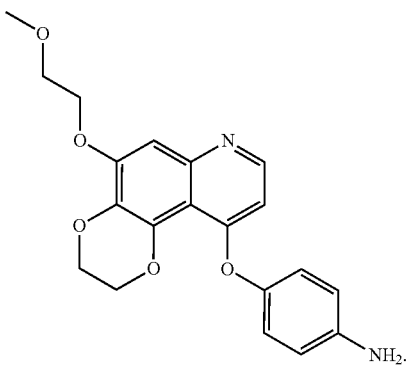
4-((5-(2-methoxyethoxy)-2,3-dihydro-[1,4]dioxino[2,3-f]quinolin-10-yl)oxy)aniline
Intermediate D-40
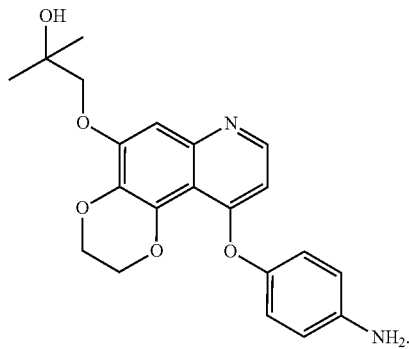
4-((5-(2-hydroxy-2-methyl-propoxy)-2,3-dihydro-[1,4]dioxino[2,3-f]quinolin-10-yl)oxy)aniline
Intermediate D-41
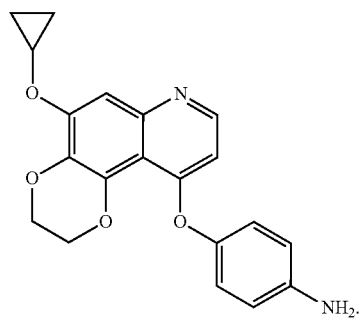
4-((5-(cyclopropyloxy)-2,3-dihydro-[1,4]dioxino[2,3-f]quinolin-10-yl)oxy)aniline TABLE 3-continued
Structures and names of intermediates D-4 to D-48
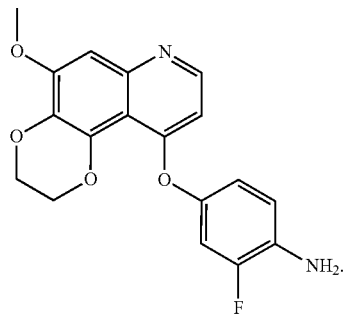
2-fluoro-4-((5-methoxy-2,3-
dihydro-[1,4]dioxino[2,3-f]quinolin-10-
yl)oxy)aniline
Intermediate D-42
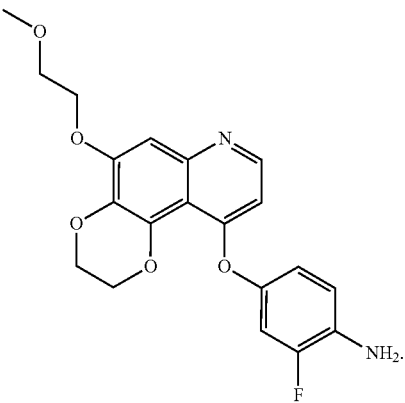
2-fluoro-4-((5-(2-methoxyethoxy)-
2,3-dihydro-[1,4]dioxino[2,3-f]
quinolin-10-yl)oxy)aniline
Intermediate D-43
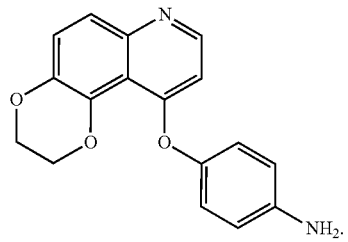
4-((2,3-dihydro-[1,4]dioxino
[2,3-f]quinolin-10-yl)oxy)aniline
Intermediate D-44
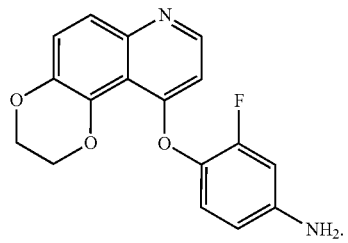
4-((2,3-dihydro-[1,4]dioxino[2,3-f]
quinolin-10-yl)oxy)-3-fluoroaniline
Intermediate D-45

TABLE 3-continued
Structures and names of intermediates D-4 to D-48
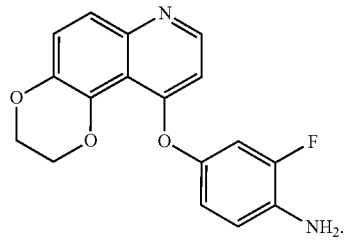
4-((2,3-dihydro-[1,4]dioxino
[2,3-f]quinolin-10-yl)oxy)-2-
fluoroaniline
Intermediate D-46
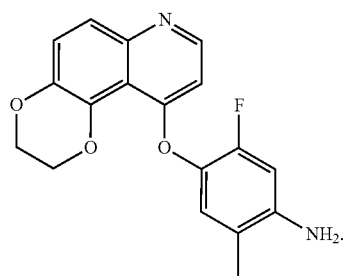
4-((2,3-dihydro-[1,4]dioxino
[2,3-f]quinolin-10-yl)oxy)-5-
fluoro-2-methylaniline
Intermediate D-47
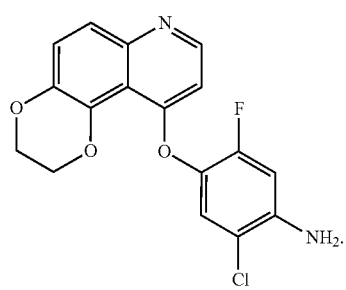
2-chloro-4-((2,3-dihydro-[1,4]
dioxino[2,3-f]quinolin-10-yl)oxy)-5-
fluoroaniline
Intermediate D-48

Intermediate E

The starting materials, i.e., 10-chloro-5-methoxy-2,3-dihydro-[1,4]dioxino[2,3-f]quinazoline and 10-chloro-5-(3-morpholinopropoxy)-2,3-dihydro-[1,4]dioxino[2,3-f]quinazoline, of intermediates E1 and E2 are described in patent application WO 2016112847.

Intermediate E-1. 3-fluoro-4-((5-methoxy-2,3-dihydro-[1,4]dioxino[2,3-f]quinazolin-10-yl)oxy)aniline

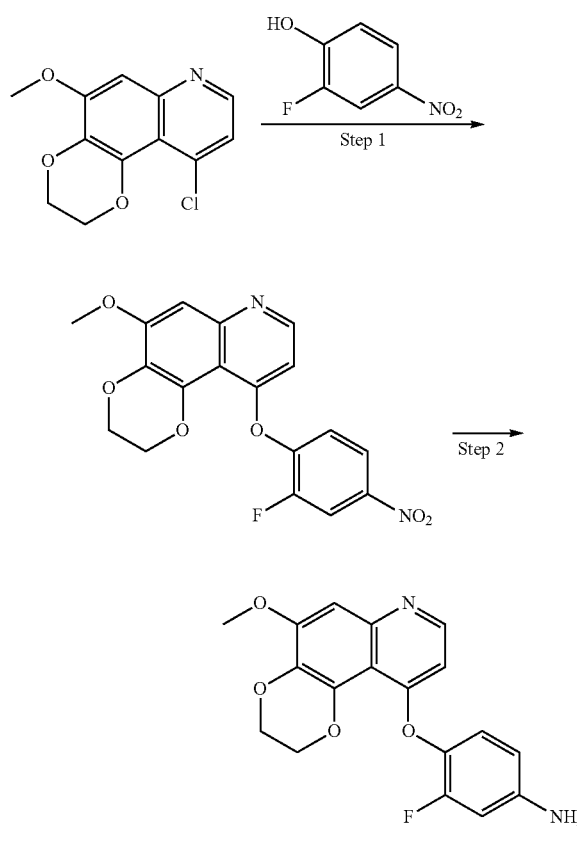

Step 1): A solution of 10-chloro-5-methoxy-2,3-dihydro-[1,4]dioxino[2,3-f]quinazoline (2.5 g, 10 mmol), 2-fluoro-4-nitrophenol (1.6 g, 10 mmol) and potassium carbonate (2.1 g, 15 mmol) in DMF (20 mL) was heated and reacted at 80° C. for 3 hours. The reaction solution was cooled, slurried with water, and filtered. The filter cake was dried to afford 10-(2-fluoro-4-nitrophenoxy)-5-methoxy-2,3-dihydro-[1,4]dioxino[2,3-f]quinazoline as an off-white solid (3.5 g, yield: 94%);

Step 2): Raney nickel was added to a solution of 10-(2-fluoro-4-nitrophenoxy)-5-methoxy-2,3-dihydro-[1,4]dioxino[2,3-f]quinazoline (370 mg, 1 mmol) in ethanol (30 mL) and ethyl acetate (10 mL), and reacted with stirring under hydrogen atmosphere at room temperature for 5 hours. The reaction solution was filtered, and the filtrate was concentrated to afford 3-fluoro-4-((5-methoxy-2,3-dihydro-[1,4]dioxino[2,3-f]quinazolin-10-yl)oxy)aniline as a light purple solid (330 mg, yield: 96%), MS: 344 [M+H]$^+$.

Intermediate E-2. 3-fluoro-4-((5-(3-morpholinopropoxy)-2,3-dihydro-[1,4]dioxino[2,3-f]quinazolin-10-yl)oxy) aniline

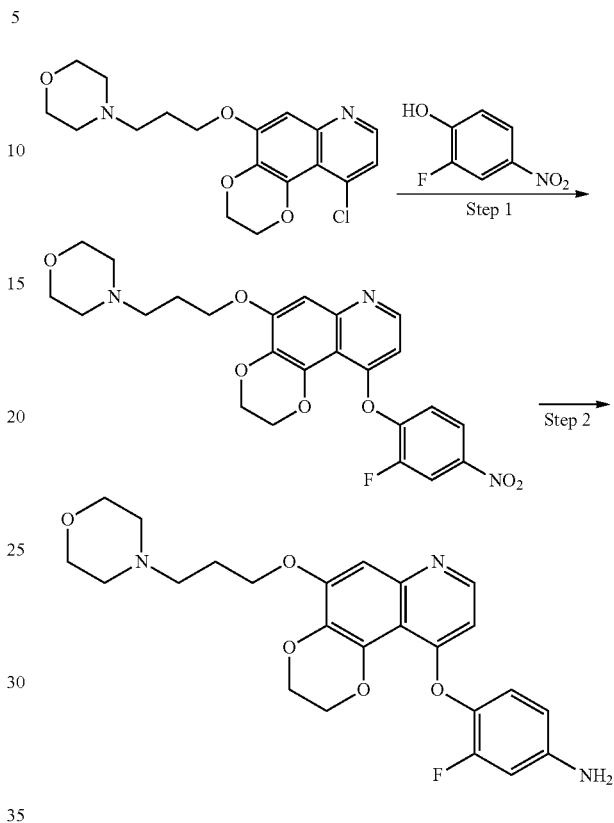

Step 1): A solution of 10-chloro-5-(3-morpholinopropoxy)-2,3-dihydro-[1,4]dioxino[2,3-f]quinazoline (3.7 g, 10 mmol), 2-fluoro-4-nitrophenol (1.6 g, 10 mmol) and potassium carbonate (2.1 g, 15 mmol) in DMF (20 mL) was heated and reacted at 80° C. for 3 hours. The reaction solution was cooled, slurried with water, and filtered. The filter cake was dried to afford 10-(2-fluoro-4-nitrophenoxy)-5-(3-morpholinopropoxy)-2,3-dihydro-[1,4]dioxino[2,3-f] quinazoline as an off-white solid (3.9 g, yield: 80%), MS: 487 [M+H]$^+$.

Step 2): Raney nickel was added to a solution of 10-(2-fluoro-4-nitrophenoxy)-5-(3-morpholinopropoxy)-2,3-dihydro-[1,4]dioxino[2,3-f]quinazoline (490 mg, 1 mmol) in methanol (30 mL), and reacted with stirring under hydrogen atmosphere at room temperature for 5 hours. The reaction solution was filtered, and the filtrate was concentrated to afford 3-fluoro-4-((5-(3-morpholinopropoxy)-2,3-dihydro-[1,4]dioxino[2,3-f]quinazolin-10-yl)oxy) aniline as a light purple solid (4.2 g, yield: 92%), MS: 457 [M+H]$^+$.

EXAMPLES

Example 1: N-(3-fluoro-4-((5-methoxy-2,3-dihydro-[1,4]dioxino[2,3-f]quinazolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (40 mg, 0.16 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (52 mg, 0.15 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 30%); $^1$H NMR (400 MHz, DMSO-$d_6$) δ 12.07 (s, 1H), 8.60 (dd, J=7.3, 2.2 Hz, 1H), 8.46 (s, 1H), 8.13 (dd, J=6.6, 2.2 Hz, 1H), 7.95 (dd, J=12.6, 2.4 Hz, 1H), 7.62 (dd, J=8.9, 4.8 Hz, 2H), 7.49-7.32 (m, 4H), 7.08 (s, 1H), 6.73 (t, J=7.0 Hz, 1H), 4.46-4.40 (m, 4H), 3.98 (s, 3H). MS: 559 [M+H]$^+$.

Example 1

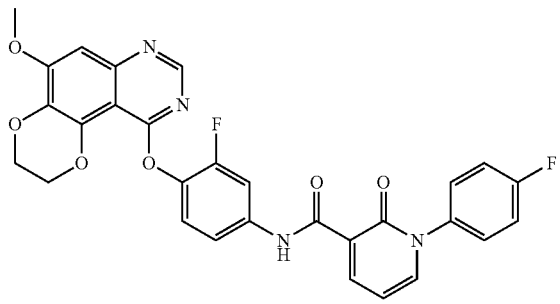

Example 2

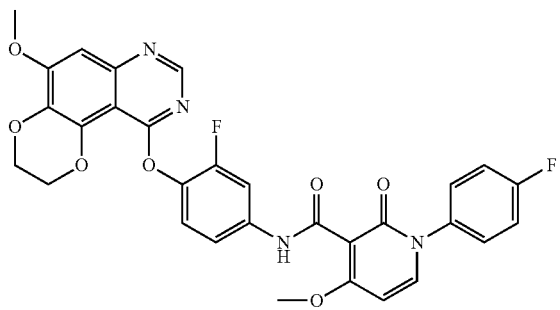

Example 2: N-(3-fluoro-4-((5-methoxy-2,3-dihydro-[1,4]dioxino[2,3-f]quinazolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 32%); $^1$H NMR (400 MHz, DMSO-$d_6$) δ 10.55 (s, 1H), 8.44 (s, 1H), 7.94-7.78 (m, 2H), 7.51-7.26 (m, 6H), 7.08 (s, 1H), 6.54 (d, J=7.9 Hz, 1H), 4.50-4.37 (m, 4H), 3.98 (s, 3H), 3.94 (s, 3H). MS: 589 [M+H]$^+$.

Example 3: N-(3-fluoro-4-((5-methoxy-2,3-dihydro-[1,4]dioxino[2,3-f]quinazolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 25%); $^1$H NMR (400 MHz, DMSO-$d_6$) δ 10.51 (s, 1H), 8.44 (s, 1H), 7.84 (dd, J=9.0, 5.7 Hz, 2H), 7.51-7.31 (m, 6H), 7.08 (s, 1H), 6.51 (d, J=7.9 Hz, 1H), 4.47-4.40 (m, 4H), 4.26 (q, J=6.9 Hz, 2H), 3.98 (s, 3H), 1.31 (t, J=7.0 Hz, 3H). MS: 603 [M+H]$^+$.

Example 3

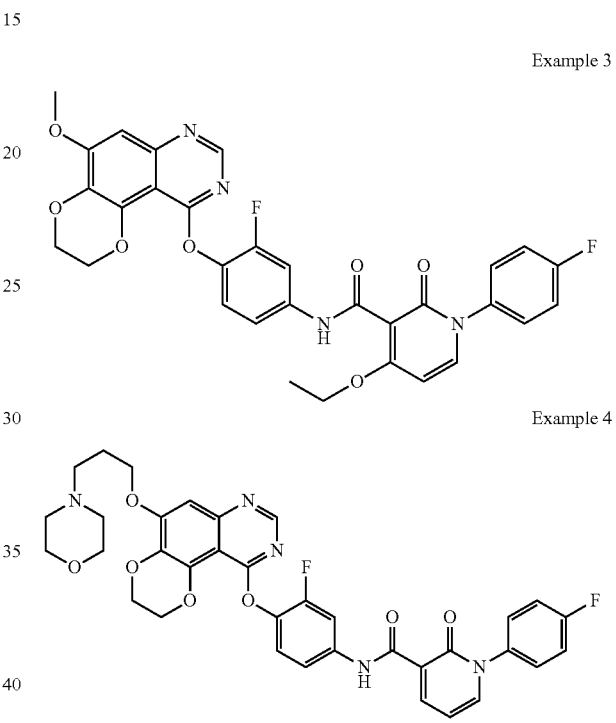

Example 4

Example 4: N-(3-fluoro-4-((5-(3-morpholinopropoxy)-2,3-dihydro-[1,4]dioxino[2,3-f]quinazolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 33%); $^1$H NMR (400 MHz, DMSO-$d_6$) δ 12.07 (s, 1H), 8.63-8.56 (m, 1H), 8.45 (s, 1H), 8.13 (dd, J=6.6, 2.2 Hz, 1H), 7.99-7.91 (m, 1H), 7.62 (dd, J=8.7, 4.8 Hz, 2H), 7.47-7.34 (m, 4H), 7.07 (s, 1H), 6.73 (t, J=6.9 Hz, 1H), 4.49-4.38 (m, 4H), 4.23 (t, J=6.4 Hz, 2H), 3.59 (t, J=4.6 Hz, 4H), 2.46 (t, J=7.2 Hz, 2H), 2.39 (s, 4H), 1.97 (t, J=6.9 Hz, 2H). MS: 672 [M+H]$^+$.

Example 5: N-(3-fluoro-4-((5-(3-morpholinopropoxy)-2,3-dihydro-[1,4]dioxino[2,3-f]quinazolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg, yield: 37%); $^1$H NMR (400 MHz, DMSO-$d_6$) δ 10.55 (s, 1H), 8.43 (s, 1H), 7.92-7.79 (m, 2H), 7.48-7.31 (m, 6H), 7.07 (s, 1H), 6.54 (d, J=7.9 Hz, 1H), 4.49-4.40 (m, 4H), 4.24 (t, J=6.4 Hz, 2H), 3.94 (s, 3H), 3.59 (t, J=4.6 Hz, 4H), 2.45 (d, J=7.1 Hz, 2H), 2.39 (t, J=4.6 Hz, 4H), 1.97 (t, J=6.9 Hz, 2H). MS: 702 [M+H]$^+$.

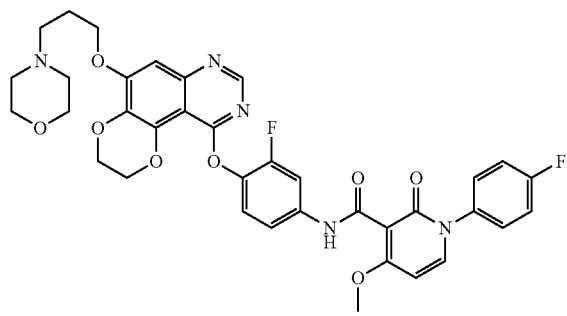

Example 5

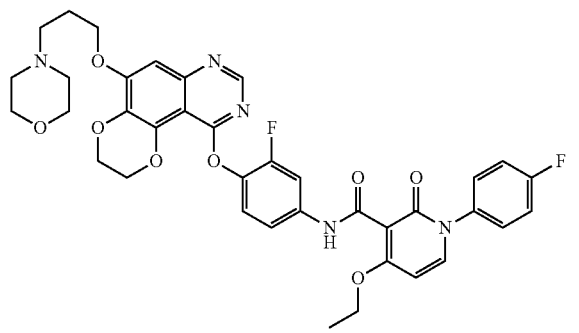

Example 6

Example 6: N-(3-fluoro-4-((5-(3-morpholinopropoxy)-2,3-dihydro-[1,4]dioxino[2,3-f]quinazolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 31%); $^1$H NMR (400 MHz, DMSO-$d_6$) δ 10.51 (s, 1H), 8.43 (s, 1H), 7.88-7.79 (m, 2H), 7.51-7.30 (m, 6H), 7.07 (s, 1H), 6.51 (d, J=7.9 Hz, 1H), 4.53-4.36 (m, 4H), 4.29-4.20 (m, 4H), 3.59 (t, J=4.4 Hz, 4H), 2.50-2.38 (m, 2H), 2.39 (s, 4H), 1.97 (t, J=6.9 Hz, 2H), 1.34-1.31 (m, 3H). MS: 716 [M+H]$^+$.

Example 7: 1-(4-fluoro-2-methylphenyl)-N-(3-fluoro-4-((5-methoxy-2,3-dihydro-[1,4]dioxino[2,3-f]quinazolin-10-yl)oxy)phenyl)-1H-pyrazole-3-carboxamide A solution of 1-(4-fluoro-2-methylphenyl)-1H-pyrazol-3-carbonyl chloride (25 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 35%); $^1$H NMR (400 MHz, DMSO-$d_6$) δ 10.42 (s, 1H), 8.46 (s, 1H), 8.19 (d, J=2.5 Hz, 1H), 8.00-7.91 (m, 1H), 7.73 (d, J=8.8 Hz, 1H), 7.55 (dd, J=8.7, 5.4 Hz, 1H), 7.36 (t, J=8.9 Hz, 2H), 7.24 (t, J=8.3 Hz, 1H), 7.11-7.00 (m, 2H), 4.47 (d, J=4.6 Hz, 2H), 4.40 (s, 2H), 3.98 (s, 3H), 2.22 (s, 3H). MS: 546 [M+H]$^+$.

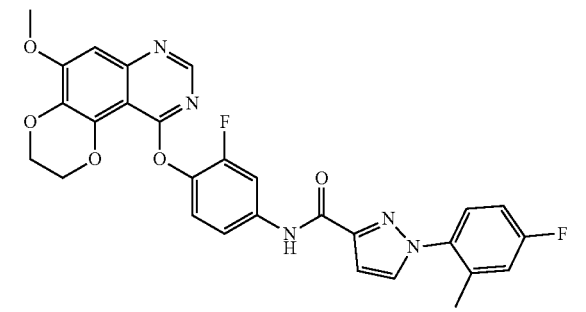

Example 7

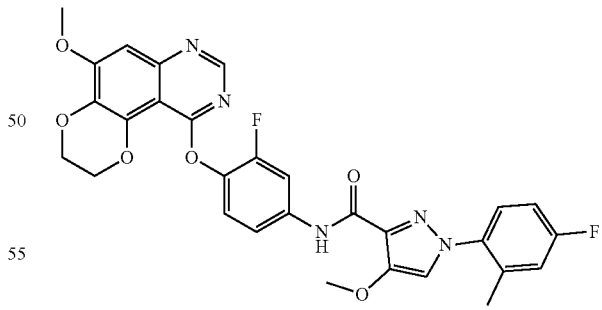

Example 8

Example 8: 1-(4-fluoro-2-methylphenyl)-N-(3-fluoro-4-((5-methoxy-2,3-dihydro-[1,4]dioxino[2,3-f]quinazolin-10-yl)oxy)phenyl)-4-methoxy-1H-pyrazole-3-carboxamide A solution of 1-(4-fluoro-2-methylphenyl)-4-methoxy-1H-pyrazol-3-carbonyl chloride (30 mg, 0.11 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (23 mg, yield: 40%); $^1$H NMR (400 MHz, DMSO-$d_6$) δ 10.08 (s, 1H), 8.46 (s, 1H), 8.05 (s, 1H), 7.91 (dd, J=13.0, 2.4 Hz, 1H), 7.65 (d, J=8.8 Hz, 1H), 7.53 (dd, J=8.7, 5.4 Hz, 1H), 7.35 (t, J=8.8 Hz, 2H), 7.28-7.20 (m, 1H), 7.08 (s, 1H)), 4.47 (s, 2H), 4.40 (s, 2H), 3.98 (s, 3H), 3.84 (s, 3H), 2.27 (s, 3H). MS: 576 [M+H]$^+$.

Example 9: 1-(4-fluoro-2-methylphenyl)-N-(3-fluoro-4-((5-methoxy-2,3-dihydro-[1,4]dioxino[2,3-f]quinazolin-10-yl)oxy)phenyl)-4-ethoxy-1H-pyrazole-3-carboxamide A solution of 1-(4-fluoro-2-methylphenyl)-4-ethoxy-1H-pyrazol-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 31%); $^1$H NMR (400 MHz, DMSO-$d_6$) δ 10.06 (s, 1H), 8.46 (s, 1H), 8.03 (s, 1H), 7.92 (dd, J=13.1, 2.3 Hz, 1H), 7.64 (d, J=8.8 Hz, 1H), 7.52 (dd, J=8.7, 5.5 Hz, 1H), 7.35 (t, J=9.3 Hz, 2H), 7.29-7.19 (m, 1H), 7.08 (s, 1H), 4.47 (s, 2H), 4.40 (s, 2H), 4.07 (q, J=7.0 Hz, 2H), 3.98 (s, 3H), 2.27 (s, 3H), 1.38 (t, J=7.0 Hz, 3H). MS: 590 [M+H]$^+$.

Example 10: 1-(4-fluoro-2-methylphenyl)-N-(3-fluoro-4-((5-(3-morpholinopropoxy)-2,3-dihydro-[1,4]dioxino[2,3-f]quinazolin-10-yl)oxy)phenyl)-1H-pyrazole-3-carboxamide A solution of 1-(4-fluoro-2-methylphenyl)-1H-pyrazol-3-carbonyl chloride (25 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 29%); $^1$H NMR (400 MHz, DMSO-$d_6$) δ 10.43 (s, 1H), 8.45 (s, 1H), 8.19 (d, J=2.4 Hz, 1H), 7.95 (dd, J=12.9, 2.4 Hz, 1H), 7.77-7.69 (m, 1H), 7.55 (dd, J=8.8, 5.4 Hz, 1H), 7.41-7.31 (m, 2H), 7.24 (td, J=8.6, 3.0 Hz, 1H), 7.09-7.01 (m, 2H), 4.44 (dt, J=22.8, 3.3 Hz, 4H), 4.24 (t, J=6.4 Hz, 2H), 3.59 (t, J=4.6 Hz, 4H), 2.43 (dt, J=26.3, 5.8 Hz, 6H), 2.22 (s, 3H), 1.97 (t, J=6.8 Hz, 2H). MS: 659 [M+H]$^+$.

Example 11: 1-(4-fluoro-2-methylphenyl)-N-(3-fluoro-4-((5-(3-morpholinopropoxy)-2,3-dihydro-[1,4]dioxino[2,3-f]quinazolin-10-yl)oxy)phenyl)-4-methoxy-1H-pyrazole-3-carboxamide A solution of 1-(4-fluoro-2-methylphenyl)-4-methoxy-1H-pyrazol-3-carbonyl chloride (30 mg, 0.11 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (23 mg, yield: 33%); $^1$H NMR (400 MHz, DMSO-$d_6$) δ 10.07 (s, 1H), 8.45 (s, 1H), 8.04 (s, 1H), 7.91 (d, J=12.8 Hz, 1H), 7.65 (d, J=9.0 Hz, 1H), 7.53 (dd, J=8.8, 5.6 Hz, 1H), 7.34 (t, J=8.9 Hz, 2H), 7.23 (t, J=8.7 Hz, 1H), 7.07 (s, 1H), 4.44 (d, J=23.1 Hz, 4H), 4.24 (t, J=6.2 Hz, 2H), 3.84 (s, 3H), 3.59 (t, J=4.4 Hz, 4H), 2.50-2.38 (m, 2H), 2.39 (s, 4H), 2.27 (s, 3H), 2.01-1.93 (m, 2H). MS: 689 [M+H]$^+$.

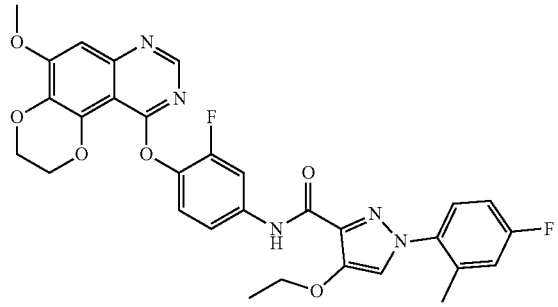

Example 9

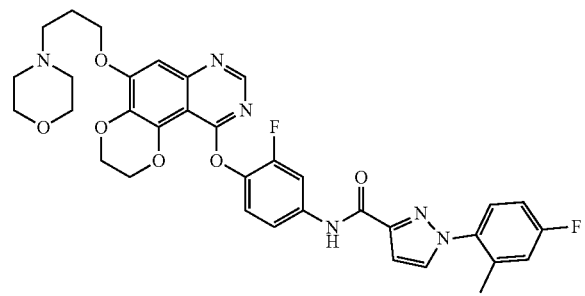

Example 10

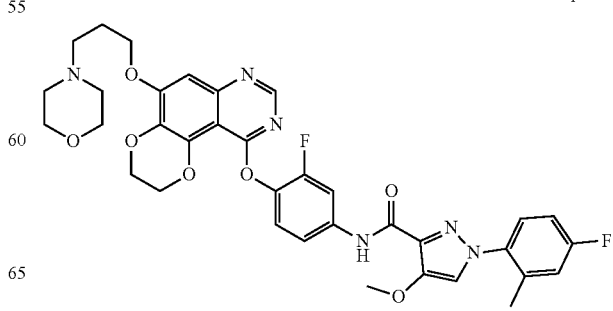

Example 11

Example 12

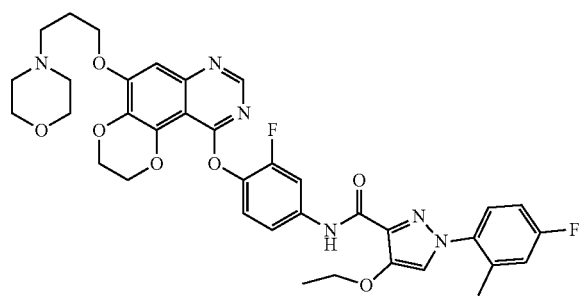

Example 12: 1-(4-fluoro-2-methylphenyl)-N-(3-fluoro-4-((5-(3-morpholinopropoxy)-2,3-dihydro-[1,4]dioxino[2,3-f]quinazolin-10-yl)oxy)phenyl)-4-ethoxy-1H-pyrazole-3-carboxamide A solution of 1-(4-fluoro-2-methylphenyl)-4-ethoxy-1H-pyrazol-3-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 30%); $^1$H NMR (400 MHz, DMSO-$d_6$) δ 10.05 (s, 1H), 8.45 (s, 1H), 8.03 (s, 1H), 7.92 (d, J=12.7 Hz, 1H), 7.64 (d, J=8.8 Hz, 1H), 7.52 (dd, J=8.7, 5.4 Hz, 1H), 7.34 (t, J=9.2 Hz, 2H), 7.28-7.18 (m, 1H), 7.07 (s, 1H), 4.50-4.39 (m, 4H), 4.24 (t, J=6.4 Hz, 2H), 4.07 (q, J=7.1 Hz, 2H), 3.59 (t, J=4.6 Hz, 4H), 2.46 (t, J=7.0 Hz, 2H), 2.39 (s, 4H), 2.27 (s, 3H), 2.01-1.93 (m, 2H), 1.38 (t, J=7.0 Hz, 3H). MS: 703 [M+H]$^+$.

Example 13: N-(3-fluoro-4-((5-methoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 36%); $^1$H NMR (400 MHz, DMSO-$d_6$) δ 10.98 (s, 1H), 8.86 (s, 1H), 8.43 (d, J=5.2 Hz, 1H), 7.95 (d, J=12.8 Hz, 1H), 7.49-7.33 (m, 5H), 7.24 (t, J=9.0 Hz, 1H), 7.08 (s, 1H), 6.47 (d, J=5.3 Hz, 1H), 4.34 (s, 4H), 3.93 (s, 3H), 3.54 (s, 3H). MS: 589 [M+H]$^+$.

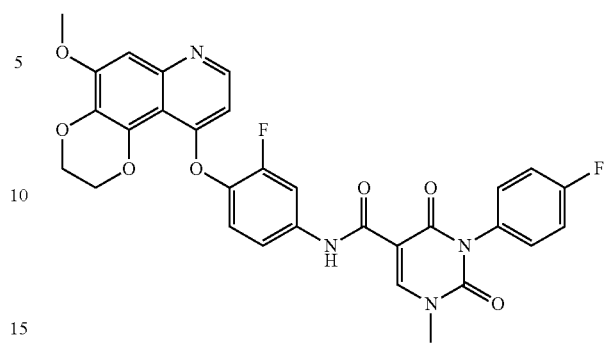

Example 14: N-(3-fluoro-4-((5-methoxy-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide

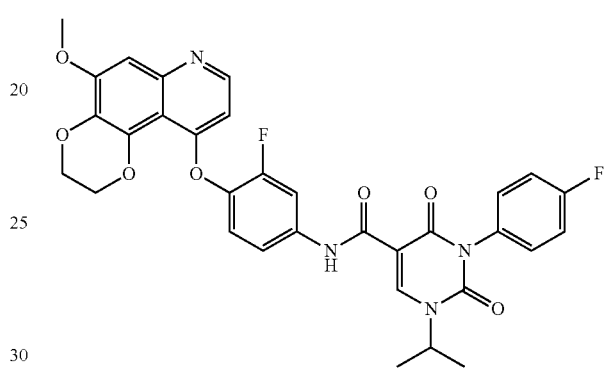

A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 31%); $^1$H NMR (600 MHz, DMSO-$d_6$) δ 11.00 (s, 1H), 8.67 (s, 1H), 8.43 (d, J=5.2 Hz, 1H), 7.97 (dd, J=13.0, 2.5 Hz, 1H), 7.49-7.40 (m, 3H), 7.36 (t, J=8.8 Hz, 2H), 7.25 (t, J=9.0 Hz, 1H), 7.08 (s, 1H), 6.47 (dd, J=5.2, 0.8 Hz, 1H), 4.81-4.75 (m, 1H), 4.34 (s, 4H), 3.92 (s, 3H), 1.43 (d, J=6.8 Hz, 6H). MS: 617 [M+H]$^+$.

Example 15: N-(3-fluoro-4-((5-(3-morpholinopropoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 36%); $^1$H NMR (400 MHz, DMSO-d$_6$) δ 10.98 (s, 1H), 8.86 (s, 1H), 8.42 (d, J=5.2 Hz, 1H), 7.95 (dd, J=13.1, 2.3 Hz, 1H), 7.50-7.31 (m, 5H), 7.23 (t, J=9.0 Hz, 1H), 7.07 (s, 1H), 6.46 (d, J=5.3 Hz, 1H), 4.34 (s, 4H), 4.18 (t, J=6.4 Hz, 2H), 3.59 (t, J=4.6 Hz, 4H), 3.54 (s, 3H), 2.46 (d, J=7.0 Hz, 2H), 2.39 (s, 4H), 1.96 (q, J=7.2 Hz, 2H). MS: 702 [M+H]$^+$.

and filtered to afford a light-yellow solid. The solid was purified by preparative liquid chromatography to afford a white solid product (21 mg, 29%); $^1$H NMR (600 MHz, DMSO-d$_6$) δ 11.00 (s, 1H), 8.67 (s, 1H), 8.42 (d, J=5.2 Hz, 1H), 7.97 (dd, J=12.9, 2.5 Hz, 1H), 7.49-7.40 (m, 3H), 7.36 (t, J=8.8 Hz, 2H), 7.24 (t, J=9.0 Hz, 1H), 7.06 (s, 1H), 6.46 (d, J=5.2 Hz, 1H), 4.78 (p, J=6.8 Hz, 1H), 4.34 (p, J=4.6, 3.6 Hz, 4H), 4.17 (t, J=6.4 Hz, 2H), 3.59 (t, J=4.6 Hz, 4H), 2.46 (t, J=7.1 Hz, 2H), 2.38 (s, 4H), 1.96 (q, J=6.8 Hz, 2H), 1.42 (d, J=6.9 Hz, 6H). MS: 730 [M+H]$^+$.

Example 15

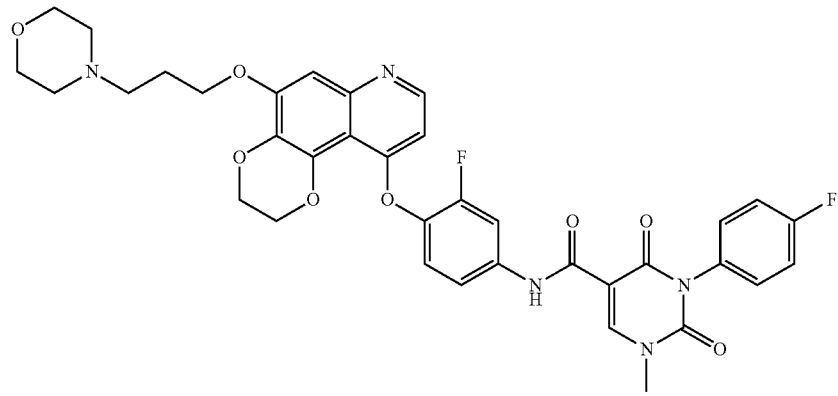

Example 16

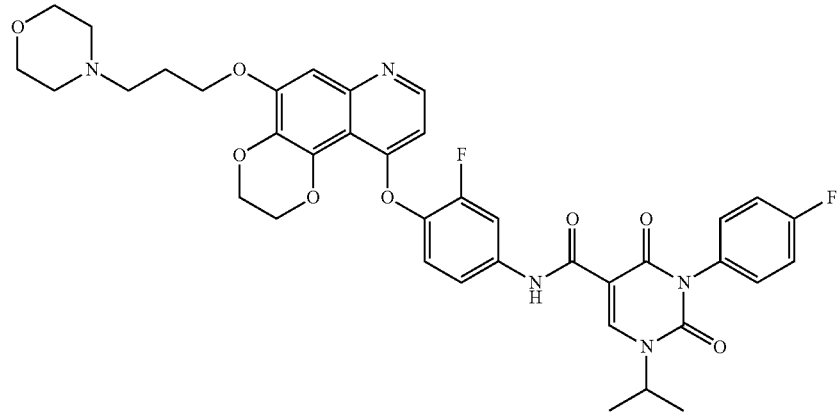

Example 16: N-(3-fluoro-4-((5-(3-morpholinopropoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, Example 17: N-(3-fluoro-4-((5-methoxy-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 32%); $^1$H NMR (400 MHz, DMSO-d$_6$) δ 12.07 (s, 1H), 8.59 (dd, J=7.3, 2.1 Hz, 1H), 8.44 (d, J=5.2 Hz, 1H), 8.12 (dd, J=6.5, 2.1 Hz, 1H), 8.01 (dd, J=13.0, 2.4 Hz, 1H), 7.60 (dd, J=8.9, 4.8 Hz, 2H), 7.43 (q, J=8.3 Hz, 3H), 7.24 (t, J=8.9 Hz, 1H), 7.08 (s, 1H), 6.73 (t, J=6.9 Hz, 1H), 6.48 (d, J=5.2 Hz, 1H), 4.34 (s, 4H), 3.93 (s, 3H). MS: 558 [M+H]$^+$.

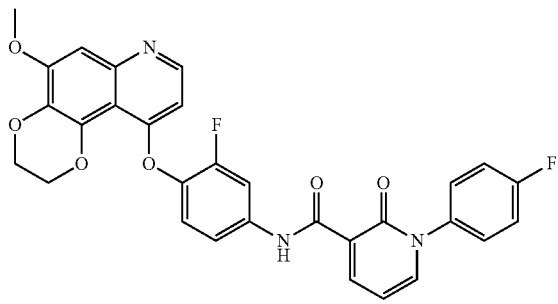

Example 17

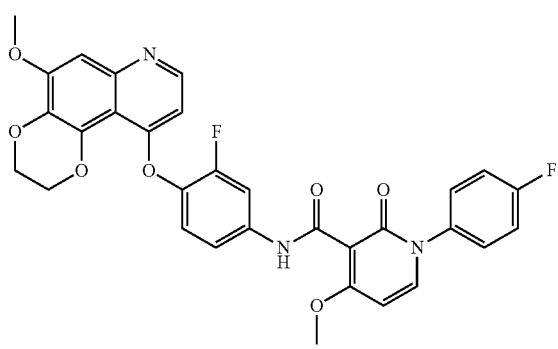

Example 18

Example 18: N-(3-fluoro-4-((5-methoxy-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 34%); $^1$H NMR (400 MHz, DMSO-$d_6$) δ 10.57 (s, 1H), 8.41 (d, J=5.3 Hz, 1H), 7.95-7.85 (m, 2H), 7.46 (td, J=7.6, 6.3, 3.5 Hz, 3H), 7.37 (t, J=8.6 Hz, 2H), 7.25 (t, J=9.0 Hz, 1H), 7.08 (s, 1H), 6.54 (d, J=7.9 Hz, 1H), 6.44 (d, J=5.2 Hz, 1H), 4.38-4.33 (m, 4H), 3.96-3.90 (m, 6H). MS: 588 [M+H]$^+$.

Example 19: N-(3-fluoro-4-((5-methoxy-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 32%); $^1$H NMR (400 MHz, DMSO-$d_6$) δ 10.53 (s, 1H), 8.41 (d, J=5.2 Hz, 1H), 7.88 (dd, J=19.7, 10.1 Hz, 2H), 7.46 (dd, J=8.8, 5.6 Hz, 3H), 7.37 (t, J=8.5 Hz, 2H), 7.26 (t, J=9.0 Hz, 1H), 7.08 (s, 1H), 6.51 (d, J=7.9 Hz, 1H), 6.44 (d, J=5.2 Hz, 1H), 4.36 (s, 4H), 4.26 (q, J=6.9 Hz, 2H), 3.93 (s, 3H), 1.31 (t, J=7.0 Hz, 3H). MS: 602 [M+H]$^+$.

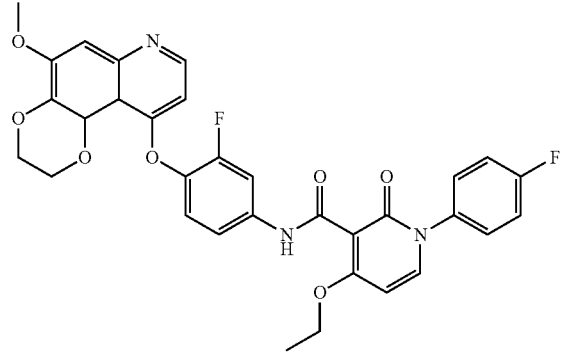

Example 19

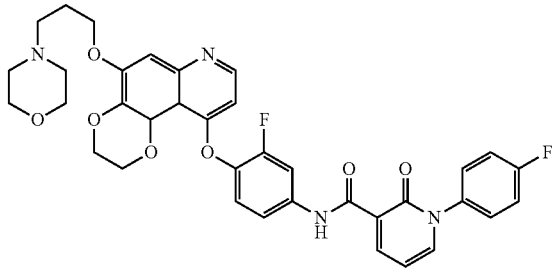

Example 20

Example 20: N-(3-fluoro-4-((5-(3-morpholinopropoxy)-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 33%); $^1$H NMR (400 MHz, DMSO-$d_6$) δ 12.07 (s, 1H), 8.59 (dd, J=7.4, 2.2 Hz, 1H), 8.43 (d, J=5.2 Hz, 1H), 8.12 (dd, J=6.6, 2.2 Hz, 1H), 8.05-7.96 (m, 1H), 7.61 (dd, J=8.5, 5.1 Hz, 2H), 7.43 (q, J=8.6, 8.2 Hz, 3H), 7.24 (t, J=8.9 Hz, 1H), 7.07 (s, 1H), 6.73 (t, J=7.0 Hz, 1H), 6.48 (d, J=5.2 Hz, 1H), 4.34 (s, 4H), 4.18 (t, J=6.4 Hz, 2H), 3.59 (t, J=4.5 Hz, 4H), 2.47 (t, J=7.1 Hz, 2H), 2.39 (s, 4H), 1.96 (t, J=6.9 Hz, 2H). MS: 671 [M+H]$^+$.

Example 21: N-(3-fluoro-4-((5-(3-morpholinopropoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 36%); $^1$H NMR (400 MHz, DMSO-$d_6$) δ 10.57 (s, 1H), 8.40 (d, J=5.2 Hz, 1H), 7.95-7.86 (m, 2H), 7.51-7.32 (m, 5H), 7.25 (t, J=9.0 Hz, 1H), 7.07 (s, 1H), 6.54 (d, J=7.8 Hz, 1H), 6.43 (d, J=5.2 Hz, 1H), 4.36 (s, 4H), 4.18 (t, J=6.4 Hz, 2H), 3.93 (s, 3H), 3.60 (t, J=4.6 Hz, 4H), 2.49 (br, 2H), 2.42 (s, 4H), 1.98 (q, J=7.2 Hz, 2H). MS: 701 [M+H]$^+$.

Example 21

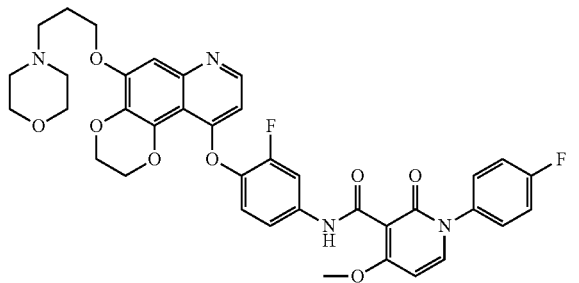

Example 22

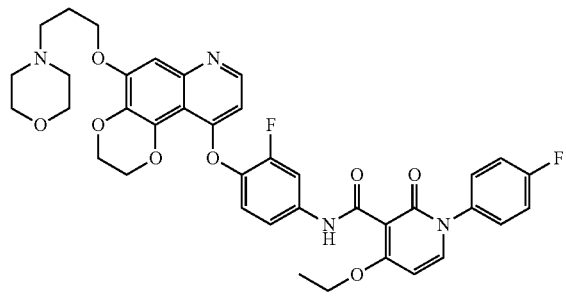

Example 22: N-(3-fluoro-4-((5-(3-morpholinopropoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 25%); $^1$H NMR (400 MHz, DMSO-$d_6$) δ 10.53 (s, 1H), 8.40 (d, J=5.2 Hz, 1H), 7.87 (dd, J=18.6, 10.2 Hz, 2H), 7.46 (dd, J=8.9, 5.9 Hz, 3H), 7.37 (t, J=8.6 Hz, 2H), 7.26 (t, J=9.0 Hz, 1H), 7.07 (s, 1H), 6.48 (dd, J=30.9, 6.6 Hz, 2H), 4.36 (s, 4H), 4.26 (d, J=7.0 Hz, 2H), 4.18 (t, J=6.4 Hz, 2H), 3.60 (s, 4H), 2.46 (br, 2H), 2.40 (s, 4H), 1.97 (s, 2H), 1.31 (t, J=7.0 Hz, 3H). MS: 715 [M+H]$^+$.

Example 23: 1-(4-fluoro-2-methylphenyl)-N-(3-fluoro-4-((5-methoxy-2,3-dihydro-[1,4]dioxino[2,3-f]quinolin-10-yl)oxy)phenyl)-1H-pyrazole-3-carboxamide A solution of 1-(4-fluoro-2-methylphenyl)-1H-pyrazol-3-carbonyl chloride (24 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (14 mg, yield: 26%); $^1$H NMR (400 MHz, DMSO-$d_6$) δ 10.45 (s, 1H), 8.43 (d, J=5.3 Hz, 1H), 8.19 (d, J=2.4 Hz, 1H), 8.03 (d, J=12.8 Hz, 1H), 7.75 (dd, J=8.9, 2.1 Hz, 1H), 7.55 (dd, J=8.7, 5.4 Hz, 1H), 7.41-7.18 (m, 3H), 7.08 (s, 1H), 7.03 (d, J=2.5 Hz, 1H), 6.45 (d, J=5.2 Hz, 1H), 4.35 (s, 4H), 3.93 (s, 3H), 2.22 (s, 3H). MS: 545 [M+H]$^+$.

Example 23

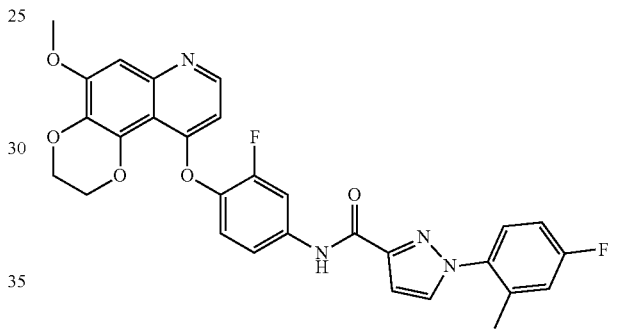

Example 24

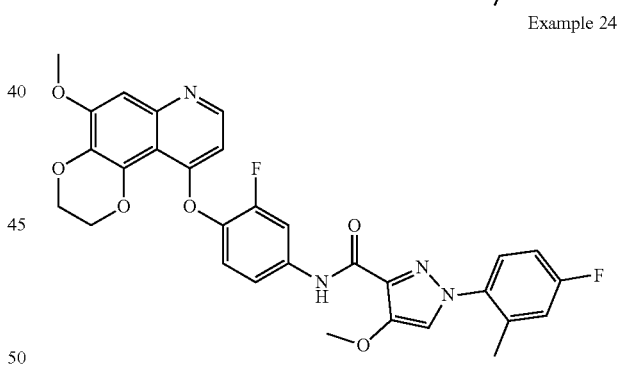

Example 24: 1-(4-fluoro-2-methylphenyl)-N-(3-fluoro-4-((5-methoxy-2,3-dihydro-[1,4]dioxino[2,3-f]quinolin-10-yl)oxy)phenyl)-4-methoxy-1H-pyrazole-3-carboxamide A solution of 1-(4-fluoro-2-methylphenyl)-4-methoxy-1H-pyrazol-3-carbonyl chloride (28 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 31%); ¹H NMR (400 MHz, DMSO-d₆) δ 10.10 (s, 1H), 8.43 (dd, J=5.3, 1.7 Hz, 1H), 8.07-7.94 (m, 2H), 7.68 (dd, J=8.9, 2.0 Hz, 1H), 7.52 (dd, J=8.7, 5.5 Hz, 1H), 7.37-7.20 (m, 3H), 7.08 (s, 1H), 6.45 (d, J=5.2 Hz, 1H), 4.35 (s, 4H), 3.93 (s, 3H), 3.84 (d, J=1.8 Hz, 3H), 2.27 (s, 3H). MS: 575 [M+H]⁺.

Example 25: 1-(4-fluoro-2-methylphenyl)-N-(3-fluoro-4-((5-methoxy-2,3-dihydro-[1,4]dioxino[2,3-f]quinolin-10-yl)oxy)phenyl)-4-ethoxy-1H-pyrazole-3-carboxamide A solution of 1-(4-fluoro-2-methylphenyl)-4-ethoxy-1H-pyrazol-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 25%); ¹H NMR (400 MHz, DMSO-d₆) δ 10.08 (s, 1H), 8.43 (d, J=5.2 Hz, 1H), 8.06-7.95 (m, 2H), 7.66 (d, J=8.7 Hz, 1H), 7.52 (dd, J=8.7, 5.4 Hz, 1H), 7.37-7.18 (m, 3H), 7.08 (s, 1H), 6.45 (d, J=5.3 Hz, 1H), 4.36 (s, 4H), 4.07 (q, J=7.0 Hz, 2H), 3.93 (s, 3H), 2.26 (s, 3H), 1.37 (t, J=7.0 Hz, 3H). MS: 589 [M+H]⁺.

a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 29%); ¹H NMR (400 MHz, DMSO-d₆) δ 10.45 (s, 1H), 8.42 (d, J=5.2 Hz, 1H), 8.19 (d, J=2.4 Hz, 1H), 8.03 (dd, J=13.4, 2.4 Hz, 1H), 7.75 (d, J=8.6 Hz, 1H), 7.55 (dd, J=8.7, 5.4 Hz, 1H), 7.39-7.20 (m, 3H), 7.10-7.00 (m, 2H), 6.45 (d, J=5.2 Hz, 1H), 4.36 (s, 4H), 4.18 (t, J=6.5 Hz, 2H), 3.59 (t, J=4.5 Hz, 4H), 2.43 (dt, J=27.6, 5.7 Hz, 6H), 2.22 (s, 3H), 2.01-1.92 (m, 2H). MS: 658 [M+H]⁺.

Example 27: 1-(4-fluoro-2-methylphenyl)-N-(3-fluoro-4-((5-(3-morpholinopropoxy)-2,3-dihydro-[1,4]dioxino[2,3-f]quinolin-10-yl)oxy)phenyl)-4-methoxy-1H-pyrazole-3-carboxamide A solution of 1-(4-fluoro-2-methylphenyl)-4-methoxy-1H-pyrazol-3-carbonyl chloride (27 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (24 mg, yield: 35%); ¹H NMR (400 MHz, DMSO-d₆) δ 10.10 (s, 1H), 8.42 (d, J=5.2 Hz, 1H), 8.07-7.94 (m, 2H), 7.67 (d, J=8.9 Hz, 1H), 7.52 (dd, J=8.7, 5.4 Hz, 1H), 7.37-7.18 (m, 3H), 7.07 (s, 1H), 6.44 (d, J=5.2 Hz, 1H), 4.36 (s, 4H), 4.18 (t, J=6.3 Hz, 2H), 3.84 (s, 3H), 3.59 (t, J=4.5 Hz, 4H), 2.49-2.38 (m, 2H), 2.39 (s, 4H), 2.27 (s, 3H), 1.97 (t, J=6.8 Hz, 2H). MS: 688 [M+H]⁺.

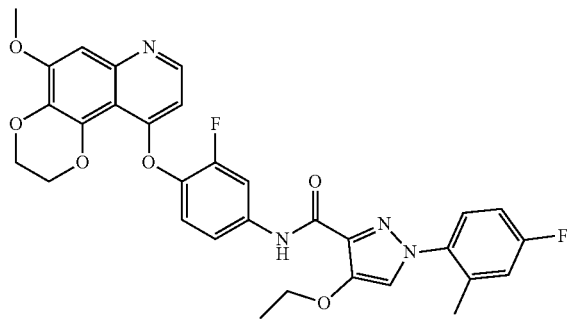

Example 25

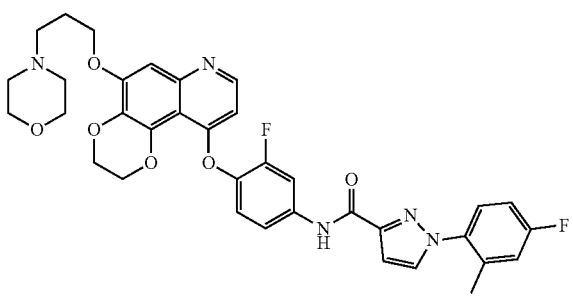

Example 26

Example 26: 1-(4-fluoro-2-methylphenyl)-N-(3-fluoro-4-((5-(3-morpholinopropoxy)-2,3-dihydro-[1,4]dioxino[2,3-f]quinolin-10-yl)oxy)phenyl)-1H-pyrazole-3-carboxamide A solution of 1-(4-fluoro-2-methylphenyl)-1H-pyrazol-3-carbonyl chloride (24 mg, 0.1 mmol) in dichloromethane (0.5 mL) followed by triethylamine (0.1 mL) were added to

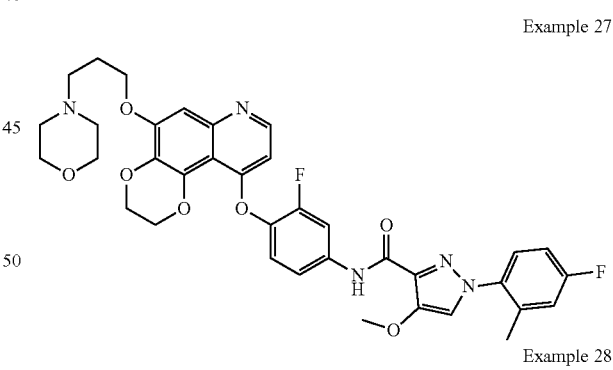

Example 27

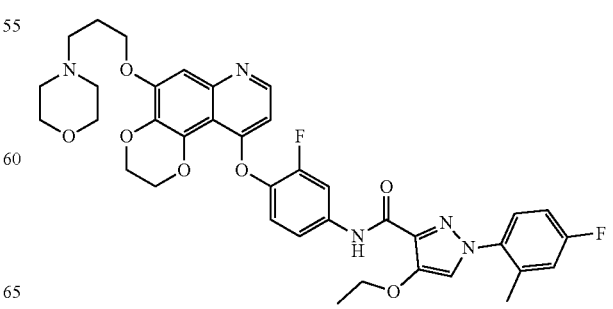

Example 28

Example 28: 1-(4-fluoro-2-methylphenyl)-N-(3-fluoro-4-((5-(3-morpholinopropoxy)-2,3-dihydro-[1,4]dioxino[2,3-f]quinolin-10-yl)oxy)phenyl)-4-ethoxy-1H-pyrazole-3-carboxamide A solution of 1-(4-fluoro-2-methylphenyl)-4-ethoxy-1H-pyrazol-3-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (24 mg, yield: 34%); $^1$H NMR (400 MHz, DMSO-$d_6$) δ 10.08 (s, 1H), 8.42 (d, J=5.1 Hz, 1H), 8.05-7.95 (m, 2H), 7.65 (d, J=8.9 Hz, 1H), 7.52 (dd, J=8.8, 5.5 Hz, 1H), 7.37-7.21 (m, 3H), 7.07 (s, 1H), 6.44 (d, J=5.2 Hz, 1H), 4.36 (s, 4H), 4.18 (t, J=6.5 Hz, 2H), 4.07 (q, J=7.0 Hz, 2H), 3.59 (t, J=4.5 Hz, 4H), 2.49-2.38 (m, 2H), 2.39 (s, 4H), 2.26 (s, 3H), 1.97 (t, J=7.0 Hz, 2H), 1.37 (t, J=7.0 Hz, 3H). MS: 702 [M+H]$^+$.

Example 29: N-(3-fluoro-4-((5-methoxy-2,3-dihydro-[1,4]dioxino[2,3-f]quinazolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinazolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 37%); $^1$H NMR (400 MHz, DMSO-$d_6$) δ 10.98 (s, 1H), 8.87 (s, 1H), 8.45 (s, 1H), 7.89 (dd, J=12.5, 2.4 Hz, 1H), 7.47-7.35 (m, 6H), 7.08 (s, 1H), 4.49-4.35 (m, 4H), 3.97 (s, 3H), 3.54 (s, 3H). MS: 590 [M+H]$^+$.

Example 29

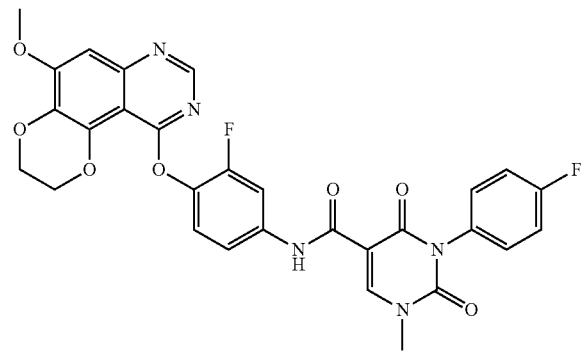

Example 30

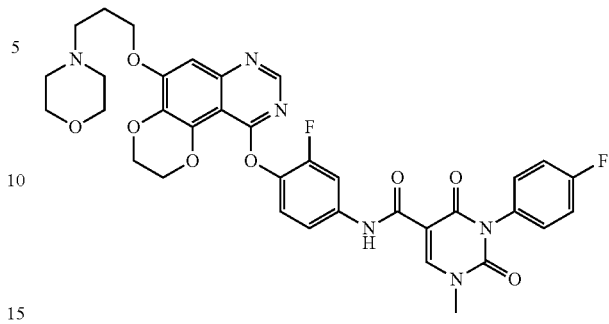

Example 30: N-(3-fluoro-4-((5-(3-morpholinopropoxy)-2,3-dihydro-[1,4]dioxino[2,3-f]quinazolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinazolin-10-yl)oxy) aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 27%); $^1$H NMR (400 MHz, DMSO-$d_6$) δ 10.98 (s, 1H), 8.87 (s, 1H), 8.44 (s, 1H), 7.89 (dd, J=12.9, 2.4 Hz, 1H), 7.44-7.31 (m, 6H), 7.07 (s, 1H), 4.49-4.38 (m, 4H), 4.23 (t, J=6.4 Hz, 2H), 3.59 (t, J=4.6 Hz, 4H), 3.54 (s, 3H), 2.46 (t, J=7.0 Hz, 2H), 2.39 (s, 4H), 2.02-1.92 (m, 2H). MS:703 [M+H]$^+$.

Example 31: N-(3-fluoro-4-((5-(3-(piperidin-1-yl)propoxy)-2,3-dihydro-[1,4]dioxino[2,3-f]quinolin-10-yl) oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 33%); $^1$H NMR (400 MHz, DMSO-$d_6$) δ 12.08 (s, 1H), 8.58 (dd, J=7.3, 2.2 Hz, 1H), 8.42 (d, J=5.2 Hz, 1H), 8.13 (dd, J=6.6, 2.2 Hz, 1H), 8.01 (dd, J=13.0, 2.5 Hz, 1H), 7.65-7.57 (m, 2H), 7.50-7.38 (m, 3H), 7.24 (t, J=9.0 Hz, 1H), 7.05 (s, 1H), 6.73 (t, J=7.0 Hz, 1H), 6.46 (d, J=5.2 Hz, 1H), 4.34 (s, 4H), 4.15 (t, J=6.4 Hz, 2H), 2.42 (t, J=7.2 Hz, 2H), 2.35 (s, 4H), 1.94 (t, J=6.9 Hz, 2H), 1.50 (p, J=5.5 Hz, 4H), 1.39 (q, J=5.9 Hz, 2H). MS: 669 [M+H]$^+$.

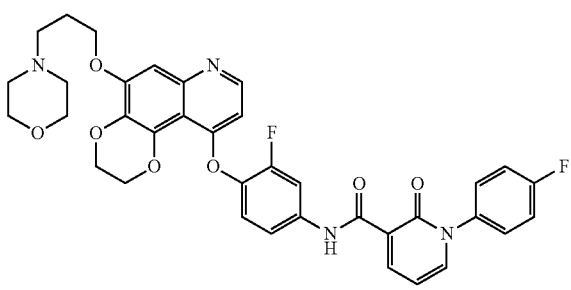

Example 31

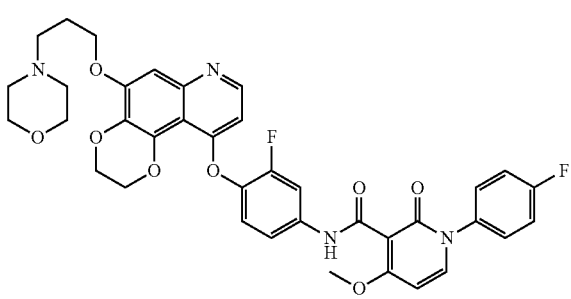

Example 32

Example 32: N-(3-fluoro-4-((5-(3-(piperidin-1-yl)propoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 28.6%); $^1$H NMR (400 MHz, DMSO-$d_6$) δ 10.60 (s, 1H), 8.40 (d, J=5.3 Hz, 1H), 7.95-7.86 (m, 2H), 7.51-7.32 (m, 5H), 7.26 (t, J=9.0 Hz, 1H), 7.08 (s, 1H), 6.54 (d, J=7.8 Hz, 1H), 6.43 (d, J=5.2 Hz, 1H), 4.37 (t, J=3.4 Hz, 4H), 4.20 (t, J=6.3 Hz, 2H), 3.93 (s, 3H), 2.95-2.62 (s, 6H), 2.12 (br, 2H), 1.66 (br, 4H), 1.48 (br, 2H). MS: 699 [M+H]$^+$.

Example 33: N-(3-fluoro-4-((5-(3-(piperidin-1-yl)propoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 27%); $^1$H NMR (400 MHz, DMSO-$d_6$) δ 10.54 (s, 1H), 8.39 (d, J=5.2 Hz, 1H), 7.98-7.80 (m, 2H), 7.50-7.33 (m, 5H), 7.26 (t, J=9.0 Hz, 1H), 7.05 (s, 1H), 6.52 (d, J=7.9 Hz, 1H), 6.43 (dd, J=5.3, 1.0 Hz, 1H), 4.36 (s, 4H), 4.26 (q, J=7.0 Hz, 2H), 4.16 (t, J=6.4 Hz, 2H), 2.48-2.33 (m, 6H), 1.96 (q, J=6.8 Hz, 2H), 1.51 (q, J=5.6 Hz, 4H), 1.39 (s, 2H), 1.30 (t, J=7.0 Hz, 3H). MS: 713 [M+H]$^+$.

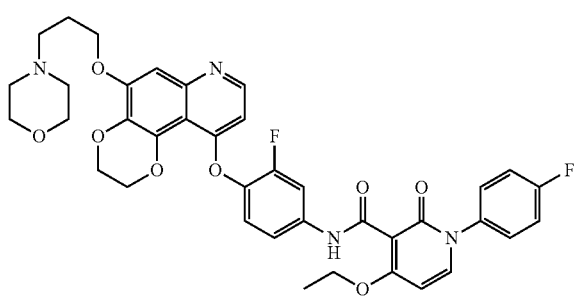

Example 33

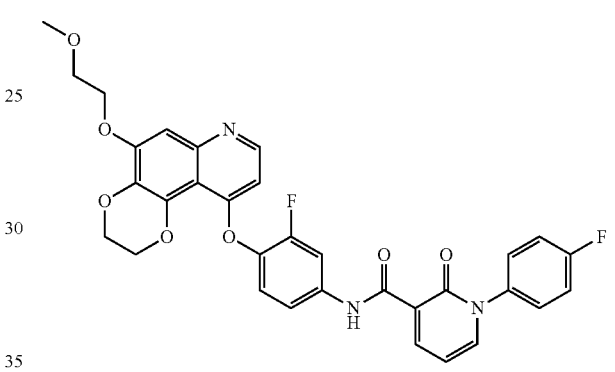

Example 34

Example 34: N-(3-fluoro-4-((5-(2-methoxyethoxy)-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 27%); $^1$H NMR (400 MHz, DMSO-$d_6$) δ 12.09 (s, 1H), 8.58 (dd, J=7.3, 2.2 Hz, 1H), 8.43 (d, J=5.2 Hz, 1H), 8.13 (dd, J=6.6, 2.2 Hz, 1H), 8.02 (dd, J=13.0, 2.5 Hz, 1H), 7.66-7.56 (m, 2H), 7.50-7.37 (m, 3H), 7.26 (t, J=9.0 Hz, 1H), 7.09 (s, 1H), 6.73 (t, J=7.0 Hz, 1H), 6.48 (dd, J=5.3, 0.9 Hz, 1H), 4.35 (s, 4H), 4.29-4.21 (m, 2H), 3.78-3.70 (m, 2H), 3.35 (s, 3H). MS: 602 [M+H]$^+$.

Example 35: N-(3-fluoro-4-((5-(2-methoxyethoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy) aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 24%); $^1$H NMR (400 MHz, DMSO-$d_6$) δ 10.61 (s, 1H), 8.41 (d, J=5.3 Hz, 1H), 7.96-7.86 (m, 2H), 7.51-7.41 (m, 3H), 7.37 (t, J=8.8 Hz, 2H), 7.28 (t, J=9.0 Hz, 1H), 7.09 (s, 1H), 6.54 (d, J=7.9 Hz, 1H), 6.45 (d, J=5.3 Hz, 1H), 4.37 (s, 4H), 4.29-4.22 (m, 2H), 3.93 (s, 3H), 3.78-3.71 (m, 2H), 3.35 (s, 3H). MS: 632 [M+H]$^+$.

Example 35

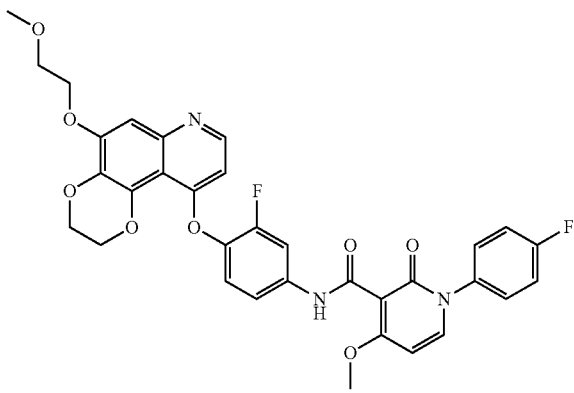

Example 36

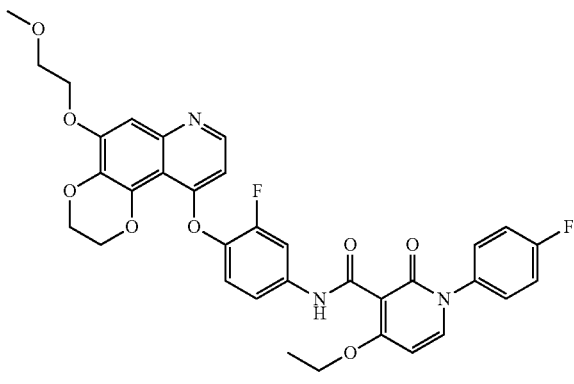

Example 36: N-(3-fluoro-4-((5-(2-methoxyethoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy) aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 34%); $^1$H NMR (400 MHz, DMSO-$d_6$) δ 10.54 (s, 1H), 8.40 (d, J=5.1 Hz, 1H), 7.96-7.75 (m, 2H), 7.49-7.42 (m, 3H), 7.37 (t, J=8.6 Hz, 2H), 7.27 (s, 1H), 7.08 (s, 1H), 6.52 (d, J=7.8 Hz, 1H), 6.44 (d, J=5.2 Hz, 1H), 4.37 (s, 4H), 4.26 (q, J=5.2, 4.4 Hz, 4H), 3.74 (t, J=4.4 Hz, 2H), 3.35 (s, 3H), 1.31 (t, J=7.0 Hz, 3H). MS: 646 [M+H]$^+$.

Example 37: N-(3-fluoro-4-((5-methoxy-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl) oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 33%); $^1$H NMR (400 MHz, DMSO-$d_6$) δ 10.99 (s, 1H), 8.88 (s, 1H), 8.43 (d, J=5.2 Hz, 1H), 7.96 (dd, J=12.9, 2.4 Hz, 1H), 7.51-7.31 (m, 5H), 7.25 (t, J=9.0 Hz, 1H), 7.08 (s, 1H), 6.47 (d, J=5.1 Hz, 1H), 4.34 (s, 4H), 4.05-3.97 (m, 2H), 3.92 (s, 3H), 1.30 (t, J=7.1 Hz, 3H). MS: 603 [M+H]+.

Example 37

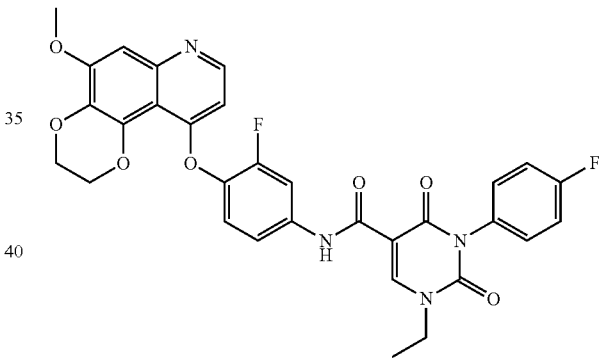

Example 38

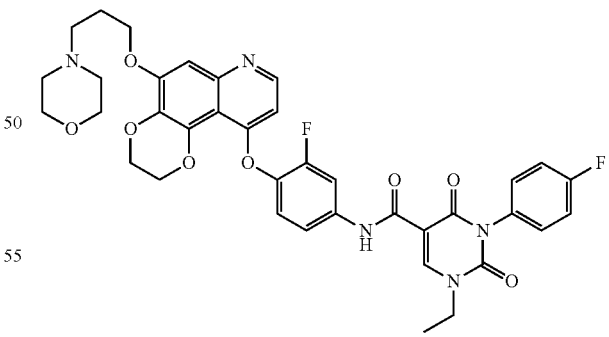

Example 38: N-(3-fluoro-4-((5-(3-morpholinopropoxy)-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-(3-morpholinopropoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 31%); $^1$H NMR (400 MHz, DMSO-$d_6$) δ 10.99 (s, 1H), 8.88 (s, 1H), 8.42 (d, J=5.2 Hz, 1H), 8.00-7.92 (m, 1H), 7.50-7.31 (m, 5H), 7.24 (t, J=8.9 Hz, 1H), 7.07 (s, 1H), 6.46 (d, J=5.2 Hz, 1H), 4.34 (s, 4H), 4.17 (s, 2H), 4.02 (d, J=7.3 Hz, 2H), 3.59 (t, J=4.4 Hz, 4H), 2.46 (t, J=7.2 Hz, 2H), 2.39 (s, 4H), 2.00-1.92 (m, 2H), 1.30 (t, J=7.0 Hz, 3H). MS: 716 [M+H]$^+$.

Example 39: N-(3-fluoro-4-((5-(3-(piperidin-1-yl)propoxy)-2,3-dihydro-[1,4]dioxino[2,3-f]quinolin-10-yl) oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 36%); $^1$H NMR (400 MHz, DMSO-$d_6$) δ 11.00 (s, 1H), 8.88 (s, 1H), 8.42 (d, J=5.2 Hz, 1H), 7.96 (dd, J=13.0, 2.5 Hz, 1H), 7.47 (dd, J=9.1, 1.7 Hz, 1H), 7.44-7.31 (m, 4H), 7.25 (t, J=9.0 Hz, 1H), 7.06 (s, 1H), 6.46 (d, J=5.2 Hz, 1H), 4.34 (s, 4H), 4.16 (t, J=6.4 Hz, 2H), 3.54 (s, 3H), 2.48-2.36 (m, 6H), 1.97 (d, J=14.2 Hz, 2H), 1.52 (s, 4H), 1.40 (s, 2H). MS: 700 [M+H]$^+$.

Example 39

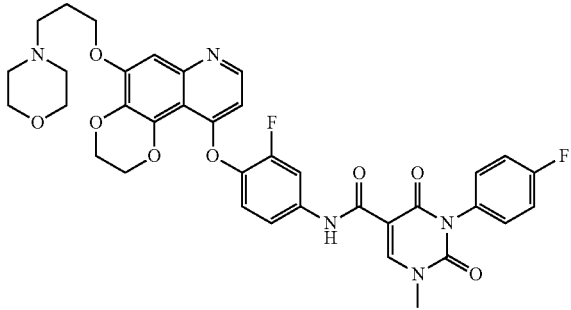

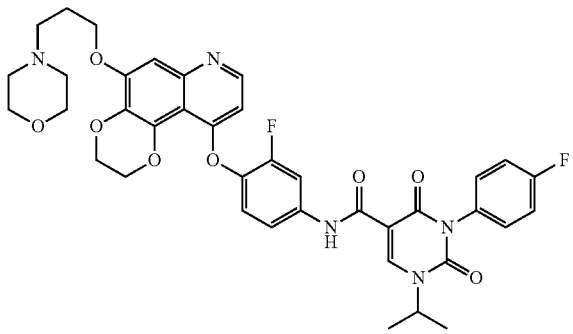

Example 40: N-(3-fluoro-4-((5-(3-(piperidin-1-yl)propoxy)-2,3-dihydro-[1,4]dioxino[2,3-f]quinolin-10-yl) oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (24 mg, yield: 33%); $^1$H NMR (600 MHz, DMSO-$d_6$) δ 10.93 (s, 1H), 8.60 (s, 1H), 8.35 (d, J=5.2 Hz, 1H), 7.90 (dd, J=13.0, 2.5 Hz, 1H), 7.42-7.33 (m, 3H), 7.29 (td, J=9.4, 8.8, 2.6 Hz, 2H), 7.17 (t, J=9.0 Hz, 1H), 6.99 (s, 1H), 6.40 (d, J=5.2 Hz, 1H), 4.71 (q, J=6.7 Hz, 1H), 4.27 (dq, J=8.3, 4.5, 4.0 Hz, 4H), 4.09 (t, J=6.4 Hz, 2H), 2.37 (br, 6H), 1.94-1.84 (m, 2H), 1.51-1.41 (m, 4H), 1.35 (d, J=6.8 Hz, 6H), 1.33 (s, 2H). MS: 728 [M+H]$^+$.

Example 41: N-(3-fluoro-4-((5-(3-(piperidin-1-yl)propoxy)-2,3-dihydro-[1,4]dioxino[2,3-f]quinolin-10-yl) oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-(3-(piperidin-1-yl)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg, yield: 36%); $^1$H NMR (400 MHz, DMSO-$d_6$) δ 10.99 (s, 1H), 8.88 (s, 1H), 8.42 (d, J=5.2 Hz, 1H), 7.96 (dd, J=13.0, 2.4 Hz, 1H), 7.48-7.32 (m, 5H), 7.24 (t, J=9.0 Hz, 1H), 7.05 (s, 1H), 6.48-6.42 (m, 1H), 4.34 (s, 4H), 4.15 (t, J=6.5 Hz, 2H), 4.01 (q, J=7.1 Hz, 2H), 2.45-2.32 (m, 6H), 1.95 (q, J=6.8 Hz, 2H), 1.51 (s, 4H), 1.39 (q, J=5.9 Hz, 2H), 1.29 (t, J=7.1 Hz, 3H). MS: 714 [M+H]$^+$.

Example 41

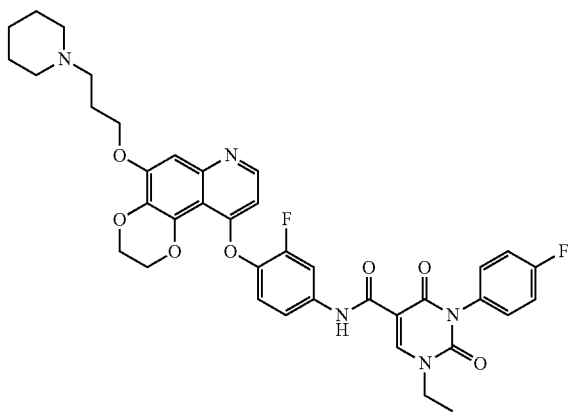

Example 42

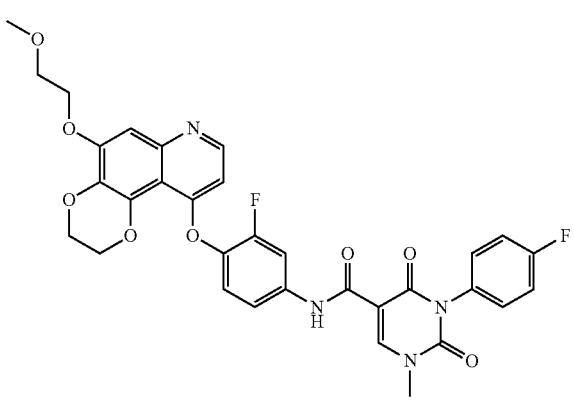

Example 42: N-(3-fluoro-4-((5-(2-methoxyethoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (400 MHz, DMSO-$d_6$) δ 10.99 (s, 1H), 8.87 (s, 1H), 8.42 (d, J=5.2 Hz, 1H), 7.96 (d, J=12.6 Hz, 1H), 7.47 (d, J=8.8 Hz, 1H), 7.41-7.35 (m, 4H), 7.25 (t, J=9.1 Hz, 1H), 7.08 (s, 1H), 6.46 (d, J=5.1 Hz, 1H), 4.35 (s, 4H), 4.25 (s, 3H), 3.74 (d, J=5.2 Hz, 2H), 3.54 (s, 2H), 3.34 (s, 3H). MS: 633 [M+H]$^+$.

Example 43: N-(3-fluoro-4-((5-(2-methoxyethoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 38%); $^1$H NMR (600 MHz, DMSO-$d_6$) δ 11.00 (s, 1H), 8.67 (s, 1H), 8.42 (d, J=5.2 Hz, 1H), 7.97 (dd, J=12.9, 2.5 Hz, 1H), 7.49-7.40 (m, 3H), 7.36 (t, J=8.8 Hz, 2H), 7.25 (t, J=9.0 Hz, 1H), 7.08 (s, 1H), 6.47 (d, J=5.2 Hz, 1H), 4.90-4.58 (m, 1H), 4.34 (q, J=4.7 Hz, 4H), 4.27-4.22 (m, 2H), 3.76-3.71 (m, 2H), 3.30 (s, 3H), 1.42 (d, J=6.7 Hz, 6H). MS: 661 [M+H]$^+$.

Example 43

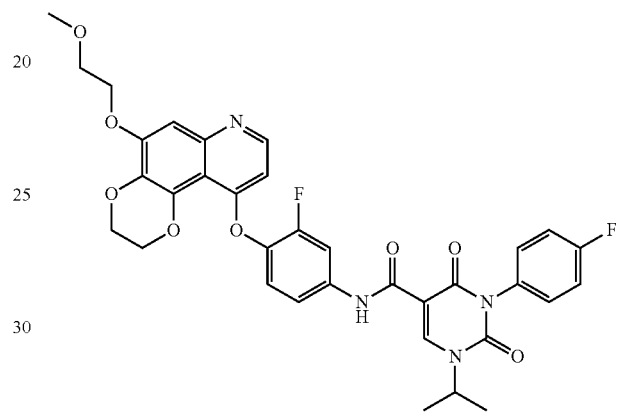

Example 44

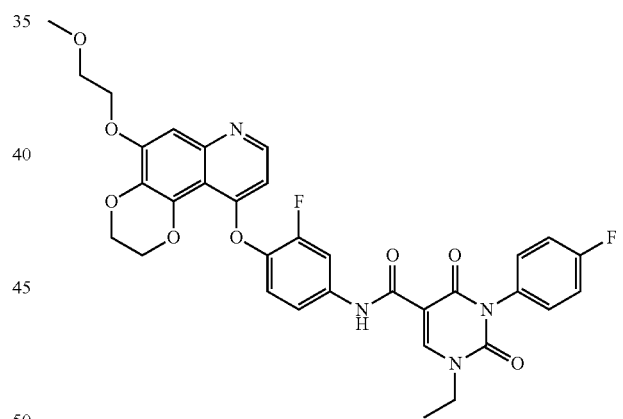

Example 44: N-(3-fluoro-4-((5-(2-methoxyethoxy)-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 39%); $^1$H NMR (400 MHz, DMSO-$d_6$) δ 10.99 (s, 1H), 8.87 (s, 1H), 8.42 (d, J=5.2 Hz, 1H), 7.96 (d, J=12.7 Hz, 1H), 7.48-7.36 (m, 5H), 7.25 (t, J=9.0 Hz, 1H), 7.08 (s, 1H), 6.47 (d, J=5.1 Hz, 1H), 4.35 (s, 4H), 4.25 (s, 2H), 4.02 (d, J=7.3 Hz, 2H), 3.74 (d, J=4.8 Hz, 2H), 3.34 (s, 3H), 1.30 (t, J=7.1 Hz, 3H). MS: 647 [M+H]$^+$.

Example 45: N-(3-fluoro-4-((5-methoxy-2,3-dihydro-[1,4]dioxino[2,3-f]quinolin-10-yl)oxy)phenyl)-3-(4-fluorophenyl)-1-(2-hydroxyethyl)-2,4-dioxo-1,2,3,4-tetrahydropyrimidine-5-carboxamide A solution of 3-(4-fluorophenyl)-1-(2-hydroxyethyl)-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 32%); $^1$H NMR (400 MHz, DMSO-$d_6$) δ 10.97 (s, 1H), 8.73 (s, 1H), 8.42 (d, J=5.2 Hz, 1H), 7.96 (d, J=11.9 Hz, 1H), 7.46 (d, J=9.2 Hz, 1H), 7.45-7.31 (m, 3H), 7.25 (d, J=9.1 Hz, 1H), 7.07 (s, 1H), 6.52 (s, 1H), 6.46 (d, J=5.2 Hz, 1H), 5.03 (t, J=5.7 Hz, 1H), 4.33 (s, 4H), 4.04 (s, 2H), 3.92 (s, 3H), 3.66 (br, 2H). MS: 619 [M+H]$^+$.

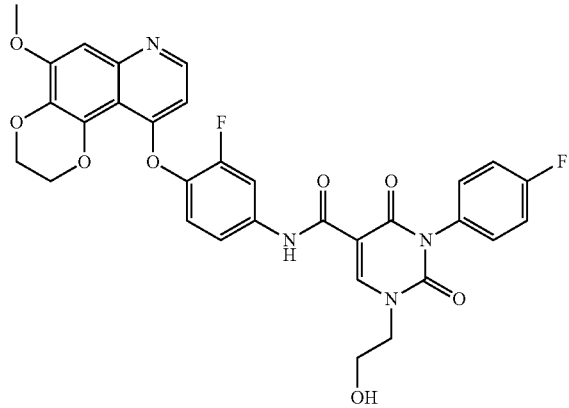

Example 45

Example 46: N-(3-fluoro-4-((5-methoxy-2,3-dihydro-[1,4]dioxino[2,3-f]quinolin-10-yl)oxy)phenyl)-3-(4-fluorophenyl)-1-(2-methoxyethyl)-2,4-dioxo-1,2,3,4-tetrahydropyrimidine-5-carboxamide A solution of 3-(4-fluorophenyl)-1-(2-methoxyethyl)-2,4-dioxo-1,2,3,4-tetrahydropyrimidine-5-carbonyl chloride (33 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 44%); $^1$H NMR (400 MHz, DMSO-$d_6$) δ 10.96 (s, 1H), 8.73 (s, 1H), 8.43 (d, J=5.2 Hz, 1H), 7.96 (dd, J=13.0, 2.5 Hz, 1H), 7.50-7.40 (m, 3H), 7.36 (t, J=8.8 Hz, 2H), 7.25 (t, J=9.0 Hz, 1H), 7.08 (s, 1H), 6.46 (d, J=5.2 Hz, 1H), 4.33 (s, 4H), 4.17 (t, J=5.0 Hz, 2H), 3.92 (s, 3H), 3.61 (t, J=5.0 Hz, 2H), 3.32 (s, 3H). MS: 633 [M+H]$^+$.

Example 47: N-(3-fluoro-4-((5-methoxy-2,3-dihydro-[1,4]dioxino[2,3-f]quinolin-10-yl)oxy)phenyl)-3-(4-fluorophenyl)-1-isobutyl-2,4-dioxo-1,2,3,4-tetrahydropyrimidine-5-carboxamide A solution of 3-(4-fluorophenyl)-1-isobutyl-2,4-dioxo-1,2,3,4-tetrahydropyrimidine-5-carbonyl chloride (33 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (17 mg, yield: 27%); $^1$H NMR (400 MHz, DMSO-$d_6$) δ 11.00 (s, 1H), 8.80 (s, 1H), 8.43 (d, J=5.2 Hz, 1H), 7.96 (dd, J=13.0, 2.5 Hz, 1H), 7.50-7.32 (m, 5H), 7.25 (t, J=9.0 Hz, 1H), 7.08 (s, 1H), 6.50-6.43 (m, 1H), 4.33 (s, 4H), 3.92 (s, 3H), 3.82 (d, J=7.3 Hz, 2H), 2.05 (dt, J=13.7, 6.8 Hz, 1H), 0.93 (d, J=6.7 Hz, 6H). MS: 631 [M+H]$^+$.

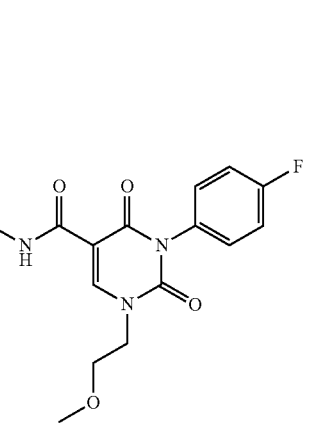

Example 46

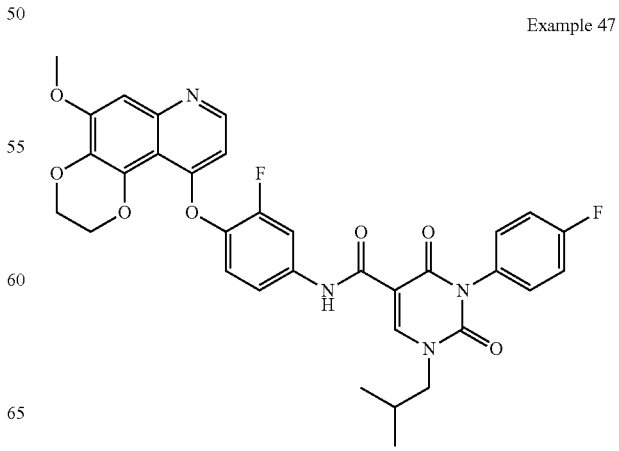

Example 47

Example 48

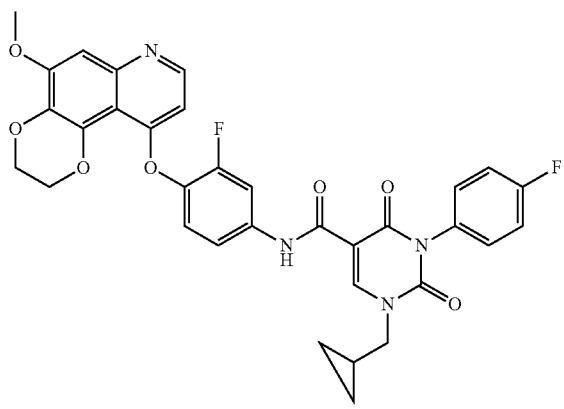

Example 48: N-(3-fluoro-4-((5-methoxy-2,3-dihydro-[1,4]dioxino[2,3-f]quinolin-10-yl)oxy)phenyl)-3-(4-fluorophenyl)-1-(cyclopropylmethyl)-2,4-dioxo-1,2,3,4-tetrahydropyrimidine-5-carboxamide A solution of 3-(4-fluorophenyl)-1-(cyclopropylmethyl)-2,4-dioxo-1,2,3,4-tetrahydropyrimidine-5-carbonyl chloride (32 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 30%); $^1$H NMR (400 MHz, DMSO-$d_6$) δ 10.99 (s, 1H), 8.91 (s, 1H), 8.43 (d, J=5.2 Hz, 1H), 7.97 (dd, J=12.9, 2.4 Hz, 1H), 7.50-7.40 (m, 3H), 7.36 (t, J=8.8 Hz, 2H), 7.25 (t, J=9.0 Hz, 1H), 7.08 (s, 1H), 6.47 (d, J=5.2 Hz, 1H), 4.34 (s, 4H), 3.92 (s, 3H), 3.86 (d, J=7.2 Hz, 2H), 1.28-1.24 (m, 1H), 0.62-0.53 (m, 2H), 0.44 (d, J=5.0 Hz, 2H). MS: 629 [M+H]$^+$.

Example 49: N-(3-fluoro-4-((5-(3-(4-methylpiperazin-1-yl)propoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(4-methylpiperazin-1-yl)propoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 34%); $^1$H NMR (600 MHz, DMSO-$d_6$) δ 10.55 (s, 1H), 8.40 (d, J=5.2 Hz, 1H), 7.90 (dd, J=13.1, 2.4 Hz, 1H), 7.86 (d, J=7.8 Hz, 1H), 7.49-7.43 (m, 3H), 7.37 (t, J=8.8 Hz, 2H), 7.27 (d, J=9.0 Hz, 1H), 7.06 (s, 1H), 6.52 (d, J=7.9 Hz, 1H), 6.43 (d, J=5.2 Hz, 1H), 4.36 (s, 4H), 4.26 (q, J=7.0 Hz, 2H), 4.17 (t, J=6.4 Hz, 2H), 2.76-2.56 (m, 10H), 2.39 (s, 3H), 1.98 (t, J=6.8 Hz, 2H), 1.30 (t, J=7.0 Hz, 3H). MS: 728 [M+H]$^+$.

Example 49

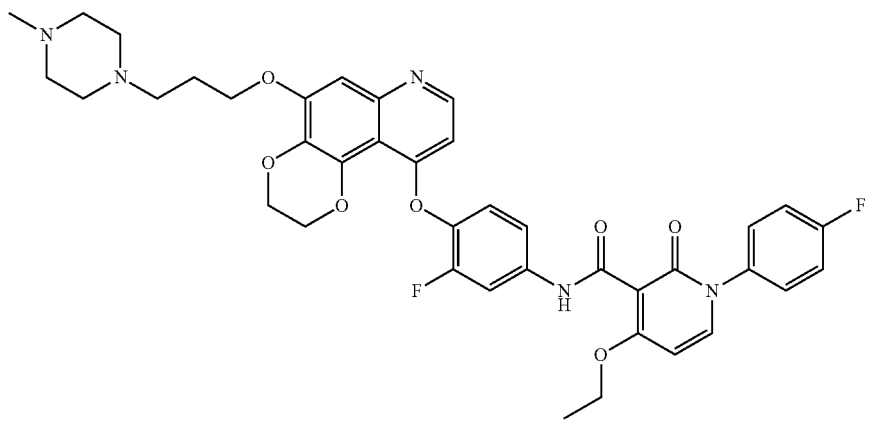

Example 50

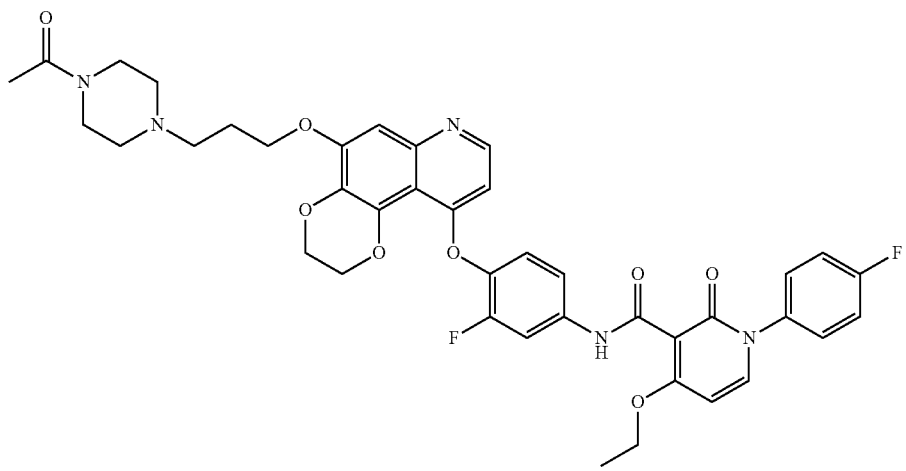

Example 50: N-(4-((5-(3-(4-acetyl-piperazin-1-yl)propoxy)-2,3-dihydro-[1,4]dioxino[2,3-f]quinolin-10-yl) oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(4-acetylpiperazin-1-yl)propoxy)-2,3-dihydro-[1,4]dioxino[2,3-f]quinolin-1 0-yl)oxy)aniline (50 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 37%); $^1$H NMR (400 MHz, DMSO-$d_6$) δ 10.48 (s, 1H), 8.33 (d, J=5.2 Hz, 1H), 7.88-7.75 (m, 2H), 7.44-7.34 (m, 3H), 7.30 (t, J=8.8 Hz, 2H), 7.20 (t, J=9.0 Hz, 1H), 7.00 (s, 1H), 6.45 (d, J=7.9 Hz, 1H), 6.36 (dd, J=5.2, 1.0 Hz, 1H), 4.29 (s, 4H), 4.19 (q, J=7.0 Hz, 2H), 4.11 (t, J=6.3 Hz, 2H), 3.37 (q, J=5.5 Hz, 4H), 2.45-2.40 (m, 2H), 2.35-2.26 (m, 4H), 1.92 (s, 5H), 1.23 (t, J=7.0 Hz, 3H). MS: 756 [M+H]$^+$.

Example 51: N-(4-((5-(3-(1,1-dioxidothiomorpholino)propoxy)-2,3-dihydro-[1,4]dioxino[2,3-f]quinolin-1 0-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(1,1-dioxidothiomorpholino)propoxy)-2,3-dihydro-[1,4]dioxino[2,3-f]quinolin-10-yl)oxy)aniline (50 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 25%); $^1$H NMR (600 MHz, DMSO-$d_6$) δ 10.54 (s, 1H), 8.40 (d, J=5.2 Hz, 1H), 7.93-7.83 (m, 2H), 7.49-7.42 (m, 3H), 7.37 (t, J=8.7 Hz, 2H), 7.26 (t, J=9.0 Hz, 1H), 7.09 (s, 1H), 6.51 (d, J=7.9 Hz, 1H), 6.43 (d, J=5.2 Hz, 1H), 4.36 (s, 4H), 4.26 (q, J=7.0 Hz, 2H), 4.19 (t, J=6.4 Hz, 2H), 3.11 (t, J=5.2 Hz, 4H), 2.92 (dd, J=6.9, 3.6 Hz, 4H), 2.65 (t, J=7.0 Hz, 2H), 1.97 (q, J=6.7 Hz, 2H), 1.30 (t, J=7.0 Hz, 3H). MS: 763 [M+H]$^+$.

Example 51

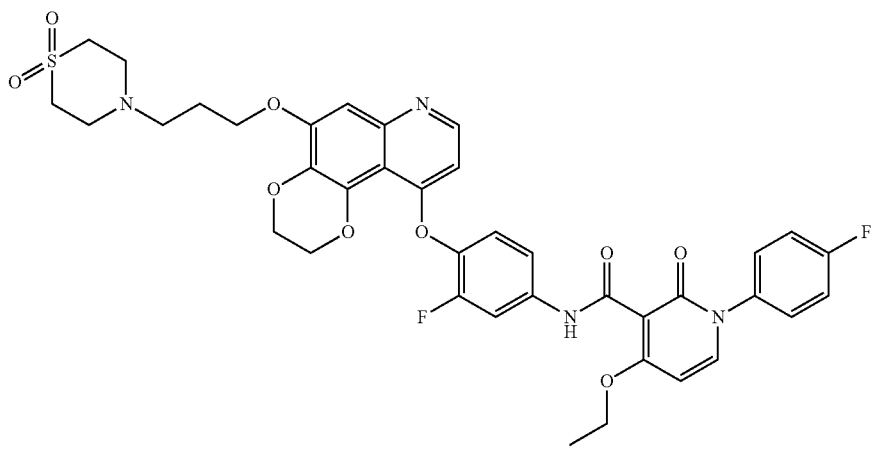

Example 52

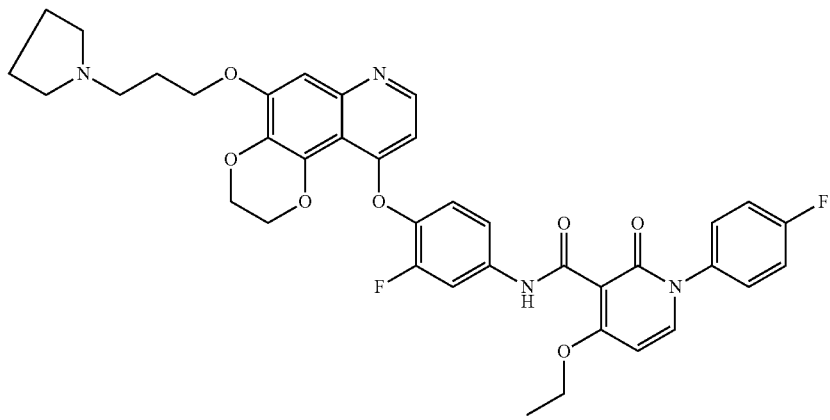

Example 52: N-(4-((5-(3-(pyrrolidin-1-yl)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(pyrrolidin-1-yl)propoxy)-2,3-dihydro-[1,4]dioxino[2,3-f]quinolin-10-yl)oxy)aniline (44 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 29%); $^1$H NMR (600 MHz, DMSO-$d_6$) δ 10.55 (s, 1H), 8.40 (d, J=5.2 Hz, 1H), 7.93-7.83 (m, 2H), 7.45 (qd, J=6.8, 5.9, 2.3 Hz, 3H), 7.37 (t, J=8.7 Hz, 2H), 7.26 (t, J=9.0 Hz, 1H), 7.06 (s, 1H), 6.51 (d, J=7.9 Hz, 1H), 6.43 (d, J=5.2 Hz, 1H), 4.36 (s, 4H), 4.26 (q, J=7.0 Hz, 2H), 4.18 (t, J=6.4 Hz, 2H), 2.68 (t, J=7.3 Hz, 2H), 2.60 (d, J=6.2 Hz, 4H), 2.01 (t, J=6.9 Hz, 2H), 1.76-1.70 (m, 4H), 1.30 (t, J=7.0 Hz, 3H). MS: 699 [M+H]$^+$.

Example 53: N-(4-((5-(2-hydroxyethoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(2-hydroxyethoxy)-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (600 MHz, DMSO-$d_6$) δ 10.55 (s, 1H), 8.40 (d, J=5.3 Hz, 1H), 7.92-7.82 (m, 2H), 7.47-7.44 (m, 3H), 7.37 (t, J=8.6 Hz, 2H), 7.27 (t, J=9.0 Hz, 1H), 7.07 (s, 1H), 6.52 (d, J=7.9 Hz, 1H), 6.44 (d, J=5.3 Hz, 1H), 4.94 (t, J=5.5 Hz, 1H), 4.36 (q, J=4.7 Hz, 4H), 4.26 (q, J=7.0 Hz, 2H), 4.15 (t, J=4.9 Hz, 2H), 3.80 (q, J=4.9 Hz, 2H), 1.30 (t, J=7.0 Hz, 3H). MS: 632 [M+H]$^+$.

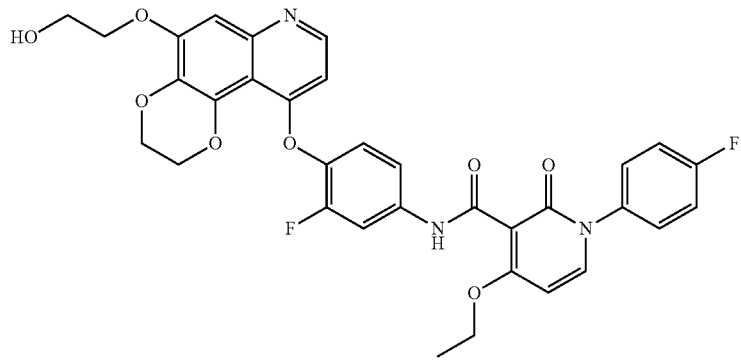

Example 53

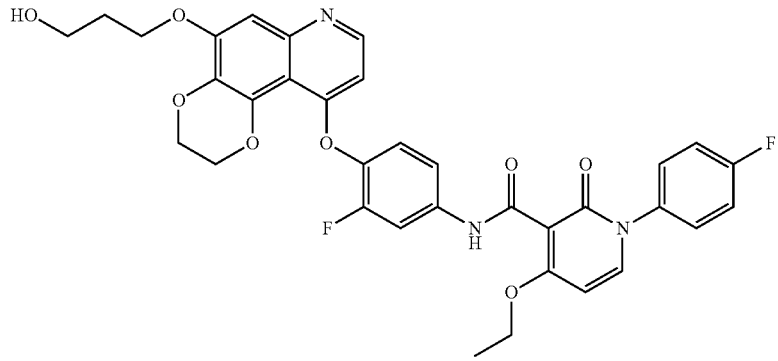

Example 54

Example 54: N-(4-((5-(3-hydroxypropoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-hydroxypropoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 34%); $^1$H NMR (600 MHz, DMSO-$d_6$) δ 10.54 (s, 1H), 8.39 (d, J=5.2 Hz, 1H), 7.93-7.83 (m, 2H), 7.49-7.42 (m, 3H), 7.37 (t, J=8.8 Hz, 2H), 7.27 (d, J=9.0 Hz, 1H), 7.06 (s, 1H), 6.51 (d, J=7.9 Hz, 1H), 6.43 (d, J=5.2 Hz, 1H), 4.60 (br, 1H), 4.36 (s, 4H), 4.26 (q, J=7.0 Hz, 2H), 4.19 (t, J=6.4 Hz, 2H), 3.60 (t, J=6.2 Hz, 2H), 1.98-1.92 (m, 2H), 1.30 (t, J=7.0 Hz, 3H). MS: 646 [M+H]$^+$.

Example 55: N-(4-((5-(3-methoxypropoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-methoxypropoxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 42%); $^1$H NMR (600 MHz, DMSO-$d_6$) δ 10.63 (s, 1H), 8.60 (d, J=6.1 Hz, 1H), 7.96 (dd, J=13.1, 2.4 Hz, 1H), 7.87 (d, J=7.8 Hz, 1H), 7.51 (dd, J=9.0, 2.4 Hz, 1H), 7.46 (dd, J=8.8, 4.9 Hz, 2H), 7.39 (dt, J=19.9, 8.9 Hz, 3H), 7.19 (s, 1H), 6.71 (d, J=6.1 Hz, 1H), 6.53 (d, J=7.9 Hz, 1H), 4.50-4.38 (m, 4H), 4.33-4.18 (m, 4H), 3.52 (t, J=6.2 Hz, 2H), 3.27 (s, 3H), 2.07 (t, J=6.3 Hz, 2H), 1.30 (t, J=7.0 Hz, 3H). MS: 660 [M+H]$^+$.

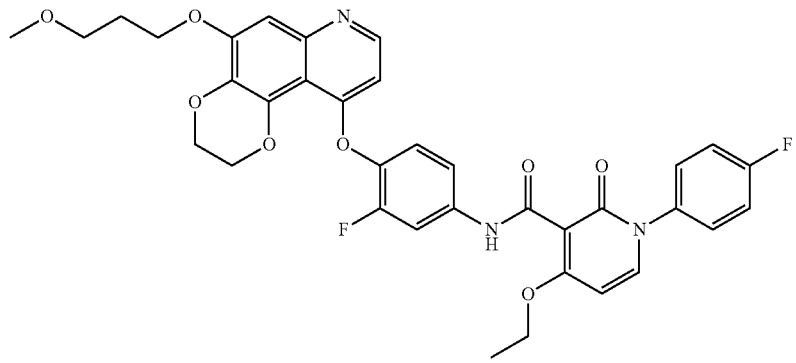

Example 55

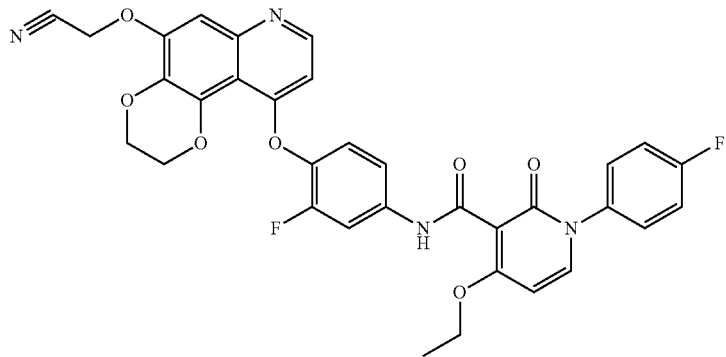

Example 56

Example 56: N-(4-((5-(cyanomethoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(cyanomethoxy)-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, yield: 18%); $^1$H NMR (600 MHz, DMSO-$d_6$) δ 10.55 (d, J=6.9 Hz, 1H), 8.46 (d, J=7.4 Hz, 1H), 7.92-7.85 (m, 3H), 7.48-7.44 (m, 2H), 7.39-7.34 (m, 2H), 7.28 (dd, J=14.3, 6.8 Hz, 2H), 6.51 (d, J=6.6 Hz, 2H), 5.37 (br, 2H), 4.39 (br, 4H), 4.26 (br, 2H), 1.35-1.22 (m, 3H). MS: 627 [M+H]$^+$.

Example 57: N-(4-((5-(3-cyanopropoxy)-2,3-dihydro-[1,4]dioxino[2,3-f]quinolin-10-yl)oxy)-3-fluorophen yl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-cyanopropoxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 23%); $^1$H NMR (600 MHz, DMSO-$d_6$) δ 10.54 (s, 1H), 8.40 (d, J=5.4 Hz, 1H), 7.88 (dd, J=28.9, 10.2 Hz, 2H), 7.47-7.43 (m, 4H), 7.39-7.33 (m, 2H), 7.27 (t, J=8.8 Hz, 1H), 7.09 (s, 1H), 6.52-6.44 (m, 1H), 4.37 (s, 4H), 4.30-4.17 (m, 4H), 2.69 (t, J=7.3 Hz, 2H), 2.13 (dt, J=13.3, 6.5 Hz, 2H), 1.31 (s, 3H). MS: 655 [M+H]$^+$.

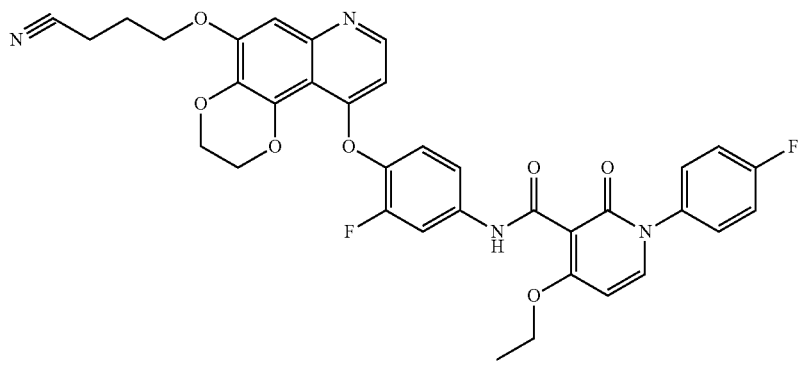

Example 57

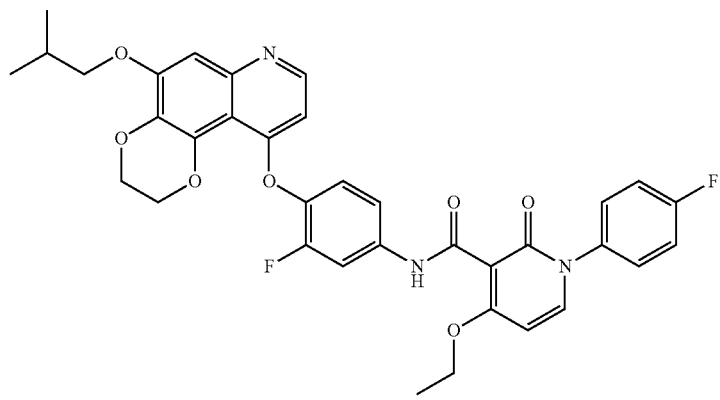

Example 58

Example 58: N-(4-((5-(isobutyloxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(isobutyloxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 31%); $^1$H NMR (400 MHz, DMSO-$d_6$) δ 10.53 (s, 1H), 8.39 (d, J=5.2 Hz, 1H), 7.97-7.70 (m, 2H), 7.45 (qd, J=6.2, 5.5, 3.6 Hz, 3H), 7.37 (t, J=8.8 Hz, 2H), 7.26 (t, J=9.0 Hz, 1H), 7.05 (s, 1H), 6.51 (d, J=7.9 Hz, 1H), 6.43 (d, J=5.2 Hz, 1H), 4.36 (s, 4H), 4.26 (q, J=7.0 Hz, 2H), 3.91 (d, J=6.6 Hz, 2H), 2.11 (dt, J=13.3, 6.6 Hz, 1H), 1.30 (t, J=7.0 Hz, 3H), 1.03 (d, J=6.7 Hz, 6H). MS: 644 [M+H]$^+$.

Example 59: N-(4-((5-(cyclopropylmethoxy)-2,3-dihydro-[1,4]dioxino[2,3-f]quinolin-10-yl)oxy)-3-fluoro phenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(cyclopropylmethoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 25%); $^1$H NMR (400 MHz, DMSO-$d_6$) δ 10.53 (s, 1H), 8.39 (d, J=5.2 Hz, 1H), 7.99-7.76 (m, 2H), 7.48-7.42 (m, 3H), 7.37 (dd, J=9.9, 7.7 Hz, 2H), 7.26 (t, J=9.0 Hz, 1H), 7.01 (s, 1H), 6.56-6.48 (m, 1H), 6.42 (dd, J=5.2, 1.0 Hz, 1H), 4.36 (s, 4H), 4.26 (q, J=7.0 Hz, 2H), 3.97 (d, J=7.0 Hz, 2H), 1.30 (t, J=7.0 Hz, 3H), 1.24 (s, 1H), 0.62 (dd, J=8.0, 1.8 Hz, 2H), 0.39 (dd, J=4.7, 1.6 Hz, 2H). MS: 642 [M+H]$^+$.

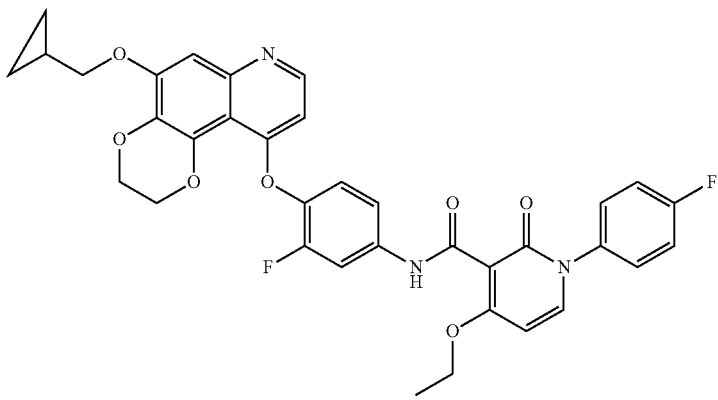

Example 59

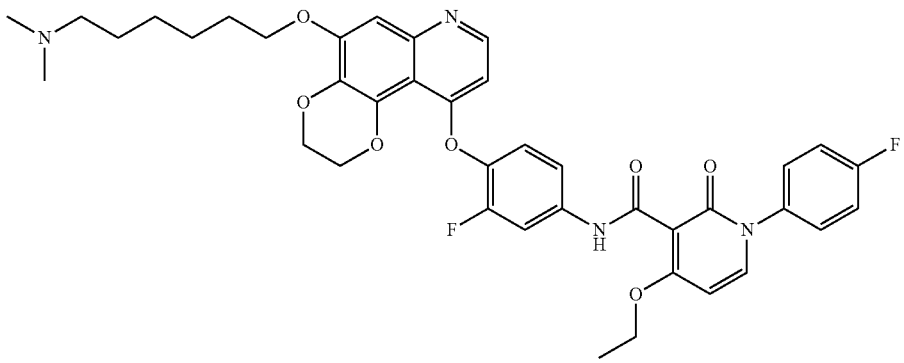

Example 60

Example N-(4-((5-(((6-dimethylamino)hexyloxy)-2, 3-dihydro-[1,4]dioxino[2,3-f]quinolin-10-yl)oxy)-3-fluorophenyl)-4-ethoxy-1-(4-fluorophenyl)-2-oxo-1, 2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(((6-dimethylamino)hexyloxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, yield: 15%); $^1$H NMR (600 MHz, DMSO-$d_6$) δ 10.55 (s, 1H), 8.39 (d, J=5.2 Hz, 1H), 7.93-7.83 (m, 2H), 7.47-7.43 (m, 3H), 7.36 (t, J=8.5 Hz, 2H), 7.26 (t, J=8.9 Hz, 1H), 7.05 (s, 1H), 6.51 (d, J=7.8 Hz, 1H), 6.43 (d, J=5.2 Hz, 1H), 4.36 (s, 4H), 4.26 (q, J=7.0 Hz, 2H), 4.12 (t, J=6.5 Hz, 2H), 2.34 (t, J=7.4 Hz, 2H), 2.22 (s, 6H), 1.80 (t, J=7.4 Hz, 2H), 1.47 (p, J=7.6 Hz, 4H), 1.39-1.34 (m, 2H), 1.30 (t, J=6.9 Hz, 3H). MS: 715 [M+H]$^+$.

Example 61: N-(4-((5-((3-dimethylamino)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(((3-dimethylamino)propyloxy)-2,3-dihydro-[1,4]dioxino[2,3-f]quinolin-10-yl) oxy)aniline (42 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 22%); $^1$H NMR (400 MHz, DMSO-$d_6$) δ 10.54 (s, 1H), 8.39 (d, J=5.2 Hz, 1H), 7.96-7.80 (m, 2H), 7.50-7.41 (m, 3H), 7.41-7.31 (m, 2H), 7.26 (t, J=9.1 Hz, 1H), 7.05 (s, 1H), 6.51 (d, J=7.9 Hz, 1H), 6.43 (dd, J=5.3, 1.0 Hz, 1H), 4.36 (s, 4H), 4.26 (q, J=7.0 Hz, 2H), 4.16 (t, J=6.5 Hz, 2H), 2.41 (t, J=7.1 Hz, 2H), 2.18 (s, 6H), 1.94 (q, J=6.8 Hz, 2H), 1.30 (t, J=7.0 Hz, 3H). MS: 673 [M+H]$^+$.

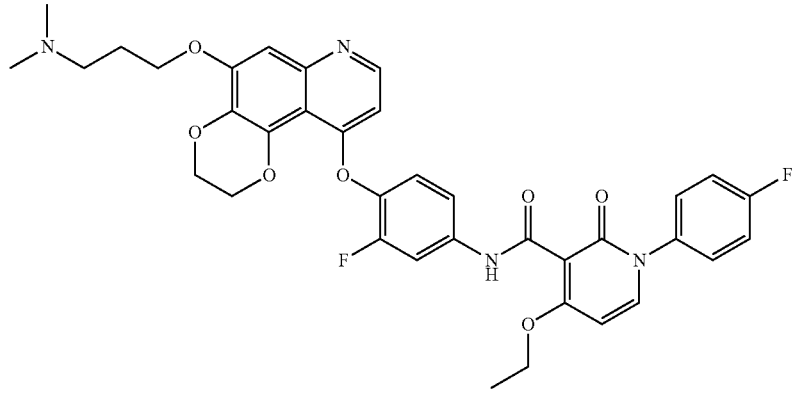

Example 61

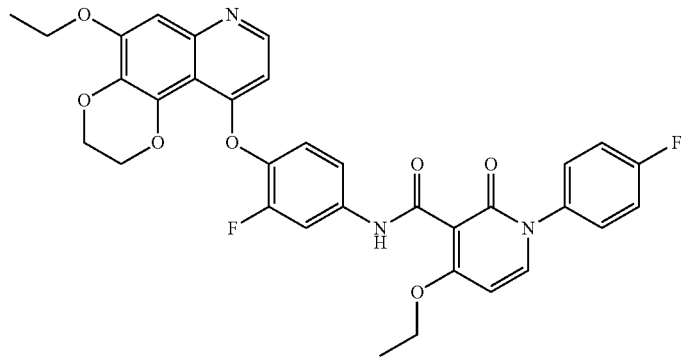

Example 62

Example 62: N-(4-((5-ethoxy-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-ethoxy-2,3-dihydro-[1,4]dioxino[2,3-f]quinolin-10-yl)oxy)aniline (36 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 41%); $^1$H NMR (600 MHz, DMSO-$d_6$) δ 10.54 (s, 1H), 8.39 (d, J=5.2 Hz, 1H), 7.93-7.83 (m, 2H), 7.49-7.42 (m, 3H), 7.37 (t, J=8.8 Hz, 2H), 7.27 (t, J=9.0 Hz, 1H), 7.05 (s, 1H), 6.52 (d, J=8.0 Hz, 1H), 6.43 (d, J=5.2 Hz, 1H), 4.36 (t, J=3.5 Hz, 4H), 4.26 (q, J=7.0 Hz, 2H), 4.18 (q, J=7.0 Hz, 2H), 1.41 (t, J=7.0 Hz, 3H), 1.30 (t, J=7.0 Hz, 3H). MS: 616 [M+H]$^+$.

Example 63: N-(4-((5-isopropoxy-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-isopropoxy-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (27 mg, yield: 43%); $^1$H NMR (600 MHz, DMSO-$d_6$) δ 10.55 (s, 1H), 8.39 (d, J=5.2 Hz, 1H), 7.90 (dd, J=13.1, 2.5 Hz, 1H), 7.85 (d, J=7.8 Hz, 1H), 7.46 (qd, J=6.6, 5.8, 2.4 Hz, 3H), 7.41-7.33 (m, 2H), 7.26 (t, J=9.0 Hz, 1H), 7.06 (s, 1H), 6.52 (d, J=7.9 Hz, 1H), 6.42 (d, J=5.2 Hz, 1H), 4.86-4.75 (m, 1H), 4.38-4.31 (m, 4H), 4.26 (q, J=7.0 Hz, 2H), 1.36 (d, J=6.0 Hz, 6H), 1.30 (t, J=7.0 Hz, 3H). MS: 630 [M+H]$^+$.

Example 63

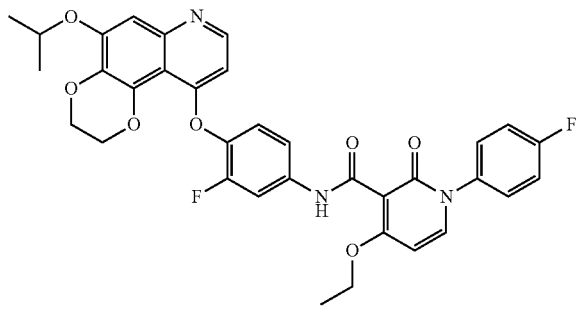

Example 64

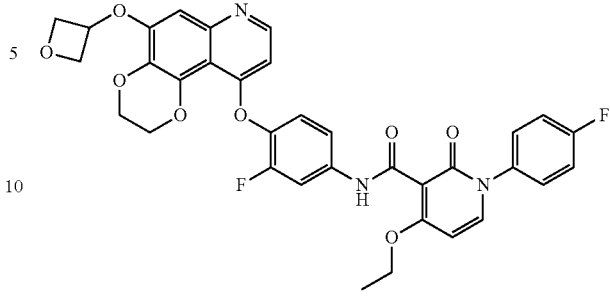

Example 64: N-(4-((5-((oxetan-3-yl)oxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-((oxetan-3-yl)oxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 25%); $^1$H NMR (600 MHz, DMSO-$d_6$) δ 10.55 (s, 1H), 8.40 (d, J=5.2 Hz, 1H), 7.93-7.84 (m, 2H), 7.49-7.43 (m, 3H), 7.37 (t, J=8.8 Hz, 2H), 7.27 (t, J=9.0 Hz, 1H), 6.70 (s, 1H), 6.52 (d, J=7.9 Hz, 1H), 6.46 (d, J=5.2 Hz, 1H), 5.46 (t, J=5.4 Hz, 1H), 5.05-4.99 (m, 2H), 4.63 (dd, J=7.5, 4.8 Hz, 2H), 4.39 (s, 4H), 4.26 (q, J=7.0 Hz, 2H), 1.30 (t, J=7.0 Hz, 3H). MS: 644 [M+H]$^+$.

Example 65: N-(4-((5-((tetrahydrofuran-3-yl)oxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-((tetrahydrofuran-3-yl)oxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 27%); $^1$H NMR (600 MHz, DMSO-$d_6$) δ 10.48 (s, 1H), 8.33 (d, J=5.2 Hz, 1H), 7.83 (dd, J=13.1, 2.4 Hz, 1H), 7.79 (d, J=7.8 Hz, 1H), 7.39 (ddd, J=8.9, 6.7, 3.6 Hz, 3H), 7.30 (t, J=8.7 Hz, 2H), 7.20 (t, J=9.0 Hz, 1H), 6.97 (s, 1H), 6.45 (d, J=7.9 Hz, 1H), 6.37 (d, J=5.2 Hz, 1H), 5.14 (t, J=5.4 Hz, 1H), 4.30 (t, J=4.1 Hz, 4H), 4.19 (q, J=7.0 Hz, 2H), 3.90 (dd, J=10.3, 4.6 Hz, 1H), 3.85-3.78 (m, 2H), 3.72 (td, J=8.3, 4.7 Hz, 1H), 2.28-2.24 (m, 1H), 2.00 (h, J=5.3 Hz, 1H), 1.23 (t, J=7.0 Hz, 3H). MS: 658 [M+H]$^+$.

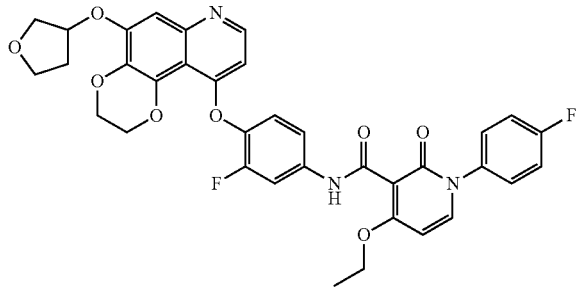

Example 65

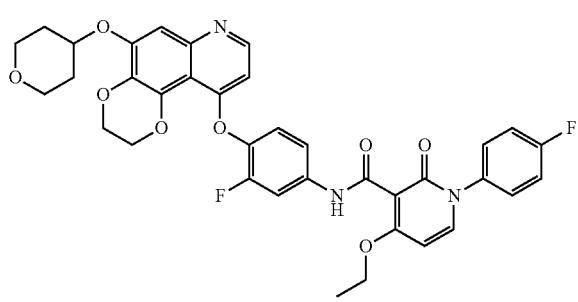

Example 66

Example 66: N-(4-((5-((tetrahydropyran-4-yl)oxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-((tetrahydropyran-4-yl)oxy)-2,3-dihydro-[1,4]dioxino[2,3-f]quinolin-10-yl)ox y)aniline (41 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 33%); $^1$H NMR (600 MHz, DMSO-$d_6$) δ 10.48 (s, 1H), 8.33 (d, J=5.2 Hz, 1H), 7.83 (dd, J=13.1, 2.4 Hz, 1H), 7.79 (d, J=7.8 Hz, 1H), 7.42-7.35 (m, 3H), 7.30 (t, J=8.7 Hz, 2H), 7.20 (t, J=9.0 Hz, 1H), 7.10 (s, 1H), 6.45 (d, J=7.9 Hz, 1H), 6.38-6.33 (m, 1H), 4.78-4.70 (m, 1H), 4.30 (s, 4H), 4.19 (q, J=7.0 Hz, 2H), 3.82 (dt, J=11.4, 4.3 Hz, 2H), 3.48 (ddd, J=11.8, 9.8, 2.7 Hz, 2H), 2.03-1.96 (m, 2H), 1.73-1.67 (m, 2H), 1.23 (t, J=7.0 Hz, 3H). MS: 672 [M+H]$^+$.

Example 67: N-(4-((5-(3-(4,4-dimethylpiperidin-1-yl)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(4,4-dimethylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 20%); $^1$H NMR (600 MHz, DMSO-$d_6$) δ 10.54 (s, 1H), 8.40 (d, J=5.2 Hz, 1H), 7.93-7.84 (m, 2H), 7.49-7.42 (m, 3H), 7.37 (t, J=8.8 Hz, 2H), 7.27 (t, J=9.0 Hz, 1H), 7.05 (s, 1H), 6.52 (d, J=7.9 Hz, 1H), 6.43 (d, J=5.2 Hz, 1H), 4.36 (s, 4H), 4.26 (q, J=7.0 Hz, 2H), 4.15 (t, J=6.4 Hz, 2H), 2.47 (s, 2H), 2.36 (s, 4H), 2.00-1.88 (m, 2H), 1.34 (t, J=5.6 Hz, 4H), 1.30 (t, J=7.0 Hz, 3H), 0.90 (s, 6H). MS: 741 [M+H]$^+$.

Example 67

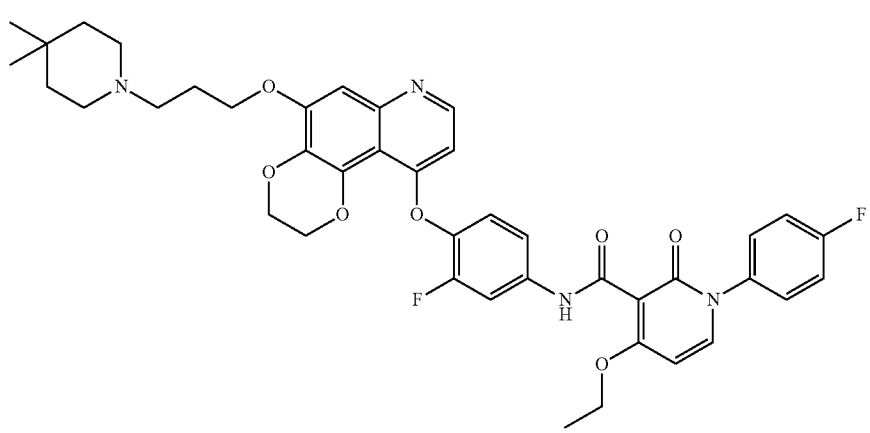

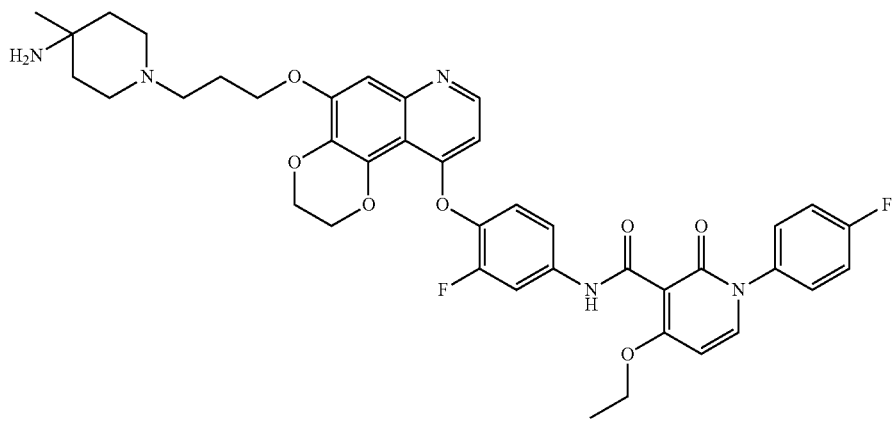

Example 68

Example 68: N-(4-((5-(3-(4-amino-4-methylpiperidin-1-yl)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(4-amino-4-methylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, yield: 15%); $^1$H NMR (600 MHz, DMSO-$d_6$) δ 10.49 (s, 1H), 8.36-8.28 (m, 1H), 7.83 (dd, J=13.1, 2.4 Hz, 1H), 7.79 (d, J=7.8 Hz, 1H), 7.39 (ddd, J=7.9, 6.3, 3.5 Hz, 3H), 7.30 (t, J=8.7 Hz, 2H), 7.20 (t, J=9.0 Hz, 1H), 6.98 (s, 1H), 6.45 (d, J=7.9 Hz, 1H), 6.36 (d, J=5.2 Hz, 1H), 4.29 (q, J=4.9 Hz, 4H), 4.19 (q, J=7.0 Hz, 2H), 4.09 (t, J=6.4 Hz, 2H), 2.59-2.49 (m, 2H), 2.42 (s, 2H), 2.21 (s, 2H), 1.93-1.83 (m, 2H), 1.62-1.45 (m, 4H), 1.23 (t, J=7.0 Hz, 3H), 1.12 (s, 3H). MS: 742 [M+H]$^+$.

Example 69: N-(4-((5-(3-(4-hydroxy-4-methylpiperidin-1-yl)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(4-hydroxy-4-methylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, yield: 15%); $^1$H NMR (600 MHz, DMSO-$d_6$) δ 10.54 (s, 1H), 8.39 (d, J=5.2 Hz, 1H), 8.19 (s, 1H), 7.93-7.83 (m, 2H), 7.49-7.42 (m, 3H), 7.37 (t, J=8.8 Hz, 2H), 7.26 (t, J=9.0 Hz, 1H), 7.05 (s, 1H), 6.51 (d, J=7.9 Hz, 1H), 6.43 (d, J=5.2 Hz, 1H), 4.36 (t, J=3.1 Hz, 4H), 4.26 (q, J=7.0 Hz, 2H), 4.16 (t, J=6.4 Hz, 2H), 4.11 (s, 1H), 2.48 (s, 4H), 2.41 (s, 2H), 1.99-1.93 (m, 2H), 1.48 (t, J=5.6 Hz, 4H), 1.30 (t, J=7.0 Hz, 3H), 1.10 (s, 3H). MS: 743 [M+H]+.

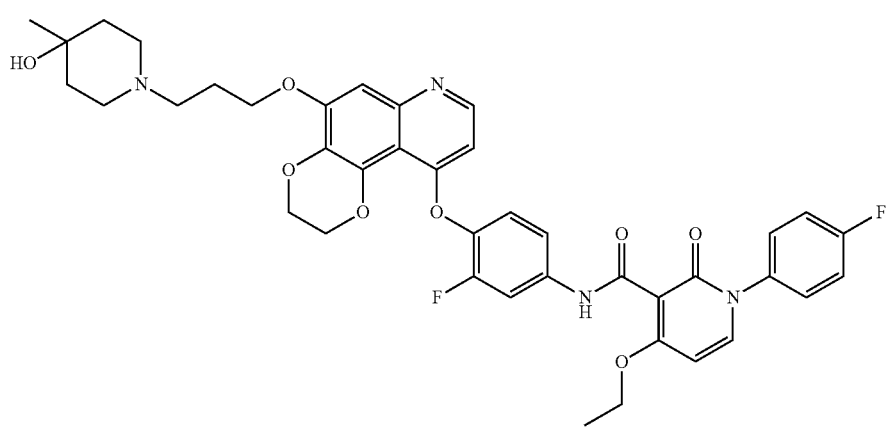

Example 69

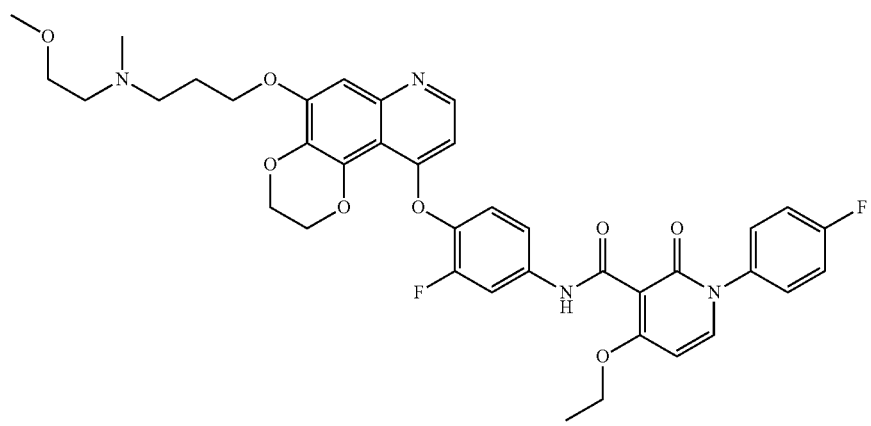

Example 70

Example 70: N-(4-((5-(3-((2-methoxyethyl)(methyl)amino)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-((2-methoxyethyl)(methyl)amino)propoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 35%); $^1$H NMR (600 MHz, DMSO-$d_6$) δ 10.54 (s, 1H), 8.39 (d, J=5.2 Hz, 1H), 7.92-7.83 (m, 2H), 7.49-7.41 (m, 3H), 7.36 (t, J=8.8 Hz, 2H), 7.26 (t, J=9.0 Hz, 1H), 7.04 (s, 1H), 6.51 (d, J=7.9 Hz, 1H), 6.43 (dd, J=5.2, 1.0 Hz, 1H), 4.36 (s, 4H), 4.26 (q, J=7.0 Hz, 2H), 4.15 (t, J=6.5 Hz, 2H), 3.41 (t, J=6.0 Hz, 2H), 3.21 (s, 3H), 2.53 (s, 4H), 2.21 (s, 3H), 1.95-1.89 (m, 2H), 1.30 (t, J=7.0 Hz, 3H). MS: 717 [M+H]$^+$.

Example 71: N-(4-((5-(3-(cyclobutyl(methyl)amino)propoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-(3-(cyclobutyl(methyl)amino)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 29%); $^1$H NMR (600 MHz, DMSO-$d_6$) δ 10.54 (s, 1H), 8.39 (d, J=5.2 Hz, 1H), 7.93-7.83 (m, 2H), 7.49-7.42 (m, 3H), 7.37 (t, J=8.8 Hz, 2H), 7.26 (t, J=9.0 Hz, 1H), 7.05 (s, 1H), 6.52 (d, J=7.9 Hz, 1H), 6.43 (d, J=5.2 Hz, 1H), 4.36 (t, J=4.1 Hz, 4H), 4.26 (q, J=7.0 Hz, 2H), 4.15 (t, J=6.4 Hz, 2H), 2.78-2.76 (m, 1H), 2.36 (t, J=7.0 Hz, 2H), 2.04 (s, 3H), 2.02-1.86 (m, 4H), 1.75 (tt, J=11.5, 9.0 Hz, 2H), 1.62-1.52 (m, 2H), 1.30 (t, J=7.0 Hz, 3H). MS: 713 [M+H]+.

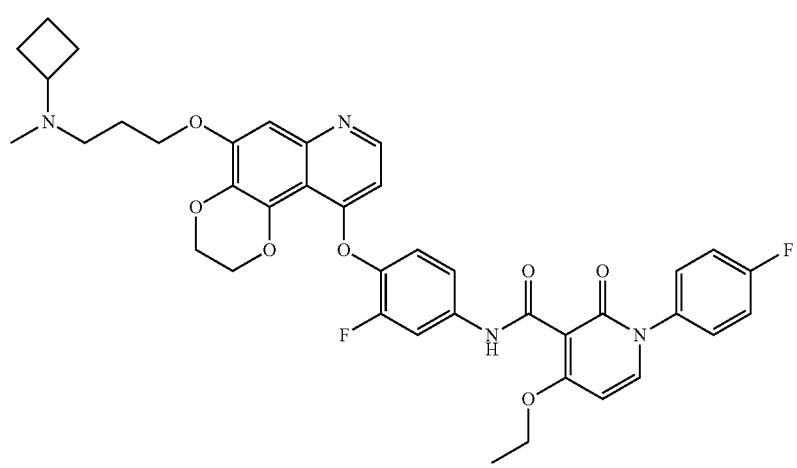

Example 71

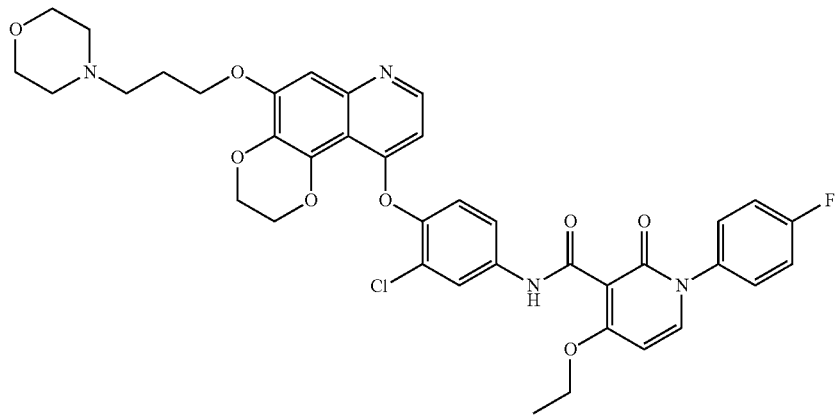

Example 72

Example 72: N-(4-((5-(3-morpholinopropoxy)-2,3-dihydro-[1,4]dioxino[2,3-f]quinolin-10-yl)oxy)-3-chlorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 3-chloro-4-((5-(3-morpholinopropoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 38%); $^1$H NMR (600 MHz, DMSO-$d_6$) δ 10.51 (s, 1H), 8.40 (d, J=5.2 Hz, 1H), 8.10 (d, J=2.5 Hz, 1H), 7.86 (d, J=7.8 Hz, 1H), 7.58 (dd, J=8.9, 2.5 Hz, 1H), 7.49-7.43 (m, 2H), 7.37 (t, J=8.8 Hz, 2H), 7.21 (d, J=8.8 Hz, 1H), 7.06 (s, 1H), 6.51 (d, J=7.9 Hz, 1H), 6.36 (d, J=5.2 Hz, 1H), 4.34 (s, 4H), 4.26 (q, J=7.0 Hz, 2H), 4.17 (t, J=6.4 Hz, 2H), 3.59 (t, J=4.6 Hz, 4H), 2.46 (t, J=7.1 Hz, 2H), 2.39 (s, 4H), 1.97 (q, J=6.8 Hz, 2H), 1.30 (t, J=6.9 Hz, 3H). MS: 731 [M+H]$^+$.

Example 73: N-(2-chloro-4-((5-(3-morpholinopropoxy)-2,3-dihydro-[1,4]dioxino[2,3-f]quinolin-10-yl)oxy)phenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 2-chloro-4-((5-(3-morpholinopropoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 30%); $^1$H NMR (600 MHz, DMSO-$d_6$) δ 10.96 (s, 1H), 8.47 (d, J=5.1 Hz, 1H), 8.21 (d, J=9.0 Hz, 1H), 7.92 (d, J=7.8 Hz, 1H), 7.50 (dd, J=8.7, 4.9 Hz, 2H), 7.38 (t, J=8.7 Hz, 2H), 7.27 (d, J=2.8 Hz, 1H), 7.07 (brs, 2H), 6.61 (d, J=5.1 Hz, 1H), 6.55 (d, J=7.9 Hz, 1H), 4.34-4.25 (m, 6H), 4.17 (t, J=6.4 Hz, 2H), 3.59 (t, J=4.6 Hz, 4H), 2.46 (t, J=7.1 Hz, 2H), 2.38 (s, 4H), 1.99-1.93 (m, 2H), 1.36 (t, J=6.9 Hz, 3H). MS:731 [M+H]$^+$.

Example 73

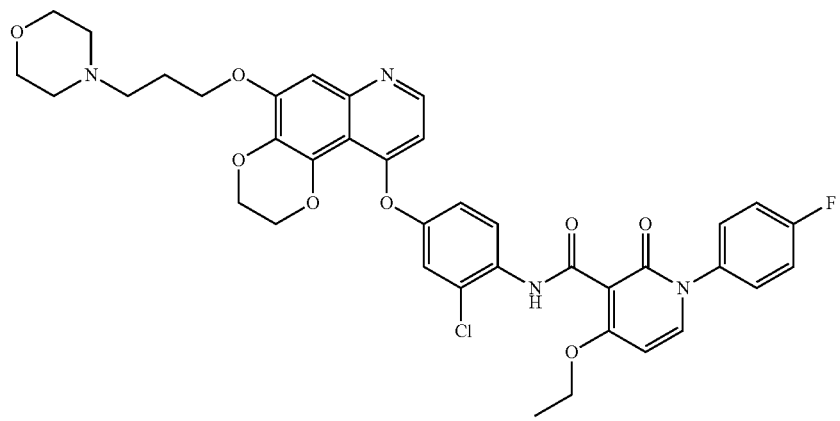

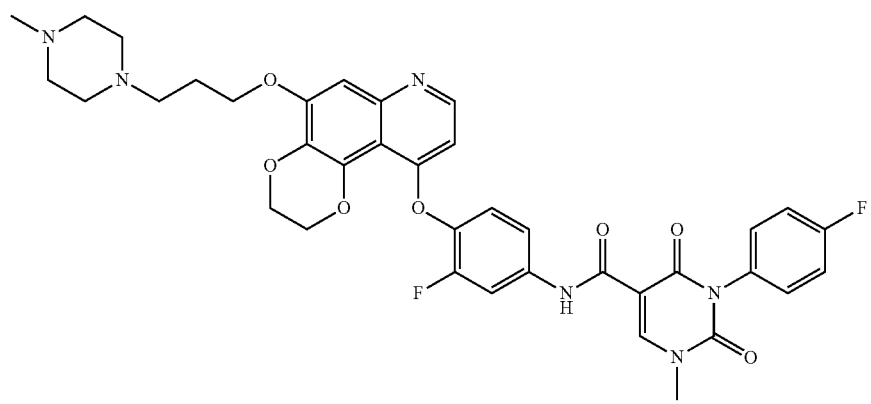

Example 74

Example 74: N-(3-fluoro-4-((5-(3-(4-methylpiperazin-1-yl)propoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(3-(4-methylpiperazin-1-yl)propoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 29%); $^1$H NMR (600 MHz, DMSO-$d_6$) δ 10.99 (s, 1H), 8.87 (s, 1H), 8.41 (d, J=5.2 Hz, 1H), 7.96 (dd, J=13.0, 2.5 Hz, 1H), 7.46 (dd, J=8.6, 2.5 Hz, 1H), 7.42-7.33 (m, 4H), 7.24 (t, J=9.0 Hz, 1H), 7.05 (s, 1H), 6.45 (d, J=5.1 Hz, 1H), 4.34 (t, J=3.4 Hz, 4H), 4.15 (t, J=6.4 Hz, 2H), 3.53 (s, 3H), 2.46 (t, J=7.1 Hz, 2H), 2.38 (br, 8H), 2.19 (s, 3H), 1.95 (q, J=6.8 Hz, 2H). MS: 715 [M+H]$^+$.

Example 75: N-(3-fluoro-4-((5-(3-(4-acetylpiperazin-1-yl)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-(4-acetylpiperazin-1-yl)propoxy)-2,3-dihydro-[1,4]dioxino[2,3-f]quinolin-1 0-yl)oxy)aniline (50 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg yield: 29%); $^1$H NMR (400 MHz, DMSO-$d_6$) δ 10.93 (s, 1H), 8.60 (s, 1H), 8.35 (d, J=5.2 Hz, 1H), 7.90 (dd, J=13.0, 2.5 Hz, 1H), 7.43-7.34 (m, 3H), 7.29 (t, J=8.8 Hz, 2H), 7.17 (t, J=9.0 Hz, 1H), 7.00 (s, 1H), 6.40 (dd, J=5.2, 1.0 Hz, 1H), 4.78-4.64 (m, 1H), 4.27 (s, 4H), 4.11 (t, J=6.4 Hz, 2H), 3.36 (br, 4H), 2.40 (s, 2H), 2.35-2.24 (m, 4H), 1.92 (s, 5H), 1.36 (d, J=6.8 Hz, 6H). MS: 771 [M+H]$^+$.

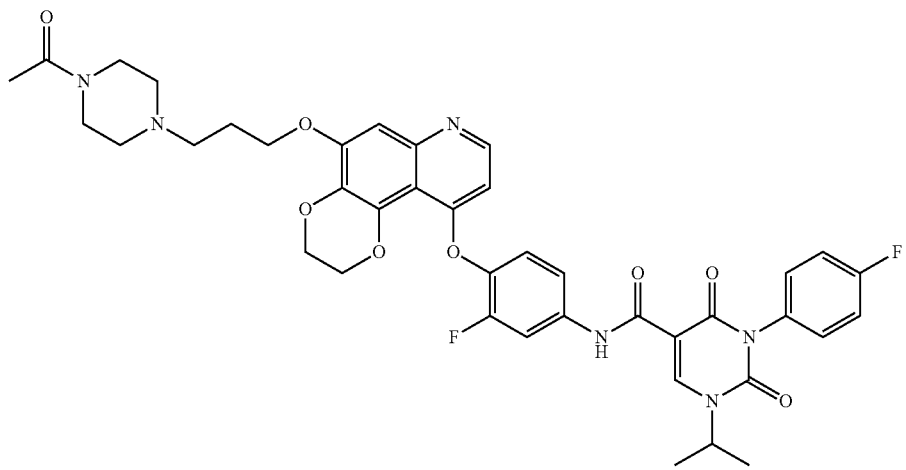

Example 75

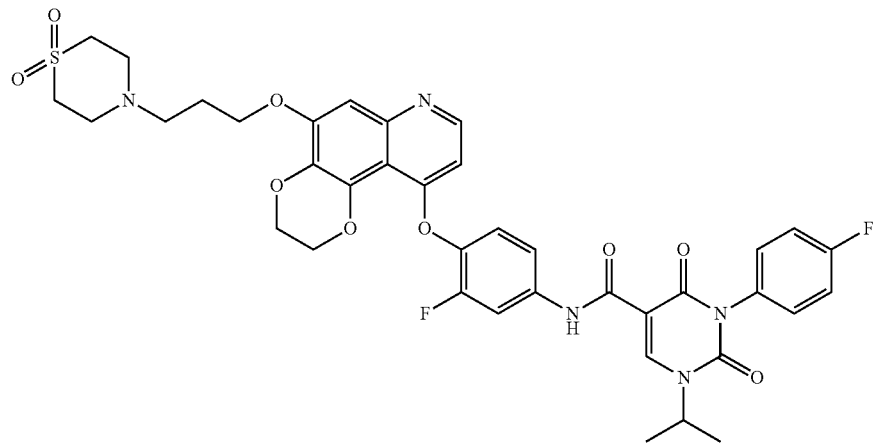

Example 76

Example 76: N-(3-fluoro-4-((5-(3-(1,1-dioxidothiomorpholino)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-(1,1-dioxidothiomorpholino)propoxy)-2,3-dihydro-[1,4]dioxino[2,3-f]quinolin-10-yl)oxy)aniline (50 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 32%); $^1$H NMR (600 MHz, DMSO-$d_6$) δ 10.99 (s, 1H), 8.67 (s, 1H), 8.42 (d, J=5.3 Hz, 1H), 7.97 (d, J=12.8 Hz, 1H), 7.49-7.40 (m, 3H), 7.36 (t, J=8.6 Hz, 2H), 7.24 (t, J=9.0 Hz, 1H), 7.09 (s, 1H), 6.46 (d, J=5.2 Hz, 1H), 4.87-4.70 (m, 1H), 4.36-4.32 (m, 4H), 4.18 (t, J=6.4 Hz, 2H), 3.11 (t, J=5.1 Hz, 4H), 2.96-2.85 (m, 4H), 2.65 (t, J=7.0 Hz, 2H), 1.96 (q, J=6.8 Hz, 2H), 1.42 (d, J=6.8 Hz, 6H). MS: 778 [M+H]$^+$.

Example 77: N-(3-fluoro-4-((5-(3-(pyrrolidin-1-yl)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-(pyrrolidin-1-yl)propoxy)-2,3-dihydro-[1,4]dioxino[2,3-f]quinolin-10-yl)oxy)aniline (44 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (12 mg, yield: 17%); $^1$H NMR (600 MHz, DMSO-$d_6$) δ 10.93 (s, 1H), 8.60 (s, 1H), 8.36 (d, J=5.2 Hz, 1H), 7.90 (dd, J=12.9, 2.4 Hz, 1H), 7.40-7.35 (m, 3H), 7.29 (t, J=8.6 Hz, 2H), 7.17 (t, J=8.9 Hz, 1H), 6.99 (s, 1H), 6.40 (d, J=5.2 Hz, 1H), 4.85-4.60 (m, 1H), 4.27 (q, J=5.0 Hz, 4H), 4.11 (t, J=6.4 Hz, 2H), 2.64 (t, J=7.3 Hz, 2H), 2.43 (s, 4H), 1.95 (q, J=6.8 Hz, 2H), 1.68 (q, J=3.8, 3.4 Hz, 4H), 1.35 (d, J=6.7 Hz, 6H). MS: 714 [M+H]$^+$.

Example 77

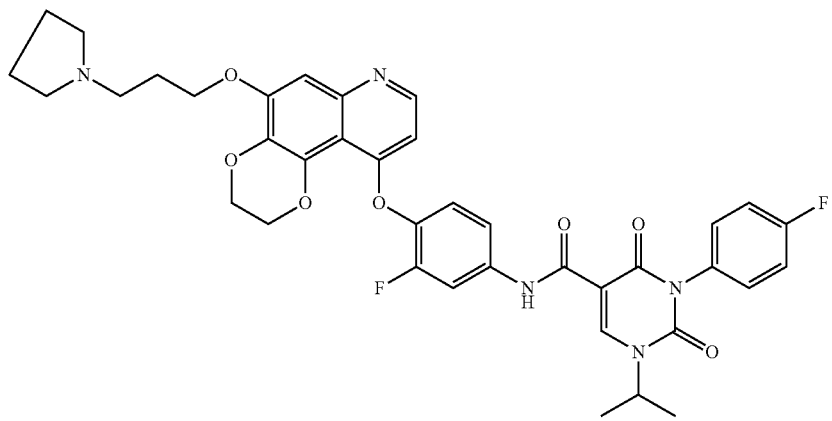

Example 78

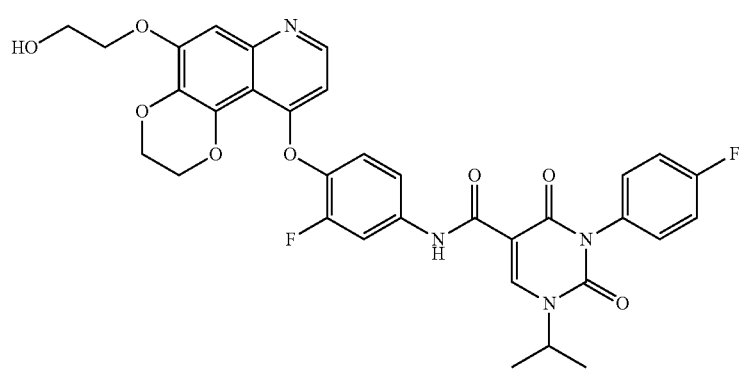

Example 78: N-(3-fluoro-4-((5-(2-hydroxyethoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(2-hydroxyethoxy)-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, 17%); $^1$H NMR (600 MHz, DMSO-$d_6$) δ 11.04 (s, 1H), 8.67 (s, 1H), 8.56 (d, J=5.9 Hz, 1H), 8.02 (dd, J=12.9, 2.5 Hz, 1H), 7.53 (dd, J=8.9, 2.3 Hz, 1H), 7.43 (dd, J=8.7, 5.1 Hz, 2H), 7.36 (t, J=8.8 Hz, 3H), 7.16 (s, 1H), 6.65 (d, J=5.9 Hz, 1H), 4.96 (s, 1H), 4.84-4.71 (m, 1H), 4.40 (s, 4H), 4.18 (t, J=4.9 Hz, 2H), 3.82 (t, J=4.9 Hz, 2H), 1.43 (d, J=6.8 Hz, 6H). MS: 647 [M+H]$^+$.

Example 79: N-(3-fluoro-4-((5-(3-hydroxypropoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-hydroxypropoxy)-2,3-dihydro-[1,4]dioxino[2,3-f]quinolin-10-yl)oxy)aniline (39 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (14 mg, yield: 21%); $^1$H NMR (400 MHz, DMSO-$d_6$) δ 10.99 (s, 1H), 8.67 (s, 1H), 8.42 (d, J=5.2 Hz, 1H), 7.97 (dd, J=13.0, 2.5 Hz, 1H), 7.50-7.31 (m, 5H), 7.24 (t, J=9.0 Hz, 1H), 7.06 (s, 1H), 6.46 (dd, J=5.2, 1.0 Hz, 1H), 4.77 (p, J=6.7 Hz, 1H), 4.60 (t, J=5.2 Hz, 1H), 4.36-4.31 (m, 4H), 4.19 (t, J=6.4 Hz, 2H), 3.60 (q, J=6.0 Hz, 2H), 1.94 (t, J=6.3 Hz, 2H), 1.42 (d, J=6.8 Hz, 6H). MS: 661 [M+H]$^+$.

Example 79

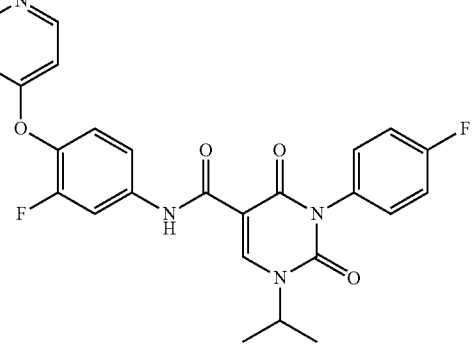

Example 80

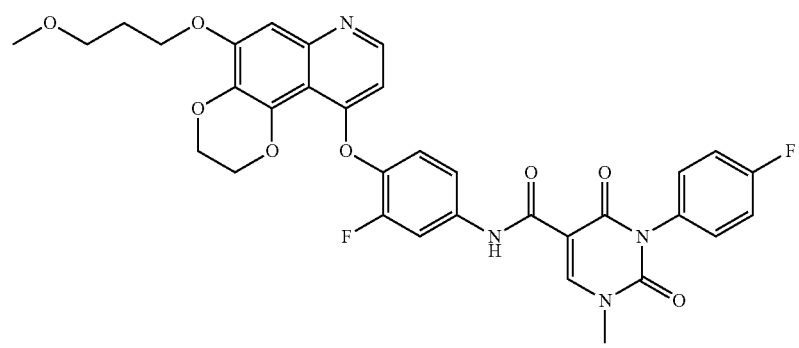

Example 80: N-(3-fluoro-4-((5-(3-methoxy-propoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(3-methoxypropoxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (20 mg, yield: 31%); $^1$H NMR (600 MHz, DMSO-$d_6$) δ 11.00 (s, 1H), 8.87 (s, 1H), 8.43 (d, J=5.3 Hz, 1H), 7.96 (dd, J=12.9, 2.5 Hz, 1H), 7.47 (dd, J=8.8, 2.4 Hz, 1H), 7.43-7.33 (m, 4H), 7.26 (t, J=9.0 Hz, 1H), 7.06 (s, 1H), 6.48 (d, J=5.3 Hz, 1H), 4.35 (d, J=1.9 Hz, 4H), 4.18 (t, J=6.4 Hz, 2H), 3.55-3.48 (m, 5H), 3.27 (s, 3H), 2.04 (p, J=6.4 Hz, 2H). MS: 647 [M+H]$^+$.

Example 81: N-(3-fluoro-4-((5-(cyanomethoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(cyanomethoxy)-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (12 mg, yield: 19%); $^1$H NMR (600 MHz, DMSO-$d_6$) δ 11.01 (d, J=3.9 Hz, 1H), 8.67 (t, J=4.5 Hz, 1H), 8.48 (t, J=4.7 Hz, 1H), 7.98 (d, J=12.9 Hz, 1H), 7.47 (s, 1H), 7.39 (ddq, J=40.3, 9.2, 4.1 Hz, 4H), 7.29-7.24 (m, 2H), 6.53 (t, J=4.8 Hz, 1H), 5.37 (t, J=4.6 Hz, 2H), 4.80-4.75 (m, 1H), 4.39-4.35 (m, 4H), 1.42 (dd, J=6.8, 3.8 Hz, 6H). MS: 642 [M+H]$^+$.

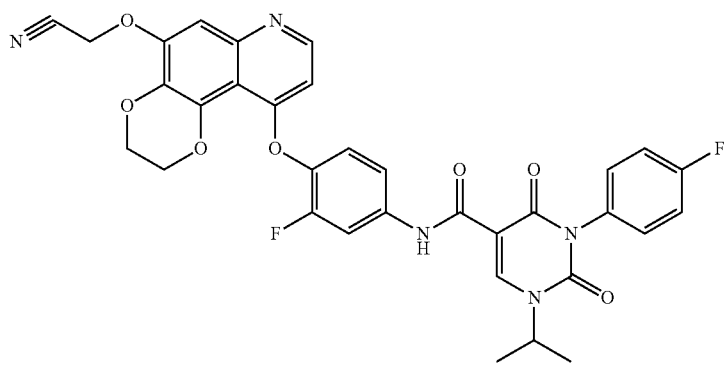

Example 81

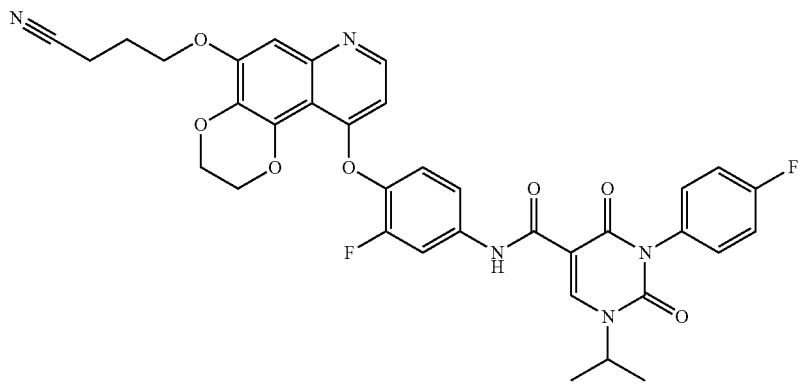

Example 82

Example 82: N-(3-fluoro-4-((5-(3-cyanopropoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-cyanopropoxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 24%); $^1$H NMR (600 MHz, DMSO-$d_6$) δ 11.00 (s, 1H), 8.67 (d, J=5.1 Hz, 1H), 8.43 (d, J=5.2 Hz, 1H), 7.97 (dd, J=13.1, 2.5 Hz, 1H), 7.49-7.40 (m, 3H), 7.36 (t, J=8.5 Hz, 2H), 7.25 (t, J=8.8 Hz, 1H), 7.10 (d, J=5.3 Hz, 1H), 6.48 (d, J=5.2 Hz, 1H), 4.89-4.66 (m, 1H), 4.37-4.32 (m, 4H), 4.20 (t, J=6.1 Hz, 2H), 2.69 (t, J=7.2 Hz, 2H), 2.12 (q, J=6.7 Hz, 2H), 1.42 (d, J=6.7 Hz, 6H). MS:670 [M+H]$^+$.

Example 83: N-(3-fluoro-4-((5-(isobutoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(isobutoxy)-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (400 MHz, DMSO-$d_6$) δ 10.98 (s, 1H), 8.87 (s, 1H), 8.42 (d, J=5.3 Hz, 1H), 7.95 (dd, J=12.9, 2.5 Hz, 1H), 7.50-7.31 (m, 5H), 7.24 (t, J=9.0 Hz, 1H), 7.05 (s, 1H), 6.45 (d, J=5.1 Hz, 1H), 4.34 (d, J=2.9 Hz, 4H), 3.90 (d, J=6.5 Hz, 2H), 3.53 (s, 3H), 2.11 (dt, J=13.3, 6.7 Hz, 1H), 1.03 (d, J=6.7 Hz, 6H). MS: 631 [M+H]$^+$.

Example 83

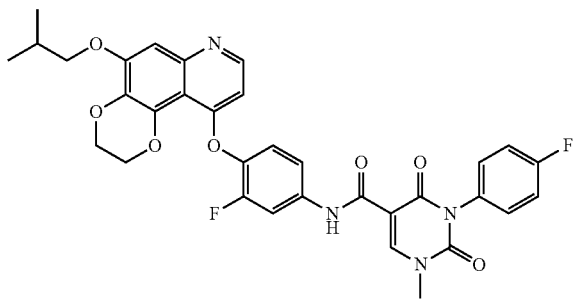

Example 84

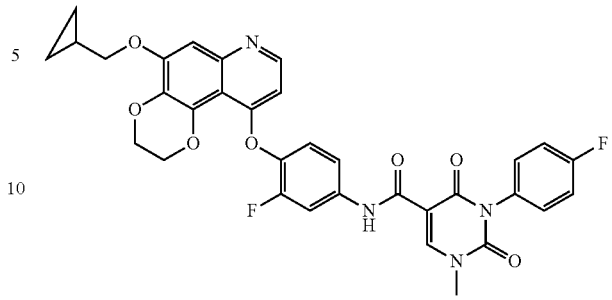

Example N-(3-fluoro-4-((5-(cyclopropylmethoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-(cyclopropylmethoxy)-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 35%); $^1$H NMR (400 MHz, DMSO-$d_6$) δ 10.98 (s, 1H), 8.87 (s, 1H), 8.41 (d, J=5.2 Hz, 1H), 7.95 (dd, J=13.0, 2.5 Hz, 1H), 7.48-7.41 (m, 1H), 7.40-7.35 (m, 3H), 7.23 (t, J=9.0 Hz, 1H), 7.02 (s, 1H), 6.51 (s, 1H), 6.45 (d, J=5.0 Hz, 1H), 4.40-4.33 (m, 4H), 3.97 (d, J=6.9 Hz, 2H), 3.53 (s, 3H), 0.90-0.80 (m, 1H), 0.66-0.57 (m, 2H), 0.38 (q, J=5.0 Hz, 2H). MS: 629 [M+H]$^+$.

Example 85: N-(3-fluoro-4-((5-((6-dimethylamino)hexyloxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-((6-dimethylamino)hexyloxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 22%); $^1$H NMR (600 MHz, DMSO-$d_6$) δ 10.99 (s, 1H), 8.67 (s, 1H), 8.42 (d, J=5.2 Hz, 1H), 7.97 (dd, J=12.9, 2.5 Hz, 1H), 7.49-7.40 (m, 3H), 7.36 (t, J=8.8 Hz, 2H), 7.24 (t, J=9.0 Hz, 1H), 7.06 (s, 1H), 6.46 (d, J=5.2 Hz, 1H), 4.83-4.62 (m, 1H), 4.34 (p, J=4.7, 4.0 Hz, 4H), 4.12 (t, J=6.5 Hz, 2H), 2.32 (t, J=7.4 Hz, 2H), 2.21 (s, 6H), 1.82-1.77 (m, 2H), 1.49-1.44 (m, 4H), 1.42 (d, J=6.8 Hz, 6H), 1.39-1.31 (m, 2H). MS: 730 [M+H]$^+$.

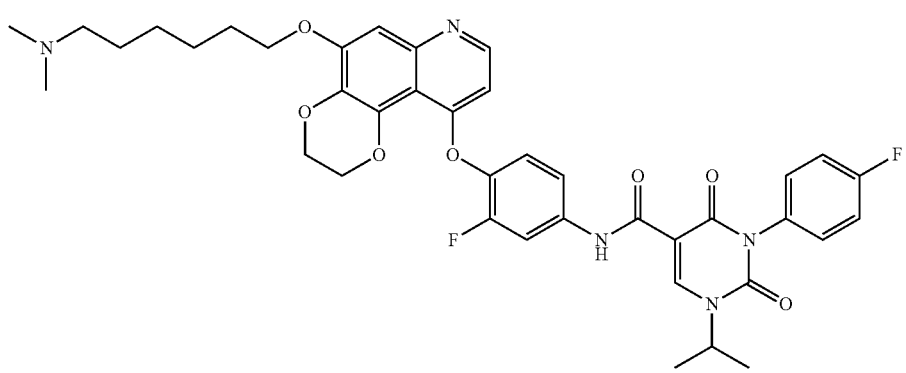

Example 85

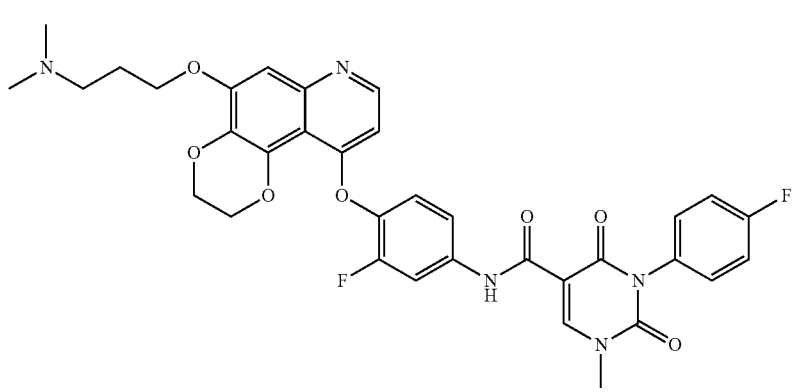

Example 86

Example 86: N-(3-fluoro-4-((5-((3-dimethylamino)propoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-((3-dimethylamino)propoxy)-2,3-dihydro-[1,4]dioxino[2,3-f]quinolin-10-yl)ox y)aniline (41 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 23%); $^1$H NMR (400 MHz, DMSO-$d_6$) δ 10.98 (s, 1H), 8.86 (s, 1H), 8.41 (d, J=5.2 Hz, 1H), 7.95 (dd, J=12.9, 2.5 Hz, 1H), 7.49-7.32 (m, 5H), 7.24 (t, J=9.0 Hz, 1H), 7.05 (s, 1H), 6.45 (d, J=5.2 Hz, 1H), 4.34 (s, 4H), 4.15 (t, J=6.5 Hz, 2H), 3.53 (s, 3H), 2.42 (t, J=7.1 Hz, 2H), 2.19 (s, 6H), 1.94 (p, J=6.7 Hz, 2H). MS: 660 [M+H]$^+$.

Example 87: N-(3-fluoro-4-((5-ethoxy-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-ethoxy-2,3-dihydro-[1,4]dioxino[2,3-f]quinolin-10-yl)oxy)aniline (36 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 40%); $^1$H NMR (600 MHz, DMSO-$d_6$) δ 11.00 (s, 1H), 8.67 (s, 1H), 8.42 (d, J=5.2 Hz, 1H), 7.97 (dd, J=12.9, 2.5 Hz, 1H), 7.49-7.40 (m, 3H), 7.36 (t, J=8.7 Hz, 2H), 7.24 (t, J=9.0 Hz, 1H), 7.05 (s, 1H), 6.47 (d, J=5.2 Hz, 1H), 4.78 (p, J=6.8 Hz, 1H), 4.34 (t, J=4.3 Hz, 4H), 4.18 (q, J=7.0 Hz, 2H), 1.41 (dd, J=10.2, 6.8 Hz, 9H). MS: 631 [M+H]+.

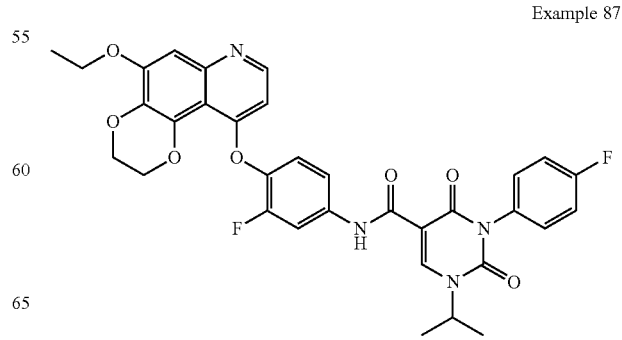

Example 87

Example 88

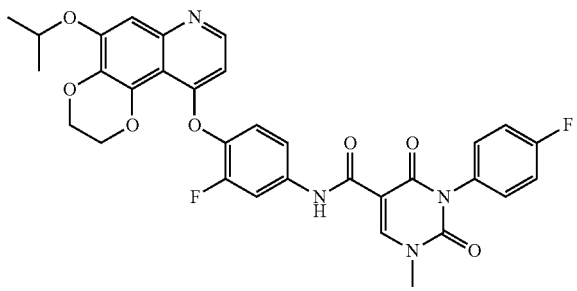

Example 88: N-(3-fluoro-4-((5-isopropoxy-2,3-di-hydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-isopropoxy-2,3-dihydro-[1,4]dioxino[2,3-f]quinolin-10-yl)oxy)aniline (37 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 34%); $^1$H NMR (600 MHz, DMSO-$d_6$) δ 10.99 (s, 1H), 8.87 (s, 1H), 8.40 (d, J=5.2 Hz, 1H), 7.95 (dd, J=12.9, 2.5 Hz, 1H), 7.46 (dd, J=8.4, 2.2 Hz, 1H), 7.43-7.33 (m, 4H), 7.24 (t, J=9.0 Hz, 1H), 7.06 (s, 1H), 6.44 (d, J=5.2 Hz, 1H), 4.81 (p, J=6.0 Hz, 1H), 4.32 (s, 4H), 3.53 (s, 3H), 1.35 (d, J=6.0 Hz, 6H). MS: 617 [M+H]$^+$.

Example 89: N-(3-fluoro-4-((5-((oxetan-3-yl)oxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-((oxetan-3-yl)oxy)-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 29%); $^1$H NMR (600 MHz, DMSO-$d_6$) δ 11.01 (s, 1H), 8.68 (s, 1H), 8.43 (d, J=5.2 Hz, 1H), 7.98 (dd, J=12.9, 2.5 Hz, 1H), 7.50-7.41 (m, 3H), 7.36 (t, J=8.8 Hz, 2H), 7.26 (t, J=9.0 Hz, 1H), 6.71 (s, 1H), 6.54-6.47 (m, 1H), 5.47 (t, J=5.3 Hz, 1H), 5.05-4.99 (m, 2H), 4.81-4.76 (m, 1H), 4.63 (dd, J=7.5, 4.8 Hz, 2H), 4.38 (br, 4H), 1.43 (d, J=6.8 Hz, 6H). MS: 659 [M+H]$^+$.

Example 89

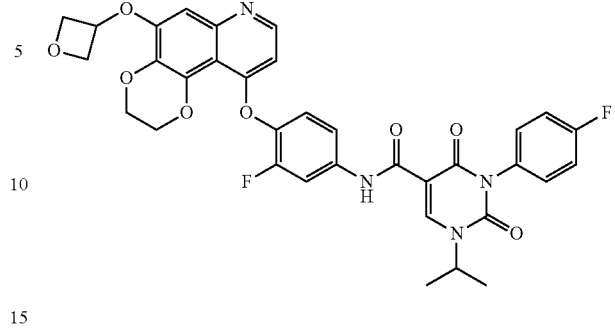

Example 90

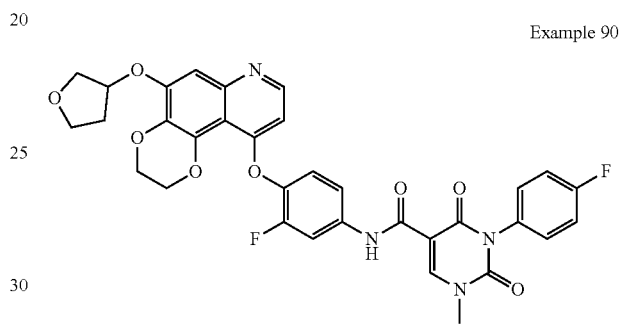

Example 90: N-(3-fluoro-4-((5-((tetrahydrofuran-3-yl)oxy)-2,3-dihydro-[1,4]dioxino[2,3-f]quinolin-10-yl) oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-((tetrahydrofuran-3-yl)oxy)-2,3-dihydro-[1,4]dioxino[2,3-f]quinolin-10-yl)oxy)aniline (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg, yield: 40%); $^1$H NMR (600 MHz, DMSO-$d_6$) δ 10.93 (s, 1H), 8.81 (s, 1H), 8.36 (d, J=5.2 Hz, 1H), 7.89 (dd, J=12.9, 2.4 Hz, 1H), 7.42-7.37 (m, 1H), 7.36-7.26 (m, 4H), 7.18 (t, J=9.0 Hz, 1H), 6.97 (s, 1H), 6.39 (d, J=5.2 Hz, 1H), 5.14 (s, 1H), 4.27 (s, 4H), 3.89 (dd, J=10.3, 4.5 Hz, 1H), 3.81 (dd, J=15.2, 8.1 Hz, 2H), 3.71 (td, J=8.3, 4.7 Hz, 1H), 3.47 (s, 3H), 2.29-2.23 (m, 1H), 2.02-1.97 (m, 1H). MS: 645 [M+H]$^+$.

Example 91: N-(3-fluoro-4-((5-((tetrahydropyran-4-yl)oxy)-2,3-dihydro-[1,4]dioxino[2,3-f]quinolin-10-yl) oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 3-fluoro-4-((5-((tetrahydropyran-4-yl)oxy)-2,3-dihydro-[1,4]dioxino[2,3-f]quinolin-10-yl)ox y)aniline (41 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 29%); $^1$H NMR (600 MHz, DMSO-$d_6$) δ 10.93 (s, 1H), 8.81 (s, 1H), 8.35 (d, J=5.1 Hz, 1H), 7.89 (dd, J=12.9, 2.5 Hz, 1H), 7.42-7.38 (m, 1H), 7.36-7.27 (m, 3H), 7.18 (t, J=9.0 Hz, 1H), 7.12 (d, J=15.3 Hz, 1H), 6.59 (s, 1H), 6.38 (d, J=5.2 Hz, 1H), 4.74 (dt, J=8.9, 4.6 Hz, 1H), 4.29-4.27 (m, 4H), 3.82 (dt, J=11.7, 4.3 Hz, 2H), 3.54-3.44 (m, 5H), 1.92-1.89 (m, 4H). MS: 659 [M+H]$^+$.

((5-(3-(4,4-dimethylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (15 mg, yield: 20%); $^1$H NMR (600 MHz, DMSO-$d_6$) δ 10.99 (s, 1H), 8.67 (s, 1H), 8.42 (d, J=5.2 Hz, 1H), 7.97 (dd, J=12.9, 2.5 Hz, 1H), 7.49-7.40 (m, 3H), 7.36 (t, J=8.8 Hz, 2H), 7.24 (t, J=9.0 Hz, 1H), 7.05 (s, 1H), 6.46 (dd, J=5.2, 0.9 Hz, 1H), 4.78 (p, J=6.8 Hz, 1H), 4.34 (d, J=4.1 Hz, 4H), 4.15 (t, J=6.4 Hz, 2H), 2.46 (s, 2H), 2.36 (s, 4H), 2.00-1.92 (m, 2H), 1.42 (d, J=6.8 Hz, 6H), 1.33 (t, J=5.7 Hz, 4H), 0.89 (s, 6H). MS: 756 [M+H]$^+$.

Example 93: N-(3-fluoro-4-((5-(3-(4-amino-4-methylpiperidin-1-yl)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, Example 91

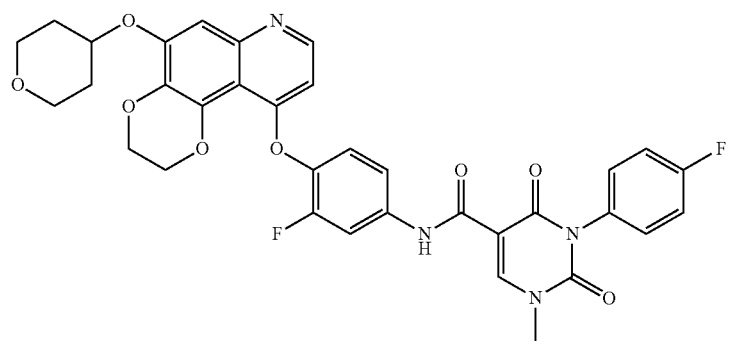

Example 92

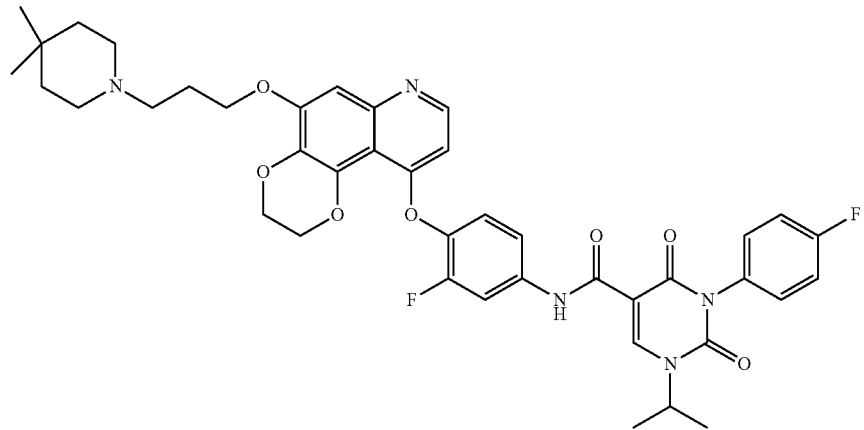

Example 92: N-(3-fluoro-4-((5-(3-(4,4-dimethylpiperidin-1-yl)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-

0.1 mmol) in dichloromethane (0.5 mL) followed by triethylamine (0.1 mL) were added to a solution of 3-fluoro-4-((5-(3-(4-amino-4-methylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 28%); $^1$H NMR (600 MHz, DMSO-$d_6$) δ 11.00 (s, 1H), 8.67 (s, 1H), 8.42 (d, J=5.2 Hz, 1H), 7.97 (dd, J=13.0, 2.5 Hz, 1H), 7.47 (ddd, J=9.0, 2.5, 1.2 Hz, 1H), 7.46-7.40 (m, 2H), 7.39-7.32 (m, 2H), 7.24 (t, J=9.0 Hz, 1H), 7.05 (s, 1H), 6.47 (d, J=5.1 Hz, 1H), 4.78 (p, J=6.8 Hz, 1H), 4.34 (d, J=1.9 Hz, 4H), 4.16 (t, J=6.4 Hz, 2H), 2.62 (d, J=5.7 Hz, 2H), 2.49 (s, 2H), 2.26 (s, 2H), 2.02-1.90 (m, 2H), 1.73-1.56 (m, 4H), 1.42 (d, J=6.8 Hz, 6H), 1.21 (s, 3H). MS: 757 [M+H]$^+$.

1H), 8.60 (s, 1H), 8.35 (d, J=5.2 Hz, 1H), 7.90 (dd, J=13.0, 2.5 Hz, 1H), 7.42-7.33 (m, 3H), 7.29 (t, J=8.8 Hz, 2H), 7.17 (t, J=9.0 Hz, 1H), 6.99 (s, 1H), 6.40 (d, J=5.2 Hz, 1H), 4.71 (p, J=6.8 Hz, 1H), 4.27 (t, J=4.4 Hz, 4H), 4.09 (t, J=6.4 Hz, 2H), 4.05 (s, 1H), 2.38 (br, 6H), 1.90 (q, J=6.8 Hz, 2H), 1.42 (t, J=5.6 Hz, 4H), 1.36 (d, J=6.8 Hz, 6H), 1.03 (s, 3H). MS: 758 [M+H]$^+$.

Example 93

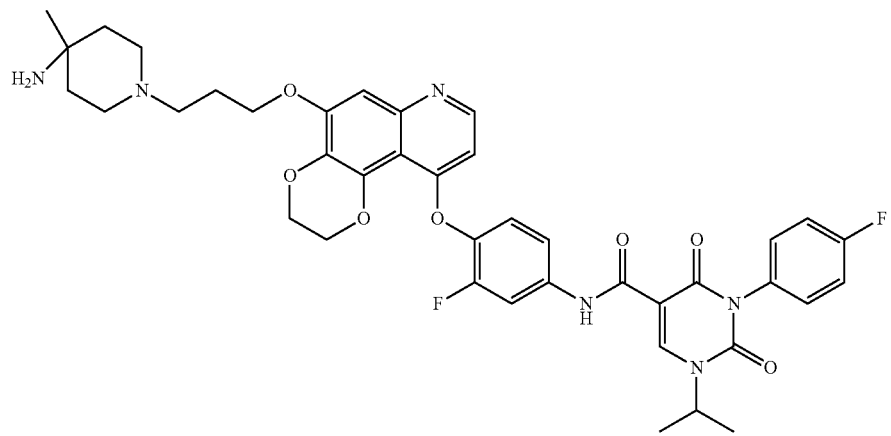

Example 94

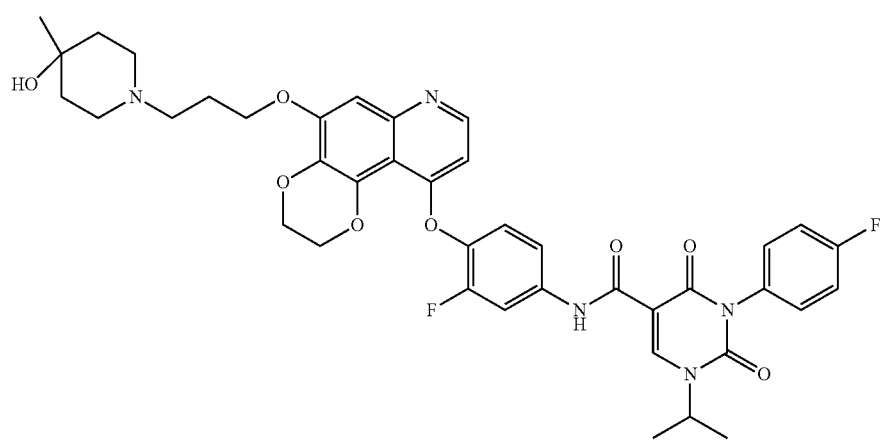

Example N-(3-fluoro-4-((5-(3-(4-methyl-4-hydroxypiperidin-1-yl)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-(4-hydroxy-4-methylpiperidin-1-yl)propoxy)-2,3-dihydro-[1,4]dioxino[2,3-f]quinolin-10-yl)oxy)aniline (48 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (12 mg, yield: 16%); $^1$H NMR (600 MHz, DMSO-d$_6$) δ 10.93 (s, Example 95: N-(3-fluoro-4-((5-(3-((2-methoxyethyl)(methyl)amino)propoxy)-2,3-dihydro-[1,4]dioxino[2, 3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-((2-methoxyethyl)(methyl)amino)propoxy)-2,3-dihydro-[1,4]dioxino[2,3-f]quinolin-10-yl)oxy)aniline (46 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg yield: 36%); $^1$H NMR (600 MHz, DMSO-d$_6$) δ 10.99 (s, 1H), 8.67 (s, 1H), 8.42 (d, J=5.2 Hz, 1H), 7.97 (dd, J=13.0, 2.5 Hz, 1H), 7.49-7.40 (m, 3H), 7.36 (t, J=8.8 Hz, 2H), 7.24 (t, J=9.0 Hz, 1H), 7.05 (s, 1H), 6.46 (d, J=5.1 Hz, 1H), 4.80-4.75 (m, 1H), 4.34 (tt, J=6.9, 2.7 Hz, 4H), 4.15 (t, J=6.5 Hz, 2H), 3.41 (t, J=5.9 Hz, 2H), 3.21 (s, 3H), 2.51 (br, 4H), 2.21 (s, 3H)), 1.94-1.89 (m, 2H), 1.42 (d, J=6.8 Hz, 6H). MS: 732 [M+H]⁺.

4.36-4.30 (m, 4H), 4.15 (t, J=6.4 Hz, 2H), 2.81-2.73 (m, 1H), 2.36 (t, J=7.0 Hz, 2H), 2.05 (s, 3H), 1.96 (dt, J=9.6, 2.8 Hz, 2H), 1.90 (t, J=6.8 Hz, 2H), 1.76-1.73 (m, 2H), 1.61-1.55 (m, 2H), 1.42 (d, J=6.8 Hz, 6H). MS: 728 [M+H]⁺.

Example 95

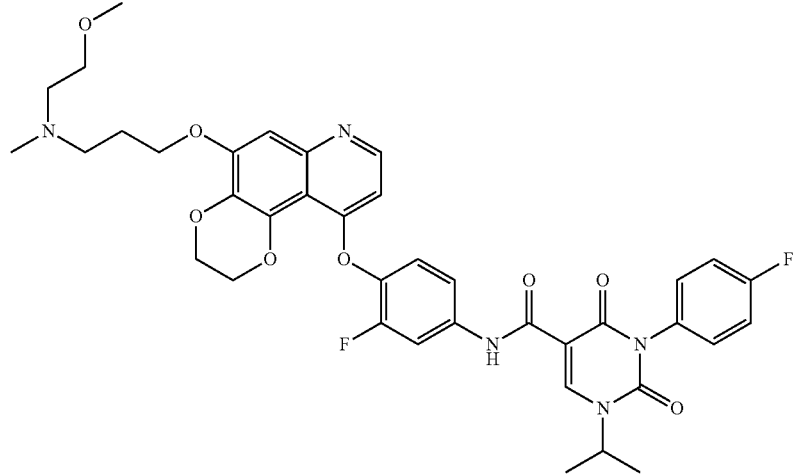

Example 96

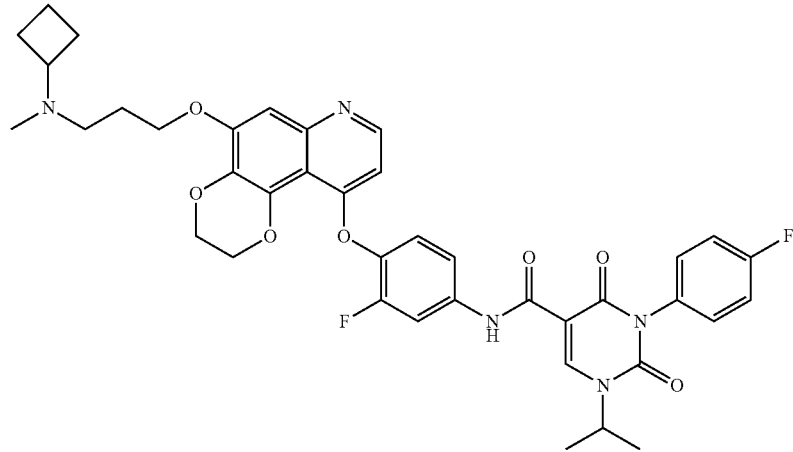

Example 96: N-(3-fluoro-4-((5-(3-((cyclobutyl)(methyl)amino)propoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-(3-((cyclobutyl)(methyl)amino)propoxy)-2,3-dihydro-[1,4]dioxino[2,3-f]quinolin-10-yl)oxy)aniline (45 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 30%); ¹H NMR (600 MHz, DMSO-d₆) δ 10.99 (s, 1H), 8.67 (s, 1H), 8.42 (d, J=5.2 Hz, 1H), 7.97 (dd, J=12.9, 2.5 Hz, 1H), 7.49-7.40 (m, 3H), 7.35 (t, J=8.8 Hz, 2H), 7.24 (t, J=9.0 Hz, 1H), 7.06 (s, 1H), 6.46 (d, J=5.2 Hz, 1H), 4.80-4.75 (m, 1H), Example 97: N-(3-chloro-4-((5-(3-morpholinopropoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-chloro-4-((5-(3-morpholinopropoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 34%); ¹H NMR (600 MHz, DMSO-d₆) δ 10.96 (s, 1H), 8.66 (s, 1H), 8.43 (d, J=5.1 Hz, 1H), 8.15 (d, J=2.5 Hz, 1H), 7.59 (dd, J=8.9, 2.6 Hz, 1H), 7.45-7.40 (m, 2H), 7.36 (t, J=8.8 Hz, 2H), 7.17 (d, J=8.9 Hz, 1H), 7.07 (s, 1H), 6.41 (d, J=5.2 Hz, 1H), 4.90-4.73 (m, 1H), 4.36-4.27 (m, 4H), 4.17 (t, J=6.4 Hz, 2H), 3.59 (t, J=4.6 Hz, 4H), 2.46 (t, J=7.1 Hz, 2H), 2.38 (d, J=6.8 Hz, 4H), 1.96 (q, J=6.8 Hz, 2H), 1.42 (d, J=6.8 Hz, 6H). MS: 746 [M+H]⁺.

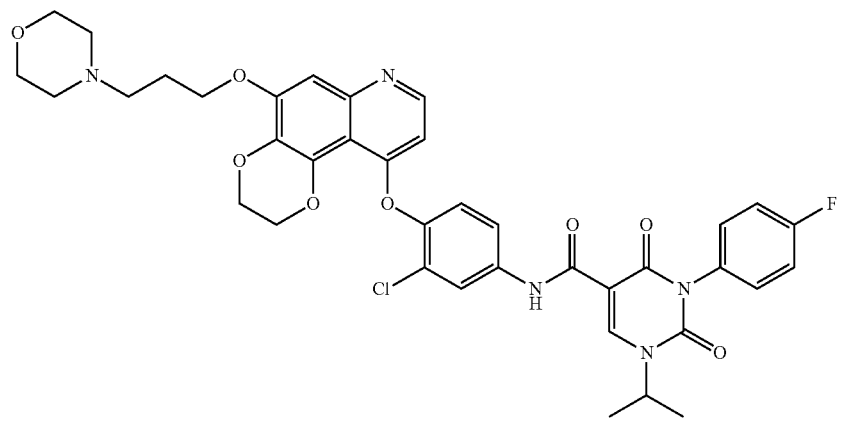

Example 97

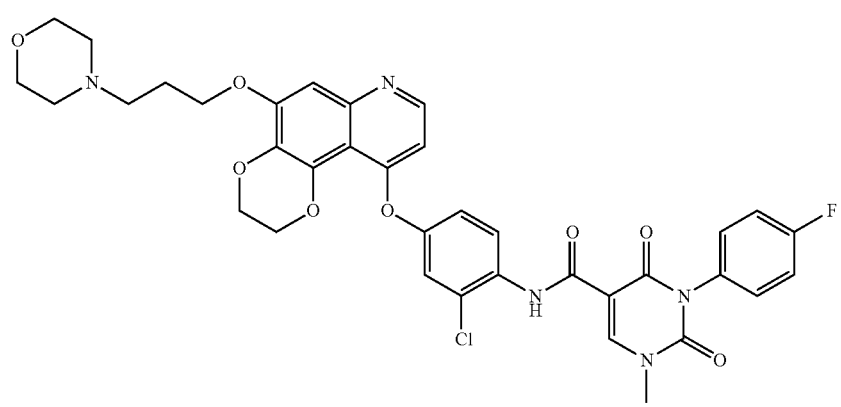

Example 98

Example 98: N-(2-chloro-4-((5-(3-morpholino-propoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-4-((5-(3-morpholinopropoxy)-2,3-dihydro-[1,4]dioxino[2,3-f]quinolin-10-yl)oxy)aniline (47 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 29%); ¹H NMR (600 MHz, DMSO-d₆) δ 11.29 (s, 1H), 8.89 (s, 1H), 8.53 (d, J=9.1 Hz, 1H), 8.48 (d, J=5.1 Hz, 1H), 7.42-7.32 (m, 4H), 7.14-7.06 (m, 3H), 6.62 (d, J=5.1 Hz, 1H), 4.29 (ddd, J=31.5, 5.9, 3.1 Hz, 4H), 4.18 (t, J=6.4 Hz, 2H), 3.64 (d, J=17.4 Hz, 4H), 3.53 (s, 3H), 2.53 (s, 2H), 2.35 (d, J=80.3 Hz, 4H), 2.00 (q, J=7.1 Hz, 2H). MS: 718 [M+H]⁺.

Example 99: N-(3-fluoro-4-((5-methoxy-2,3-dihydro-[1,4]dioxino[2,3-f]quinolin-10-yl)oxy)phenyl)-3-(4-fluorophenyl)-1-(3-hydroxypropyl)-2,4-dioxo-1,2,3,4-tetrahydropyrimidine-5-carboxamide A solution of 3-(4-fluorophenyl)-1-(3-hydroxypropyl)-2,4-dioxo-1,2,3,4-tetrahydropyrimidine-5-carbonyl chloride (33 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (11 mg, yield: 17%); ¹H NMR (600 MHz, DMSO-d₆) δ 11.00 (s, 1H), 8.81 (s, 1H), 8.44 (d, J=5.2 Hz, 1H), 7.97 (dd, J=12.9, 2.5 Hz, 1H), 7.45 (ddd, J=27.9, 9.0, 3.7 Hz, 3H), 7.36 (t, J=8.8 Hz, 2H), 7.25 (t, J=9.0 Hz, 1H), 7.08 (s, 1H), 6.47 (d, J=5.2 Hz, 1H), 4.65 (t, J=5.0 Hz, 1H), 4.34 (s, 4H), 4.05 (t, J=6.9 Hz, 2H), 3.93 (s, 3H), 3.51 (q, J=5.7 Hz, 2H), 1.87-1.83 (m, 2H). MS: 633 [M+H]⁺.

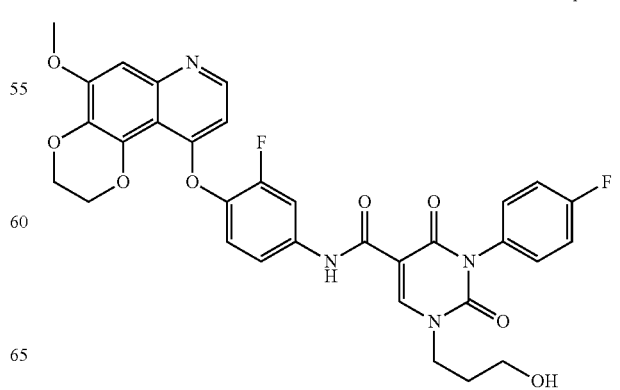

Example 99

Example 100

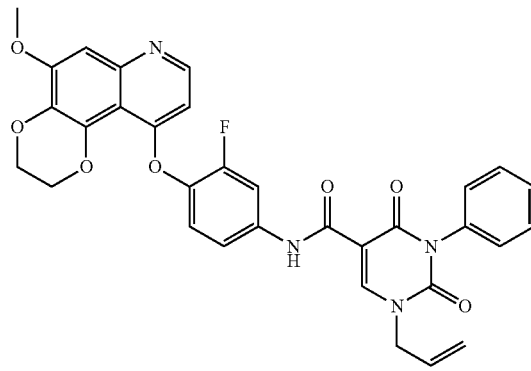

Example 101

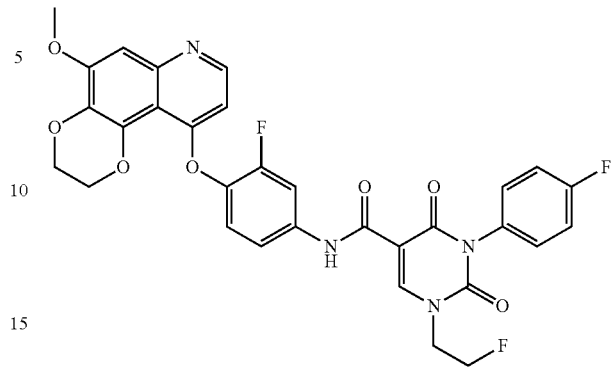

Example 102

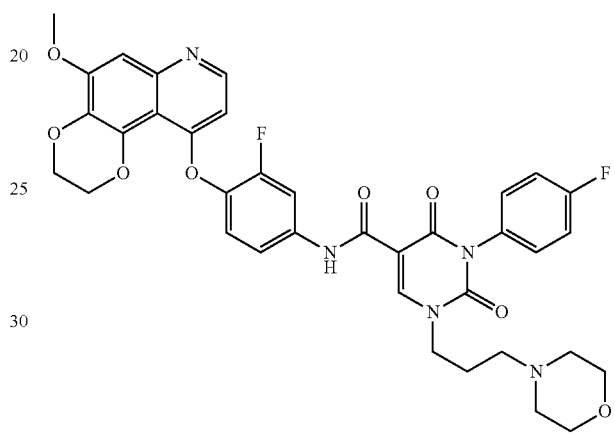

Example 100: N-(3-fluoro-4-((5-methoxy-2,3-dihydro-[1,4]dioxino[2,3-f]quinolin-10-yl)oxy)phenyl)-3-(4-fluorophenyl)-1-allyl-2,4-dioxo-1,2,3,4-tetrahydropyrimidine-5-carboxamide A solution of 3-(4-fluorophenyl)-1-allyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 31%); $^1$H NMR (600 MHz, DMSO-$d_6$) δ 10.98 (s, 1H), 8.79 (d, J=1.3 Hz, 1H), 8.43 (d, J=5.3 Hz, 1H), 7.96 (dd, J=12.8, 2.4 Hz, 1H), 7.50-7.40 (m, 3H), 7.36 (t, J=8.7 Hz, 2H), 7.25 (t, J=8.9 Hz, 1H), 7.08 (s, 1H), 6.47 (d, J=5.2 Hz, 1H), 5.98 (td, J=10.7, 5.1 Hz, 1H), 5.41-5.34 (m, 1H), 5.31-5.26 (m, 1H), 4.62 (d, J=5.5 Hz, 2H), 4.33 (s, 4H), 3.92 (s, 3H). MS: 615 [M+H]$^+$.

Example 101: N-(3-fluoro-4-((5-methoxy-2,3-dihydro-[1,4]dioxino[2,3-f]quinolin-10-yl)oxy)phenyl)-3-(4-fluorophenyl)-1-(2-fluoroethyl)-2,4-dioxo-1,2,3,4-tetrahydropyrimidine-5-carboxamide A solution of 3-(4-fluorophenyl)-1-(2-fluoroethyl)-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 35%); $^1$H NMR (600 MHz, DMSO-$d_6$) δ 10.96 (s, 1H), 8.81 (s, 1H), 8.43 (d, J=5.2 Hz, 1H), 7.99-7.93 (m, 1H), 7.45 (dt, J=8.5, 4.3 Hz, 3H), 7.37 (d, J=8.7 Hz, 2H), 7.26 (d, J=9.0 Hz, 1H), 7.08 (s, 1H), 6.47 (d, J=5.3 Hz, 1H), 4.37 (br, 6H), 3.94 (s, 2H), 3.92 (s, 3H). MS: 621 [M+H]$^+$.

Example 102: N-(3-fluoro-4-((5-methoxy-2,3-dihydro-[1,4]dioxino[2,3-f]quinolin-10-yl)oxy)phenyl)-3-(4-fluorophenyl)-1-(3-morpholinopropyl)-2,4-dioxo-1,2,3,4-tetrahydropyrimidine-5-carboxamide A solution of 3-(4-fluorophenyl)-1-(3-morpholinopropyl)-2,4-dioxo-1,2,3,4-tetrahydropyrimidine-5-carbonyl chloride (40 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (22 mg, yield: 31%); $^1$H NMR (600 MHz, DMSO-$d_6$) δ 11.00 (s, 1H), 8.90 (s, 1H), 8.43 (d, J=5.2 Hz, 1H), 7.95 (dd, J=12.9, 2.5 Hz, 1H), 7.48 (dd, J=8.8, 2.4 Hz, 1H), 7.42 (dd, J=8.9, 5.1 Hz, 2H), 7.37 (t, J=8.7 Hz, 2H), 7.26 (t, J=9.0 Hz, 1H), 7.08 (s, 1H), 6.47 (d, J=5.2 Hz, 1H), 4.34 (s, 4H), 4.03 (t, J=6.7 Hz, 2H), 3.93 (s, 3H), 3.61 (t, J=4.6 Hz, 4H), 2.35 (br, 4H), 2.00 (dt, J=12.8, 6.8 Hz, 2H), 1.89-1.83 (m, 2H). MS: 702 [M+H]$^+$.

Example 103: tert-butyl 2-(5-((3-fluoro-4-((5-methoxy-2,3-dihydro-[1,4]dioxino[2,3-f]quinolin-10-yl)oxy)phenyl)carbamoyl)-3-(4-fluorophenyl)-2,4-dioxo-3,4-dihydropyrimidin-1(2H)-yl)acetate

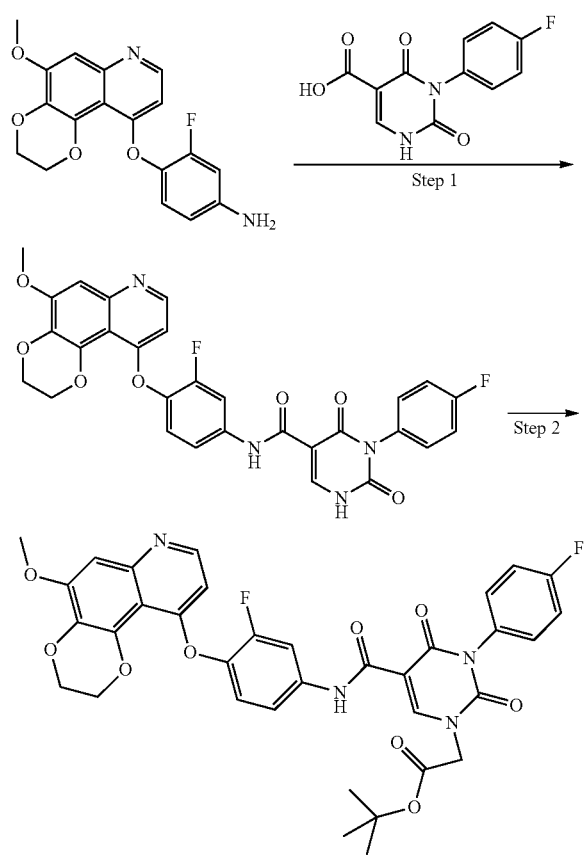

Step 1): N-(3-fluoro-4-((5-methoxy-2,3-dihydro-[1,4]dioxino[2,3-f]quinolin-10-yl)oxy)phenyl)-3-(4-fluorophenyl)-2,4-dioxo-1,2,3,4-tetrahydropyrimidine-5-carboxamide 3-(4-Fluorophenyl)-2,4-dioxo-1,2,3,4-tetrahydropyrimidine-5-carboxylic acid (275 mg, 1.1 mmol), HATU (1 mmol), and DIEA (2 mmol) were added to a solution of 3-fluoro-4-((5-methoxy-2,3-dihydro-[1,4]dioxino[2,3-f]quinolin-10-yl)oxy)aniline (340 mg, 1 mmol) in anhydrous DMF (5 mL), and reacted with stirring at room temperature for 10 hours. The reaction solution was slurried with water, and filtered. The filter cake was dried to afford a white solid (170 mg, yield: 30%), MS: 575 [M+H]+;

Step 2): A solution of N-(3-fluoro-4-((5-methoxy-2,3-dihydro-[1,4]dioxino[2,3-f]quinolin-10-yl)oxy)phenyl)-3-(4-fluorophenyl)-2,4-dioxo-1,2,3,4-tetrahydropyrimidine-5-carboxamide (115 mg, 0.2 mmol), tert-butyl 2-bromoacetate (40 mg, 0.2 mmol) and potassium carbonate (70 mg, 0.5 mmol) in DMF (1 mL) was heated and reacted at 50° C. for two hours. Water was added, and the mixture was extracted with ethyl acetate. The organic phase was washed with saturated sodium chloride solution, dried, and concentrated to afford a yellow oil, which was purified by preparative liquid chromatography to afford a white solid product (60 mg, yield: 43%); ¹H NMR (600 MHz, DMSO-d₆) δ 10.90 (s, 1H), 8.94 (s, 1H), 8.44 (d, J=5.2 Hz, 1H), 7.96 (dd, J=12.9, 2.4 Hz, 1H), 7.52-7.46 (m, 1H), 7.44-7.35 (m, 4H), 7.26 (t, J=9.0 Hz, 1H), 7.08 (s, 1H), 6.47 (d, J=5.2 Hz, 1H), 4.76 (s, 2H), 4.34 (s, 4H), 3.93 (s, 3H), 1.45 (s, 9H). MS: 689 [M+H]+.

Example 104: 2-(5-(((3-fluoro-4-((5-methoxy-2,3-dihydro-[1,4]dioxino[2,3-f]quinolin-10-yl)oxy)phenyl)carbamoyl)-3-(4-fluorophenyl)-2,4-dioxo-3,4-dihydropyrimidin-1(2H)-yl)acetic acid Tert-butyl 2-(5-(((3-fluoro-4-((5-methoxy-2,3-dihydro-[1,4]dioxino[2,3-f]quinolin-10-yl)oxy)phenyl)carbamoyl)-3-(4-fluorophenyl)-2,4-dioxo-3,4-dihydropyrimidin-1(2H)-yl)acetate (20 mg, 0.3 mmol) was added to a 4 M solution of hydrogen chloride in dioxane (2 mL), and stirred at room temperature for 2 hours. The reaction solution was concentrated, and purified by preparative liquid chromatography to afford a white solid product (12 mg, yield: 65%); ¹H NMR (400 MHz, DMSO-d₆) δ 10.91 (s, 1H), 8.91 (s, 1H), 8.43 (d, J=5.2 Hz, 1H), 7.96 (d, J=12.8 Hz, 1H), 7.48 (d, J=8.9 Hz, 1H), 7.39-7.34 (m, 4H), 7.26 (t, J=9.0 Hz, 1H), 7.08 (s, 1H), 6.47 (d, J=5.2 Hz, 1H), 4.74 (s, 2H), 4.34 (s, 4H), 3.92 (s, 3H). MS: 633 [M+H]+.

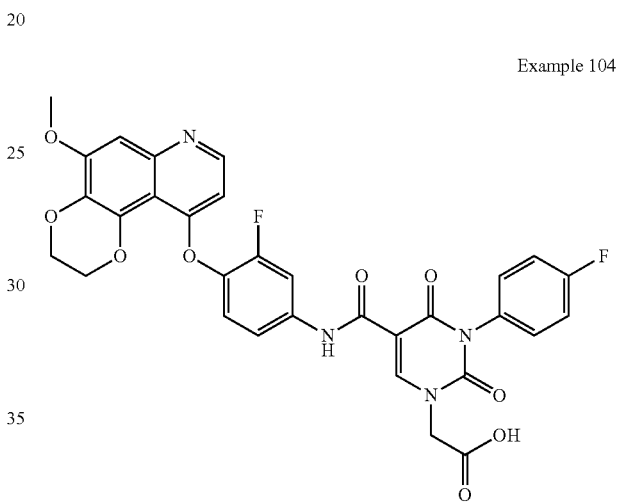

Example 104

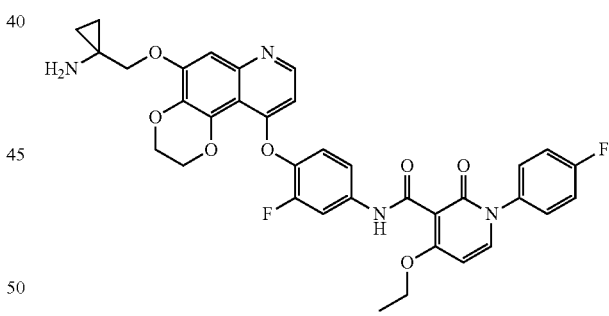

Example 105

Example 105: N-(4-((5-(((1-aminocyclopropyl)methoxy)-2,3-dihydro-[1,4]dioxino[2,3-f]quinolin-10-yl)oxy)-3-fluorophenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of tert-butyl (1-(((10-(4-amino-2-fluorophenoxy)-2,3-dihydro-[1,4]dioxino[2,3-f]quinolin-5-yl)oxy)methyl)cyclopropyl)carbamate (50 mg, 0.1 mmol) in anhydrous DMF (1 mL), and reacted with stirring at room temperature for 5 hours. The reaction solution was quenched with water, and filtered to afford a light-yellow solid. The yellow solid was added to a solution of trifluoroacetic acid (1 mL) in dichloromethane (3 mL), and reacted with stirring at room temperature for 2 hours. The reaction solution was concentrated to afford a yellow oil. The oil was purified by preparative liquid chromatography to afford a white solid product (15 mg, yield 23%); $^1$H NMR (400 MHz, DMSO-d$_6$) δ 10.48 (s, 1H), 8.33 (d, J=5.2 Hz, 1H), 7.88-7.75 (m, 2H), 7.44-7.34 (m, 3H), 7.30 (t, J=8.8 Hz, 2H), 7.20 (t, J=9.0 Hz, 1H), 6.97 (s, 1H), 6.45 (d, J=7.9 Hz, 1H), 6.37 (d, J=5.2 Hz, 1H), 4.31 (s, 4H), 4.19 (q, J=7.0 Hz, 2H), 3.97 (s, 2H), 1.23 (t, J=7.0 Hz, 3H), 0.64-0.53 (m, 4H). MS: 657 [M+H]$^+$.

Example 106: N-(3-fluoro-4-((5-((1-aminocyclopropyl)methoxy)-2,3-dihydro-[1,4]dioxino[2,3-f]quinolin-1 0-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of tert-butyl (1-(((10-(4-amino-2-fluorophenoxy)-2,3-dihydro-[1,4]dioxino[2,3-f]quinolin-5-yl)oxy)methyl)cyclopropyl)carbamate (50 mg, 0.1 mmol) in anhydrous DMF (1 mL), and reacted with stirring at room temperature for 5 hours. The reaction solution was quenched with water, and filtered to afford a light-yellow solid. The yellow solid was added to a solution of trifluoroacetic acid (1 mL) in dichloromethane (3 mL), and reacted with stirring at room temperature for 2 hours. The reaction solution was concentrated to afford a yellow oil. The oil was purified by preparative liquid chromatography to afford a white solid product (11 mg, yield: 16%); $^1$H NMR (400 MHz, DMSO-d$_6$) δ 10.99 (s, 1H), 8.67 (s, 1H), 8.42 (d, J=5.2 Hz, 1H), 7.97 (dd, J=13.0, 2.5 Hz, 1H), 7.50-7.31 (m, 5H), 7.24 (t, J=9.0 Hz, 1H), 7.03 (s, 1H), 6.47 (d, J=5.1 Hz, 1H), 4.82-4.73 (m, 1H), 4.41-4.30 (m, 4H), 4.02 (s, 2H), 1.42 (d, J=6.8 Hz, 6H), 0.63 (dt, J=10.2, 2.1 Hz, 4H). MS: 672 [M+H]$^+$.

Example 106

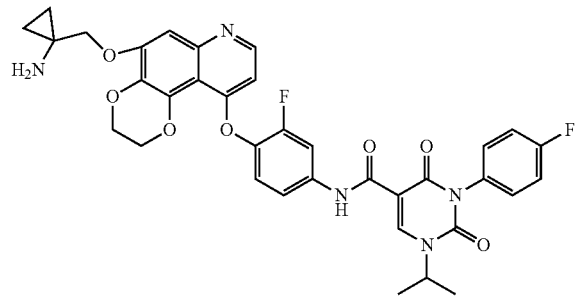

Example 107

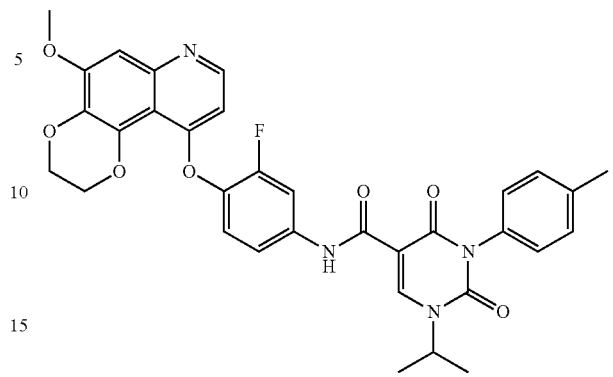

Example 107: N-(3-fluoro-4-((5-methoxy-2,3-dihydro-[1,4]dioxino[2,3-f]quinolin-10-yl)oxy)phenyl)-3-(4-methylphenyl)-1-isopropyl-2,4-dioxo-1,2,3,4-tetrahydropyrimidine-5-carboxamide A solution of 3-(4-methylphenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (18 mg, yield: 29%); $^1$H NMR (600 MHz, DMSO-d$_6$) δ 11.05 (s, 1H), 8.66 (s, 1H), 8.43 (d, J=5.2 Hz, 1H), 7.97 (dd, J=12.9, 2.4 Hz, 1H), 7.47-7.42 (m, 1H), 7.32 (d, J=8.0 Hz, 2H), 7.28-7.20 (m, 3H), 7.08 (s, 1H), 6.48 (d, J=5.2 Hz, 1H), 4.88-4.65 (m, 1H), 4.34 (s, 4H), 3.93 (s, 3H), 2.38 (s, 3H), 1.42 (d, J=6.8 Hz, 6H). MS: 613 [M+H]$^+$.

Example 108: N-(3-fluoro-4-((5-methoxy-2,3-dihydro-[1,4]dioxino[2,3-f]quinolin-10-yl)oxy)phenyl)-3-(4-chlorophenyl)-1-isopropyl-2,4-dioxo-1,2,3,4-tetrahydropyrimidine-5-carboxamide A solution of 3-(4-chlorophenyl)-1-isopropyl-2,4-dioxo-1,2,3,4-tetrahydropyrimidine-5-carbonyl chloride (33 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (600 MHz, DMSO-d$_6$) δ 10.98 (s, 1H), 8.68 (s, 1H), 8.44 (d, J=5.2 Hz, 1H), 7.97 (dd, J=12.9, 2.5 Hz, 1H), 7.63-7.58 (m, 2H), 7.49-7.40 (m, 3H), 7.25 (t, J=9.0 Hz, 1H), 7.08 (s, 1H), 6.48 (d, J=5.2 Hz, 1H), 4.78 (p, J=6.8 Hz, 1H), 4.34 (s, 4H), 3.93 (s, 3H), 1.43 (d, J=6.8 Hz, 6H). MS: 633 [M+H]$^+$.

Example 108

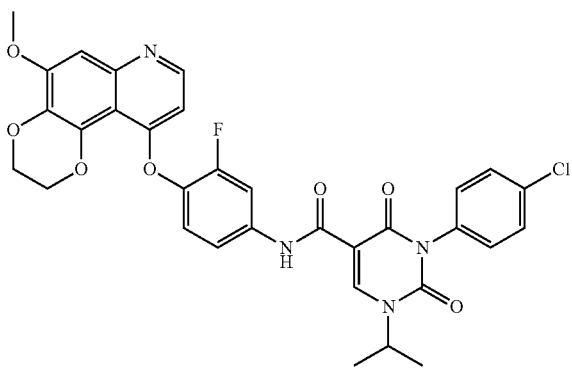

Example 109

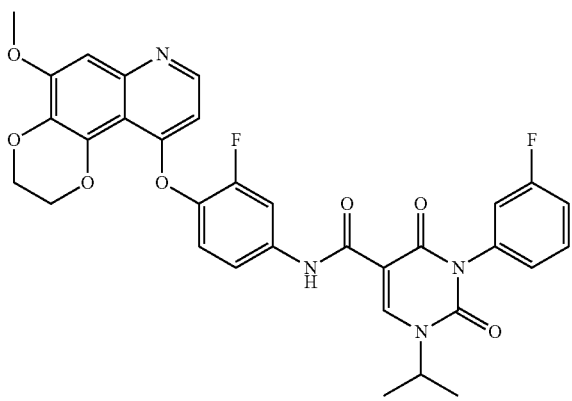

Example 109: N-(3-fluoro-4-((5-methoxy-2,3-dihydro-[1,4]dioxino[2,3-f]quinolin-10-yl)oxy)phenyl)-3-(3-fluorophenyl)-1-isopropyl-2,4-dioxo-1,2,3,4-tetrahydropyrimidine-5-carboxamide A solution of 3-(3-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 41%); $^1$H NMR (400 MHz, DMSO-$d_6$) δ 10.90 (s, 1H), 8.61 (s, 1H), 8.38 (d, J=5.3 Hz, 1H), 7.91 (dd, J=13.0, 2.5 Hz, 1H), 7.57-7.46 (m, 1H), 7.41 (dt, J=8.7, 1.6 Hz, 1H), 7.27 (ddd, J=9.0, 4.1, 1.9 Hz, 2H), 7.23-7.15 (m, 2H), 7.02 (s, 1H), 6.42 (d, J=5.2 Hz, 1H), 4.83-4.64 (m, 1H), 4.27 (s, 4H), 3.86 (s, 3H), 1.36 (d, J=6.7 Hz, 6H). MS: 617 [M+H]$^+$.

Example 110: N-(3-fluoro-4-((5-methoxy-2,3-dihydro-[1,4]dioxino[2,3-f]quinolin-10-yl)oxy)phenyl)-3-(2-fluorophenyl)-1-isopropyl-2,4-dioxo-1,2,3,4-tetrahydropyrimidine-5-carboxamide A solution of 3-(2-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 31%); $^1$H NMR (400 MHz, DMSO-$d_6$) δ 10.84 (s, 1H), 8.72 (s, 1H), 8.43 (d, J=5.2 Hz, 1H), 7.96 (dd, J=13.0, 2.5 Hz, 1H), 7.60-7.33 (m, 5H), 7.25 (t, J=9.0 Hz, 1H), 7.08 (s, 1H), 6.47 (dd, J=5.1, 1.0 Hz, 1H), 4.82-4.73 (m, 1H), 4.33 (s, 4H), 3.92 (s, 3H), 1.44 (d, J=6.8 Hz, 6H). MS: 617 [M+H]$^+$.

Example 110

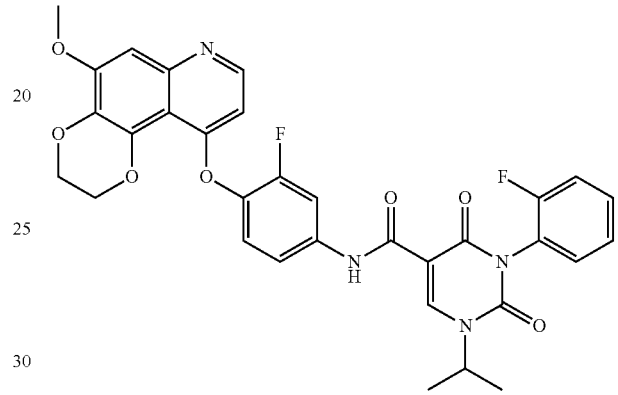

Example 111

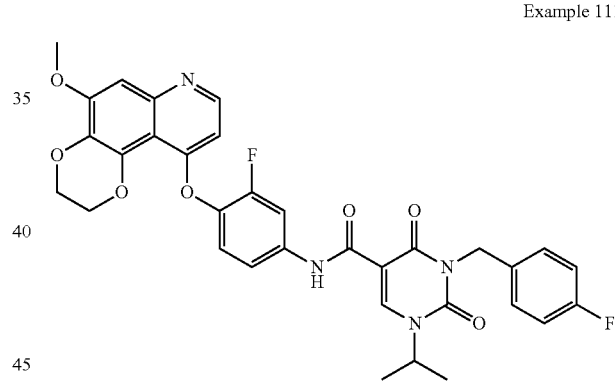

Example 111: N-(3-fluoro-4-((5-methoxy-2,3-dihydro-[1,4]dioxino[2,3-f]quinolin-10-yl)oxy)phenyl)-3-(4-fluorobenzyl)-1-isopropyl-2,4-dioxo-1,2,3,4-tetrahydropyrimidine-5-carboxamide A solution of 3-(4-fluorobenzyl)-1-isopropyl-2,4-dioxo-1,2,3,4-tetrahydropyrimidine-5-carbonyl chloride (32 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (600 MHz, DMSO-$d_6$) δ 11.05 (s, 1H), 8.60 (s, 1H), 8.44 (d, J=5.2 Hz, 1H), 7.98 (dd, J=12.9, 2.5 Hz, 1H), 7.50-7.45 (m, 1H), 7.42 (dd, J=8.5, 5.6 Hz, 2H), 7.26 (t, J=9.0 Hz, 1H), 7.17 (t, J=8.9 Hz, 2H), 7.09 (s, 1H), 6.49 (d, J=5.2 Hz, 1H), 5.09 (s, 2H), 4.79 (p, J=6.8 Hz, 1H), 4.34 (s, 4H), 3.93 (s, 3H), 1.40 (d, J=6.8 Hz, 6H). MS: 631 [M+H]$^+$.

Example 112: N-(3-fluoro-4-((5-methoxy-2,3-dihydro-[1,4]dioxino[2,3-f]quinolin-10-yl)oxy)phenyl)-2-oxo-4-ethoxy-1-(4-methylphenyl)-1,2-dihydropyridin-3-carboxamide A solution of 4-ethoxy-1-(4-methylphenyl)-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 35%); $^1$H NMR (400 MHz, DMSO-d$_6$) δ 10.55 (s, 1H), 8.41 (d, J=5.3 Hz, 1H), 7.91 (dd, J=13.1, 2.4 Hz, 1H), 7.81 (d, J=7.8 Hz, 1H), 7.45 (dt, J=8.9, 1.7 Hz, 1H), 7.36-7.19 (m, 5H), 7.08 (s, 1H), 6.46 (dd, J=17.4, 6.5 Hz, 2H), 4.36 (q, J=4.8 Hz, 4H), 4.25 (q, J=7.0 Hz, 2H), 3.92 (s, 3H), 2.37 (s, 3H), 1.30 (t, J=7.0 Hz, 3H). MS: 598 [M+H]$^+$.

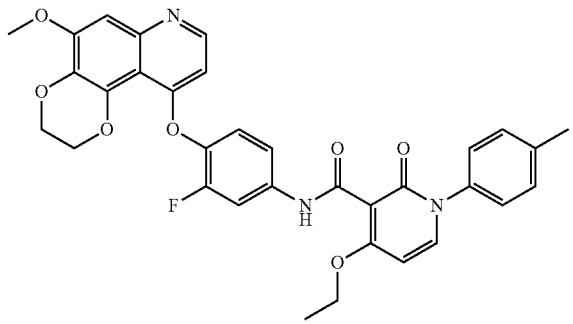

Example 112

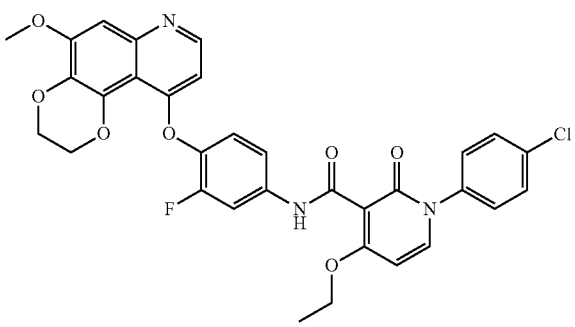

Example 113

Example 113: N-(3-fluoro-4-((5-methoxy-2,3-dihydro-[1,4]dioxino[2,3-f]quinolin-10-yl)oxy)phenyl)-2-oxo-4-ethoxy-1-(4-chlorophenyl)-1,2-dihydropyridin-3-carboxamide A solution of 4-ethoxy-1-(4-chlorophenyl)-2-oxo-1,2-dihydropyridine-3-carbonyl chloride (31 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 40%); $^1$H NMR (400 MHz, DMSO-d$_6$) δ 10.54 (s, 1H), 8.40 (d, J=5.3 Hz, 1H), 7.94-7.83 (m, 2H), 7.63-7.56 (m, 2H), 7.45 (dd, J=9.4, 3.0 Hz, 3H), 7.28 (d, J=9.0 Hz, 1H), 7.07 (s, 1H), 6.53 (d, J=7.9 Hz, 1H), 6.44 (d, J=5.2 Hz, 1H), 4.36 (p, J=4.6, 3.8 Hz, 4H), 4.26 (q, J=7.0 Hz, 2H), 3.92 (s, 3H), 1.30 (t, J=7.0 Hz, 3H). MS: 618 [M+H]$^+$.

Example 114: N-(3-fluoro-4-((5-methoxy-2,3-dihydro-[1,4]dioxino[2,3-f]quinolin-10-yl)oxy)phenyl)-2-oxo-4-ethoxy-1-(3-fluorophenyl)-1,2-dihydropyridin-3-carboxamide A solution of 4-ethoxy-1-(3-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (16 mg, yield: 27%); $^1$H NMR (400 MHz, DMSO-d$_6$) δ 10.55 (s, 1H), 8.41 (d, J=5.2 Hz, 1H), 7.95-7.85 (m, 2H), 7.58 (td, J=8.1, 6.4 Hz, 1H), 7.45 (dt, J=8.9, 1.6 Hz, 1H), 7.41-7.23 (m, 4H), 7.08 (s, 1H), 6.54 (d, J=7.9 Hz, 1H), 6.44 (d, J=5.2 Hz, 1H), 4.36 (q, J=4.8 Hz, 4H), 4.27 (q, J=7.0 Hz, 2H), 3.92 (s, 3H), 1.30 (t, J=7.0 Hz, 3H). MS: 602 [M+H]$^+$.

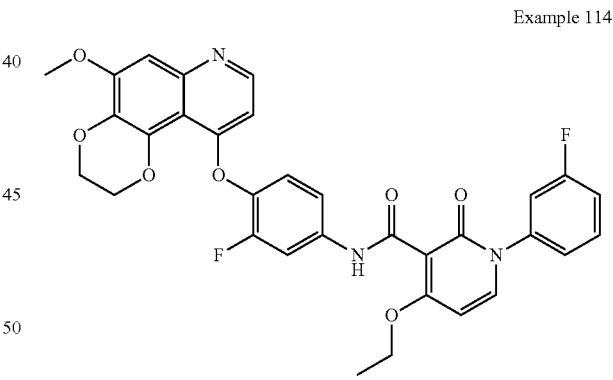

Example 114

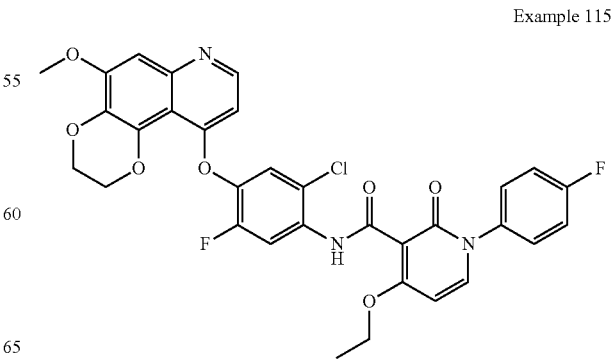

Example 115

Example 115: N-(2-chloro-5-fluoro-4-((5-methoxy-2,3-dihydro-[1,4]dioxino[2,3-f]quinolin-10-yl)oxy)phenyl)-4-ethoxy-2-oxo-1-(4-fluorophenyl)-1,2-dihydropyridin-3-carboxamide A solution of 4-ethoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 2-chloro-5-fluoro-4-((5-methoxy-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 47%); $^1$H NMR (400 MHz, DMSO-$d_6$) δ 11.62 (s, 1H), 8.50-8.42 (m, 2H), 7.98 (d, J=7.8 Hz, 1H), 7.52 (dd, J=8.6, 4.7 Hz, 3H), 7.39 (t, J=8.8 Hz, 2H), 7.09 (s, 1H), 6.59 (dd, J=12.6, 6.5 Hz, 2H), 4.32 (d, J=7.4 Hz, 6H), 3.92 (s, 3H), 1.38 (t, J=7.0 Hz, 3H). MS: 636 [M+H]$^+$.

Example 116: N-(2-chloro-5-fluoro-4-((5-methoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-5-fluoro-4-((5-methoxy-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg, yield: 42%); $^1$H NMR (400 MHz, DMSO-$d_6$) δ 11.49 (s, 1H), 8.93 (s, 1H), 8.62 (d, J=13.1 Hz, 1H), 8.45 (d, J=5.2 Hz, 1H), 7.58 (d, J=8.1 Hz, 1H), 7.45-7.32 (m, 4H), 7.09 (s, 1H), 6.59 (d, J=5.2 Hz, 1H), 4.33 (s, 4H), 3.92 (s, 3H), 3.54 (s, 3H). MS: 623 [M+H]$^+$.

Example 116

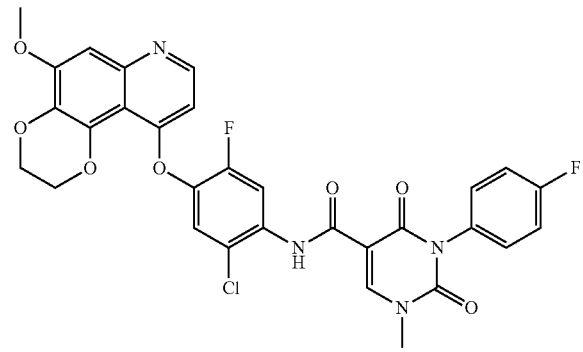

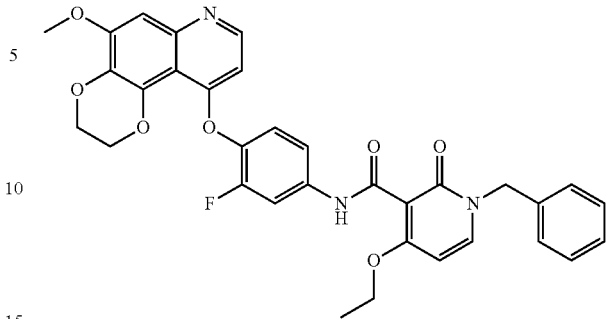

Example 117: N-(3-fluoro-4-((5-methoxy-2,3-dihydro-[1,4]dioxino[2,3-f]quinolin-10-yl)oxy)phenyl)-2-oxo-4-ethoxy-1-benzyl-1,2-dihydropyridin-3-carboxamide A solution of 4-ethoxy-1-benzyl-2-oxo-1,2-dihydropyridine-3-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (19 mg, yield: 32%); $^1$H NMR (400 MHz, DMSO-$d_6$) δ 10.46 (s, 1H), 8.42 (d, J=5.6 Hz, 1H), 7.96-7.81 (m, 2H), 7.41 (dt, J=8.9, 1.7 Hz, 1H), 7.32-7.28 (m, 4H), 7.26-7.21 (m, 2H), 7.07 (s, 1H), 6.49 (d, J=5.5 Hz, 1H), 6.37 (d, J=7.8 Hz, 1H), 5.04 (s, 2H), 4.38-4.27 (m, 4H), 4.12 (q, J=7.0 Hz, 2H), 3.88 (s, 3H), 1.19 (t, J=7.0 Hz, 3H). MS: 598 [M+H]$^+$.

Example 118: N-(2-chloro-5-fluoro-4-((5-methoxy-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 2-chloro-5-fluoro-4-((5-methoxy-2,3-dihydro-[1,4]dioxino[2,3-f]quinolin-10-yl)oxy)aniline (38 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (30 mg, yield: 46%); $^1$H NMR (400 MHz, DMSO-$d_6$) δ 11.49 (s, 1H), 8.72 (s, 1H), 8.61 (d, J=13.1 Hz, 1H), 8.46 (d, J=5.2 Hz, 1H), 7.58 (d, J=8.1 Hz, 1H), 7.46-7.32 (m, 4H), 7.09 (s, 1H), 6.60 (d, J=5.1 Hz, 1H), 4.82-4.74 (m, 1H), 4.33 (s, 4H), 3.92 (s, 3H), 1.43 (d, J=6.7 Hz, 6H). MS: 651 [M+H]$^+$.

Example 118

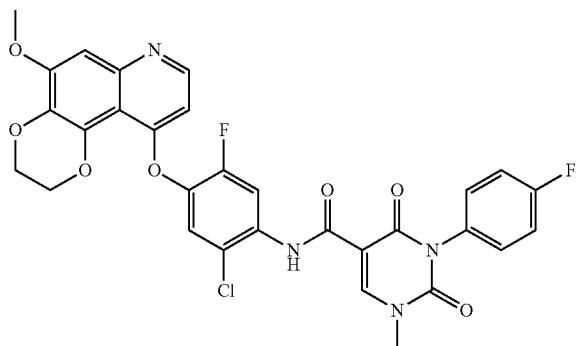

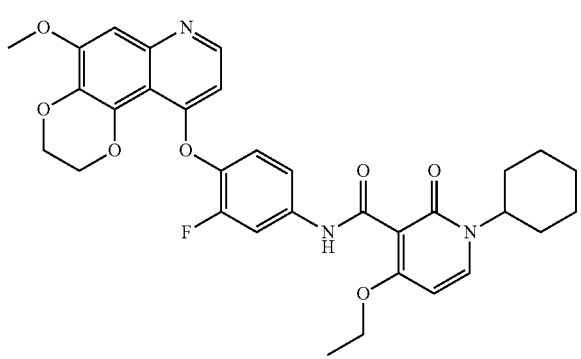

Example 119

Example 119: 1-cyclohexyl-4-ethoxy-N-(3-fluoro-4-((5-methoxy-2,3-dihydro-[1,4]dioxino[2,3-f]quinolin-1 0-yl)oxy)phenyl)-2-oxo-1,2-dihydropyridine-3-carboxamide A solution of 4-ethoxy-1-cyclohexyl-2-oxo-1,2-dihydropyridine-3-carbonyl chloride (29 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (29 mg, yield: 40%); $^1$H NMR (400 MHz, DMSO-d$_6$) δ 10.51 (s, 1H), 8.42 (d, J=5.2 Hz, 1H), 8.11 (d, J=6.0 Hz, 1H), 7.88 (dd, J=13.0, 2.4 Hz, 1H), 7.51-7.40 (m, 1H), 7.29 (t, J=9.0 Hz, 1H), 7.08 (s, 1H), 6.84 (d, J=6.1 Hz, 1H), 6.45 (d, J=5.2 Hz, 1H), 5.06 (dt, J=8.3, 4.4 Hz, 1H), 4.36 (s, 4H), 4.18 (q, J=7.0 Hz, 2H), 3.93 (s, 3H), 1.84 (s, 2H), 1.64 (s, 2H), 1.54-1.24 (m, 9H). MS: 590 [M+H]$^+$.

Example 120: N-(3-fluoro-4-((5-(2-hydroxy-2-methylpropoxy)-2,3-dihydro-[1,4]dioxino[2,3-f]quinolin-10-yl)oxy)phenyl)-4-ethoxy-1-(4-fluorophenyl)-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 1-((10-(4-amino-2-fluorophenoxy)-2,3-dihydro-[1,4]dioxino[2,3-f]quinolin-5-yl) oxy)-2-meth ylpropyl-2-ol (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (21 mg, yield: 32%); $^1$H NMR (400 MHz, DMSO-d$_6$) δ 10.55 (s, 1H), 8.40 (d, J=5.2 Hz, 1H), 7.97-7.81 (m, 2H), 7.46 (ddt, J=8.5, 6.1, 2.9 Hz, 3H), 7.37 (t, J=8.7 Hz, 2H), 7.27 (t, J=9.0 Hz, 1H), 7.04 (s, 1H), 6.52 (d, J=8.0 Hz, 1H), 6.44 (d, J=5.2 Hz, 1H), 4.69 (s, 1H), 4.38 (s, 4H), 4.26 (q, J=7.0 Hz, 2H), 3.87 (s, 2H), 1.31 (t, J=7.0 Hz, 3H), 1.26 (s, 6H). MS: 660 [M+H]$^+$.

Example 120

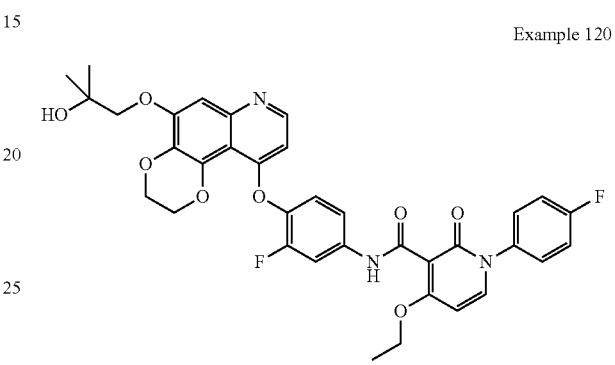

Example 121

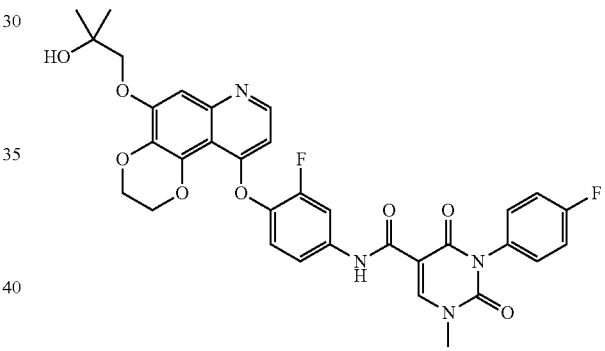

Example 121: N-(3-fluoro-4-((5-(2-hydroxy-2-methylpropoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 1-((10-(4-amino-2-fluorophenoxy)-2,3-dihydro-[1,4]dioxino[2,3-f]quinolin-5-yl)oxy)-2-meth ylpropyl-2-ol (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (28 mg, yield: 43%); $^1$H NMR (400 MHz, DMSO-d$_6$) δ 10.99 (s, 1H), 8.87 (d, J=1.6 Hz, 1H), 8.42 (d, J=5.3 Hz, 1H), 7.96 (dd, J=13.0, 2.5 Hz, 1H), 7.52-7.44 (m, 1H), 7.44-7.32 (m, 4H), 7.25 (t, J=9.0 Hz, 1H), 7.05 (d, J=1.6 Hz, 1H), 6.46 (dd, J=5.2, 1.0 Hz, 1H), 4.68 (d, J=1.6 Hz, 1H), 4.36 (q, J=4.7 Hz, 4H), 3.87 (s, 2H), 3.54 (s, 3H), 1.26 (s, 6H). MS: 647 [M+H]$^+$.

Example 122: N-(3-fluoro-4-((5-(2-hydroxy-2-methylpropoxy)-2,3-dihydro-[1,4]dioxino[2,3-f]quinolin-10-yl)oxy)phenyl)-3-(4-fluorophenyl)-1-isopropyl-2,4-dioxo-1,2,3,4-tetrahydropyrimidine-5-carboxamide A solution of 3-(4-fluorophenyl)-1-isopropyl-2,4-dioxo-1,2,3,4-tetrahydropyrimidine-5-carbonyl chloride (31 mg, 0.1 mmol) in dichloromethane (0.5 mL) followed by triethylamine (0.1 mL) were added to a solution of 1-((10-(4-amino-2-fluorophenoxy)-2,3-dihydro-[1,4]dioxino[2,3-f]quinolin-5-yl)oxy)-2-methylpropyl-2-ol (40 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (25 mg, yield: 37%); $^1$H NMR (400 MHz, DMSO-$d_6$) δ 10.99 (s, 1H), 8.67 (s, 1H), 8.42 (d, J=5.2 Hz, 1H), 7.97 (dd, J=13.0, 2.4 Hz, 1H), 7.50-7.39 (m, 3H), 7.39-7.31 (m, 2H), 7.24 (t, J=9.0 Hz, 1H), 7.04 (s, 1H), 6.47 (dd, J=5.2, 1.0 Hz, 1H), 4.83-4.72 (m, 1H), 4.68 (s, 1H), 4.35 (q, J=4.8 Hz, 4H), 3.86 (s, 2H), 1.42 (d, J=6.8 Hz, 6H), 1.25 (s, 6H). MS: 675 [M+H]$^+$.

with stirring at room temperature for 5 hours. The reaction solution was quenched with water, and filtered to afford a light-yellow solid. The solid was purified by preparative liquid chromatography to afford a white solid product (35 mg, yield: 61%); $^1$H NMR (400 MHz, DMSO-$d_6$) δ 12.32 (s, 1H), 8.62 (d, J=8.9 Hz, 2H), 8.50 (d, J=5.2 Hz, 1H), 8.13 (dd, J=6.6, 2.2 Hz, 1H), 7.62 (dd, J=8.7, 4.9 Hz, 2H), 7.43 (t, J=8.6 Hz, 2H), 7.36 (d, J=2.8 Hz, 1H), 7.14 (dd, J=9.2, 2.8 Hz, 1H), 7.10 (s, 1H), 6.73 (t, J=7.0 Hz, 1H), 6.64 (d, J=5.2 Hz, 1H), 4.30 (dd, J=13.4, 4.5 Hz, 4H), 3.93 (s, 3H). MS: 574 [M+H]$^+$.

Example 124: N-(2-chloro-4-((5-methoxy-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 2-chloro-4-((5-methoxy-2,3-dihydro-[1,4]dioxino[2,3-f]quinolin-10-yl)oxy)aniline (36 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 41%); $^1$H NMR (400 MHz, DMSO-$d_6$) δ 11.10 (s, 1H), 8.49 (d, J=5.1 Hz, 1H), 8.26 (d, J=9.1 Hz, 1H), 7.99 (d, J=7.8 Hz, 1H), 7.56-7.47 (m, 2H), 7.39 (dd, J=9.8, 7.8 Hz, 2H), 7.29 (d, J=2.8 Hz, 1H), 7.08 (d, J=11.0 Hz, 2H), 6.61 (dd, J=7.9, 6.5 Hz, 2H), 4.35-4.25 (m, 4H), 3.98 (s, 3H), 3.93 (s, 3H). MS: 604 [M+H]$^+$.

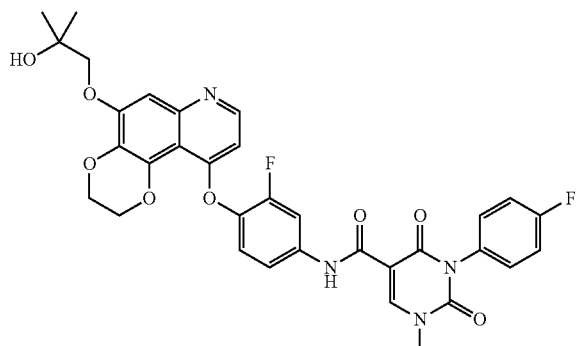

Example 122

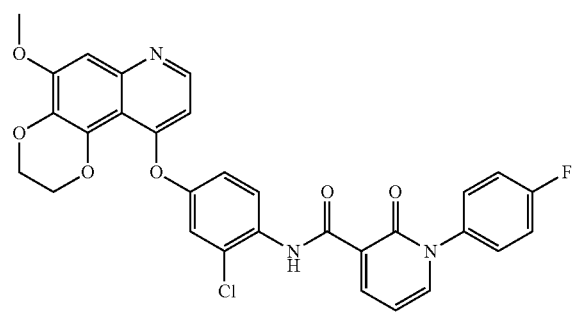

Example 123

Example 123: N-(2-chloro-4-((5-methoxy-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 2-chloro-4-((5-methoxy-2,3-dihydro-[1,4]dioxino[2,3-f]quinolin-10-yl)oxy)aniline (36 mg, 0.1 mmol) in anhydrous DMF (0.5 mL), and reacted

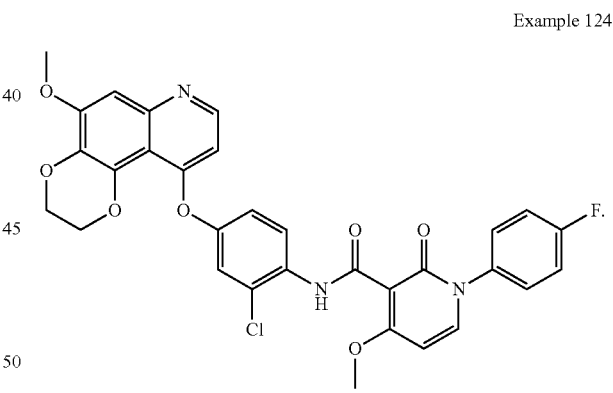

Example 124

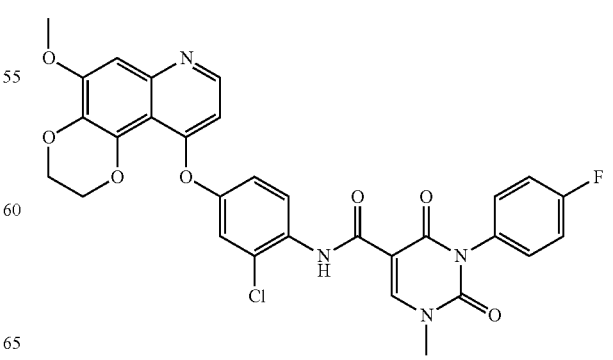

Example 125

149

Example 125: N-(2-chloro-4-((5-methoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-4-((5-methoxy-2,3-dihydro-[1,4]dioxino[2,3-f]quinolin-10-yl)oxy)aniline (36 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (22 mg, yield: 36%); $^1$H NMR (400 MHz, DMSO-$d_6$) δ 11.31 (s, 1H), 8.90 (s, 1H), 8.57-8.45 (m, 2H), 7.45-7.32 (m, 5H), 7.13 (dd, J=9.1, 2.8 Hz, 1H), 7.09 (s, 1H), 6.62 (d, J=5.1 Hz, 1H), 4.34-4.23 (m, 4H), 3.92 (s, 3H), 3.54 (s, 3H). MS: 605 [M+H]$^+$.

Example 126: N-(2-chloro-4-((5-methoxy-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 2-chloro-4-((5-methoxy-2,3-dihydro-[1,4]dioxino[2,3-f]quinolin-10-yl)oxy)aniline (36 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 40%); $^1$H NMR (400 MHz, DMSO-$d_6$) δ 10.97 (s, 1H), 8.49 (d, J=5.1 Hz, 1H), 8.21 (d, J=9.0 Hz, 1H), 7.93 (d, J=7.8 Hz, 1H), 7.55-7.46 (m, 2H), 7.39 (t, J=8.8 Hz, 2H), 7.28 (d, J=2.8 Hz, 1H), 7.13-7.05 (m, 2H), 6.62-6.55 (m, 2H), 4.33-4.28 (m, 6H), 3.93 (s, 3H), 1.36 (t, J=7.0 Hz, 3H). MS: 618 [M+H]+.

Example 126

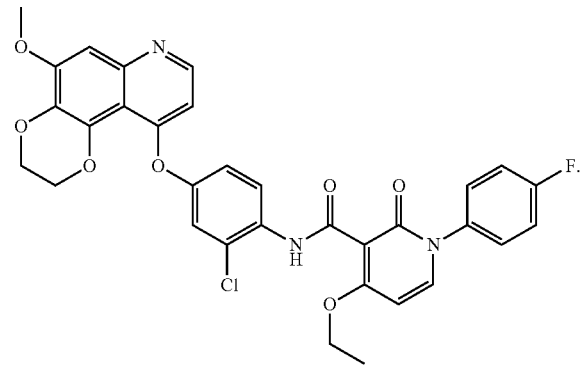

150

-continued

Example 127

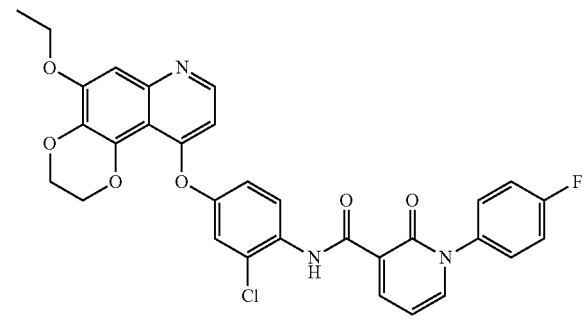

Example 126. Example 127

Example 127: N-(2-chloro-4-((5-ethoxy-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 2-chloro-4-((5-ethoxy-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (21 mg, yield: 36%); $^1$H NMR (400 MHz, DMSO-$d_6$) δ 12.33 (s, 1H), 8.66-8.59 (m, 2H), 8.49 (d, J=5.2 Hz, 1H), 8.14 (dd, J=6.6, 2.2 Hz, 1H), 7.66-7.58 (m, 2H), 7.48-7.39 (m, 2H), 7.37 (d, J=2.8 Hz, 1H), 7.15 (dd, J=9.1, 2.8 Hz, 1H), 7.08 (s, 1H), 6.78-6.69 (m, 1H), 6.63 (d, J=5.2 Hz, 1H), 4.36-4.25 (m, 4H), 4.19 (q, J=6.9 Hz, 2H), 1.42 (t, J=7.0 Hz, 3H). MS: 588 [M+H]$^+$.

Example 128: N-(2-chloro-4-((5-ethoxy-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 2-chloro-4-((5-ethoxy-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (24 mg, yield: 39%); $^1$H NMR (400 MHz, DMSO-$d_6$) δ 11.10 (s, 1H), 8.47 (d, J=5.1 Hz, 1H), 8.26 (d, J=9.0 Hz, 1H), 7.99 (d, J=7.8 Hz, 1H), 7.56-7.47 (m, 2H), 7.39 (t, J=8.8 Hz, 2H), 7.29 (d, J=2.8 Hz, 1H), 7.08 (d, J=8.2 Hz, 2H), 6.64-6.56 (m, 2H), 4.36-4.25 (m, 4H), 4.18 (q, J=7.0 Hz, 2H), 3.98 (s, 3H), 1.41 (t, J=6.9 Hz, 3H). MS: 618 [M+H]$^+$.

Example 128

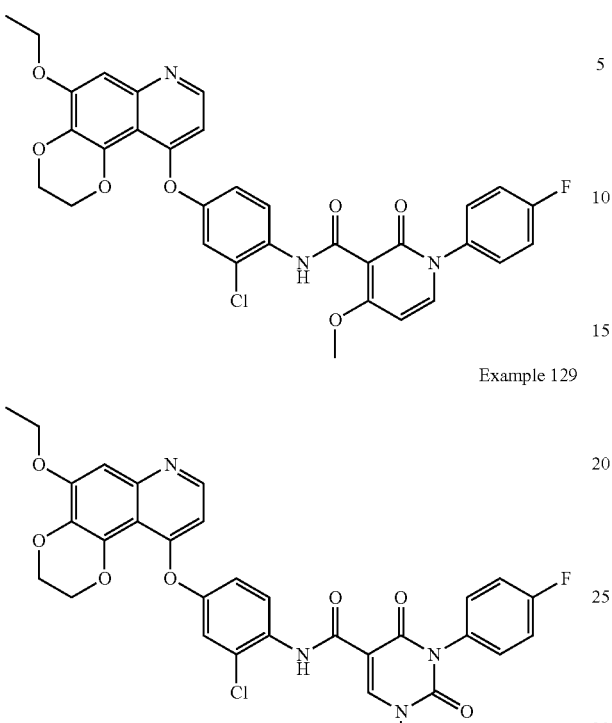

Example 129

Example N-(2-chloro-4-((5-ethoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-4-((5-ethoxy-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 40%); $^1$H NMR (400 MHz, DMSO-$d_6$) δ 11.31 (s, 1H), 8.91 (s, 1H), 8.54 (d, J=9.1 Hz, 1H), 8.47 (d, J=5.1 Hz, 1H), 7.44-7.32 (m, 5H), 7.13 (d, J=9.1 Hz, 1H), 7.07 (s, 1H), 6.60 (d, J=5.1 Hz, 1H), 4.35-4.24 (m, 4H), 4.18 (d, J=7.0 Hz, 2H), 3.54 (s, 3H), 1.41 (t, J=6.9 Hz, 3H). MS: 619 [M+H]$^+$.

Example 130: N-(2-chloro-4-((5-ethoxy-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 2-chloro-4-((5-ethoxy-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 44%); $^1$H NMR (400 MHz, DMSO-$d_6$) δ 10.98 (s, 1H), 8.48 (d, J=5.1 Hz, 1H), 8.21 (d, J=9.0 Hz, 1H), 7.94 (d, J=7.8 Hz, 1H), 7.55-7.47 (m, 2H), 7.39 (dd, J=9.9, 7.7 Hz, 2H), 7.29 (d, J=2.8 Hz, 1H), 7.13-7.06 (m, 1H), 7.07 (s, 1H), 6.58 (dd, J=15.4, 6.5 Hz, 2H), 4.36-4.24 (m, 6H), 4.19 (q, J=6.9 Hz, 2H), 1.43-1.34 (m, 6H). MS: 632 [M+H]$^+$.

Example 130

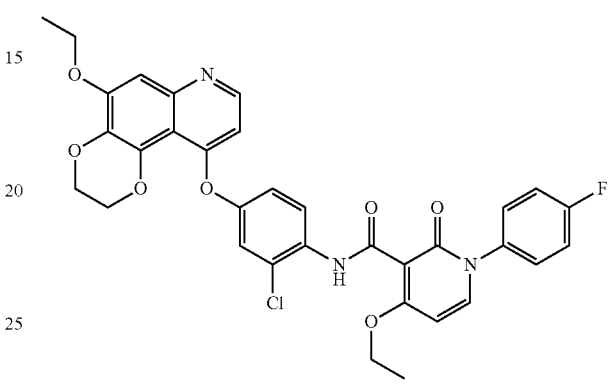

Example 131

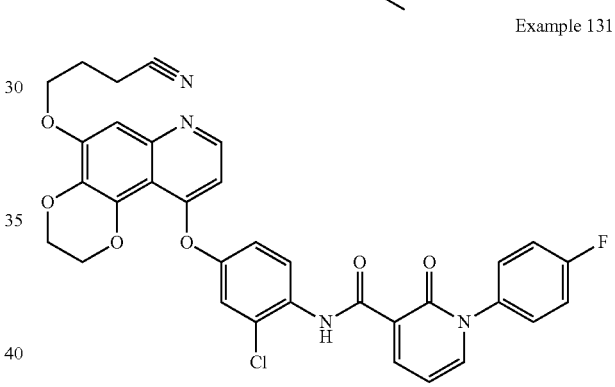

Example 131: N-(2-chloro-4-((5-(3-cyanopropoxy)-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 4-((10-(4-amino-3-chlorophenoxy)-2,3-dihydro-[1,4]dioxino[2,3-f]quinolin-5-yl)oxy)butyronitrile (41 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 45%); $^1$H NMR (400 MHz, DMSO-$d_6$) δ 12.32 (s, 1H), 8.66-8.58 (m, 2H), 8.49 (d, J=5.1 Hz, 1H), 8.14 (dd, J=6.6, 2.2 Hz, 1H), 7.66-7.58 (m, 2H), 7.48-7.39 (m, 2H), 7.35 (d, J=2.8 Hz, 1H), 7.17-7.10 (m, 1H), 7.12 (s, 1H), 6.78-6.69 (m, 1H), 6.64 (d, J=5.1 Hz, 1H), 4.31 (dd, J=17.9, 4.7 Hz, 4H), 4.21 (t, J=6.1 Hz, 2H), 2.69 (t, J=7.2 Hz, 2H), 2.17-2.05 (m, 2H). MS: 627 [M+H]$^+$.

Example 132: N-(2-chloro-4-((5-(3-cyanopropoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 4-((10-(4-amino-3-chlorophenoxy)-2,3-dihydro-[1,4]dioxino[2,3-f]quinolin-5-yl)oxy)butyronitrile (41 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (24 mg, yield: 37%); $^1$H NMR (400 MHz, DMSO-$d_6$) δ 11.10 (s, 1H), 8.49 (d, J=5.2 Hz, 1H), 8.26 (d, J=9.0 Hz, 1H), 7.99 (d, J=7.8 Hz, 1H), 7.56-7.47 (m, 2H), 7.39 (t, J=8.8 Hz, 2H), 7.29 (d, J=2.7 Hz, 1H), 7.14-7.04 (m, 2H), 6.61 (dd, J=10.5, 6.5 Hz, 2H), 4.35-4.28 (m, 4H), 4.21 (t, J=6.1 Hz, 2H), 3.98 (s, 3H), 2.69 (t, J=7.2 Hz, 2H), 2.13 (t, J=6.7 Hz, 2H). MS: 657 [M+H]$^+$.

Example 132

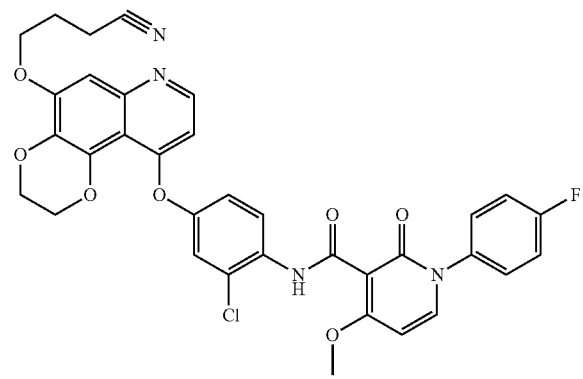

Example 133: N-(2-chloro-4-((5-(3-cyanopropoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 4-((10-(4-amino-3-chlorophenoxy)-2,3-dihydro-[1,4]dioxino[2,3-f]quinolin-5-yl)oxy)butyronitrile (41 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 38%); $^1$H NMR (400 MHz, DMSO-$d_6$) δ 11.31 (s, 1H), 8.91 (s, 1H), 8.54 (d, J=9.2 Hz, 1H), 8.49 (d, J=5.1 Hz, 1H), 7.46-7.31 (m, 5H), 7.18-7.04 (m, 2H), 6.63 (d, J=5.1 Hz, 1H), 4.30 (dd, J=18.0, 4.7 Hz, 4H), 4.21 (t, J=6.2 Hz, 2H), 3.54 (s, 3H), 2.69 (t, J=7.2 Hz, 2H), 2.12 (t, J=6.7 Hz, 2H). MS: 658 [M+H]$^+$.

Example 134: N-(2-chloro-4-((5-(3-cyanopropoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 4-((10-(4-amino-3-chlorophenoxy)-2,3-dihydro-[1,4]dioxino[2,3-f]quinolin-5-yl)oxy)butyronitrile (41 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (26 mg, yield: 39%); $^1$H NMR (400 MHz, DMSO-$d_6$) δ 10.98 (s, 1H), 8.49 (d, J=5.1 Hz, 1H), 8.21 (d, J=9.0 Hz, 1H), 7.93 (d, J=7.8 Hz, 1H), 7.55-7.46 (m, 2H), 7.39 (t, J=8.8 Hz, 2H), 7.29 (d, J=2.8 Hz, 1H), 7.14-7.05 (m, 2H), 6.65-6.52 (m, 2H), 4.31 (dd, J=15.2, 6.0 Hz, 6H), 4.21 (t, J=6.2 Hz, 2H), 2.69 (t, J=7.2 Hz, 2H), 2.12 (dq, J=12.2, 6.1, 5.4 Hz, 2H), 1.36 (t, J=6.9 Hz, 3H). MS: 671 [M+H]$^+$.

Example 133

Example 134

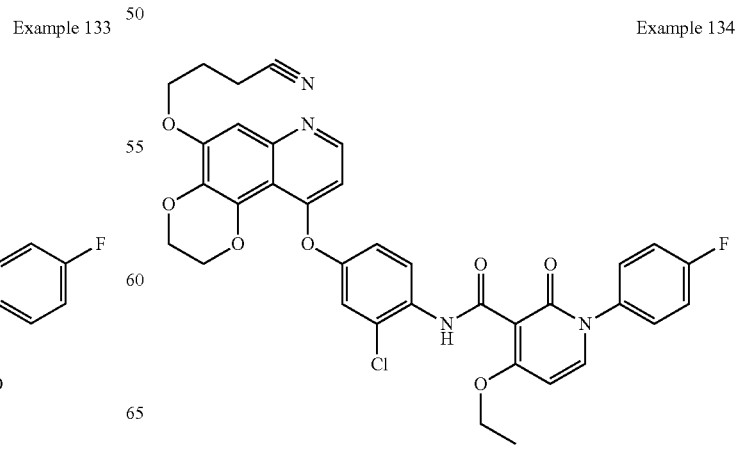

Example 135

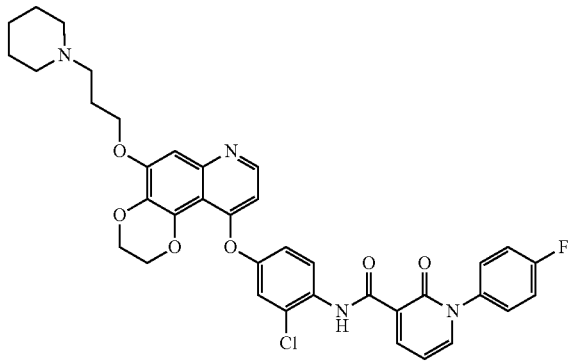

Example N-(2-chloro-4-((5-((3-piperidin-1-yl)propoxy)-2,3-dihydro-[1,4]dioxino[2,3-f]quinolin-10-yl) oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 2-chloro-4-((5-(3-(piperidin-1-yl)propoxy)-2,3-dihydro-[1,4]dioxino[2,3-f]quinolin-10-yl) ox y)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (30 mg, yield: 44%); $^1$H NMR (400 MHz, DMSO-$d_6$) δ 12.32 (s, 1H), 8.66-8.57 (m, 2H), 8.48 (d, J=5.1 Hz, 1H), 8.13 (d, J=6.6 Hz, 1H), 7.64-7.59 (m, 2H), 7.43 (t, J=8.8 Hz, 2H), 7.34 (d, J=2.8 Hz, 1H), 7.12 (dd, J=9.1, 2.8 Hz, 1H), 7.07 (s, 1H), 6.73 (t, J=7.0 Hz, 1H), 6.62 (d, J=5.1 Hz, 1H), 4.29 (dd, J=21.6, 6.0 Hz, 4H), 4.15 (t, J=6.4 Hz, 2H), 2.42 (t, J=7.1 Hz, 2H), 2.36 (s, 4H), 1.99-1.90 (m, 2H), 1.51 (p, J=5.6 Hz, 4H), 1.39 (d, J=6.6 Hz, 2H). MS: 685 [M+H]$^+$.

Example 136: N-(2-chloro-4-((5-((3-piperidin-1-yl)propoxy)-2,3-dihydro-[1,4]dioxino[2,3-f]quinolin-10-yl) oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 2-chloro-4-((5-(3-(piperidin-1-yl)propoxy)-2,3-dihydro-[1,4]dioxino[2,3-f]quinolin-10-yl)ox y)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 37%); $^1$H NMR (400 MHz, DMSO-$d_6$) δ 11.10 (s, 1H), 8.48 (d, J=5.2 Hz, 1H), 8.26 (d, J=9.0 Hz, 1H), 7.99 (d, J=7.8 Hz, 1H), 7.56-7.47 (m, 2H), 7.39 (t, J=8.8 Hz, 2H), 7.28 (d, J=2.8 Hz, 1H), 7.11-7.03 (m, 2H), 6.60 (dd, J=6.5, 4.5 Hz, 2H), 4.36-4.24 (m, 4H), 4.16 (t, J=6.4 Hz, 2H), 3.98 (s, 3H), 2.44 (t, J=7.2 Hz, 2H), 2.37 (s, 4H), 1.95 (t, J=6.9 Hz, 2H), 1.54-1.49 (m, 4H), 1.39 (d, J=6.5 Hz, 2H). MS: 715 [M+H]$^+$.

Example 136

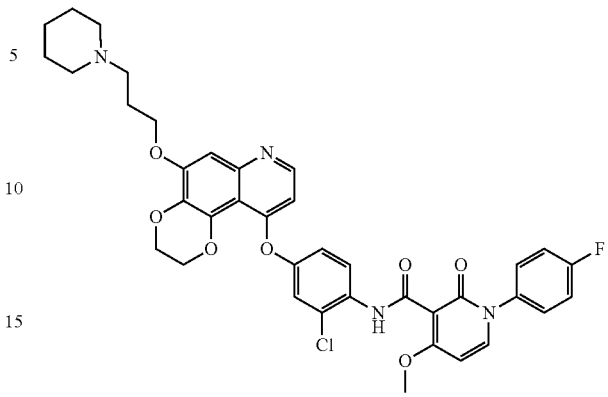

Example 137

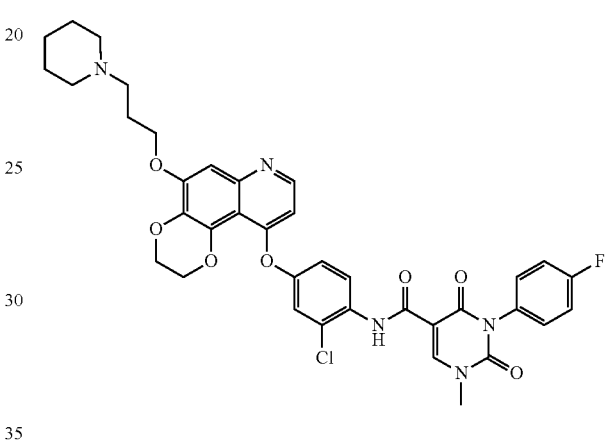

Example 137: N-(2-chloro-4-((5-((3-piperidin-1-yl)propoxy)-2,3-dihydro-[1,4]dioxino[2,3-f]quinolin-10-yl) oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-4-((5-(3-(piperidin-1-yl)propoxy)-2,3-dihydro-[1,4]dioxino[2,3-f] quinolin-10-yl)ox y)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (30 mg, yield: 42%); $^1$H NMR (400 MHz, DMSO-$d_6$) δ 11.31 (s, 1H), 8.90 (s, 1H), 8.57-8.44 (m, 2H), 7.45-7.32 (m, 5H), 7.13 (dd, J=9.1, 2.8 Hz, 1H), 7.10-7.07 (m, 2H), 6.61 (d, J=5.1 Hz, 1H), 4.29 (ddd, J=21.5, 6.1, 3.0 Hz, 4H), 4.15 (t, J=6.4 Hz, 2H), 3.54 (s, 3H), 2.44 (t, J=7.2 Hz, 2H), 2.37 (s, 4H), 1.95 (t, J=6.9 Hz, 2H), 1.54-1.49 (m, 4H), 1.39 (d, J=6.6 Hz, 2H). MS: 716 [M+H]$^+$.

Example 138: N-(2-chloro-4-((5-((3-piperidin-1-yl)propoxy)-2,3-dihydro-[1,4]dioxino[2,3-f]quinolin-10-yl) oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 2-chloro-4-((5-(3-(piperidin-1-yl)propoxy)-2,3-dihydro-[1,4]dioxino[2,3-f]quinolin-10-yl)oxy)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (32 mg, yield: 44%); $^1$H NMR (400 MHz, DMSO-$d_6$) δ 10.98 (s, 1H), 8.48 (d, J=5.1 Hz, 1H), 8.21 (d, J=9.0 Hz, 1H), 7.94 (d, J=7.8 Hz, 1H), 7.55-7.47 (m, 2H), 7.39 (t, J=8.8 Hz, 2H), 7.28 (d, J=2.8 Hz, 1H), 7.07 (s, 1H), 6.59 (dd, J=16.8, 6.5 Hz, 2H), 4.36-4.24 (m, 6H), 4.16 (t, J=6.4 Hz, 2H), 2.43 (t, J=7.2 Hz, 2H), 2.36 (s, 4H), 1.95 (t, J=6.9 Hz, 2H), 1.53-1.48 (m, 4H), 1.40-1.34 (m, 5H). MS: 729 [M+H]$^+$.

Example 138

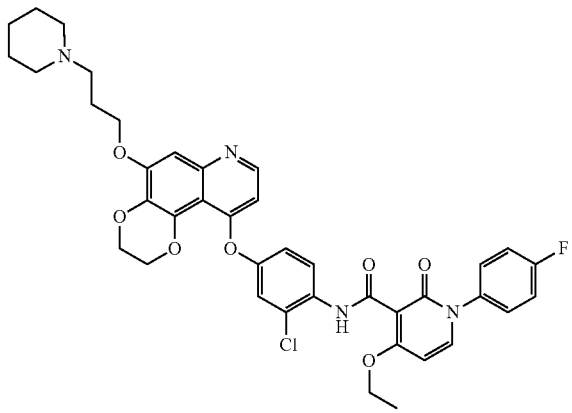

Example 139

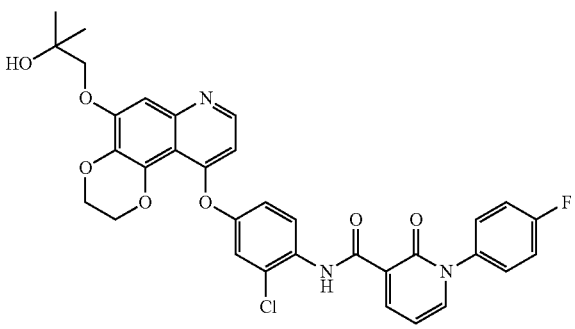

Example 139: N-(2-chloro-4-((5-(2-hydroxy-2-methylpropoxy)-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 2-chloro-4-((5-(2-hydroxy-2-methylpropoxy)-2,3-dihydro-[1,4]dioxino[2,3-f]quinolin-10-yl) oxy)aniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 40%); $^1$H NMR (400 MHz, DMSO-$d_6$) δ 12.32 (s, 1H), 8.66-8.58 (m, 2H), 8.48 (d, J=5.2 Hz, 1H), 8.14 (dd, J=6.6, 2.2 Hz, 1H), 7.66-7.58 (m, 2H), 7.44 (t, J=8.8 Hz, 2H), 7.34 (d, J=2.8 Hz, 1H), 7.13 (dd, J=9.0, 2.8 Hz, 1H), 7.06 (s, 1H), 6.73 (t, J=7.0 Hz, 1H), 6.63 (d, J=5.1 Hz, 1H), 4.70 (s, 1H), 4.31 (ddd, J=24.9, 5.9, 3.1 Hz, 4H), 3.87 (s, 2H), 1.25 (s, 6H). MS: 632 [M+H]$^+$.

Example 140: N-(2-chloro-4-((5-(2-hydroxy-2-methylpropoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 2-chloro-4-((5-(2-hydroxy-2-methylpropoxy)-2,3-dihydro-[1,4]dioxino[2,3-f]quinolin-10-yl) oxy)aniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (30 mg, yield: 45%); $^1$H NMR (400 MHz, DMSO-$d_6$) δ 11.10 (s, 1H), 8.48 (d, J=5.1 Hz, 1H), 8.26 (d, J=9.0 Hz, 1H), 7.99 (d, J=7.7 Hz, 1H), 7.56-7.47 (m, 2H), 7.39 (t, J=8.8 Hz, 2H), 7.28 (d, J=2.8 Hz, 1H), 7.07 (d, J=11.1 Hz, 2H), 6.61 (t, J=6.7 Hz, 2H), 4.70 (s, 1H), 4.38-4.26 (m, 4H), 3.98 (s, 3H), 3.87 (s, 2H), 1.25 (s, 6H). MS: 662 [M+H]$^+$.

Example 140

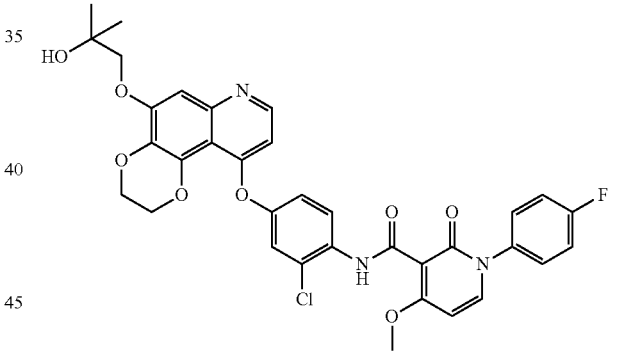

Example 141

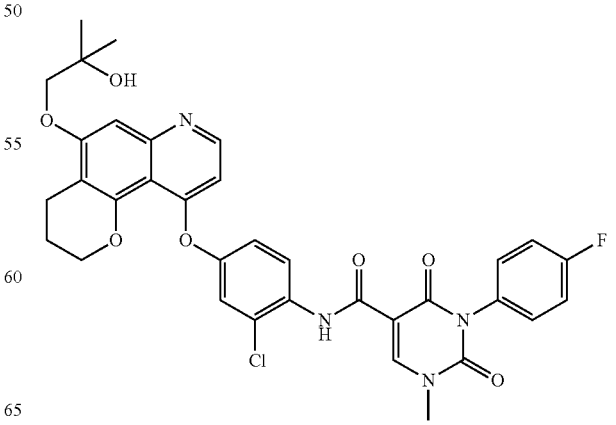

Example 141: N-(2-chloro-4-((5-(2-hydroxy-2-methylpropoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-chloro-4-((5-(2-hydroxy-2-methylpropoxy)-2,3-dihydro-[1,4]dioxino[2,3-f]quinolin-10-yl) oxy)aniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 50%); $^1$H NMR (400 MHz, DMSO-$d_6$) δ 11.30 (s, 1H), 8.90 (s, 1H), 8.57-8.45 (m, 2H), 7.45-7.31 (m, 5H), 7.13 (dd, J=9.1, 2.8 Hz, 1H), 7.06 (s, 1H), 6.62 (d, J=5.1 Hz, 1H), 4.69 (s, 1H), 4.37-4.24 (m, 4H), 3.87 (s, 2H), 3.54 (s, 3H), 1.25 (s, 6H). MS: 663 [M+H]$^+$.

Example 142: N-(2-chloro-4-((5-(2-hydroxy-2-methylpropoxy)-2,3-dihydro-[1,4]dioxino[2,3-f]quinolin-10-yl)oxy)phenyl)-1-(4-fluorophenyl)-4-ethoxy-2-oxo-1,2-dihydropyridine-3-carboxamide A solution of 1-(4-fluorophenyl)-4-ethoxy-2-oxo-1,2-dihydropyridine-3-carbonyl chloride (30 mg, 0.1 mmol) in dichloromethane (0.5 mL) followed by triethylamine (0.1 mL) were added to a solution of 2-chloro-4-((5-(2-hydroxy-2-methylpropoxy)-2,3-dihydro-[1,4]dioxino[2,3-f]quinolin-10-yl) oxy)aniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (29 mg, yield: 43%); $^1$H NMR (400 MHz, DMSO-$d_6$) δ 10.97 (s, 1H), 8.48 (d, J=5.2 Hz, 1H), 8.21 (d, J=9.0 Hz, 1H), 7.93 (d, J=7.8 Hz, 1H), 7.51 (dd, J=8.8, 4.9 Hz, 2H), 7.39 (t, J=8.8 Hz, 2H), 7.28 (d, J=2.8 Hz, 1H), 7.13-7.03 (m, 2H), 6.59 (dd, J=20.2, 6.5 Hz, 2H), 4.69 (s, 1H), 4.42-4.29 (m, 6H), 4.11 (q, J=5.2 Hz, 2H), 1.36 (t, J=7.0 Hz, 3H), 1.26 (s, 6H). MS: 676 [M+H]$^+$.

Example 142

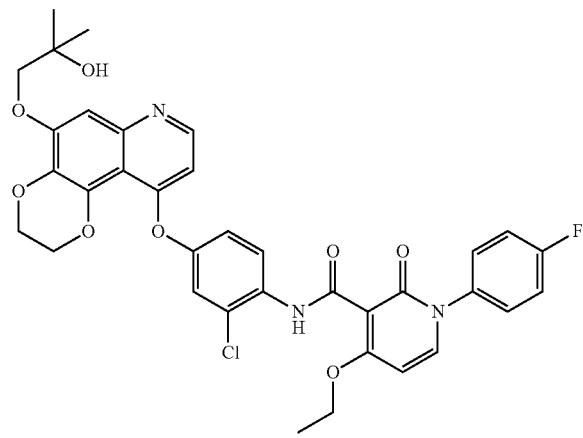

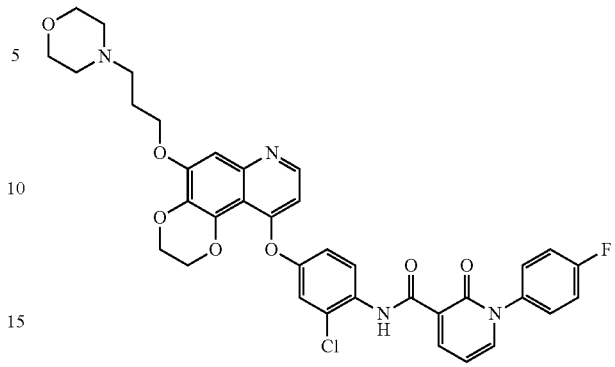

Example 143: N-(2-chloro-4-((5-(3-morpholinopropoxy)-2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 2-chloro-4-((5-(3-morpholinopropoxy)-2,3-dihydro-[1,4]dioxino[2,3-f]quinolin-10-yl) oxy)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 41%); $^1$H NMR (400 MHz, DMSO-$d_6$) δ 12.32 (s, 1H), 8.66-8.58 (m, 2H), 8.48 (d, J=5.1 Hz, 1H), 8.14 (dd, J=6.5, 2.2 Hz, 1H), 7.66-7.57 (m, 2H), 7.44 (t, J=8.8 Hz, 2H), 7.34 (d, J=2.8 Hz, 1H), 7.17-7.06 (m, 2H), 6.73 (t, J=7.0 Hz, 1H), 6.62 (d, J=5.1 Hz, 1H), 4.30 (d, J=21.4 Hz, 4H), 4.17 (t, J=6.4 Hz, 2H), 3.59 (t, J=4.6 Hz, 4H), 2.46 (t, J=7.1 Hz, 2H), 2.39 (s, 4H), 1.96 (t, J=6.9 Hz, 2H). MS: 687 [M+H]$^+$.

Example 144: N-(2-chloro-4-((5-(3-morpholinopropoxy)-2,3-dihydro-[1,4]dioxino[2,3-f]quinolin-10-yl)oxy)phenyl)-1-(4-fluorophenyl)-4-methoxy-2-oxo-1,2-dihydropyridine-3-carboxamide A solution of 1-(4-fluorophenyl)-4-methoxy-2-oxo-1,2-dihydropyridine-3-carbonyl chloride (28 mg, 0.1 mmol) in dichloromethane (0.5 mL) followed by triethylamine (0.1 mL) were added to a solution of 2-chloro-4-((5-(3-morpholinopropoxy)-2,3-dihydro-[1,4]dioxino[2,3-f]quinolin-10-yl)oxy)aniline (47 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (32 mg, yield: 45%); $^1$H NMR (400 MHz, DMSO-$d_6$) δ 11.10 (s, 1H), 8.48 (d, J=5.1 Hz, 1H), 8.26 (d, J=9.0 Hz, 1H), 7.99 (d, J=7.8 Hz, 1H), 7.52 (dd, J=8.9, 4.9 Hz, 2H), 7.39 (t, J=8.8 Hz, 2H), 7.28 (d, J=2.7 Hz, 1H), 7.09-7.06 (m, 2H), 6.64-6.56 (m, 2H), 4.36-4.24 (m, 4H), 4.17 (t, J=6.4 Hz, 2H), 3.98 (s, 3H), 3.59 (t, J=4.6 Hz, 4H), 2.50-2.35 (m, 6H), 1.96 (t, J=6.9 Hz, 2H). MS: 717 [M+H]$^+$.

Example 144

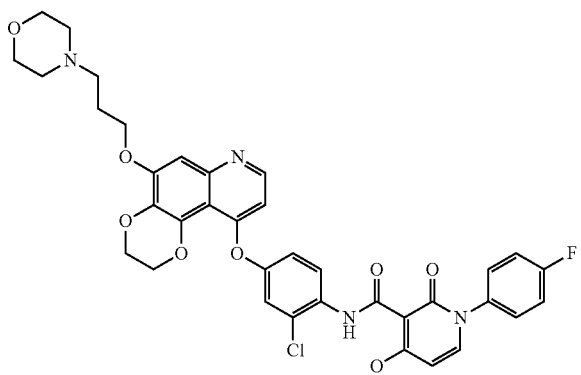

Example 145

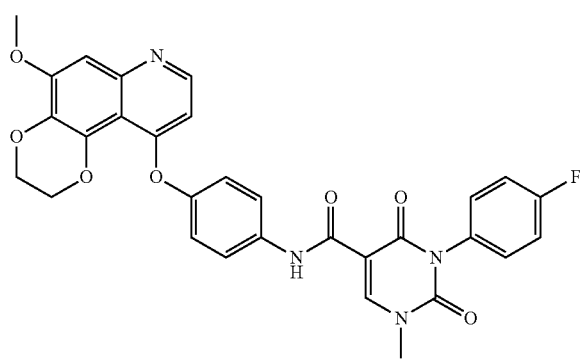

Example 145: N-(4-((5-methoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 4-((5-methoxy-2,3-dihydro-[1,4]dioxino[2,3-f]quinolin-10-yl)oxy)aniline (33 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (21 mg, yield: 37%); $^1$H NMR (400 MHz, DMSO-d$_6$) δ 10.88 (s, 1H), 8.86 (s, 1H), 8.44 (d, J=5.2 Hz, 1H), 7.78-7.71 (m, 2H), 7.44-7.32 (m, 4H), 7.14-7.05 (m, 3H), 6.49 (d, J=5.2 Hz, 1H), 4.31 (q, J=5.0 Hz, 4H), 3.92 (s, 3H), 3.53 (s, 3H). MS: 571 [M+H]$^+$.

Example 146: N-(4-((5-methoxy-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((5-methoxy-2,3-dihydro-[1,4]dioxino[2,3-f]quinolin-10-yl)oxy)aniline (33 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 43%); $^1$H NMR (400 MHz, DMSO-d$_6$) δ 10.89 (s, 1H), 8.86 (s, 1H), 8.43 (d, J=5.1 Hz, 1H), 7.78-7.71 (m, 2H), 7.47-7.31 (m, 4H), 7.14-7.04 (m, 3H), 6.49 (d, J=5.2 Hz, 1H), 4.31 (tt, J=5.0, 3.3 Hz, 4H), 4.01 (q, J=7.1 Hz, 2H), 3.92 (s, 3H), 1.29 (t, J=7.1 Hz, 3H). MS: 585 [M+H]$^+$.

Example 146

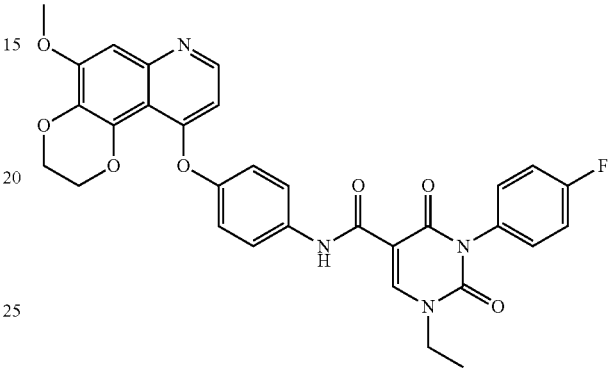

Example 147

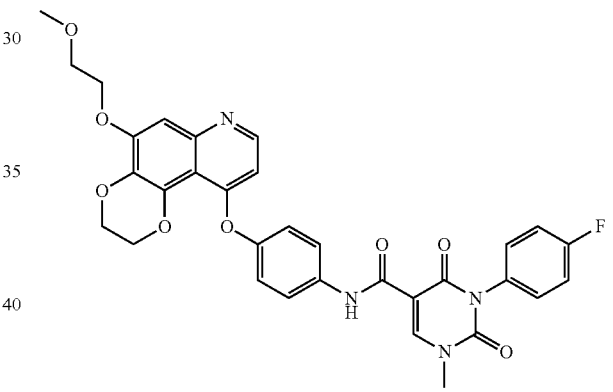

Example 147: N-(4-((5-(2-methoxyethoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 4-((5-(2-methoxyethoxy)-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (27 mg, yield: 44%); $^1$H NMR (400 MHz, DMSO-d$_6$) δ 10.88 (s, 1H), 8.86 (s, 1H), 8.43 (d, J=5.2 Hz, 1H), 7.78-7.71 (m, 2H), 7.44-7.32 (m, 4H), 7.14-7.05 (m, 3H), 6.48 (d, J=5.2 Hz, 1H), 4.37-4.21 (m, 6H), 3.78-3.70 (m, 2H), 3.53 (s, 3H), 3.35 (s, 3H). MS: 615 [M+H]$^+$.

Example 148: N-(4-((5-(2-methoxyethoxy)-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((5-(2-methoxyethoxy)-2,3-dihydro-[1,4]dioxino[2,3-f]quinolin-10-yl)oxy)aniline (37 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (21 mg, yield: 33%); $^1$H NMR (400 MHz, DMSO-$d_6$) δ 10.89 (s, 1H), 8.86 (s, 1H), 8.43 (d, J=5.2 Hz, 1H), 7.78-7.71 (m, 2H), 7.47-7.31 (m, 4H), 7.14-7.05 (m, 3H), 6.48 (d, J=5.2 Hz, 1H), 4.36-4.27 (m, 4H), 4.27-4.20 (m, 2H), 4.01 (d, J=7.1 Hz, 2H), 3.78-3.70 (m, 2H), 3.35 (s, 3H), 1.29 (t, J=7.1 Hz, 3H). MS: 629 [M+H]$^+$.

Example 149: N-(4-((5-(2-hydroxy-2-methylpropoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 4-((5-(2-hydroxy-2-methylpropoxy)-2,3-dihydro-[1,4]dioxino[2,3-f]quinolin-10-yl)oxy)aniline (39 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (31 mg, yield: 48%); $^1$H NMR (400 MHz, DMSO-$d_6$) δ 10.88 (s, 1H), 8.86 (s, 1H), 8.43 (d, J=5.2 Hz, 1H), 7.81-7.66 (m, 2H), 7.48-7.30 (m, 4H), 7.16-7.06 (m, 2H), 7.03 (s, 1H), 6.48 (d, J=5.2 Hz, 1H), 4.69 (s, 1H), 4.42-4.21 (m, 4H), 3.86 (s, 2H), 3.53 (s, 3H), 1.25 (s, 6H). MS: 629 [M+H]$^+$.

Example 150: N-(4-((5-(2-hydroxy-2-methylpropoxy)-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((5-(2-hydroxy-2-methylpropoxy)-2,3-dihydro-[1,4]dioxino[2,3-f]quinolin-10-yl)oxy)aniline (39 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (30 mg, yield: 47%); $^1$H NMR (400 MHz, DMSO-$d_6$) δ 10.88 (s, 1H), 8.86 (s, 1H), 8.43 (d, J=5.2 Hz, 1H), 7.80-7.70 (m, 2H), 7.49-7.30 (m, 4H), 7.16-7.06 (m, 2H), 7.03 (s, 1H), 6.49 (d, J=5.1 Hz, 1H), 4.69 (s, 1H), 4.41-4.25 (m, 4H), 4.01 (d, J=7.2 Hz, 2H), 3.86 (s, 2H), 1.31-1.25 (m, 9H). MS: 643 [M+H]$^+$.

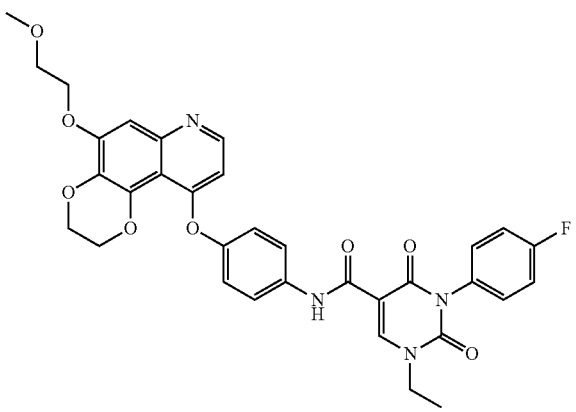

Example 148

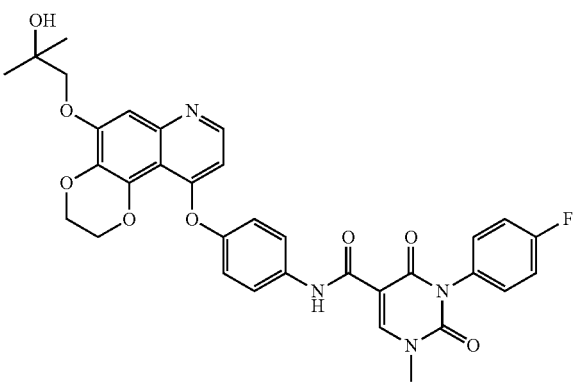

Example 149

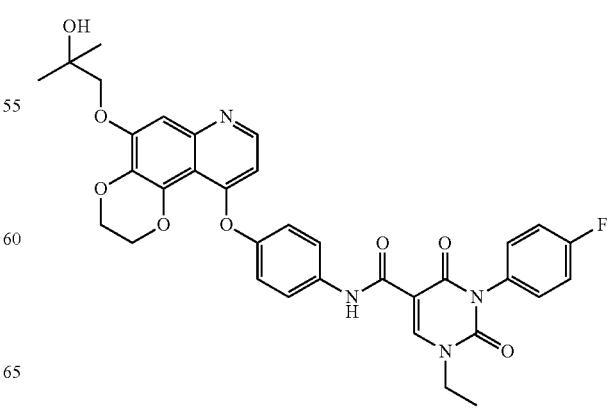

Example 150

Example 151

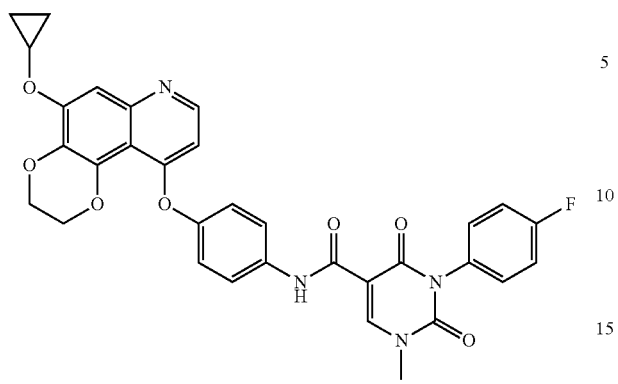

Example 152

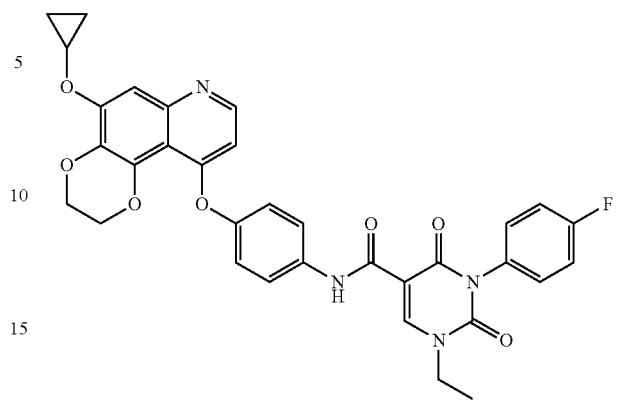

Example 153

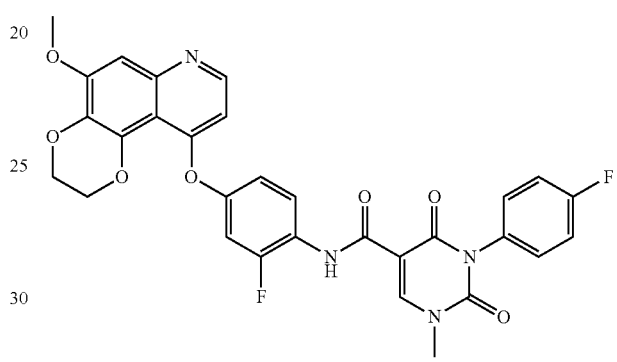

Example 151: N-(4-((5-cyclopropyloxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 4-((5-cyclopropyloxy-2,3-dihydro-[1,4]dioxino[2,3-f]quinolin-10-yl)oxy) aniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (20 mg, yield: 36%); $^1$H NMR (400 MHz, DMSO-$d_6$) δ 10.88 (s, 1H), 8.85 (s, 1H), 8.44 (d, J=5.2 Hz, 1H), 7.78-7.70 (m, 2H), 7.43-7.38 (m, 3H), 7.36 (s, 2H), 7.10 (d, J=8.9 Hz, 2H), 6.50 (d, J=5.2 Hz, 1H), 4.31-4.28 (m, 4H), 4.01 (dt, J=6.1, 3.1 Hz, 1H), 3.53 (s, 3H), 0.88 (d, J=6.1 Hz, 2H), 0.76 (s, 2H). MS: 597 [M+H]$^+$.

Example 152: N-(4-((5-cyclopropyloxy-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((5-cyclopropyloxy-2,3-dihydro-[1,4]dioxino[2,3-f]quinolin-10-yl)oxy) aniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (18 mg, yield: 29%); $^1$H NMR (400 MHz, DMSO-$d_6$) δ 10.88 (s, 1H), 8.86 (s, 1H), 8.44 (d, J=5.2 Hz, 1H), 7.74 (d, J=8.9 Hz, 2H), 7.43 (dd, J=8.8, 5.2 Hz, 2H), 7.39-7.35 (m, 3H), 7.10 (d, J=8.9 Hz, 2H), 6.50 (d, J=5.1 Hz, 1H), 4.30 (s, 4H), 4.04-4.00 (m, 3H), 1.29 (t, J=7.1 Hz, 3H), 0.89 (d, J=6.6 Hz, 2H), 0.76 (s, 2H). MS: 611 [M+H]$^+$.

Example 153: N-(2-fluoro-4-((5-methoxy-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-fluoro-4-((5-methoxy-2,3-dihydro-[1,4]dioxino[2,3-f]quinolin-10-yl)oxy)aniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 43%); $^1$H NMR (400 MHz, DMSO-$d_6$) δ 11.10 (d, J=2.4 Hz, 1H), 8.89 (s, 1H), 8.49 (d, J=5.1 Hz, 1H), 8.40 (t, J=9.0 Hz, 1H), 7.45-7.32 (m, 4H), 7.19 (dd, J=11.9, 2.7 Hz, 1H), 7.09 (s, 1H), 6.99-6.91 (m, 1H), 6.63 (d, J=5.1 Hz, 1H), 4.35-4.23 (m, 4H), 3.92 (s, 3H), 3.54 (s, 3H). MS: 589 [M+H]$^+$.

Example 154: N-(2-fluoro-4-((5-methoxy-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 2-fluoro-4-((5-methoxy-2,3-dihydro-[1,4]dioxino[2,3-f]quinolin-10-yl)

oxy)aniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (22 mg, yield: 37%); $^1$H NMR (400 MHz, DMSO-$d_6$) δ 11.10 (d, J=2.4 Hz, 1H), 8.89 (s, 1H), 8.49 (d, J=5.1 Hz, 1H), 8.39 (t, J=9.0 Hz, 1H), 7.47-7.38 (m, 2H), 7.41-7.31 (m, 2H), 7.19 (dd, J=11.8, 2.7 Hz, 1H), 7.09 (s, 1H), 6.99-6.91 (m, 1H), 6.63 (d, J=5.1 Hz, 1H), 4.35-4.23 (m, 4H), 4.02 (q, J=7.1 Hz, 2H), 3.92 (s, 3H), 1.29 (t, J=7.1 Hz, 3H). MS: 603 [M+H]$^+$.

1H), 6.62 (d, J=5.1 Hz, 1H), 4.36-4.21 (m, 6H), 3.77-3.70 (m, 2H), 3.54 (s, 3H), 3.36 (s, 3H). MS: 633 [M+H]$^+$.

Example 156: N-(2-fluoro-4-((5-(2-methoxy-ethoxy)-2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 2-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (24 mg, yield: 37%); $^1$H NMR (400 MHz, DMSO-$d_6$) δ 11.11 (d, J=2.4 Hz, 1H), 8.89 (s, 1H), 8.49 (d, J=5.2 Hz, 1H), 8.40 (t, J=9.0 Hz, 1H), 7.47-7.31 (m, 4H), 7.21 (dd, J=11.8, 2.7 Hz, 1H), 7.10 (s, 1H), 6.97 (dd, J=8.9, 2.5 Hz, 1H), 6.64 (d, J=5.2 Hz, 1H), 4.37-4.22 (m, 6H), 4.02 (q, J=7.1 Hz, 2H), 3.78-3.71 (m, 2H), 3.40-3.32 (m, 3H), 1.29 (t, J=7.1 Hz, 3H). MS: 647 [M+H]$^+$.

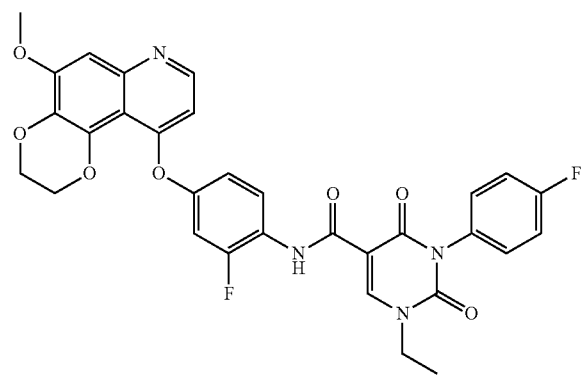

Example 154

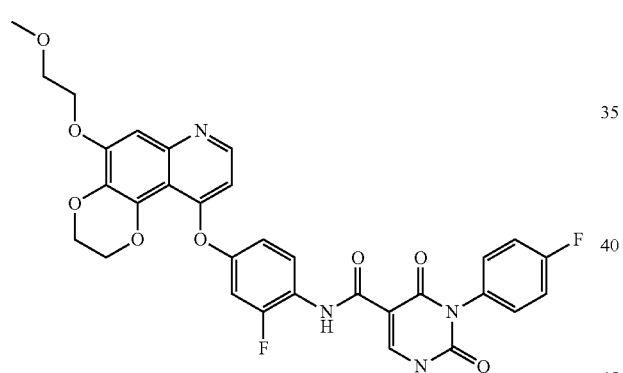

Example 155

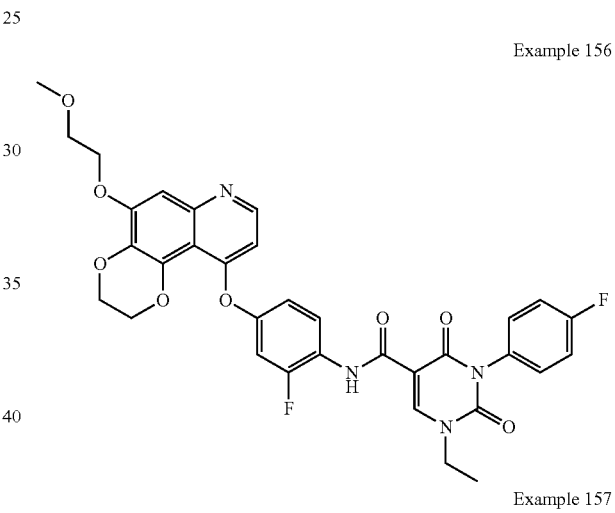

Example 156

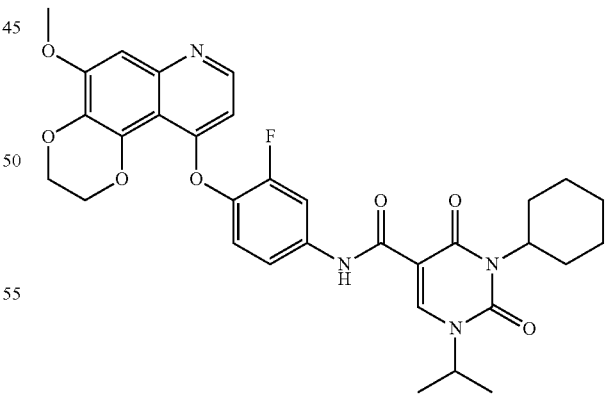

Example 157

Example 155: N-(2-fluoro-4-((5-(2-methoxy-ethoxy)-2,3-dihydro-[1,4]dioxino[2,3-f]quinolin-10-yl)oxy)phenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (28 mg, 0.1 mmol) in dichloromethane (0.5 mL) followed by triethylamine (0.1 mL) were added to a solution of 2-fluoro-4-((5-(2-methoxyethoxy)-2,3-dihydro-[1,4]dioxino[2,3-f]quinolin-10-yl)oxy)aniline (39 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (26 mg, yield: 41%); $^1$H NMR (400 MHz, DMSO-$d_6$) δ 11.10 (d, J=2.4 Hz, 1H), 8.89 (s, 1H), 8.48 (d, J=5.1 Hz, 1H), 8.40 (t, J=9.0 Hz, 1H), 7.45-7.32 (m, 4H), 7.19 (dd, J=11.9, 2.7 Hz, 1H), 7.10 (s, 1H), 6.96 (dd, J=9.9, 1.8 Hz, Example 157: N-(3-fluoro-4-((5-methoxy-2,3-dihydro-[1,4]dioxino[2,3-f]quinolin-10-yl)oxy)phenyl)-3-cyclohexyl-1-isopropyl-2,4-dioxo-1,2,3,4-tetrahydropyrimidine-5-carboxamide A solution of 3-cyclohexyl-1-isopropyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 3-fluoro-4-((5-methoxy-2,3-dihydro-[1,4]dioxino[2,3-f]quinolin-10-yl)oxy)aniline (34 mg, 0.1 mmol) in anhydrous DMF (1 mL), and reacted with stirring at room temperature for 5 hours. The reaction solution was quenched with water, and filtered to afford a light-yellow solid. The solid was purified by preparative liquid chromatography to afford a white solid product (26 mg, yield: 43%); $^1$H NMR (400 MHz, DMSO-$d_6$) δ 11.17 (s, 1H), 8.52 (s, 1H), 8.46 (d, J=5.3 Hz, 1H), 7.98 (dd, J=13.0, 2.5 Hz, 1H), 7.48 (dd, J=9.0, 2.5 Hz, 1H), 7.27 (t, J=9.0 Hz, 1H), 7.09 (s, 1H), 6.51 (d, J=5.2 Hz, 1H), 4.80-4.72 (m, 2H), 4.34 (s, 4H), 3.93 (s, 3H), 2.38-2.30 (m, 2H), 1.83-1.80 (m, 2H), 1.69-1.53 (m, 4H), 1.37-1.35 (m, 6H), 1.21-1.11 (m, 2H). MS: 605 [M+H]$^+$.

Example 158: N-(4-((2,3-dihydro-[1,4]dioxino[2,3-f]quinolin-10-yl)oxy)phenyl)-3-(4-fluorophenyl)-1-meth yl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)aniline (30 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 45%); $^1$H NMR (400 MHz, DMSO-$d_6$) δ 10.89 (s, 1H), 8.86 (s, 1H), 8.49 (d, J=5.1 Hz, 1H), 7.79-7.72 (m, 2H), 7.53 (d, J=9.1 Hz, 1H), 7.44-7.34 (m, 5H), 7.17-7.10 (m, 2H), 6.60 (d, J=5.1 Hz, 1H), 4.35-4.28 (m, 4H), 3.53 (s, 3H). MS: 541 [M+H]$^+$.

Example 159: N-(4-((2,3-dihydro-[1,4]dioxino[2,3-f]quinolin-10-yl)oxy)phenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)aniline (30 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 45%); $^1$H NMR (400 MHz, DMSO-$d_6$) δ 10.90 (s, 1H), 8.87 (s, 1H), 8.49 (d, J=5.1 Hz, 1H), 7.80-7.72 (m, 2H), 7.53 (d, J=9.1 Hz, 1H), 7.43-7.35 (m, 5H), 7.17-7.10 (m, 2H), 6.60 (d, J=5.1 Hz, 1H), 4.32 (q, J=4.8 Hz, 4H), 4.01 (d, J=7.1 Hz, 2H), 1.29 (t, J=7.1 Hz, 3H). MS: 555 [M+H]$^+$.

Example 160: N-(4-((2,3-dihydro-[1,4]dioxino[2,3-f]quinolin-10-yl)oxy)-3-fluorophenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-3-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 45%); $^1$H NMR (400 MHz, DMSO-$d_6$) δ 11.01 (s, 1H), 8.89 (s, 1H), 8.49 (d, J=5.1 Hz, 1H), 7.98 (dd, J=12.9, 2.5 Hz, 1H), 7.57-7.45 (m, 2H), 7.44-7.34 (m, 5H), 7.29 (t, J=9.0 Hz, 1H), 6.59 (d, J=5.1 Hz, 1H), 4.36 (s, 4H), 3.54 (s, 3H). MS: 559 [M+H]$^+$.

Example 158

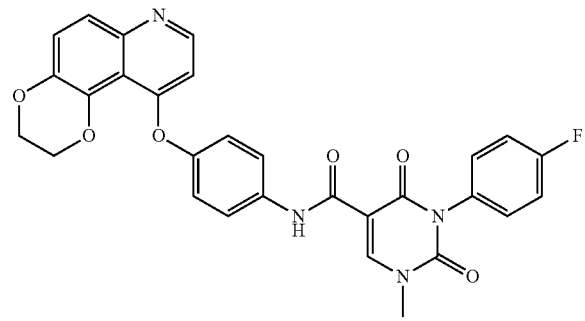

Example 159

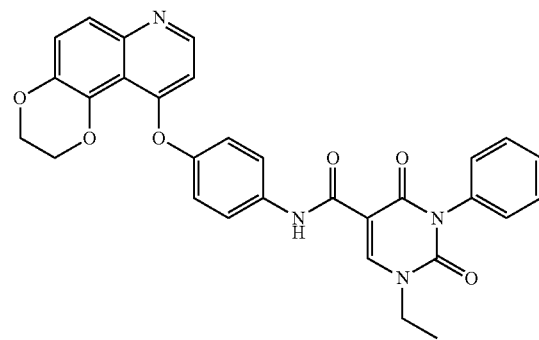

Example 160

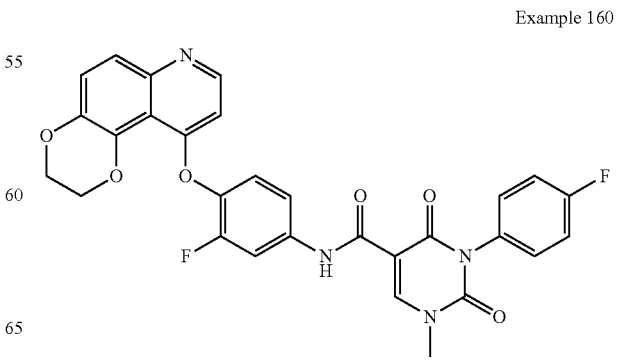

Example 161

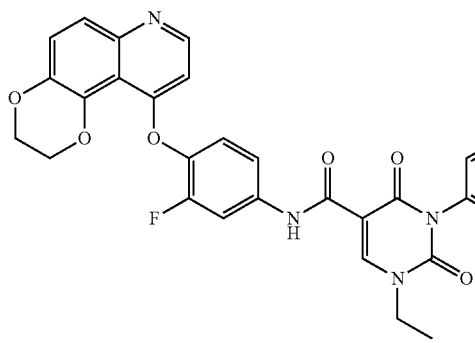

Example 161: N-(4-((2,3-dihydro-[1,4]dioxino[2,3-f]quinolin-10-yl)oxy)-3-fluorophenyl)-3-(4-fluorophenyl)-1-ethyl-2,4-dioxo-1,2,3,4-tetrahydropyrimidine-5-carboxamide

A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-3-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (38 mg, yield: 66%); $^1$H NMR (400 MHz, DMSO-$d_6$) δ 11.02 (s, 1H), 8.89 (s, 1H), 8.49 (d, J=5.1 Hz, 1H), 7.98 (dd, J=13.0, 2.5 Hz, 1H), 7.52 (dd, J=16.5, 8.7 Hz, 2H), 7.47-7.24 (m, 6H), 6.59 (d, J=5.1 Hz, 1H), 4.36 (s, 4H), 4.02 (q, J=7.1 Hz, 2H), 1.29 (t, J=7.1 Hz, 3H). MS: 573 [M+H]$^+$.

Example 162: N-(4-((2,3-dihydro-[1,4]dioxino[2,3-f]quinolin-10-yl)oxy)-2-fluorophenyl)-3-(4-fluorophenyl)-1-methyl-2,4-dioxo-1,2,3,4-tetrahydropyrimidine-5-carboxamide

A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-2-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 50%); $^1$H NMR (400 MHz, DMSO-$d_6$) δ 11.12 (s, 1H), 8.89 (s, 1H), 8.54 (d, J=5.0 Hz, 1H), 8.42 (t, J=9.0 Hz, 1H), 7.55 (d, J=9.1 Hz, 1H), 7.45-7.34 (m, 5H), 7.23 (dd, J=11.8, 2.7 Hz, 1H), 7.03-6.95 (m, 1H), 6.75 (d, J=5.0 Hz, 1H), 4.36-4.25 (m, 4H), 3.54 (s, 3H). MS: 559 [M+H]$^+$.

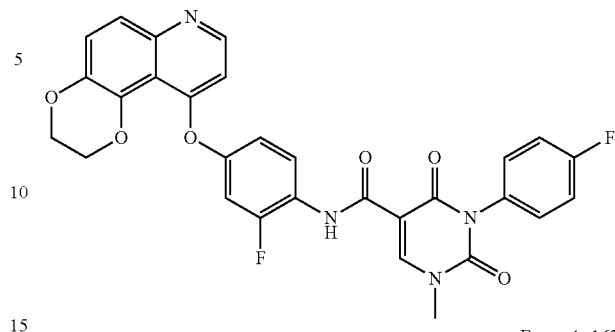

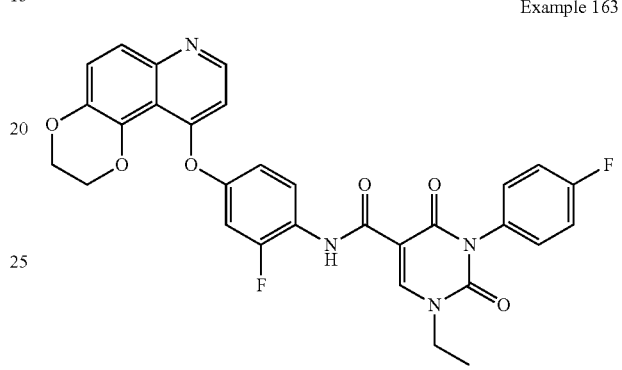

Example 163: N-(4-((2,3-dihydro-[1,4]dioxino[2,3-f]quinolin-10-yl)oxy)-2-fluorophenyl)-3-(4-fluorophenyl)-1-ethyl-2,4-dioxo-1,2,3,4-tetrahydropyrimidine-5-carboxamide

A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-2-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (32 mg, yield: 56%); $^1$H NMR (400 MHz, DMSO-$d_6$) δ 11.12 (d, J=2.4 Hz, 1H), 8.90 (s, 1H), 8.54 (d, J=5.0 Hz, 1H), 8.41 (t, J=9.0 Hz, 1H), 7.55 (d, J=9.1 Hz, 1H), 7.47-7.31 (m, 5H), 7.23 (dd, J=11.8, 2.7 Hz, 1H), 6.98 (dt, J=8.9, 1.9 Hz, 1H), 6.75 (d, J=5.0 Hz, 1H), 4.36-4.25 (m, 4H), 4.02 (d, J=7.2 Hz, 2H), 1.29 (t, J=7.1 Hz, 3H). MS: 573 [M+H]$^+$.

Example 164: N-(4-((2,3-dihydro-[1,4]dioxino[2,3-f]quinolin-10-yl)oxy)phenyl)-4-ethoxy-1-(4-fluorophenyl)-2-oxo-1,2-dihydropyridine-3-carboxamide

A solution of 4-ethoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)aniline (30 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (35 mg, yield: 63%);

¹H NMR (400 MHz, DMSO-d₆) δ 10.35 (s, 1H), 8.46 (d, J=5.1 Hz, 1H), 7.85 (d, J=7.8 Hz, 1H), 7.81-7.74 (m, 2H), 7.56-7.42 (m, 3H), 7.42-7.33 (m, 3H), 7.16-7.09 (m, 2H), 6.53 (dd, J=16.7, 6.5 Hz, 2H), 4.35 (s, 4H), 4.26 (q, J=7.0 Hz, 2H), 1.30 (t, J=7.0 Hz, 3H). MS: 554 [M+H]⁺.

Example 164

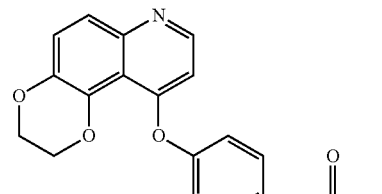

Example 165

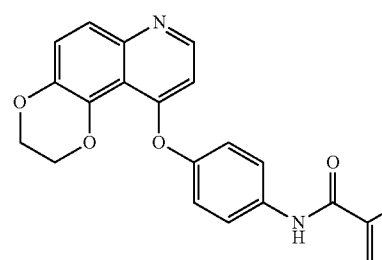

Example N-(4-((2,3-dihydro-[1,4]dioxino[2,3-f]quinolin-10-yl)oxy)phenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)aniline (30 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (28 mg, yield: 55%); ¹H NMR (400 MHz, DMSO-d₆) δ 11.98 (s, 1H), 8.59 (dd, J=7.3, 2.2 Hz, 1H), 8.50 (d, J=5.1 Hz, 1H), 8.12 (dd, J=6.6, 2.2 Hz, 1H), 7.83-7.76 (m, 2H), 7.66-7.57 (m, 2H), 7.53 (d, J=9.1 Hz, 1H), 7.48-7.35 (m, 3H), 7.17-7.10 (m, 2H), 6.72 (t, J=6.9 Hz, 1H), 6.61 (d, J=5.0 Hz, 1H), 4.33 (q, J=5.0 Hz, 4H). MS: 510 [M+H]⁺.

Example 166: N-(4-((2,3-dihydro-[1,4]dioxino[2,3-f]quinolin-10-yl)oxy)phenyl)-4-methoxy-1-(4-fluorophenyl)-2-oxo-1,2-dihydropyridine-3-carboxamide A solution of 4-methoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)aniline (30 mg, 0.1 mmol) in anhydrous DMF (0.5 mL) and reacted with stirring at room temperature for 5 hours. The reaction solution was quenched with water, and filtered to afford a light-yellow solid. The solid was purified by preparative liquid chromatography to afford a white solid product (33 mg, yield: 61%); ¹H NMR (400 MHz, DMSO-d₆) δ 10.40 (s, 1H), 8.46 (d, J=5.1 Hz, 1H), 7.89 (d, J=7.8 Hz, 1H), 7.78 (d, J=8.9 Hz, 2H), 7.59-7.44 (m, 2H), 7.38 (dd, J=9.0, 2.6 Hz, 2H), 7.32-7.21 (m, 2H), 7.12 (d, J=8.9 Hz, 1H), 7.05-6.98 (m, 1H), 6.54 (dd, J=6.5, 4.3 Hz, 2H), 4.35 (s, 4H), 3.92 (s, 3H). MS: 540 [M+H]⁺.

Example 166

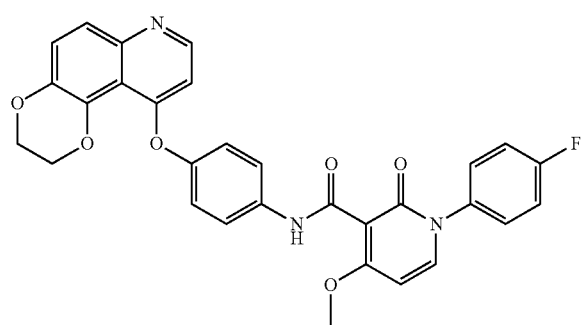

Example 167

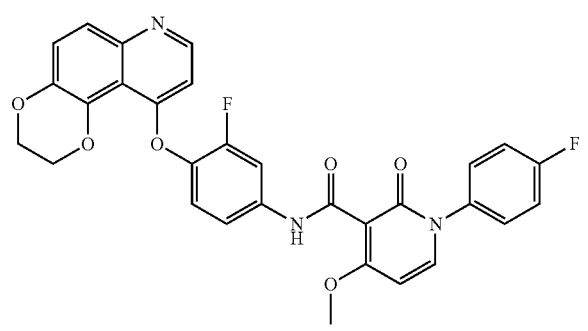

Example 167: N-(4-((2,3-dihydro-[1,4]dioxino[2,3-f]quinolin-10-yl)oxy)-3-fluorophenyl)-1-(4-fluorophenyl)-4-methoxy-2-oxo-1,2-dihydropyridine-3-carboxamide A solution of 4-methoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-3-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (31 mg, yield: 56%); ¹H NMR (400 MHz, DMSO-d₆) δ 10.62 (s, 1H), 8.46 (d, J=5.1 Hz, 1H), 7.97-7.87 (m, 2H), 7.53 (d, J=9.1 Hz, 1H), 7.51-7.43 (m, 3H), 7.44-7.33 (m, 3H), 7.30 (t, J=9.0 Hz, 1H), 6.59-6.51 (m, 2H), 4.38 (d, J=3.5 Hz, 4H), 3.93 (s, 3H). MS: 558 [M+H]⁺.

Example 168: N-(4-((2,3-dihydro-[1,4]dioxino[2,3-f]quinolin-10-yl)oxy)-3-fluorophenyl)-1-(4-fluorophenyl)-4-ethoxy-2-oxo-1,2-dihydropyridine-3-carboxamide A solution of 4-ethoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-3-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (35 mg, yield: 61%); $^1$H NMR (400 MHz, DMSO-d$_6$) δ 10.58 (s, 1H), 8.48 (d, J=5.1 Hz, 1H), 7.97-7.83 (m, 2H), 7.58-7.26 (m, 8H), 6.55 (dd, J=21.5, 6.5 Hz, 2H), 4.38 (s, 4H), 4.27 (t, J=7.0 Hz, 2H), 1.31 (t, J=7.0 Hz, 3H). MS:572 [M+H]$^+$.

Example 168

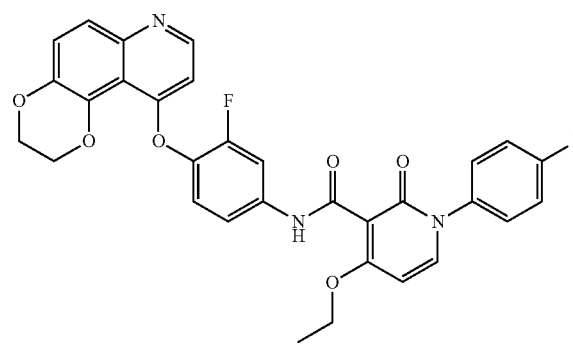

Example 169

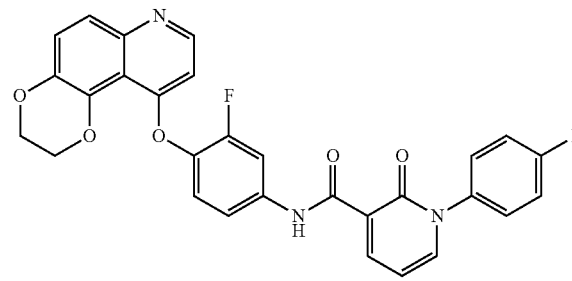

Example 169: N-(4-((2,3-dihydro-[1,4]dioxino[2,3-f]quinolin-10-yl)oxy)-3-fluorophenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-3-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 63%); $^1$H NMR (400 MHz, DMSO-d$_6$) δ 12.11 (s, 1H), 8.59 (dd, J=7.3, 2.2 Hz, 1H), 8.50 (d, J=5.1 Hz, 1H), 8.14 (dd, J=6.6, 2.2 Hz, 1H), 8.04 (dd, J=13.0, 2.4 Hz, 1H), 7.66-7.58 (m, 2H), 7.58-7.37 (m, 5H), 7.29 (t, J=9.0 Hz, 1H), 6.74 (t, J=6.9 Hz, 1H), 6.60 (d, J=5.1 Hz, 1H), 4.36 (s, 4H). MS: 528 [M+H]$^+$.

Example 170: N-(4-((2,3-dihydro-[1,4]dioxino[2,3-f]quinolin-10-yl)oxy)-2-fluorophenyl)-1-(4-fluorophenyl)-2-oxo-1,2-dihydropyridine-3-carboxamide A solution of 1-(4-fluorophenyl)-2-oxo-1,2-dihydropyridine-3-carbonyl chloride (25 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-2-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (26 mg, yield: 49%); $^1$H NMR (400 MHz, DMSO-d$_6$) δ 12.22 (s, 1H), 8.61 (dd, J=7.3, 2.2 Hz, 1H), 8.57-8.47 (m, 2H), 8.14 (dd, J=6.6, 2.2 Hz, 1H), 7.66-7.57 (m, 2H), 7.55 (d, J=9.1 Hz, 1H), 7.49-7.36 (m, 3H), 7.23 (dd, J=11.8, 2.7 Hz, 1H), 6.98 (dt, J=8.8, 1.8 Hz, 1H), 6.79-6.70 (m, 2H), 4.36-4.26 (m, 4H). MS: 528 [M+H]$^+$.

Example 170

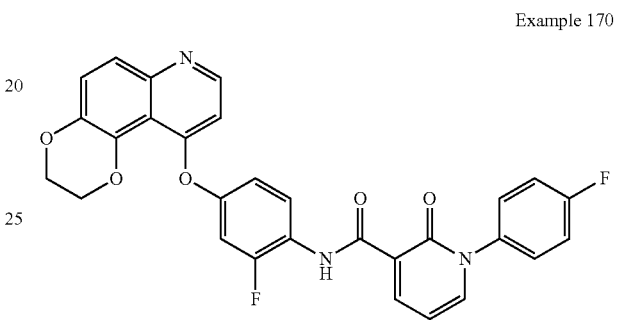

Example 171

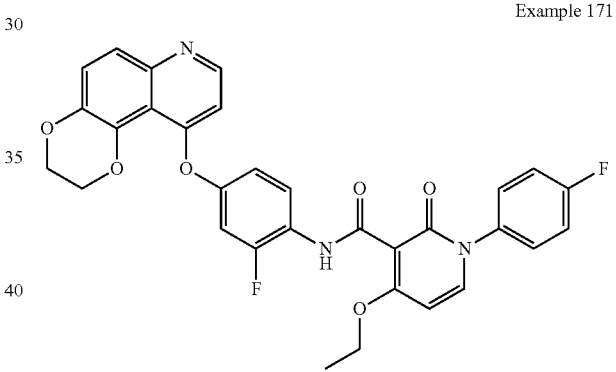

Example 171: N-(4-((2,3-dihydro-[1,4]dioxino[2,3-f]quinolin-10-yl)oxy)-2-fluorophenyl)-1-(4-fluorophenyl)-4-ethoxy-2-oxo-1,2-dihydropyridine-3-carboxamide A solution of 4-ethoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-2-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (31 mg, yield: 54%); $^1$H NMR (400 MHz, DMSO-d$_6$) δ 10.66 (s, 1H), 8.54 (d, J=5.0 Hz, 1H), 8.16 (t, J=8.9 Hz, 1H), 7.89 (d, J=7.8 Hz, 1H), 7.55 (d, J=9.1 Hz, 1H), 7.53-7.44 (m, 2H), 7.43-7.33 (m, 3H), 7.16 (dd, J=11.6, 2.7 Hz, 1H), 6.98-6.90 (m, 1H), 6.74 (d, J=5.1 Hz, 1H), 6.53 (d, J=7.9 Hz, 1H), 4.36-4.22 (m, 6H), 1.34 (t, J=6.9 Hz, 3H). MS: 572 [M+H]$^+$.

Example 172: N-(4-((2,3-dihydro-[1,4]dioxino[2,3-f]quinolin-10-yl)oxy)-2-fluorophenyl)-1-(4-fluorophenyl)-4-methoxy-2-oxo-1,2-dihydropyridine-3-carboxamide A solution of 4-methoxy-1-(4-fluorophenyl)-2-oxo-1,2-dihydropyridine-3-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-2-fluoroaniline (32 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 59%); $^1$H NMR (400 MHz, DMSO-$d_6$) δ 10.75 (s, 1H), 8.53 (d, J=5.0 Hz, 1H), 8.21 (t, J=8.9 Hz, 1H), 7.94 (d, J=7.8 Hz, 1H), 7.58-7.45 (m, 3H), 7.38 (t, J=9.2 Hz, 3H), 7.16 (dd, J=11.6, 2.7 Hz, 1H), 6.93 (dt, J=8.8, 1.6 Hz, 1H), 6.73 (d, J=5.0 Hz, 1H), 6.56 (d, J=7.9 Hz, 1H), 4.37-4.27 (m, 4H), 3.95 (s, 3H). MS:558 [M+H]$^+$.

Example 172

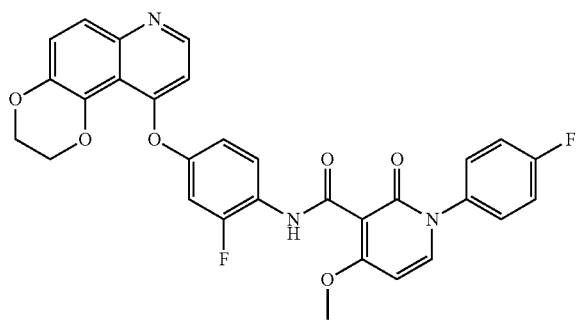

Example 173

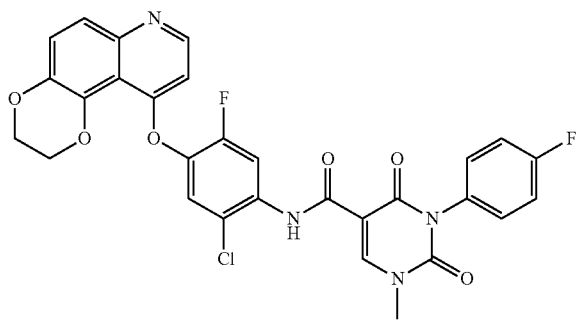

Example 173: N-(2-chloro-4-((2,3-dihydro-[1,4]dioxino[2,3-f]quinolin-10-yl)oxy)-5-fluorophenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 2-chloro-4-((2,3-dihydro-[1,4]dioxino[2,3-f]quinolin-10-yl)oxy)-5-fluoroaniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 56%); $^1$H NMR (400 MHz, DMSO-$d_6$) δ 11.52 (s, 1H), 8.95 (s, 1H), 8.64 (d, J=13.1 Hz, 1H), 8.51 (d, J=5.1 Hz, 1H), 7.65 (d, J=8.2 Hz, 1H), 7.55 (d, J=9.1 Hz, 1H), 7.46-7.32 (m, 5H), 6.72 (d, J=5.0 Hz, 1H), 4.35 (s, 4H), 3.55 (s, 3H). MS: 593 [M+H]$^+$.

Example 174: N-(2-chloro-4-((2,3-dihydro-[1,4]dioxino[2,3-f]quinolin-10-yl)oxy)-5-fluorophenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 2-chloro-4-((2,3-dihydro-[1,4]dioxino[2,3-f]quinolin-10-yl)oxy)-5-fluoroaniline (35 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (32 mg, yield: 53%); $^1$H NMR (400 MHz, DMSO-$d_6$) δ 11.52 (s, 1H), 8.96 (s, 1H), 8.63 (d, J=13.1 Hz, 1H), 8.51 (d, J=5.1 Hz, 1H), 7.65 (d, J=8.1 Hz, 1H), 7.55 (d, J=9.1 Hz, 1H), 7.48-7.32 (m, 5H), 6.72 (d, J=5.1 Hz, 1H), 4.35 (s, 4H), 4.03 (d, J=7.1 Hz, 2H), 1.30 (t, J=7.1 Hz, 3H). MS: 607 [M+H]$^+$.

Example 174

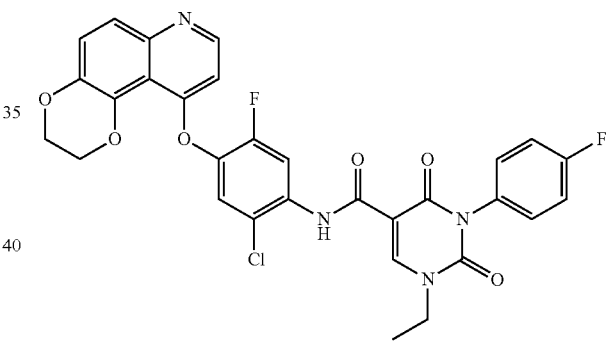

Example 175

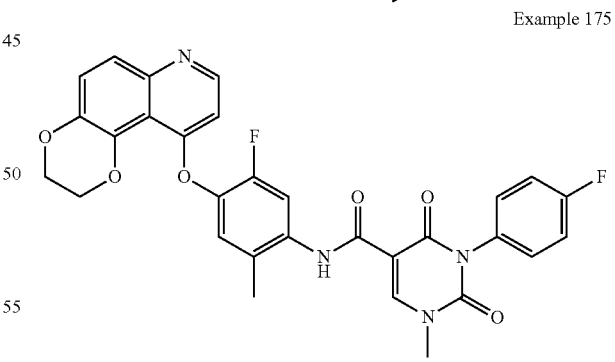

Example 175: N-(4-((2,3-dihydro-[1,4]dioxino[2,3-f]quinolin-10-yl)oxy)-5-fluoro-2-methylphenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-5-fluoro-2-methylaniline (33 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 58%); $^1$H NMR (400 MHz, DMSO-$d_6$) δ 11.01 (s, 1H), 8.93 (s, 1H), 8.47 (d, J=5.1 Hz, 1H), 8.40 (d, J=13.3 Hz, 1H), 7.53 (d, J=9.1 Hz, 1H), 7.46-7.32 (m, 5H), 7.29 (d, J=9.0 Hz, 1H), 6.56 (d, J=5.1 Hz, 1H), 4.37 (s, 4H), 3.55 (s, 3H), 2.22 (s, 3H). MS: 573 [M+H]$^+$.

Example 176: N-(4-((2,3-dihydro-[1,4]dioxino[2,3-f]quinolin-10-yl)oxy)-5-fluoro-2-methylphenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 4-((2,3-dihydro-[1,4]dioxino[2,3-f]quinolin-10-yl)oxy)-5-fluoro-2-methylaniline (33 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (31 mg, yield: 53%); $^1$H NMR (400 MHz, DMSO-$d_6$) δ 11.01 (s, 1H), 8.93 (s, 1H), 8.48 (d, J=5.1 Hz, 1H), 8.39 (d, J=13.3 Hz, 1H), 7.53 (d, J=9.1 Hz, 1H), 7.48-7.34 (m, 5H), 7.29 (d, J=8.9 Hz, 1H), 6.57 (d, J=5.1 Hz, 1H), 4.37 (s, 4H), 4.03 (d, J=7.1 Hz, 2H), 2.22 (s, 3H), 1.30 (t, J=7.1 Hz, 3H). MS:587 [M+H]$^+$.

Example 176

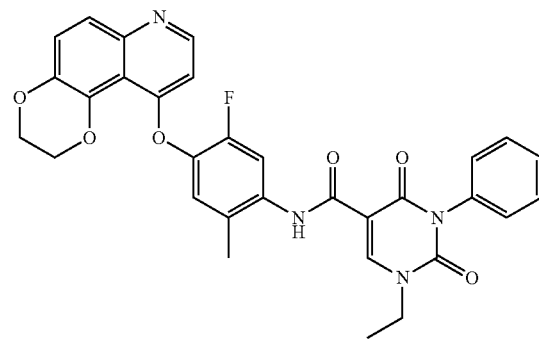

Example 177: N-(5-fluoro-4-((5-methoxy-2,3-dihydro-[1,4]dioxino[2,3-f]quinolin-10-yl)oxy)-2-methylphen yl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-methoxy-2,3-dihydro-[1,4]dioxino[2,3-f]quinolin-10-yl)oxy)-2-methylaniline (36 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (32 mg, yield: 53%); $^1$H NMR (400 MHz, DMSO-$d_6$) δ 11.00 (s, 1H), 8.93 (s, 1H), 8.44-8.35 (m, 2H), 7.44-7.34 (m, 4H), 7.26 (d, J=9.0 Hz, 1H), 7.07 (s, 1H), 6.43 (d, J=5.2 Hz, 1H), 4.35 (s, 4H), 3.92 (s, 3H), 3.55 (s, 3H), 2.21 (s, 3H). MS: 603 [M+H]$^+$.

Example 178: N-(5-fluoro-4-((5-methoxy-2,3-dihydro-[1,4]dioxino[2,3-f]quinolin-10-yl)oxy)-2-methylphen yl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-methoxy-2,3-dihydro-[1,4]dioxino[2,3-f]quinolin-10-yl)oxy)-2-methylaniline (36 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (35 mg, yield: 57%); $^1$H NMR (400 MHz, DMSO-$d_6$) δ 11.00 (s, 1H), 8.93 (s, 1H), 8.45-8.34 (m, 2H), 7.48-7.32 (m, 4H), 7.27 (d, J=9.0 Hz, 1H), 7.07 (s, 1H), 6.44 (d, J=5.2 Hz, 1H), 4.35 (s, 4H), 4.03 (d, J=7.1 Hz, 2H), 3.92 (s, 3H), 2.21 (s, 3H), 1.29 (t, J=7.1 Hz, 3H). MS: 617 [M+H]$^+$.

Example 177

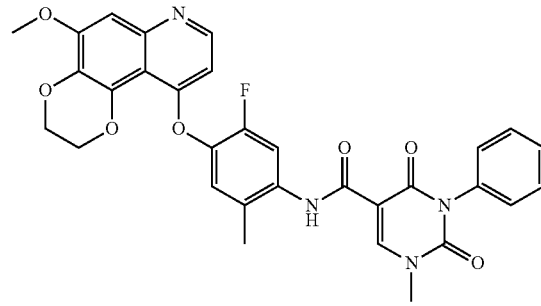

Example 178

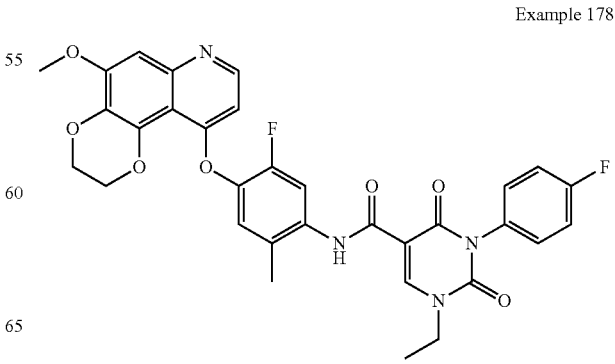

Example 179

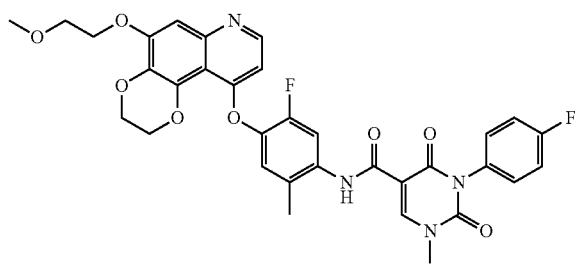

Example 180

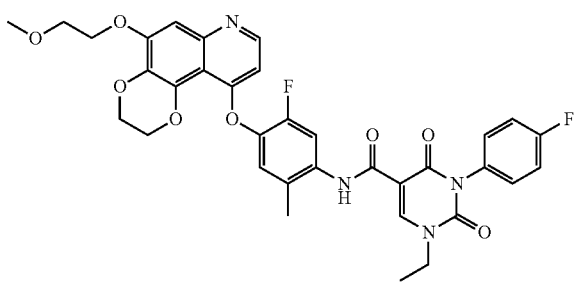 [SMILES: CCn1cc(C(=O)Nc2cc(F)c(Oc3ccnc4cc(OCCOC)c5c(c34)OCCO5)cc2C(C)C)c(=O)n(-c2ccc(F)cc2)c1=O]

Example 181

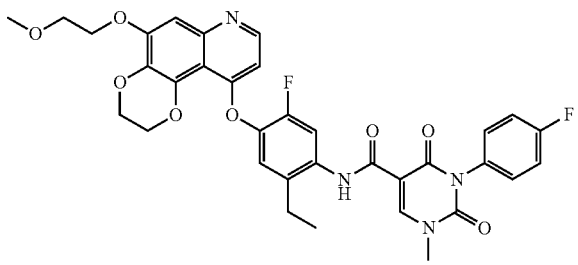

Example 179: N-(5-fluoro-4-((5-(2-methoxy-ethoxy)-2,3-dihydro-[1,4]dioxino[2,3-f]quinolin-10-yl)oxy)-2-methylphenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-methylaniline (40 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 51%); $^1$H NMR (400 MHz, DMSO-$d_6$) δ 11.05 (s, 1H), 8.93 (s, 1H), 8.61 (d, J=6.1 Hz, 1H), 8.45 (d, J=13.2 Hz, 1H), 7.46-7.33 (m, 5H), 7.20 (s, 1H), 6.72 (d, J=6.0 Hz, 1H), 4.44 (d, J=2.7 Hz, 4H), 4.35-4.27 (m, 2H), 3.81-3.74 (m, 2H), 3.56 (s, 3H), 3.35 (s, 3H), 2.24 (s, 3H). MS: 647 [M+H]$^+$.

Example 180: N-(5-fluoro-4-((5-(2-methoxy-ethoxy)-2,3-dihydro-[1,4]dioxino[2,3-f]quinolin-10-yl)oxy)-2-methylphenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-methylaniline (40 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (34 mg, yield: 51%); $^1$H NMR (400 MHz, DMSO-$d_6$) δ 11.00 (s, 1H), 8.93 (s, 1H), 8.44-8.34 (m, 2H), 7.46-7.34 (m, 4H), 7.27 (d, J=9.0 Hz, 1H), 7.08 (s, 1H), 6.43 (d, J=5.2 Hz, 1H), 4.36 (s, 4H), 4.28-4.21 (m, 2H), 4.03 (d, J=7.1 Hz, 2H), 3.74 (dd, J=5.4, 3.4 Hz, 2H), 3.34 (s, 3H), 2.21 (s, 3H), 1.29 (t, J=7.1 Hz, 3H). MS: 661 [M+H]$^+$.

Example N-(5-fluoro-4-((5-(2-methoxyethoxy)-2,3-dihydro-[1,4]dioxino[2,3-f]quinolin-10-yl)oxy)-2-ethylphenyl)-3-(4-fluorophenyl)-1-methyl-2,4-dioxo-1,2,3,4-tetrahydropyrimidine-5-carboxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-ethylaniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (29 mg, yield: 44%); $^1$H NMR (400 MHz, DMSO-$d_6$) δ 11.02 (s, 1H), 8.92 (s, 1H), 8.44-8.32 (m, 2H), 7.39 (p, J=8.9 Hz, 4H), 7.23 (d, J=9.0 Hz, 1H), 7.08 (s, 1H), 6.42 (d, J=5.2 Hz, 1H), 4.36 (s, 4H), 4.25 (t, J=4.4 Hz, 2H), 3.74 (t, J=4.3 Hz, 2H), 3.54 (s, 3H), 3.33-3.24 (m, 3H), 2.57 (q, J=7.5 Hz, 2H), 1.11 (t, J=7.5 Hz, 3H). MS: 661 [M+H]$^+$.

Example 182: N-(5-fluoro-4-((5-(2-methoxy-ethoxy)-2,3-dihydro-[1,4]dioxino[2,3-f]quinolin-10-yl)oxy)-2-ethylphenyl)-3-(4-fluorophenyl)-1-ethyl-2,4-dioxo-1,2,3,4-tetrahydropyrimidine-5-carboxamide A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-ethylaniline (42 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (33 mg, yield: 49%); $^1$H NMR (400 MHz, DMSO-d$_6$) δ 11.03 (s, 1H), 8.92 (s, 1H), 8.44-8.32 (m, 2H), 7.48-7.32 (m, 4H), 7.23 (d, J=9.0 Hz, 1H), 7.08 (s, 1H), 6.42 (dd, J=5.2, 1.1 Hz, 1H), 4.36 (s, 4H), 4.29-4.21 (m, 2H), 4.02 (q, J=7.1 Hz, 2H), 3.78-3.71 (m, 2H), 3.34 (s, 3H), 2.58 (q, J=7.5 Hz, 2H), 1.34-1.21 (m, 3H), 1.11 (t, J=7.5 Hz, 3H). MS: 675 [M+H]$^+$.

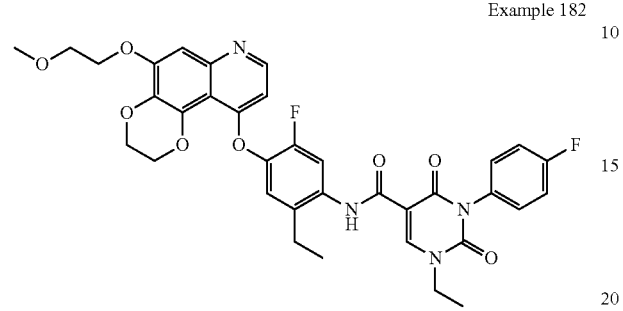

Example 182

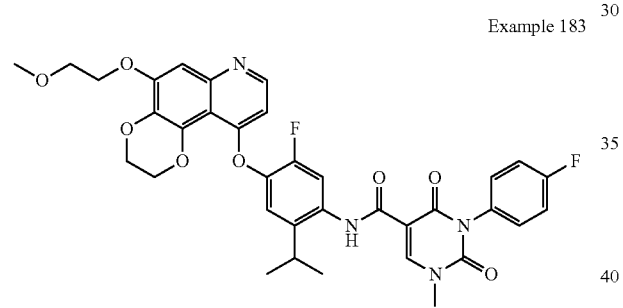

Example 183

Example 183: N-(5-fluoro-4-((5-(2-methoxyethoxy)-2,3-dihydro-[1,4]dioxino[2,3-f]quinolin-10-yl)oxy)-2-isopropylphenyl)-3-(4-fluorophenyl)-1-methyl-2,4-dioxo-1,2,3,4-tetrahydropyrimidine-5-carb oxamide A solution of 3-(4-fluorophenyl)-1-methyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-isopropylaniline (43 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (25 mg, yield: 37%); $^1$H NMR (400 MHz, DMSO-d$_6$) δ 11.01 (s, 1H), 8.91 (s, 1H), 8.41 (d, J=5.2 Hz, 1H), 8.26 (d, J=13.1 Hz, 1H), 7.40 (h, J=8.6, 7.0 Hz, 4H), 7.26 (d, J=9.0 Hz, 1H), 7.08 (s, 1H), 6.39 (d, J=5.2 Hz, 1H), 4.37 (s, 4H), 4.28-4.21 (m, 2H), 3.74 (t, J=4.2 Hz, 2H), 3.54 (s, 3H), 3.34 (s, 3H), 3.02 (dd, J=14.2, 7.5 Hz, 1H), 1.15 (d, J=6.7 Hz, 6H). MS: 675 [M+H]$^+$.

Example 184: N-(5-fluoro-4-((5-(2-methoxyethoxy)-2,3-dihydro-[1,4]dioxino[2,3-f]quinolin-10-yl)oxy)-2-isopropylphenyl)-3-(4-fluorophenyl)-1-ethyl-2,4-dioxo-1,2,3,4-tetrahydropyrimidine-5-carboxamide

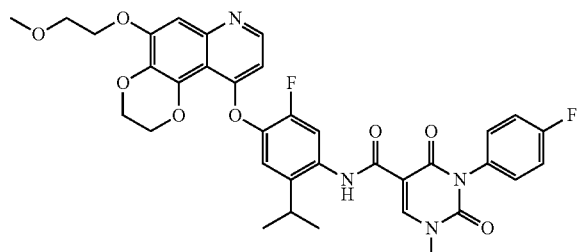

A solution of 3-(4-fluorophenyl)-1-ethyl-2,4-dioxo-1,2,3,4-tetrahydropyrimidine-5-carbonyl chloride (30 mg, 0.1 mmol) in dichloromethane (0.5 mL) followed by triethylamine (0.1 mL) were added to a solution of 5-fluoro-4-((5-(2-methoxyethoxy)-2,3-dihydro-[1,4]dioxino[2,3-f]quinolin-10-yl)oxy)-2-isopropylaniline (43 mg, 0.1 mmol) in anhydrous DMF (0.5 mL), and reacted with stirring at room temperature for 5 hours. The reaction solution was quenched with water, and filtered to afford a light-yellow solid. The solid was purified by preparative liquid chromatography to afford a white solid product (29 mg, yield: 42%); $^1$H NMR (400 MHz, DMSO-d$_6$) δ 11.02 (s, 1H), 8.92 (s, 1H), 8.41 (d, J=5.3 Hz, 1H), 8.25 (d, J=13.2 Hz, 1H), 7.48-7.32 (m, 4H), 7.27 (d, J=9.0 Hz, 1H), 7.08 (s, 1H), 6.39 (dd, J=5.3, 1.1 Hz, 1H), 4.37 (s, 4H), 4.25 (s, 2H), 4.02 (d, J=7.1 Hz, 2H), 3.74 (s, 2H), 3.35 (s, 3H), 3.04 (p, J=6.8 Hz, 1H), 1.29 (t, J=7.1 Hz, 3H), 1.16 (d, J=6.8 Hz, 6H). MS: 689 [M+H]$^+$.

Assay Example 1. Assay of Small Molecular Compounds for Inhibiting the Activity of TRKA Kinase The assay of small molecular compounds for inhibiting the activity of TRKA kinase is based on the LANCE TR-FRET technology of Perkin Elmer Inc., and the assay method is as follows:
1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 μL of the gradient-diluted compounds were taken with a transfer pipette to a 384-well plate.
3. Addition of enzyme: 5 μL of 2×TRKA kinase solution (with a concentration of 2 nM) was taken with a transfer pipette to the corresponding reaction well of the 384-well plate, mixed well and pre-reacted at room temperature for 5 minutes.
4. 2.5 μL 4× Ultra ULight-labeled TK Peptide (with a concentration of 400 nM)/ATP (with a concentration of 40 μM) mixture was taken with a transfer pipette to the corresponding reaction well of the 384-well plate.
5. Negative control: 2.5 μL/well 4× substrate/ATP mixture and 7.5 μL 1× Kinase Assay Buffer were added to the wells of the 384-well plate.

Positive control: 2.5 µL/well 4× substrate/ATP mixture, 2.5 µL/well 1× Kinase Assay Buffer containing 4% DMSO, and 5 µL/well 2×TRKA kinase solution were added to the 384-well plate. The final concentration of DMSO in the reaction system was 1%.
6. The mixture was mixed well and then centrifuged and reacted at room temperature in dark for 60 min.
7. Termination of the enzymatic reaction: 5 µL of 4× stop solution was taken with a transfer pipette to the wells of the 384-well plate, mixed and then centrifuged, and reacted at room temperature for 5 min.
8. Development of the reaction: 5 µL of 4× detection solution was taken with a transfer pipette to the wells of the 384-well plate for color development, and the mixture was mixed and then centrifuged and reacted at room temperature for 60 min.
9. The 384-well plate was placed into the Envision plate reader and the signal was detected using the appropriate program.
10. Analysis and processing of the raw data:

The drug concentrations and the corresponding inhibition rates were input into GraphPad Prism5 for calculation, and the inhibition rate of the compounds were calculated as follows: inhibition rate (%)=(reading of positive well–reading of experimental well)/(reading of positive control well–reading of negative control well)×100%. Processing with GraphPad Prism5 software yielded the corresponding $IC_{50}$ values (the concentration of the compound at which 50% of the highest inhibition of the enzyme is achieved).

Table 4 lists the assay results of the inhibitory activity of some of the compounds disclosed herein on the TRKA tyrosine kinase, wherein A indicates that $IC_{50}$ is less than or equal to 50 nM, B indicates that $IC_{50}$ is greater than 50 nM but less than or equal to 500 nM, C indicates that $IC_{50}$ is greater than 500 nM but less than or equal to 5000 nM, and D indicates that $IC_{50}$ is greater than 5000 nM. NT indicates that no assay is carried out.

Assay Example 2. Assay of Small Molecular Compounds for Inhibiting the Activity of c-MET Kinase The assay is based on the LANCE TR-FRET technology of Perkin Elmer Inc., and the assay method is as follows:
1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 µL of the gradient-diluted compounds were taken with a transfer pipette to a 384-well plate.
3. Addition of enzyme: 5 µL of 2×c-MET kinase solution (with a concentration of 2 nM) was taken with a transfer pipette to the corresponding reaction well of the 384-well plate, mixed well and pre-reacted at room temperature for 5 minutes.
4. 2.5 µL 4× Ultra ULight™-JAK-1 (Tyr1023) Peptide (with a concentration of 400 nM)/ATP (with a concentration of 40 µM) mixture was taken with a transfer pipette to the corresponding reaction well of the 384-well plate.
5. Negative control: 2.5 µL/well 4× substrate/ATP mixture and 7.5 µL 1× Kinase Assay Buffer were added to the wells of the 384-well plate.
6. Positive control: 2.5 µL/well 4× substrate/ATP mixture, 2.5 µL/well 1× Kinase Assay Buffer containing 16% DMSO, and 5 µL/well 2× c-MET kinase solution were added to the 384-well plate. The final concentration of DMSO in the reaction system was 4%.
7. The mixture was mixed well and then centrifuged and reacted at room temperature in dark for 60 min.
8. Termination of the enzymatic reaction: 5 µL of 4× stop solution was taken with a transfer pipette to the wells of the 384-well plate, mixed and then centrifuged, and reacted at room temperature for 5 min.
9. Development of the reaction: 5 µL of 4× detection solution was taken with a transfer pipette to the wells of the 384-well plate for color development, and the mixture was mixed and then centrifuged and reacted at room temperature for 60 min.
10. The 384-well plate was placed into the Envision plate reader and the signal was detected using the appropriate program.
11. Analysis and processing of the raw data:
12. The drug concentrations and the corresponding inhibition rates were input into GraphPad Prism5 for calculation, and the inhibition rate of the compounds were calculated as follows: inhibition rate (%)=(reading of positive well–reading of experimental well)/(reading of positive control well–reading of negative control well)×100%. Processing with GraphPad Prism5 software yielded the corresponding $IC_{50}$ values (the concentration of the compound at which 50% of the highest inhibition of the enzyme is achieved).

Table 4 lists the assay results of the inhibitory activity of some of the compounds disclosed herein on the c-MET tyrosine kinase, wherein A indicates that the $IC_{50}$ is less than or equal to 50 nM, B indicates that the $IC_{50}$ is greater than 50 nM but less than or equal to 500 nM, C indicates that the $IC_{50}$ is greater than 500 nM but less than or equal to 5000 nM, and D indicates that the $IC_{50}$ is greater than 5000 nM. NT indicates that no assay is carried out.

Assay Example 3. Assay of Small Molecular Compounds for Inhibiting the Activity of MER Kinase The assay of small molecular compounds for inhibiting the activity of MER kinase is based on the LANCE TR-FRET technology of Perkin Elmer Inc., and the assay method is as follows:
1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 µL of the gradient-diluted compounds were taken with a transfer pipette to a 384-well plate.
3. Addition of enzyme: 5 µL of 2×MER kinase solution (with a concentration of 1 nM) was taken with a transfer pipette to the corresponding reaction well of the 384-well plate, mixed well and pre-reacted at room temperature for 5 minutes.
4. 2.5 µL 4× ULight-labeled Ploy GT (with a concentration of 200 nM)/ATP (with a concentration of 20 µM) mixture was taken with a transfer pipette to the corresponding reaction well of the 384-well plate.
5. Negative control: 2.5 µL/well 4× substrate/ATP mixture and 7.5 µL 1× Kinase Assay Buffer were added to the wells of the 384-well plate.

Positive control: 2.5 µL/well 4× substrate/ATP mixture, 2.5 µL/well 1× Kinase Assay Buffer containing 4% DMSO, and 5 μL/well 2×MER kinase solution were added to the 384-well plate. The final concentration of DMSO in the reaction system was 1%.
6. The mixture was mixed well and then centrifuged and reacted at room temperature in dark for 60 min.
7. Termination of the enzymatic reaction: 5 μL of 4× stop solution was taken with a transfer pipette to the wells of the 384-well plate, mixed and then centrifuged, and reacted at room temperature for 5 min.
8. Development of the reaction: 5 μL of 4× detection solution was taken with a transfer pipette to the wells of the 384-well plate for color development, and the mixture was mixed and then centrifuged and reacted at room temperature for 60 min.
9. The 384-well plate was placed into the Envision plate reader and the signal was detected using the appropriate program.
10. Analysis and processing of the raw data:

The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding $IC_{50}$ values (the concentration of the compound at which 50% of the highest inhibition of the enzyme is achieved).

Table 4 lists the assay results of the inhibitory activity of some of the compounds disclosed herein on the MER tyrosine kinase, wherein A indicates that $IC_{50}$ is less than or equal to 50 nM, B indicates that $IC_{50}$ is greater than 50 nM but less than or equal to 500 nM, C indicates that $IC_{50}$ is greater than 500 nM but less than or equal to 5000 nM, and D indicates that $IC_{50}$ is greater than 5000 nM. NT indicates that no assay is carried out.

Assay Example 4. Assay of Small Molecular Compounds for Inhibiting the Activity of VEGFR-2 Kinase The assay is based on the LANCE TR-FRET technology of Perkin Elmer Inc., and the assay method is as follows:
1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 μL of the gradient-diluted compounds were taken with a transfer pipette to a 384-well plate.
3. Addition of enzyme: 5 μL of 2×VEGFR2 kinase solution (with a concentration of 0.5 nM) was taken with a transfer pipette to the corresponding reaction well of the 384-well plate, mixed well and pre-reacted at room temperature for 30 minutes.
4. 2.5 μL 4× Ultra ULight™-JAK-1 (Tyr1023) Peptide (with a concentration of 200 nM)/ATP (with a concentration of 40 μM) mixture was taken with a transfer pipette to the corresponding reaction well of the 384-well plate.
5. Negative control: 2.5 μL/well 4× substrate/ATP mixture and 7.5 μL 1× Kinase Assay Buffer were added to the wells of the 384-well plate.
6. Positive control: 2.5 μL/well 4× substrate/ATP mixture, 2.5 μL/well 1× Kinase Assay Buffer containing 16% DMSO, and 5 μL/well 2×VEGFR-2 kinase solution were added to the 384-well plate. The final concentration of DMSO in the reaction system was 4%.
7. The mixture was mixed well and then centrifuged and reacted at room temperature in dark for 60 min.
8. Termination of the enzymatic reaction: 5 μL of 4× stop solution was taken with a transfer pipette to the wells of the 384-well plate, mixed and then centrifuged, and reacted at room temperature for 5 min.
9. Development of the reaction: 5 μL of 4× detection solution was taken with a transfer pipette to the wells of the 384-well plate for color development, and the mixture was mixed and then centrifuged and reacted at room temperature for 60 min.
10. The 384-well plate was placed into the Envision plate reader and the signal was detected using the appropriate program.
11. Analysis and processing of the raw data: The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding $IC_{50}$ values (the concentration of the compound at which 50% of the highest inhibition of the enzyme is achieved).

Table 4 lists the assay results of the inhibitory activity of some of the compounds disclosed herein on the VEGFR-2 tyrosine kinase, wherein A indicates that the $IC_{50}$ is less than or equal to 50 nM, B indicates that the $IC_{50}$ is greater than 50 nM but less than or equal to 500 nM, C indicates that the $IC_{50}$ is greater than 500 nM but less than or equal to 5000 nM, and D indicates that the $IC_{50}$ is greater than 5000 nM. NT indicates that no assay is carried out.

TABLE 4

Assay results of the inhibitory activity of some of the compounds disclosed herein on TRKA, c-MET, MER, or VEGFR-2

| Example No. | TRKA $IC_{50}$ (nM) | CMET $IC_{50}$ (nM) | MER $IC_{50}$ (nM) | VEGFR2 $IC_{50}$ (nM) |
|---|---|---|---|---|
| 1 | A | A | A | A |
| 2 | A | A | A | B |
| 3 | A | A | A | B |
| 4 | A | A | A | A |
| 5 | A | A | A | B |
| 6 | A | A | A | B |
| 7 | NT | B | C | NT |
| 8 | NT | B | C | NT |
| 9 | NT | B | C | NT |
| 10 | NT | A | B | NT |
| 11 | NT | A | B | B |
| 12 | NT | A | B | C |
| 13 | A | A | A | C |
| 14 | B | A | A | NT |
| 15 | A | A | A | B |
| 16 | A | A | A | NT |
| 17 | A | A | A | A |
| 18 | A | A | A | A |
| 19 | A | A | A | A |
| 20 | A | A | A | A |
| 21 | A | A | A | A |
| 22 | A | A | A | A |
| 23 | B | B | C | NT |
| 24 | A | B | B | NT |
| 25 | B | B | B | NT |
| 26 | A | A | B | NT |
| 27 | A | A | A | A |
| 28 | A | A | A | NT |
| 29 | A | A | A | C |

TABLE 4-continued

Assay results of the inhibitory activity of some of the compounds disclosed herein on TRKA, c-MET, MER, or VEGFR-2

| Example No. | TRKA IC$_{50}$ (nM) | CMET IC$_{50}$ (nM) | MER IC$_{50}$ (nM) | VEGFR2 IC$_{50}$ (nM) |
|---|---|---|---|---|
| 30 | A | A | A | A |
| 31 | A | A | A | A |
| 32 | A | A | A | A |
| 33 | A | A | A | A |
| 34 | A | A | A | A |
| 35 | A | A | A | A |
| 36 | A | A | A | A |
| 37 | A | A | A | B |
| 38 | A | A | A | B |
| 39 | A | A | A | B |
| 40 | A | A | A | B |
| 41 | A | A | A | B |
| 42 | A | A | A | B |
| 43 | B | A | A | NT |
| 44 | A | A | A | B |
| 45 | B | A | A | C |
| 46 | B | A | A | C |
| 47 | B | A | B | NT |
| 48 | B | A | B | NT |
| 49 | A | A | A | A |
| 50 | A | A | A | A |
| 51 | A | A | A | A |
| 52 | A | A | A | A |
| 53 | A | A | A | A |
| 54 | A | A | A | A |
| 55 | A | A | A | B |
| 56 | A | A | A | B |
| 57 | A | A | A | A |
| 58 | B | A | A | A |
| 59 | B | A | A | A |
| 60 | A | A | A | A |
| 61 | A | A | A | A |
| 62 | A | A | A | A |
| 63 | B | A | A | B |
| 64 | A | A | A | B |
| 65 | A | A | A | B |
| 66 | A | A | A | B |
| 67 | A | A | A | A |
| 68 | A | A | A | A |
| 69 | A | A | A | A |
| 70 | A | A | A | A |
| 71 | A | A | A | A |
| 72 | A | A | A | A |
| 73 | A | A | A | B |
| 74 | A | A | A | A |
| 75 | A | A | A | NT |
| 76 | A | B | A | C |
| 77 | A | A | A | B |
| 78 | A | A | A | C |
| 79 | A | A | A | NT |
| 80 | A | A | A | C |
| 81 | C | B | A | NT |
| 82 | B | B | A | NT |
| 83 | B | C | B | NT |
| 84 | B | B | B | NT |
| 85 | A | B | A | B |
| 86 | A | A | A | B |
| 87 | B | B | A | NT |
| 88 | B | A | A | C |
| 89 | B | B | A | NT |
| 90 | A | A | A | B |
| 91 | A | A | A | B |
| 92 | A | B | A | C |
| 93 | A | A | A | B |
| 94 | A | A | A | C |
| 95 | A | A | A | C |
| 96 | A | A | A | C |
| 97 | A | B | A | C |
| 98 | A | B | A | C |
| 99 | B | A | A | C |
| 100 | B | A | A | C |
| 101 | B | A | A | C |
| 102 | B | A | A | NT |
| 103 | NT | NT | B | C |
| 104 | A | A | A | D |
| 105 | A | A | A | B |
| 106 | B | B | A | D |
| 107 | C | B | A | NT |
| 108 | C | B | B | NT |
| 109 | C | A | A | NT |
| 110 | C | A | A | NT |
| 111 | C | C | B | NT |
| 112 | A | A | A | B |
| 113 | A | A | A | B |
| 114 | B | A | A | B |
| 115 | A | A | A | C |
| 116 | A | A | A | D |
| 117 | B | A | A | C |
| 118 | B | B | B | NT |
| 119 | D | NT | C | D |
| 120 | A | A | A | B |
| 121 | B | B | A | C |
| 122 | A | A | A | C |
| 123 | A | NT | A | D |
| 124 | A | NT | A | C |
| 125 | A | B | B | NT |
| 126 | A | A | A | B |
| 127 | A | A | A | C |
| 128 | A | A | A | C |
| 129 | A | A | A | C |
| 130 | A | A | A | B |
| 131 | A | A | B | NT |
| 132 | A | A | A | C |
| 133 | B | A | C | NT |
| 134 | A | A | A | B |
| 135 | A | A | A | A |
| 136 | A | A | A | B |
| 137 | A | A | A | B |
| 138 | A | A | A | A |
| 139 | A | A | A | B |
| 140 | A | A | A | C |
| 141 | A | A | B | NT |
| 142 | A | A | A | B |
| 143 | A | A | A | A |
| 144 | A | A | NT | B |
| 145 | A | A | NT | C |
| 146 | A | A | NT | D |
| 147 | A | A | NT | B |
| 148 | A | A | NT | C |
| 149 | A | A | NT | C |
| 150 | A | A | NT | C |
| 151 | C | A | NT | C |
| 152 | D | A | NT | D |
| 153 | A | A | NT | C |
| 154 | A | A | NT | NT |
| 155 | A | A | NT | C |
| 156 | A | A | NT | C |
| 157 | C | NT | B | NT |
| 158 | B | NT | NT | NT |
| 159 | B | NT | NT | NT |
| 160 | B | NT | NT | NT |
| 161 | B | NT | NT | NT |
| 162 | A | C | B | C |
| 163 | B | NT | NT | NT |
| 164 | B | A | NT | NT |
| 165 | B | A | NT | NT |
| 166 | B | B | NT | NT |
| 167 | B | A | NT | NT |
| 168 | B | NT | NT | NT |
| 169 | A | A | A | B |
| 170 | A | B | A | C |
| 171 | A | A | A | C |
| 172 | A | B | A | D |
| 173 | B | NT | NT | NT |
| 174 | A | NT | NT | NT |
| 175 | A | NT | NT | NT |
| 176 | B | NT | NT | NT |
| 177 | A | A | A | C |

TABLE 4-continued

Assay results of the inhibitory activity of some of the compounds disclosed herein on TRKA, c-MET, MER, or VEGFR-2

| Example No. | TRKA IC$_{50}$ (nM) | CMET IC$_{50}$ (nM) | MER IC$_{50}$ (nM) | VEGFR2 IC$_{50}$ (nM) |
|---|---|---|---|---|
| 178 | A | A | NT | NT |
| 179 | A | A | A | C |
| 180 | A | A | NT | C |
| 181 | A | A | NT | NT |
| 182 | B | A | NT | NT |
| 183 | B | B | NT | NT |
| 184 | B | NT | NT | NT |

Assay Example 5. Assay of Small Molecular Compounds for Inhibiting the Proliferation of Ba/F3-AXL Cells Ba/F3 Axl cells were purchased from KYinno Biotechnology (Beijing) Co., Ltd. under the catalog number KC-0388.

hGas6 was purchased from R&D under the catalog number 885-GSB-050.

In particular, the steps of the method for detecting Ba/F3-AXL cell are as follows:
1) Dilution of compounds: A total of 9 concentrations were obtained using a 4-fold gradient dilution from a final concentration of 1000 nM (the maximum final concentration of the drug used in this assay was 1000 nM, and the minimum final concentration was 0.015 nM). After dilution with RPMI-1640 complete medium (100 ng/mL of hGas6 was added to the medium), the compound concentration was 5 times the final concentration, and the DMSO content was 1.25%.
2) Well-growing Ba/F3-AXL cells were collected, transferred to a 15 mL centrifuge tube, and centrifuged at 1000 rpm for 5 minutes.
3) The supernatant was discarded, to which the above-mentioned RPMI-1640 complete medium containing hGas6 was added, pipetted evenly, then stained with trypan blue and counted; and cell number and survival rate were recorded (the survival rate was required to be greater than 90%).
4) The cell suspension was seeded into each well of a 96-well plate at 20000 cells/80 L; positive and blank wells were set.
5) 20 μL of the corresponding 5×compound solution diluted with the above-mentioned medium was added to each well and mixed evenly; the final concentration of DMSO was 0.25%.
6) After 72 hours of incubation, 10 μL of CCK-8 reagent was added to each well and incubated for another 2 hours (the reaction time can be adjusted according to the color depth);
7) The OD value was read at 450 nm on a multi-function plate reader.
8) Data processing: cell survival rate (%)=[(As−Ab)/(Ac−Ab)]*100%

As: OD value of assay well (medium containing cells, CCK-8, compound),
Ac: OD value of control well (medium containing cells, CCK-8),
Ab: OD value of blank well (CCK-8, medium without cell and compound), The values were then imported into Graphpad Prism 5 software for curve fitting, and IC$_{50}$ was calculated.

Table 5 lists the assay results of the inhibitory activity of some of the compounds disclosed herein on the proliferation of Ba/F3-AXL cells, wherein A indicates that IC$_{50}$ is less than or equal to 50 nM, B indicates that IC$_{50}$ is greater than 50 nM but less than or equal to 500 nM, C indicates that IC$_{50}$ is greater than 500 nM but less than or equal to 5000 nM, and D indicates that IC$_{50}$ is greater than 5000 nM. NT indicates that no assay is carried out.

TABLE 5

The assay results of the inhibitory activity of some of the compounds disclosed herein on the proliferation of Ba/F3-AXL cells

| Example No. | Ba/F3-AXL IC$_{50}$ (nM) |
|---|---|
| 1 | A |
| 2 | A |
| 4 | A |
| 5 | A |
| 13 | A |
| 15 | A |
| 16 | A |
| 17 | A |
| 18 | A |
| 19 | A |
| 20 | A |
| 21 | A |
| 22 | A |
| 26 | A |
| 27 | A |
| 28 | A |
| 31 | A |
| 32 | A |
| 33 | A |
| 34 | A |
| 35 | A |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | A |
| 74 | A |
| 76 | A |
| 77 | A |
| 78 | A |
| 80 | A |
| 81 | A |
| 82 | A |

TABLE 5-continued

The assay results of the inhibitory activity of some of the compounds
disclosed herein on the proliferation of Ba/F3-AXL cells

| Example No. | Ba/F3-AXL IC$_{50}$ (nM) |
|---|---|
| 85 | A |
| 86 | A |
| 87 | A |
| 88 | A |
| 90 | A |
| 91 | A |
| 92 | A |
| 93 | A |
| 94 | A |
| 95 | A |
| 96 | A |
| 98 | A |
| 99 | A |
| 100 | A |
| 101 | A |
| 104 | D |
| 105 | A |
| 106 | A |
| 109 | A |
| 112 | A |
| 113 | A |
| 114 | A |
| 115 | A |
| 116 | A |
| 117 | A |
| 120 | A |
| 121 | A |
| 122 | A |
| 123 | A |
| 124 | A |
| 126 | A |
| 132 | A |
| 134 | A |
| 141 | A |
| 142 | A |

Assay Example 6. Assay of Small Molecular
Compounds for Inhibiting the Proliferation of
MHCC97H, Ba/F3 LMNA-NTRK1, Ba/F3
LMNA-NTRK1-G595R and EBC1 Cells In particular, the method of the assay of small molecular compounds for inhibiting cell proliferation is as follows:

1. Cells cultured to a logarithmic growth phase (adherent cells need to be digested with trypsin and neutralized) were taken, pipetted evenly, transferred to a 15 mL centrifuge tube, and centrifuged at 1000 rpm at room temperature for 4 minutes;
2. The supernatant was discarded; 5 mL of complete medium was added and pipetted evenly; 10 µL of cell suspension was taken out, mixed well with 10 µL of 0.4% trypan blue, and counted under a cell counter; the proportion of living cells was ensured to be above 90%;
3. 80 µL of cell suspension per well was seeded into a 96-well plate according to the conditions shown in the attached table, and cultured overnight; in the outer 36 wells of the 96-well plate, no cells were added but only sterile water was added; only the inner 60 wells were used for cell assay and control;
4. 5×compound dilution: the compounds were serially diluted 3-fold to obtain a total of 9 concentrations; 80-fold overall dilution was completed with complete medium, the resulting concentration was 5 times the final drug concentration, and DMSO concentration was 1.25%;
5. 20 µL of the corresponding compounds with different concentration gradients were added to each well of assay wells of the 96-well plate; 20 µL of complete medium was added to positive and negative control wells and shaken well; and the final concentration of DMSO in each well was 0.25%;
6. After 72 hours of incubation, 10 µL of CCK-8 reagent was added to each well and further incubated at 37° C. for 1-2 hours; and the OD value was read at 450 nm;
7. Cell survival rate (%)=[(As−Ab)/(Ac−Ab)]*100%
   As: Assay well (medium containing cells, CCK-8, compound),
   Ac: Control well (medium containing cells, CCK-8),
   Ab: Blank well (CCK-8, medium without cell and compound),
8. The values were imported into Graphpad Prism 5 software for IC$_{50}$ calculation.

Table 6 lists the assay results of the inhibitory activity of some of the compounds disclosed herein on the proliferation of MHCC97H, Ba/F3 LMNA-NTRK1, Ba/F3 LMNA-NTRK1-G595R and EBC1 cells, wherein A indicates that IC$_{50}$ is less than or equal to 50 nM, B indicates that IC$_{50}$ is greater than 50 nM but less than or equal to 200 nM, C indicates that IC$_{50}$ is greater than 200 nM but less than or equal to 1000 nM, and D indicates that IC$_{50}$ is greater than 1000 nM. NT indicates that no assay is carried out.

Basic Information and Seeding Conditions of Cells

| Cell name | Source | Medium | Seeding density |
|---|---|---|---|
| MHCC97H | Shanghai Ruilu Biotechnology Co., Ltd. | DMEM + 10% FBS | 6000/well |
| Ba/F3 LMNA-NTRK1 | KYinno Biotechnology (Beijing) Co., Ltd. | RPMI 1640 + 10% FBS | 10000/well |
| Ba/F3 LMNA-NTRK1-G595R | KYinno Biotechnology (Beijing) Co., Ltd. | RPMI 1640 + 10% FBS | 10000/well |
| EBC1 | Cobioer Biosciences (Nanjing) Co., Ltd. | MEM + 1.0 mM sodium pyruvate + 1% NEAA + 10% FBS | 8000/well |

| Example No. | MHCC97H IC$_{50}$ (nM) | Ba/F3 LMNA-NTRK1 IC$_{50}$ (nM) | Ba/F3 LMNA-NTRK1-G595R IC$_{50}$ (nM) | EBC1 IC$_{50}$ (nM) |
|---|---|---|---|---|
| 1 | A | NT | NT | B |
| 2 | C | NT | NT | B |
| 3 | B | NT | NT | B |
| 4 | A | NT | NT | A |
| 5 | B | NT | NT | A |
| 6 | B | A | NT | A |
| 11 | C | NT | NT | C |
| 12 | B | NT | NT | C |
| 13 | B | A | NT | B |
| 15 | A | A | B | A |
| 16 | NT | A | C | NT |
| 17 | A | A | NT | A |
| 18 | A | A | NT | A |
| 19 | A | A | NT | A |
| 20 | A | A | NT | A |
| 21 | A | A | NT | A |
| 22 | A | A | NT | A |
| 24 | NT | A | NT | NT |
| 25 | NT | NT | NT | NT |
| 26 | NT | A | NT | NT |

| Example No. | MHCC97H IC$_{50}$ (nM) | Ba/F3 LMNA-NTRK1 IC$_{50}$ (nM) | Ba/F3 LMNA-NTRK1-G595R IC$_{50}$ (nM) | EBC1 IC$_{50}$ (nM) |
|---|---|---|---|---|
| 27 | B | A | NT | B |
| 28 | NT | A | NT | NT |
| 29 | NT | A | C | NT |
| 30 | NT | A | C | NT |
| 31 | A | A | NT | A |
| 32 | B | A | NT | A |
| 33 | A | A | NT | A |
| 34 | A | A | NT | A |
| 35 | A | A | NT | A |
| 36 | A | A | NT | A |
| 37 | NT | A | B | NT |
| 38 | NT | A | C | NT |
| 39 | B | A | B | A |
| 40 | NT | A | NT | NT |
| 41 | B | A | B | A |
| 42 | A | A | B | A |
| 43 | NT | A | B | NT |
| 44 | A | A | A | A |
| 45 | C | NT | NT | B |
| 46 | A | A | B | A |
| 49 | A | A | NT | A |
| 50 | A | A | NT | A |
| 51 | A | A | NT | A |
| 52 | A | A | NT | NT |
| 53 | A | A | NT | A |
| 54 | A | A | NT | A |
| 55 | A | A | NT | A |
| 56 | A | A | NT | A |
| 57 | A | A | NT | A |
| 60 | B | A | NT | A |
| 61 | A | A | NT | A |
| 62 | A | A | NT | A |
| 63 | B | NT | NT | A |
| 64 | B | B | NT | B |
| 65 | A | B | NT | A |
| 66 | A | B | NT | A |
| 67 | A | A | NT | A |
| 68 | C | C | NT | A |
| 69 | B | A | NT | A |
| 70 | A | A | NT | A |
| 71 | A | A | NT | A |
| 72 | A | A | NT | A |
| 73 | A | A | NT | A |
| 74 | B | A | C | A |
| 75 | NT | A | C | NT |
| 76 | NT | A | NT | NT |
| 77 | NT | A | C | NT |
| 78 | NT | A | B | NT |
| 79 | NT | A | B | NT |
| 80 | A | A | NT | A |
| 85 | NT | A | NT | NT |
| 86 | B | A | B | A |
| 90 | NT | A | B | NT |
| 91 | NT | A | NT | NT |
| 92 | NT | B | NT | NT |
| 93 | NT | C | NT | NT |
| 94 | NT | B | NT | NT |
| 95 | NT | B | NT | NT |
| 96 | NT | A | C | NT |
| 97 | NT | A | B | NT |
| 98 | NT | A | B | NT |
| 99 | B | NT | NT | A |
| 100 | A | NT | NT | A |
| 101 | A | NT | NT | A |
| 104 | NT | D | NT | NT |
| 105 | B | B | NT | A |
| 106 | B | NT | NT | A |
| 112 | C | A | NT | B |
| 113 | B | A | NT | B |
| 114 | B | NT | NT | B |
| 115 | A | A | NT | A |
| 116 | B | A | A | A |
| 120 | NT | A | NT | NT |
| 122 | NT | A | C | NT |
| 123 | NT | A | NT | NT |
| 124 | NT | A | NT | NT |
| 125 | NT | A | A | NT |
| 126 | NT | A | NT | NT |
| 127 | NT | A | NT | NT |
| 128 | NT | A | NT | NT |
| 129 | NT | A | A | NT |
| 130 | NT | A | NT | NT |
| 131 | NT | A | NT | NT |
| 132 | NT | A | NT | NT |
| 134 | NT | A | NT | NT |
| 135 | NT | A | NT | NT |
| 136 | NT | A | NT | NT |
| 137 | NT | A | A | NT |
| 138 | NT | A | NT | NT |
| 139 | NT | A | NT | NT |
| 140 | NT | A | NT | NT |
| 141 | NT | A | B | NT |
| 142 | NT | A | NT | NT |
| 143 | NT | A | NT | NT |
| 144 | NT | A | NT | NT |
| 145 | NT | A | D | NT |
| 146 | NT | A | C | NT |
| 147 | NT | A | B | NT |
| 148 | NT | A | C | NT |
| 149 | NT | A | D | NT |
| 150 | NT | A | D | NT |
| 153 | NT | A | A | NT |
| 154 | NT | A | B | NT |
| 155 | NT | A | A | NT |
| 156 | NT | A | B | NT |
| 158 | NT | C | D | NT |
| 159 | NT | C | D | NT |
| 162 | NT | A | B | NT |
| 175 | NT | A | B | NT |
| 177 | B | A | A | NT |
| 178 | A | A | A | NT |
| 179 | A | A | A | NT |
| 180 | A | A | A | NT |
| 181 | B | NT | NT | NT |
| 182 | A | NT | NT | NT |
| 183 | D | NT | NT | NT |
| 184 | D | NT | NT | NT |

Through the above biological assay, it can be found that the compounds of the present disclosure show good inhibitory activity on CMET, MER and TRK kinases. Especially for TRK kinase, it can also be seen from cell assay that some of the compounds of the present disclosure not only show inhibitory activity on Ba/F3 LMNA-NTRK1 cells, but also show inhibitory activity on G595R mutant cells. Therefore, the compounds of the present disclosure can be used for manufacture of medicaments for the treatment of corresponding diseases.

The biological data provided by the present disclosure show that the compounds of the present disclosure are beneficial for the treatment or prevention of diseases caused by abnormal tyrosine kinases. It has been proved that the compounds of the present disclosure can strongly inhibit the activity of tyrosine kinases such as TRKA, c-MET, AXL, MER, and VEGFR2, while these kinase families are closely related to autoimmune diseases and the occurrence and metastasis of cancers. Therefore, the compounds of the present disclosure are beneficial for the treatment of autoimmune diseases and cancers. The compounds of the present disclosure can also treat cancers that are resistant to one or more other treatment methods. The compounds of the present disclosure can be used as monotherapy or combination therapy in combination with multiple compounds of the present disclosure or in combination with other drugs other than those of the present disclosure.

The above-mentioned embodiments are only preferred embodiments of the present disclosure and are not intended to limit the present disclosure. Any modification, equivalent replacement and improvement made within the spirit and principle of the present disclosure should be included within the protection scope of the present disclosure.

What is claimed is:

1. A compound of structural Formula (I):

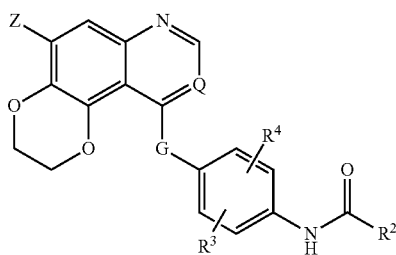

Formula (I)

or a pharmaceutically acceptable salt, stereoisomer, or tautomer thereof,
wherein:
Z is H or $OR^1$;
$R^1$ is H, $C_1$-$C_{10}$ alkyl, $(CH_2)_nR^B$, or $C_3$-$C_8$ cycloalkyl;
  wherein the $C_1$-$C_{10}$ alkyl is optionally substituted with 1, 2, or 3 substituents independently selected from the group consisting of halogen, CN, $CF_3$, $C_1$-$C_3$ acyl, $C(O)NH_2$, $NR^aR^b$, OH, $OC_1$-$C_6$ alkyl, $SC_1$-$C_6$ alkyl, and $C_3$-$C_7$ cycloalkyl; and
  wherein the $C_3$-$C_8$ cycloalkyl is optionally substituted with 1, 2, or 3 substituents independently selected from the group consisting of halogen, CN, $CF_3$, $C_1$-$C_3$ acyl, $C(O)NH_2$, $NR^aR^b$, OH, $OC_1$-$C_6$ alkyl, =O, and $SC_1$-$C_6$ alkyl;
$R^B$ is 4- to 8-membered heteroalicyclyl;
  wherein the 4- to 8-membered heteroalicyclyl contains one or two ring heteroatoms or heteroatomic groups independently selected from the group consisting of N, NH, O, and S; and
  wherein the 4- to 8-membered heteroalicyclyl is optionally substituted with 1, 2, or 3 substituents independently selected from the group consisting of halogen, CN, $C_1$-$C_3$ alkyl, $CF_3$, $C_1$-$C_3$ acyl, $NR^aR^b$, OH, $OC_1$-$C_3$ alkyl, =O, and $SC_1$-$C_3$ alkyl;
each $R^a$ is independently H, $C_1$-$C_6$ alkyl, or $C_3$-$C_6$ cycloalkyl, wherein each $C_1$-$C_6$ alkyl is optionally and independently substituted with 1 substituent selected from the group consisting of $NH_2$, $NHC_1$-$C_3$ alkyl, $N(C_1$-$C_3$ alkyl)$_2$, $OC_1$-$C_3$ alkyl, and $SC_1$-$C_3$ alkyl;
each $R^b$ is independently H, $C_1$-$C_6$ alkyl, or $C_3$-$C_6$ cycloalkyl, wherein each $C_1$-$C_6$ alkyl is optionally and independently substituted with 1 substituent selected from the group consisting of $NH_2$, $NHC_1$-$C_3$ alkyl, $N(C_1$-$C_3$ alkyl)$_2$, $OC_1$-$C_3$ alkyl, and $SC_1$-$C_3$ alkyl,
Q is CH or N;
G is —NH—, —O—, or —S—;
$R^3$ is H, halogen, $C_1$-$C_3$ alkyl, $CF_3$, or $OC_1$-$C_3$ alkyl;
$R^4$ is H, halogen, $C_1$-$C_3$ alkyl, $CF_3$, or $OC_1$-$C_3$ alkyl;

$R^2$ is

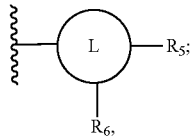

(i) ring L is unsaturated 5- or 6-membered heterocyclyl, aryl, or heteroaryl, wherein the 5- or 6-membered heterocyclyl or heteroaryl contains one, two, or three ring heteroatoms independently selected from the group consisting of N, O, and S; or
(ii) ring L is

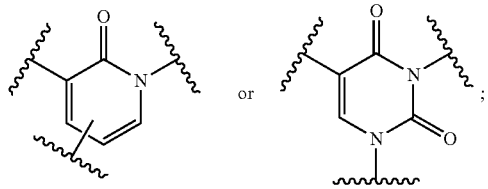

$R_5$ is H, $C_1$-$C_3$ alkyl, $C_4$-$C_6$ alkyl, or $OC_1$-$C_3$ alkyl, wherein the $C_1$-$C_3$ alkyl is substituted with 1, 2, or 3 substituents independently selected from the group consisting of halogen, alkenyl, C(O)OH, C(O)OC(CH$_3$)$_3$, OH, $OC_1$-$C_3$ alkyl, $C_3$-$C_6$ cycloalkyl, piperidinyl, 4-amino-4-methylpiperidinyl, 4-hydroxy-4-methylpiperidinyl, 4,4-dimethylpiperidinyl, piperazinyl, 4-methylpiperazinyl, morpholinyl, and pyrrolyl;
$R_6$ is $(CH_2)_tR^7$;
$R^7$ is $C_3$-$C_6$ cycloalkyl, aryl, or heteroaryl;
  wherein the $C_3$-$C_6$ cycloalkyl is optionally substituted with 1 or more substituents independently selected from the group consisting of halogen, $C_1$-$C_3$ alkyl, $CF_3$, and $OC_1$-$C_3$ alkyl; and
  wherein the aryl or heteroaryl is optionally substituted with 1 or more substituents independently selected from the group consisting of halogen, $C_1$-$C_3$ alkyl, $CF_3$, and $OC_1$-$C_3$ alkyl;
n is 0, 1, 2, 3, 4, 5, 6, 7, 8, 9, or 10; and
t is 0, 1, 2, or 3.

2. The compound according to claim 1, or a pharmaceutically acceptable salt, stereoisomer, or tautomer thereof, wherein:
$R^1$ is H, $C_1$-$C_8$ alkyl, $(CH_2)_nR^8$, or $C_3$-$C_8$ cycloalkyl, wherein the $C_1$-$C_8$ alkyl is optionally substituted with 1, 2, or 3 substituents independently selected from the group consisting of F, CN, $CF_3$, $C_1$-$C_3$ acyl, $C(O)NH_2$, $NR^aR^b$, OH, $OC_1$-$C_6$ alkyl, $SC_1$-$C_6$ alkyl, and $C_3$-$C_6$ cycloalkyl;
$R^8$ is 4- to 8-membered heteroalicyclyl;
  wherein the 4- to 8-membered heteroalicyclyl contains one or two ring heteroatoms or heteroatomic groups independently selected from the group consisting of N, NH, O, and S; and
  wherein the 4- to 8-membered heteroalicyclyl is optionally substituted with 1, 2, or 3 substituents independently selected from the group consisting of F, CN, $C_1$-$C_3$ alkyl, $CF_3$, $C_1$-$C_3$ acyl, $NR^aR^b$, OH, $OC_1$-$C_3$ alkyl, and =O;

each $R^a$ is independently H, $C_1$-$C_6$ alkyl, or $C_3$-$C_6$ cycloalkyl, wherein each $C_1$-$C_6$ alkyl is optionally and independently substituted with 1 $OC_1$-$C_3$ alkyl substituent;

each $R^b$ is independently H, $C_1$-$C_6$ alkyl, or $C_3$-$C_6$ cycloalkyl, wherein each $C_1$-$C_6$ alkyl is optionally and independently substituted with 1 $OC_1$-$C_3$ alkyl substituent; and n is 0, 1, 2, 3, 4, 5, 6, 7, or 8.

3. The compound according to claim 2, or a pharmaceutically acceptable salt, stereoisomer, or tautomer thereof, wherein:

$R^1$ is H, $C_1$-$C_6$ alkyl, $(CH_2)_nR^8$, or $C_3$-$C_6$ cycloalkyl, wherein the $C_1$-$C_6$ alkyl is optionally substituted with 1, 2, or 3 substituents independently selected from the group consisting of F, CN, $CF_3$, $C_1$-$C_3$ acyl, $C(O)NH_2$, $NR^aR^b$, OH, $OC_1$-$C_3$ alkyl, $SC_1$-$C_3$ alkyl, and $C_3$-$C_5$ cycloalkyl;

$R^8$ is 4- to 6-membered heteroalicyclyl;
wherein the 4- to 6-membered heteroalicyclyl contains one or two ring heteroatoms or heteroatomic groups independently selected from the group consisting of N, NH, O, and S; and
wherein the 4- to 6-membered heteroalicyclyl is optionally substituted with 1, 2, or 3 substituents independently selected from the group consisting of F, CN, $C_1$-$C_3$ alkyl, $CF_3$, $C_1$-$C_3$ acyl, $NR^aR^b$, OH, $OC_1$-$C_3$ alkyl, and =O;

each $R^a$ is independently H, $C_1$-$C_3$ alkyl, or $C_3$-$C_6$ cycloalkyl, wherein each $C_1$-$C_3$ alkyl is optionally and independently substituted with 1 $OC_1$-$C_3$ alkyl substituent;

each $R^b$ is independently H, $C_1$-$C_3$ alkyl, or $C_3$-$C_6$ cycloalkyl, wherein each $C_1$-$C_3$ alkyl is optionally and independently substituted with 1 $OC_1$-$C_3$ alkyl substituent; and n is 0, 1, 2, 3, 4, 5, or 6.

4. The compound according to claim 2, or a pharmaceutically acceptable salt, stereoisomer, or tautomer thereof, wherein:

$R^1$ is H, $C_1$-$C_6$ alkyl, $(CH_2)_nR^8$, cyclopropyl, cyclobutyl, cyclopentyl, or cyclohexyl, wherein the $C_1$-$C_6$ alkyl is optionally substituted with 1, 2, or 3 substituents independently selected from the group consisting of F, CN, $CF_3$, $C(O)H$, $C(O)CH_3$, $C(O)NH_2$, $NR^aR^b$, OH, $OCH_3$, $OCH_2CH_3$, $OCH_2CH_2CH_3$, $OCH(CH_3)_2$, $SCH_3$, $SCH_2CH_3$, cyclopropyl, cyclobutyl, and cyclopentyl;

$R^8$ is 4- to 6-membered azacycloalkyl, 4- to 6-membered oxacycloalkyl, 4- to 6-membered thiacycloalkyl, piperazin-1-yl, morpholin-4-yl, or thiomorpholin-4-yl;
wherein the 4- to 6-membered azacycloalkyl, 4- to 6-membered oxacycloalkyl, or 4- to 6-membered thiacycloalkyl contains one or two ring heteroatoms or heteroatomic groups independently selected from the group consisting of N, NH, O, and S; and
wherein the 4- to 6-membered azacycloalkyl, 4- to 6-membered oxacycloalkyl, 4- to 6-membered thiacycloalkyl, piperazin-1-yl, morpholin-4-yl, or thiomorpholin-4-yl is optionally substituted with 1, 2, or 3 substituents independently selected from the group consisting of F, CN, $CH_3$, $CH_2CH_3$, $CF_3$, $C(O)H$, $C(O)CH_3$, $NH_2$, OH, and =O; or each $R^a$ is independently H, $CH_3$, $CH_2OCH_3$, $CH_2CH_3$, $CH(OCH_3)CH_3$, $CH_2CH_2OCH_3$, $CH(OCH_3)CH_2CH_3$, $CH_2CH_2CH_2OCH_3$, cyclopropyl, or cyclobutyl;

each $R^b$ is independently H, $CH_3$, $CH_2OCH_3$, $CH_2CH_3$, $CH(OCH_3)CH_3$, $CH_2CH_2OCH_3$, $CH(OCH_3)CH_2CH_3$, $CH_2CH_2CH_2OCH_3$, cyclopropyl, or cyclobutyl; and n is 0, 1, 2, 3, 4, 5, or 6.

5. The compound according to claim 1, or a pharmaceutically acceptable salt, stereoisomer, or tautomer thereof, wherein:

$R^3$ is H, F, Cl, $CH_3$, $CH_2CH_3$, $CH_2CH_2CH_3$, $CH(CH_3)_2$, or $CF_3$; and $R^4$ is H, F, Cl, $CH_3$, $CH_2CH_3$, $CH_2CH_2CH_3$, $CH(CH_3)_2$, or $CF_3$.

6. The compound according to claim 1, or a pharmaceutically acceptable salt, stereoisomer, or tautomer thereof, wherein:

$R^2$ is

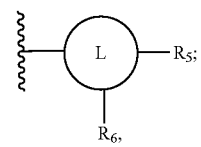

(i) ring L is pyranyl, phenyl, naphthyl, pyrrolyl, pyrazolyl, imidazolyl, oxazolyl, thiazolyl, pyridyl, or pyrimidinyl; or (ii) ring L is

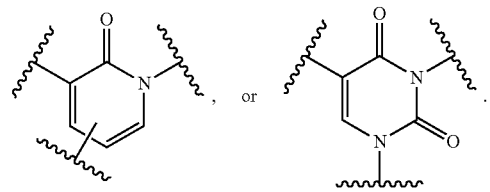

7. The compound according to claim 6, or a pharmaceutically acceptable salt, stereoisomer, or tautomer thereof, wherein:

$R^2$ is

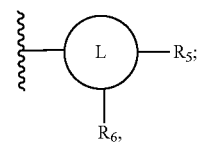

(i) ring L is

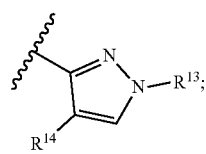

or (ii) ring L is

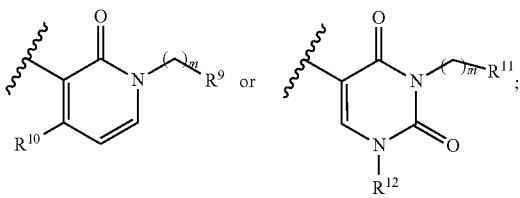

$R^5$ is $R^{10}$, $R^{12}$, or $R^{14}$;
$R_6$ is $(CH_2)_t R^7$;
$R^7$ is $R^9$, $R^{11}$, or $R^{13}$;
$R^9$ is $C_3$-$C_6$ cycloalkyl, phenyl, pyridyl, or pyrimidinyl;
  wherein the $C_3$-$C_6$ cycloalkyl is optionally substituted with 1 or more substituents independently selected from the group consisting of halogen, $C_1$-$C_3$ alkyl, $CF_3$, and $OC_1$-$C_3$ alkyl; and
  wherein the phenyl, pyridyl, or pyrimidinyl is optionally substituted with 1 or more substituents independently selected from the group consisting of halogen, $C_1$-$C_3$ alkyl, $CF_3$, and $OC_1$-$C_3$ alkyl;
$R^{10}$ is H, $C_1$-$C_3$ alkyl, or $OC_1$-$C_3$ alkyl;
$R^{11}$ is $C_3$-$C_6$ cycloalkyl, phenyl, pyridyl, or pyrimidinyl;
  wherein the $C_3$-$C_6$ cycloalkyl is optionally substituted with 1 or more substituents independently selected from the group consisting of halogen, $C_1$-$C_3$ alkyl, $CF_3$, and $OC_1$-$C_3$ alkyl; and
  wherein the phenyl, pyridyl, or pyrimidinyl is optionally substituted with 1 or more substituents independently selected from the group consisting of halogen, $C_1$-$C_3$ alkyl, $CF_3$, and $OC_1$-$C_3$ alkyl;
$R^{12}$ is H, $C_1$-$C_3$ alkyl, or $C_4$-$C_6$ alkyl, wherein the $C_1$-$C_3$ alkyl is substituted with 1, 2, or 3 substituents independently selected from the group consisting of halogen, alkenyl, C(O)OH, $C(O)OC(CH_3)_3$, OH, $OC_1$-$C_3$ alkyl, $C_3$-$C_6$ cycloalkyl, and morpholinyl;
$R^{13}$ is phenyl, pyridyl, or pyrimidinyl, wherein the phenyl, pyridyl, or pyrimidinyl is optionally substituted with 1 or more substituents independently selected from the group consisting of halogen, $C_1$-$C_3$ alkyl, $CF_3$, and $OC_1$-$C_3$ alkyl;
$R^{14}$ is H, $C_1$-$C_3$ alkyl, or $OC_1$-$C_3$ alkyl;
t is m; and
m is 0, 1, 2, or 3.

8. The compound according to claim 7, or a pharmaceutically acceptable salt, stereoisomer, or tautomer thereof, wherein:
$R^9$ is $C_3$-$C_6$ cycloalkyl, phenyl, pyridyl, or pyrimidinyl, wherein the phenyl, pyridyl, or pyrimidinyl is substituted with 1 or more substituents independently selected from the group consisting of F, Cl, $CH_3$, and $CH_2CH_3$;
$R^{10}$ is H, $OCH_3$, or $OCH_2CH_3$;
$R^{11}$ is $C_3$-$C_6$ cycloalkyl, phenyl, pyridyl, or pyrimidinyl, wherein the phenyl, pyridyl, or pyrimidinyl is substituted with 1 or more substituents independently selected from the group consisting of F, Cl, $CH_3$, and $CH_2CH_3$;
$R^{12}$ is $CH_3$, $CH_2CH=CH_2$, $CH_2C(O)OH$, $CH_2C(O)OC(CH_3)_3$, $CH_2$-cyclopropyl, $CH_2CH_3$, $CH(F)CH_3$, $CH_2CH_2F$, $CH(OH)CH_3$, $CH_2CH_2OH$, $CH(OCH_3)CH_3$, $CH_2CH_2OCH_3$, $CH(OCH_3)CH_3$, $CH_2CH_2OCH_3$, $CH(CH_3)_2$, $CH(OH)CH_2CH_3$, $CH_2CH_2CH_2OH$, $CH(OCH_3)CH_2CH_3$, $CH_2CH_2CH_2$ $OCH_3$, $CH(OCH_2CH_3)CH_2CH_3$, $CH_2CH_2CH_2OCH_2CH_3$, $CH(morpholinyl)CH_2CH_3$, $CH_2CH_2CH_2$-morpholinyl, or $CH_2CH(CH_3)_2$;
$R^{13}$ is phenyl, pyridyl, or pyrimidinyl, wherein the phenyl, pyridyl, or pyrimidinyl is substituted with 1 or more substituents independently selected from the group consisting of F and $C_1$; and
$R^{14}$ is H, $OCH_3$, or $OCH_2CH_3$.

9. The compound according to claim 1, or a pharmaceutically acceptable salt, stereoisomer, or tautomer thereof, wherein:
Z is $OR^1$;
$R^1$ is $C_1$-$C_6$ alkyl or $(CH_2)_n R^8$, wherein the $C_1$-$C_6$ alkyl is optionally substituted with 1, 2, or 3 substituents independently selected from the group consisting of F, CN, $CF_3$, C(O)H, $C(O)CH_3$, $C(O)NH_2$, $NR^a R^b$, OH, $OCH_3$, $OCH_2CH_3$, $OCH_2CH_2CH_3$, $OCH(CH_3)_2$, $SCH_3$, $SCH_2CH_3$, cyclopropyl, cyclobutyl, and cyclopentyl;
$R^8$ is 4- to 6-membered azacycloalkyl, 4- to 6-membered oxacycloalkyl, 4- to 6-membered thiacycloalkyl, piperazin-1-yl, morpholin-4-yl, or thiomorpholin-4-yl;
  wherein the 4- to 6-membered azacycloalkyl, 4- to 6-membered oxacycloalkyl, or 4- to 6-membered thiacycloalkyl contains one or two ring heteroatoms or heteroatomic groups independently selected from the group consisting of N, NH, O, and S; and
  wherein the 4- to 6-membered azacycloalkyl, 4- to 6-membered oxacycloalkyl, or 4- to 6-membered thiacycloalkyl is optionally substituted with 1, 2, or 3 substituents independently selected from the group consisting of F, CN, $CH_3$, $CH_2CH_3$, $CF_3$, C(O)H, $C(O)CH_3$, $NH_2$, OH, and =O; or
each $R^a$ is independently H, $CH_3$, $CH_2OCH_3$, $CH_2CH_3$, $CH(OCH_3)CH_3$, $CH_2CH_2OCH_3$, $CH(OCH_3)CH_2CH_3$, $CH_2CH_2CH_2OCH_3$, cyclopropyl, or cyclobutyl;
each $R^b$ is independently H, $CH_3$, $CH_2OCH_3$, $CH_2CH_3$, $CH(OCH_3)CH_3$, $CH_2CH_2OCH_3$, $CH(OCH_3)CH_2CH_3$, $CH_2CH_2CH_2OCH_3$, cyclopropyl, or cyclobutyl;
Q is CH;
G is —O—
$R^3$ is H, F, Cl, $CH_3$, or $CH_2CH_3$;
$R^4$ is H, F, Cl, $CH_3$, or $CH_2CH_3$;
$R^2$ is

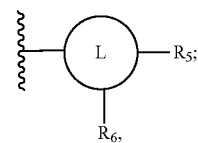

ring L is

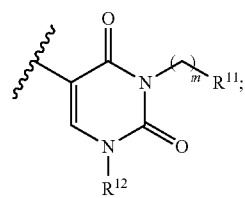

$R_5$ is $R^{12}$;
$R_6$ is $(CH_2)_t R^7$,
$R^7$ is $R^{11}$;
$R^{11}$ is phenyl, wherein the phenyl is optionally substituted with 1 or more substituents independently selected from the group consisting of F, Cl, $CH_3$, $CH_2CH_3$, $CF_3$, $OCH_3$, and $OCH_2CH_3$;
$R^{12}$ is H, $CH_3$, $CH_2CH_3$, $CH_2CH_2CH_3$, or $CH(CH_3)_2$;
n is 0, 1, 2, 3, 4, 5, or 6;
t is m; and
m is 0, 1, 2, or 3.

10. The compound according to claim 9, or a pharmaceutically acceptable salt, stereoisomer, or tautomer thereof, wherein:
$R^1$ is $C_1$-$C_4$ alkyl, $(CH_2)_n NR^a R^b$, $CH_2CN$, $CH_2$-cyclopropyl, $CH_2$-(1-aminocyclopropyl), $CH(CN)CH_3$, $CH_2CH_2CN$, $CH(OH)CH_3$, $CH_2CH_2OH$, $CH(OCH_3)CH_3$, $CH_2CH_2OCH_3$, $CH(OCH_2CH_3)CH_3$, $CH_2CH_2OCH_2CH_3$, $CH(CN)CH_2CH_3$, $CH_2CH_2CH_2CN$, $CH(OH)CH_2CH_3$, $CH_2CH_2Cl_2OH$, $CH(OCH_3)CH_2CH_3$, $CH_2CH_2CH_2OCH_3$, $CH(OCH_2CH_3)CH_2CH_3$, $CH_2CH_2CH_2OCH_2CH_3$, $CH_2CH_2CH_2$-pyrrolidin-1-yl, $CH_2CH_2CH_2$-piperidin-1-yl, $CH_2CH_2CH_2$-(4-amino-4-methylpiperidin-1-yl), $CH_2CH_2CH_2$-(4-hydroxy-4-methylpiperidin-1-yl), $CH_2CH_2CH_2$-(4,4-dimethylpiperidin-1-yl), $CH_2CH_2CH_2$-(4-methylpiperazin-1-yl), $CH_2CH_2CH_2$-(4-acetylpiperazin-1-yl), $CH_2CH_2CH_2$-morpholin-4-yl, $CH_2CH_2CH_2$-(1,1-dioxothiomorpholin-4-yl), oxetan-3-yl, tetrahydrofuran-3-yl, tetrahydropyran-3-yl, or tetrahydropyran-4-yl;
each $R^a$ is independently H, $CH_3$, $CH_2OCH_3$, $CH_2CH_3$, $CH(OCH_3)CH_3$, $CH_2CH_2OCH_3$, cyclopropyl, or cyclobutyl;
each $R^b$ is independently H, $CH_3$, $CH_2OCH_3$, $CH_2CH_3$, $CH(OCH_3)CH_3$, $CH_2CH_2OCH_3$, cyclopropyl, or cyclobutyl; and
n is 1, 2, 3, 4, 5, or 6.

11. The compound according to claim 1, wherein the compound is selected from the group consisting of:

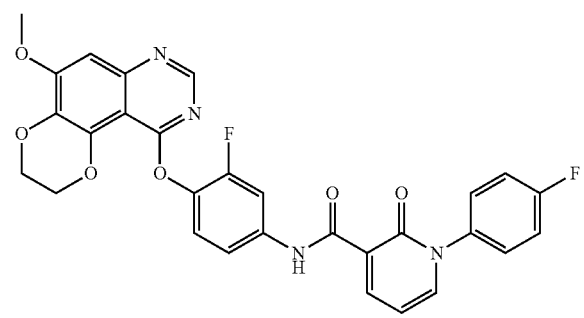

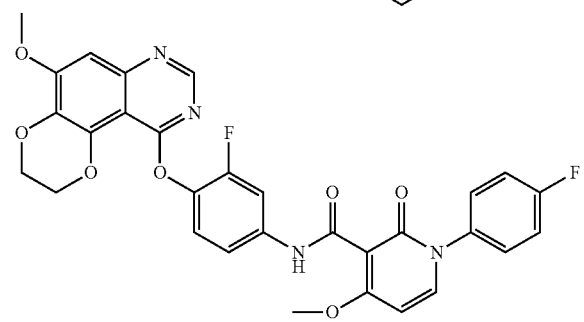

-continued

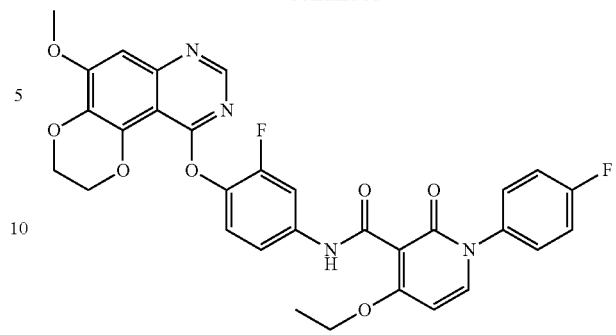

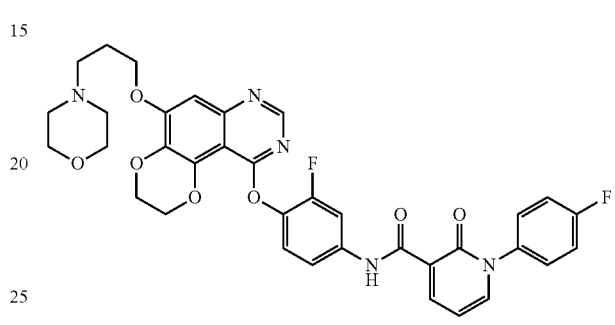

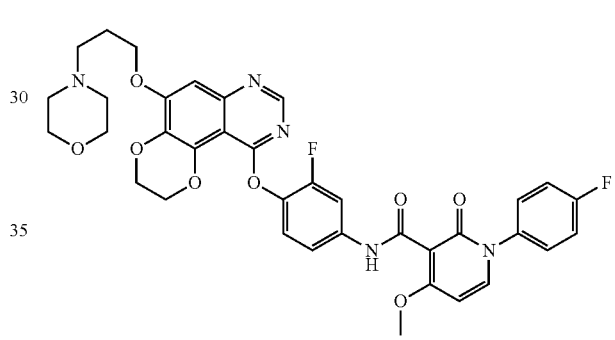

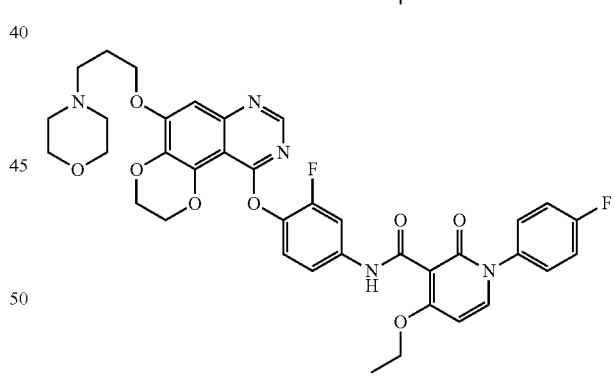

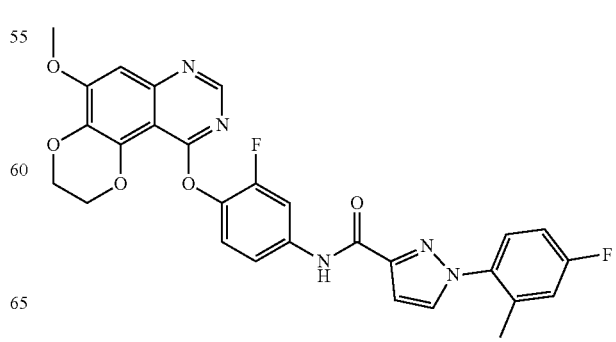

205
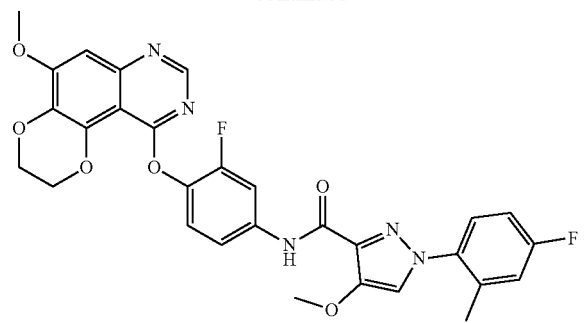
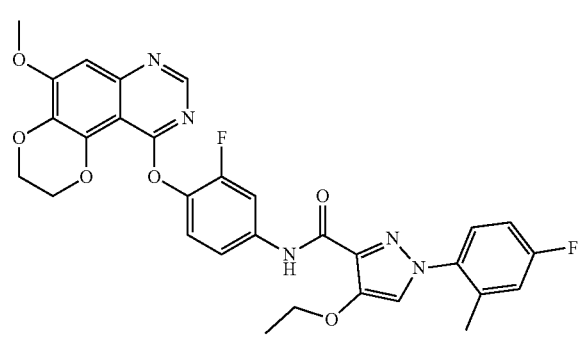
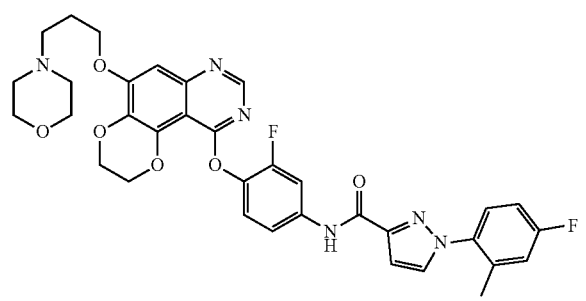
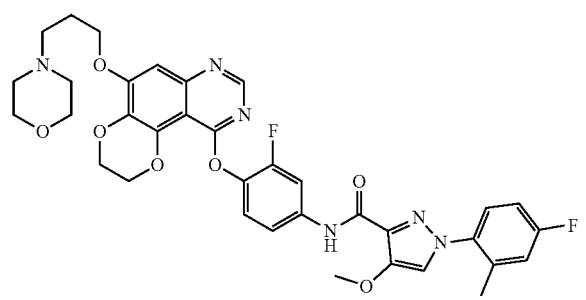
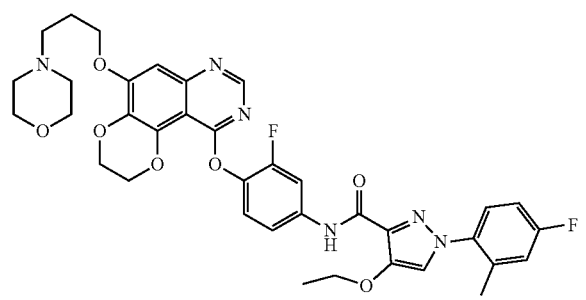
206
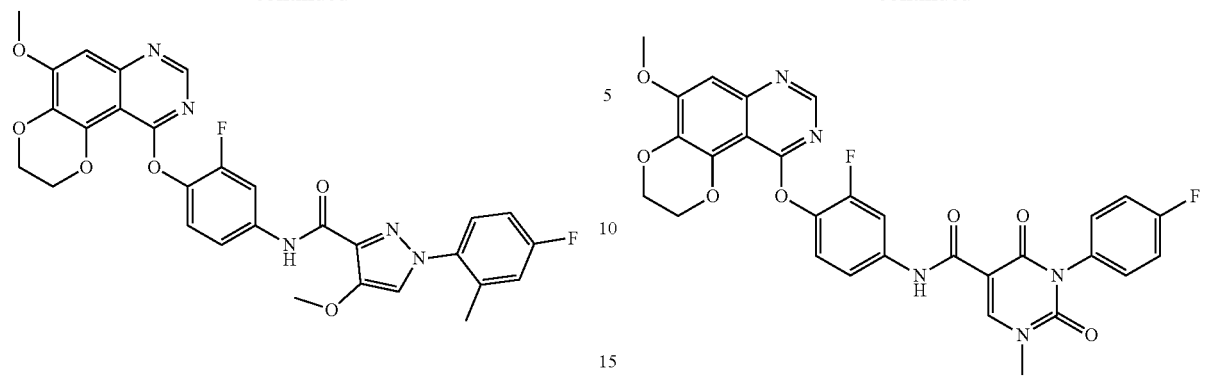
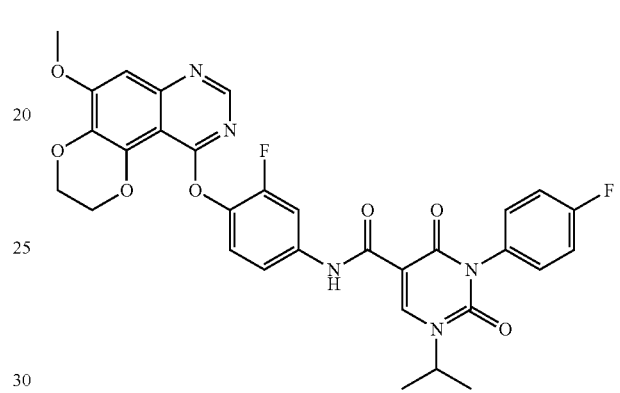
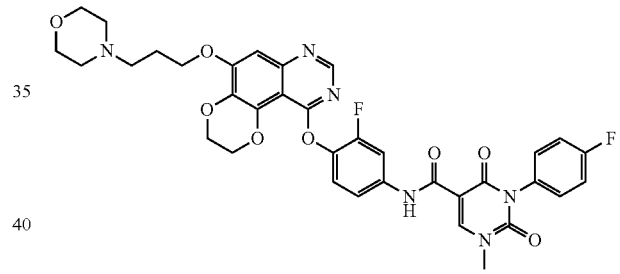
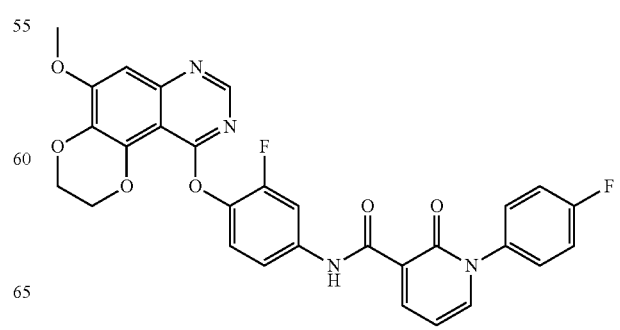

207
-continued
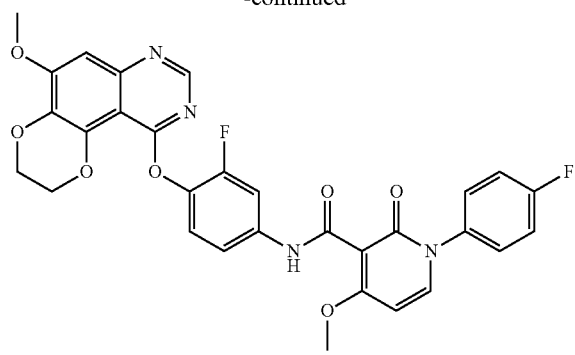
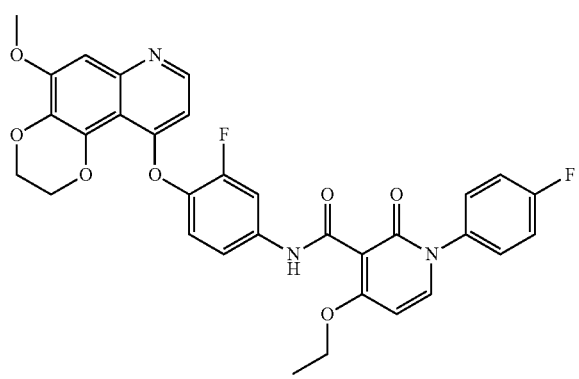
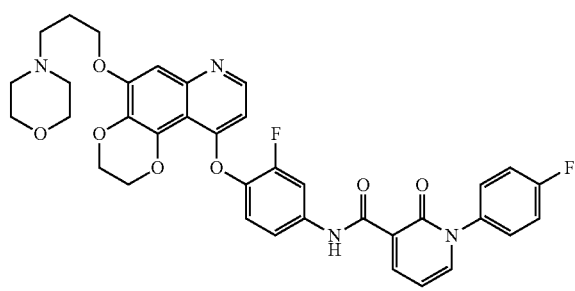
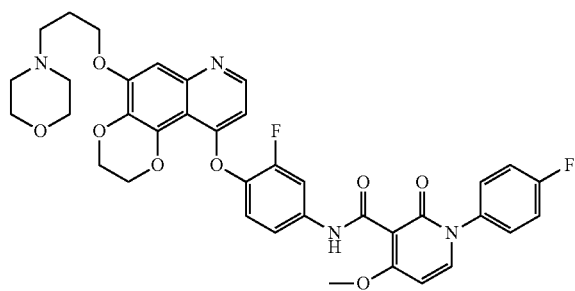
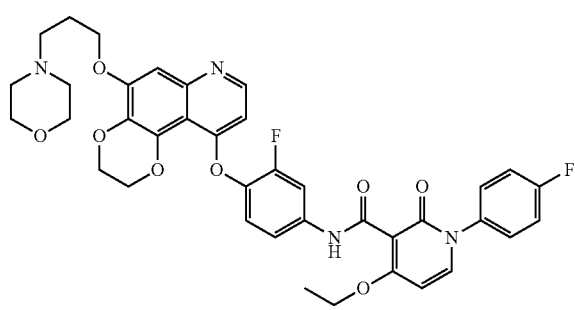
208
-continued
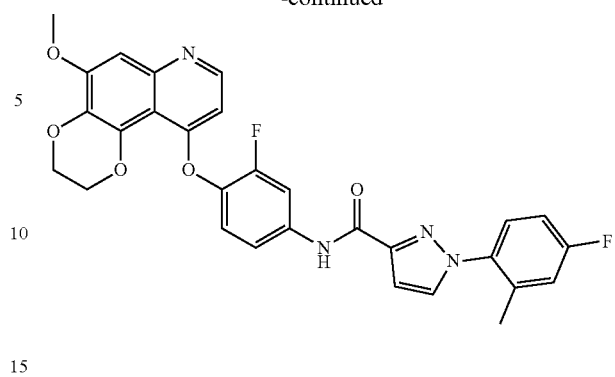
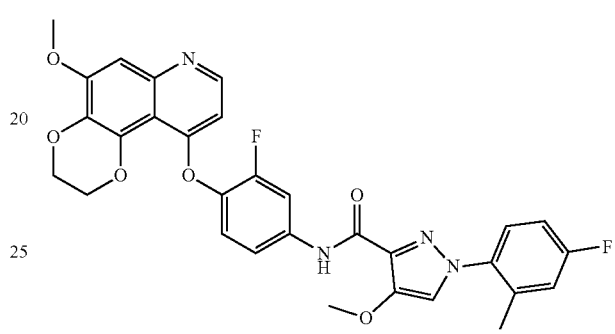
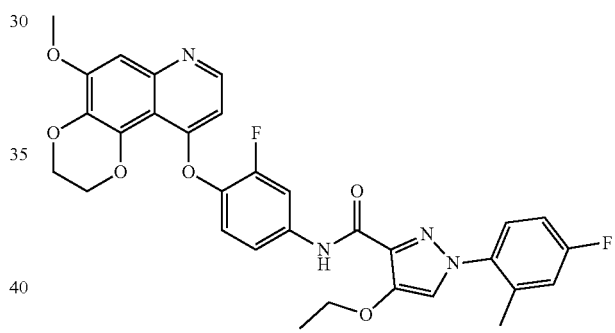
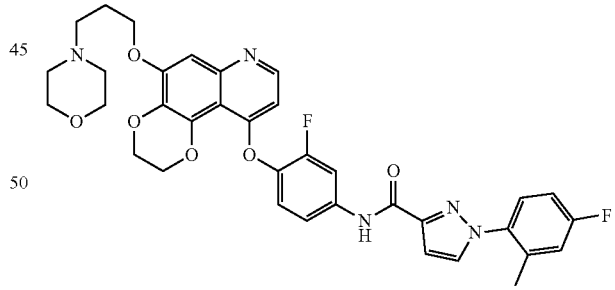
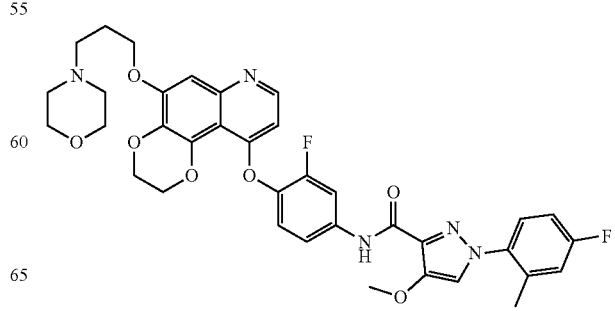

209
-continued
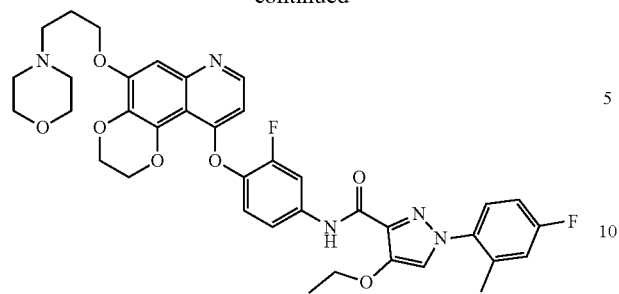
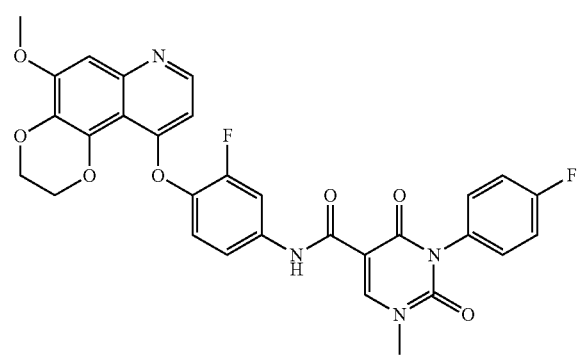
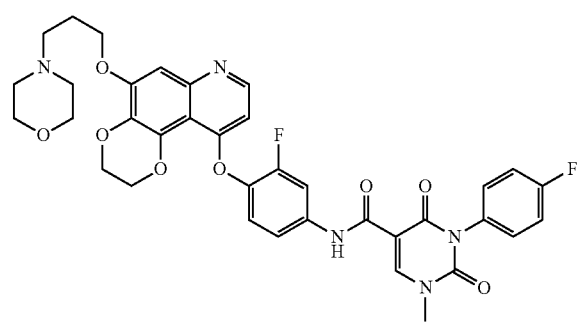
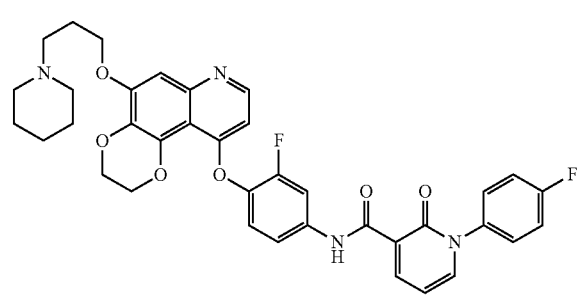
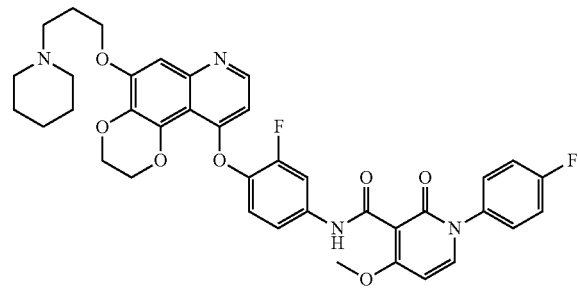
210
-continued
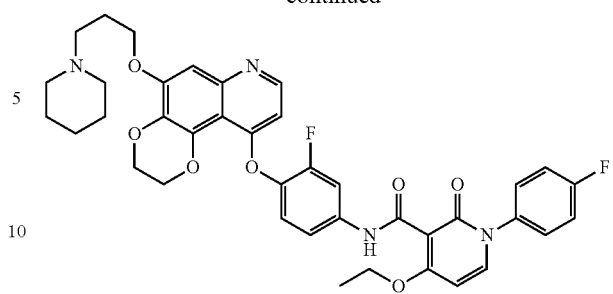
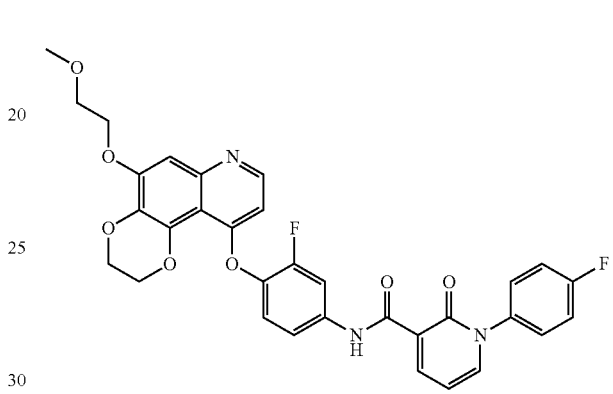
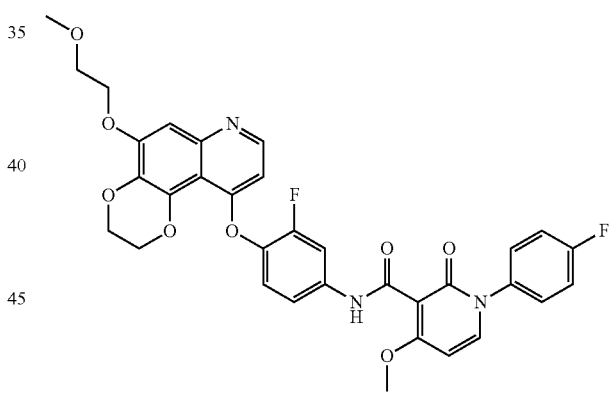
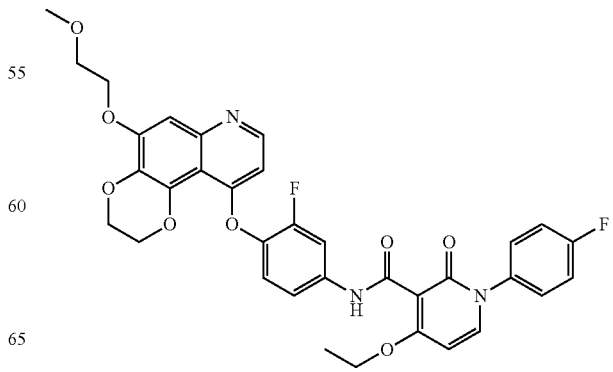
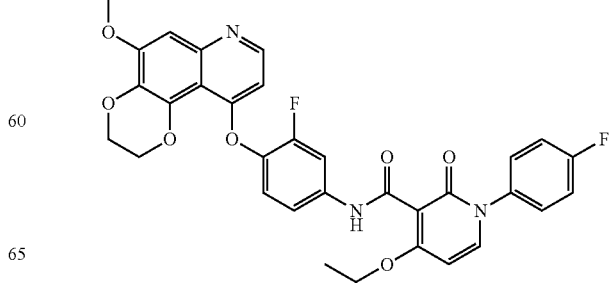

211
-continued
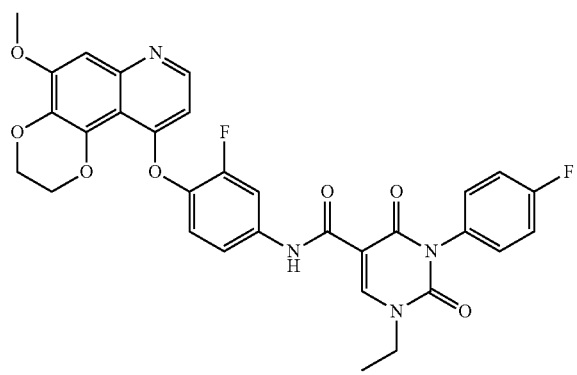
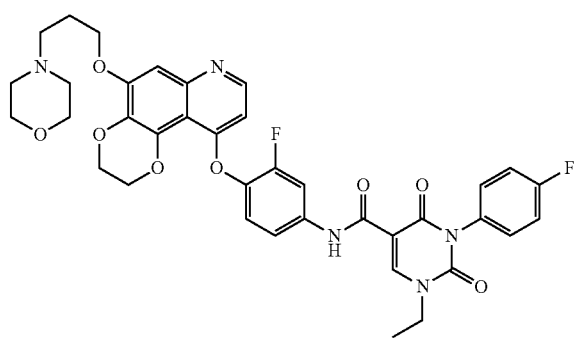
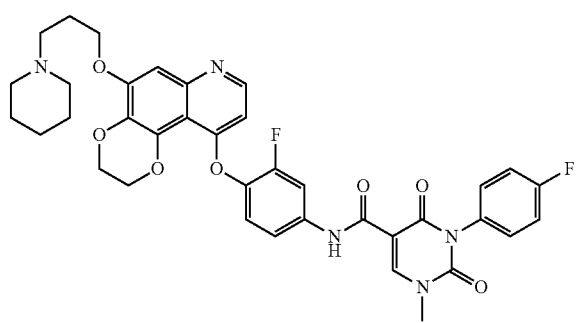
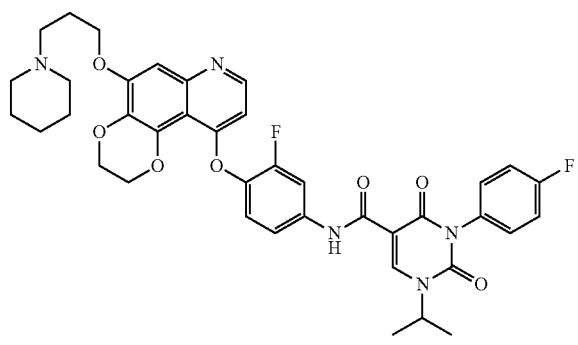
212
-continued
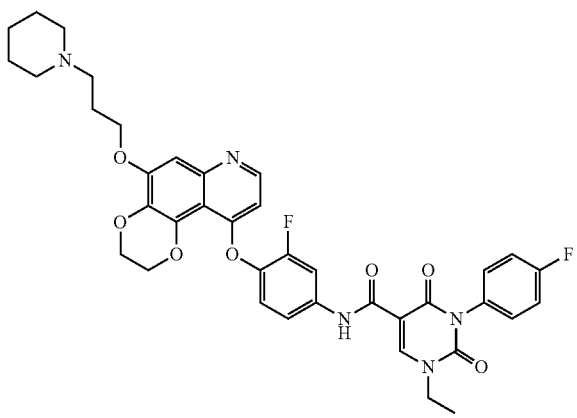
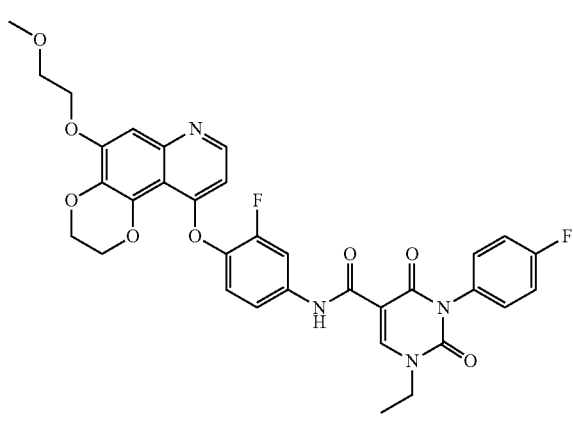

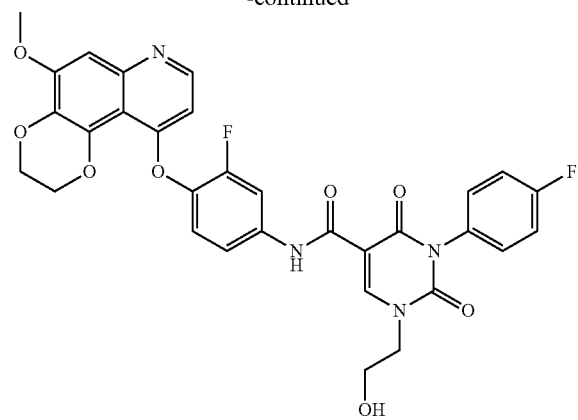
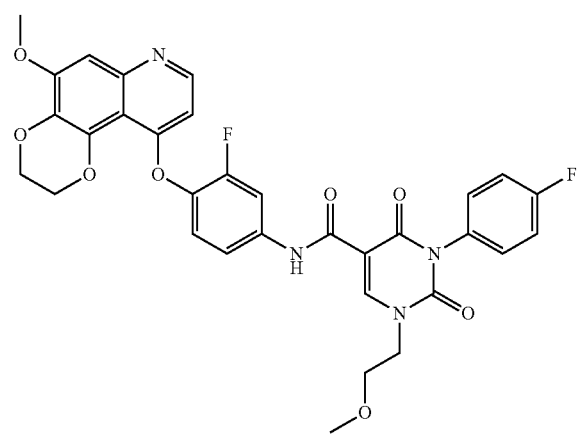
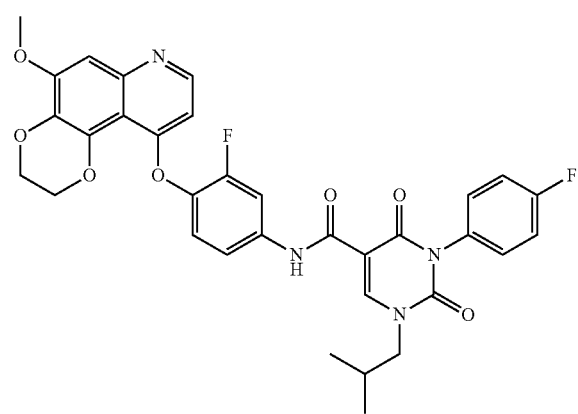
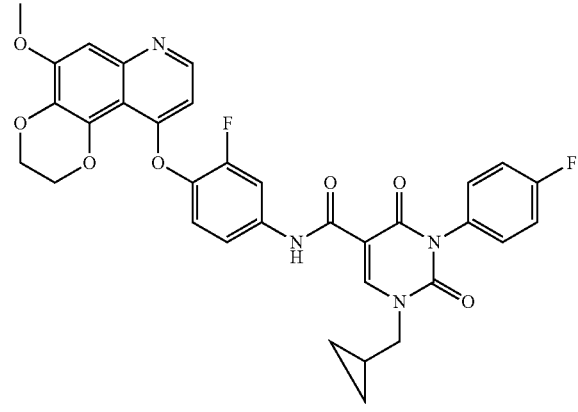
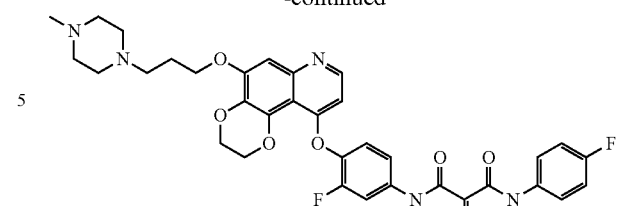
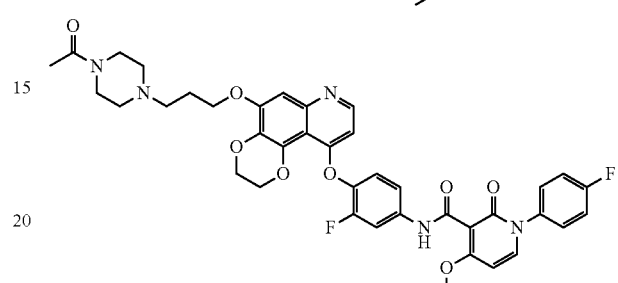
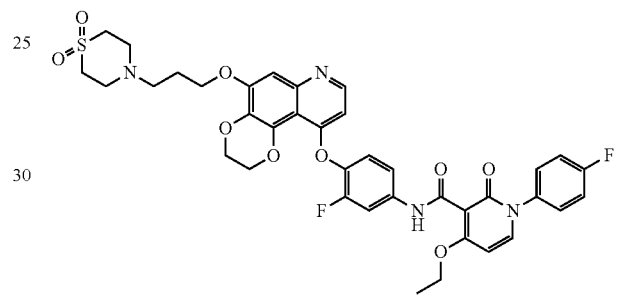
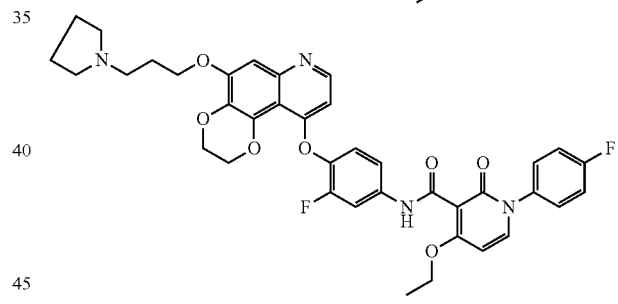
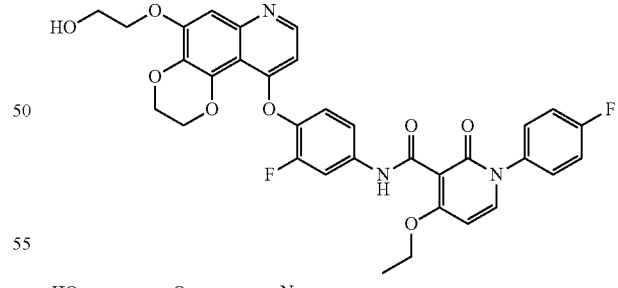
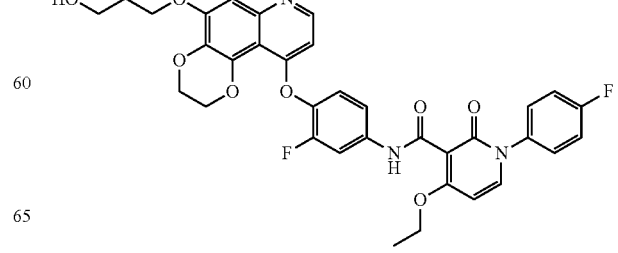

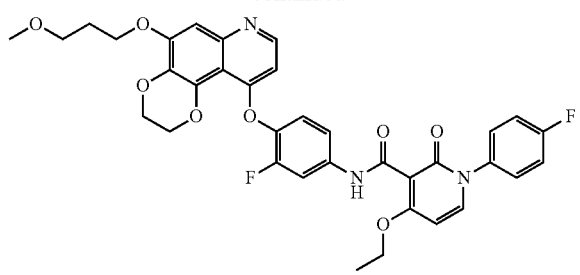
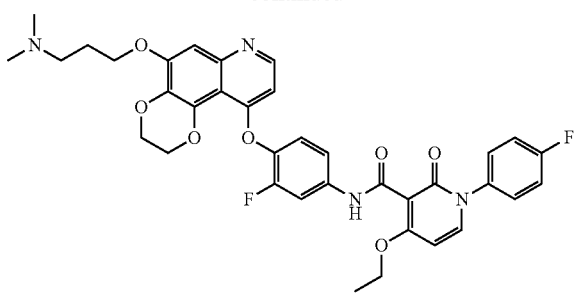
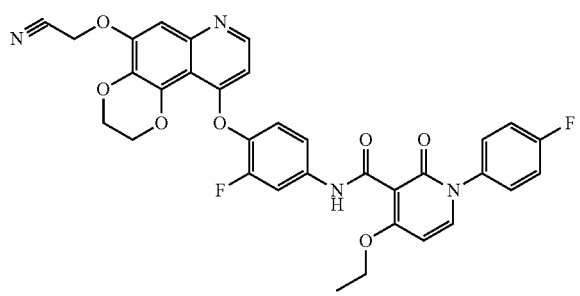
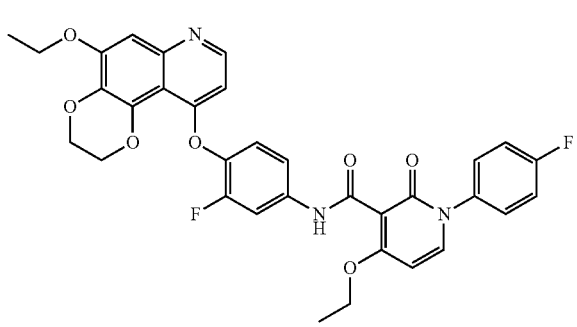
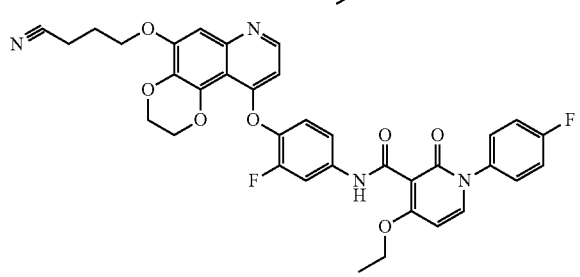
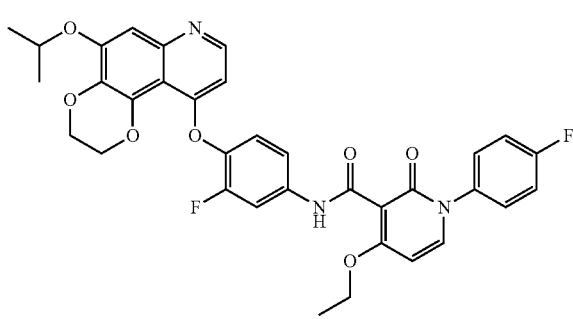
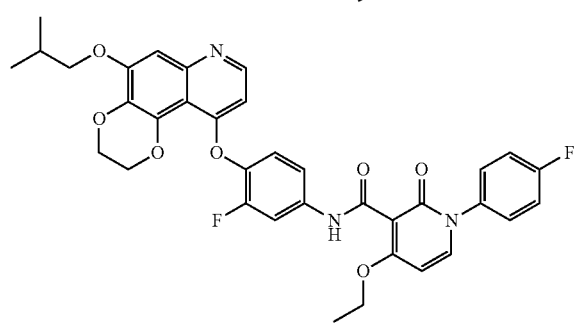
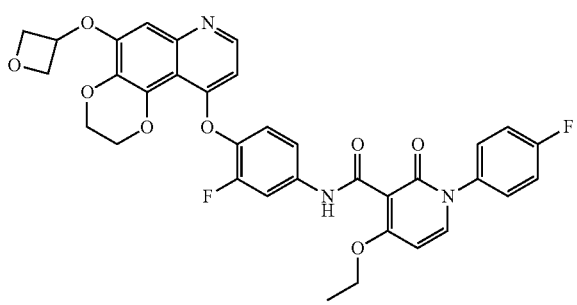
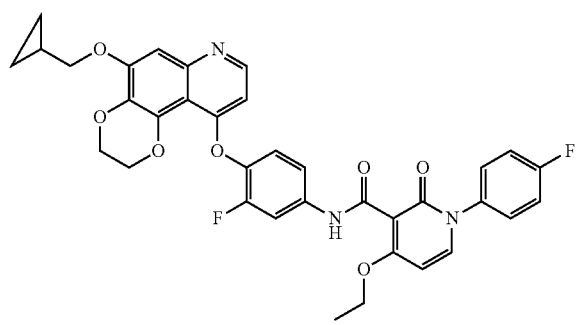
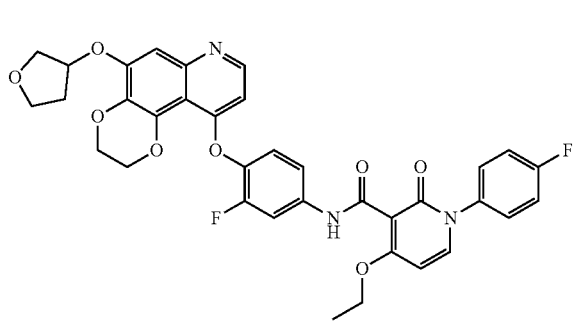

217
-continued
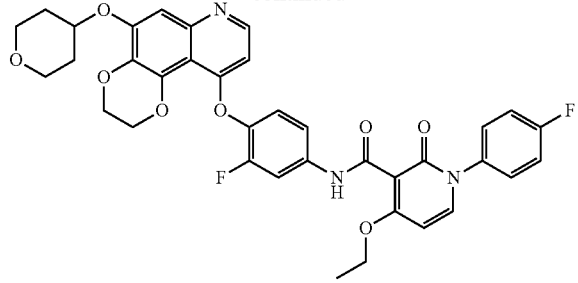
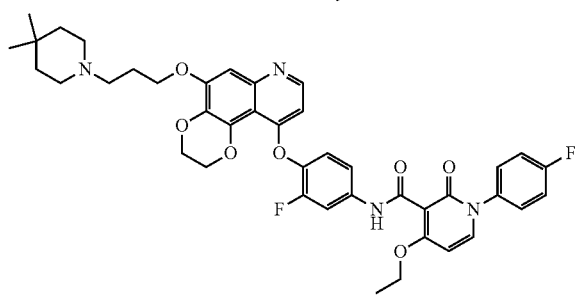
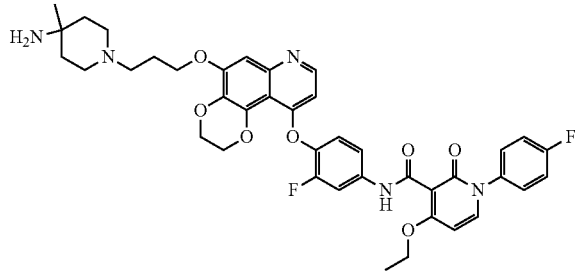
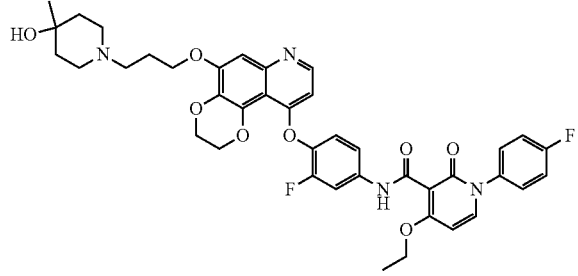
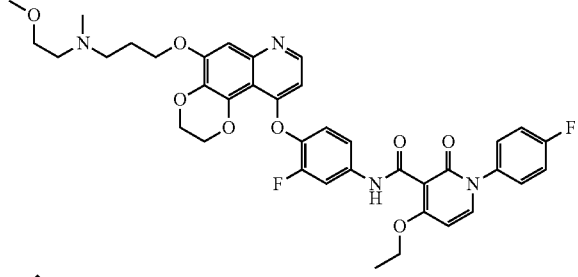
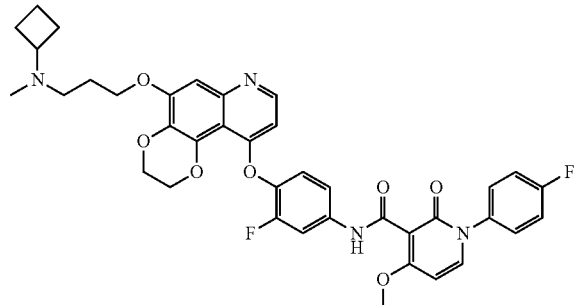
218
-continued
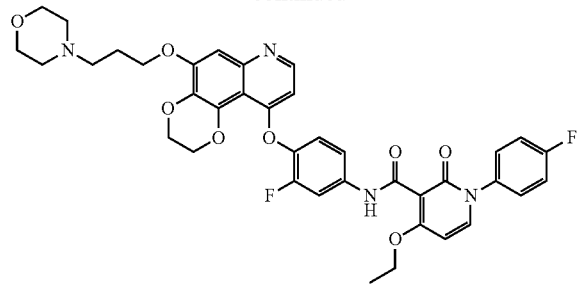
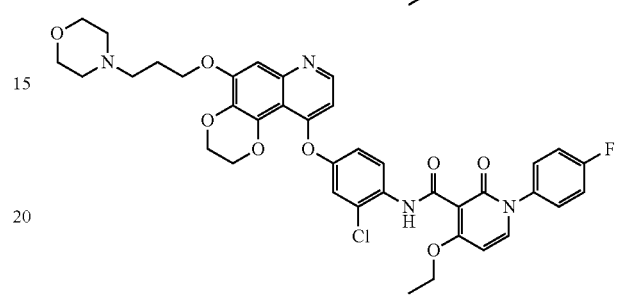
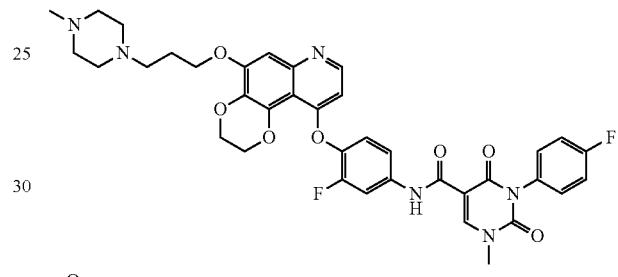
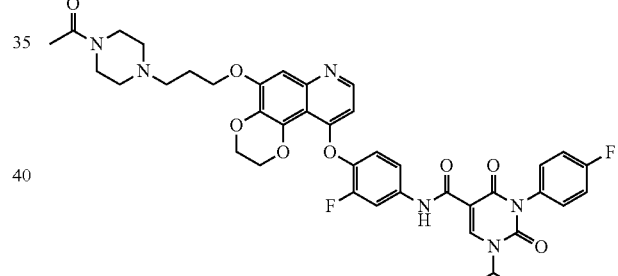
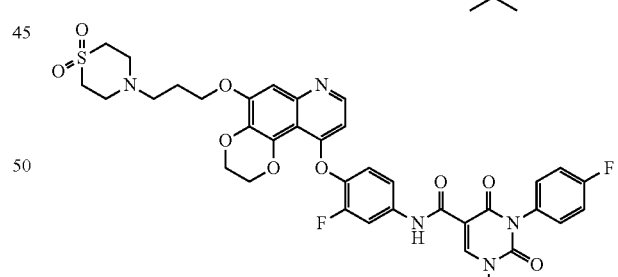
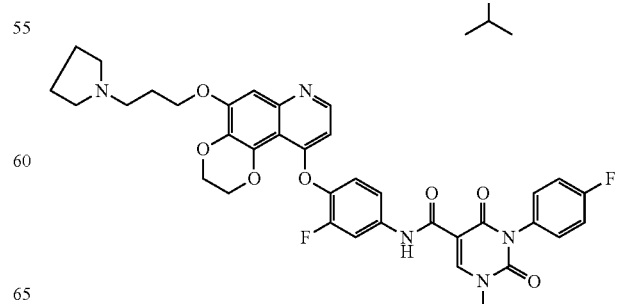

219
-continued
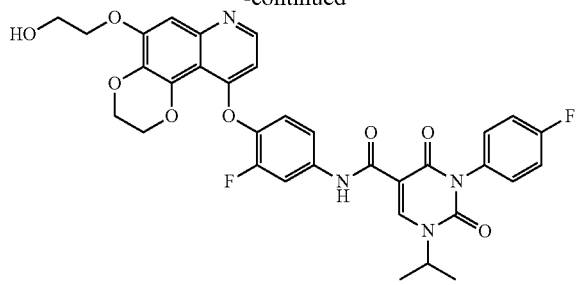
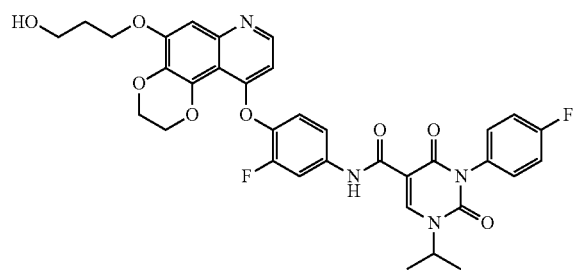
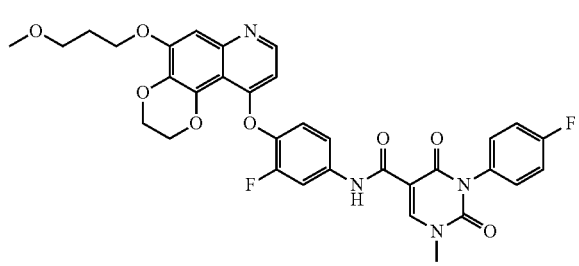
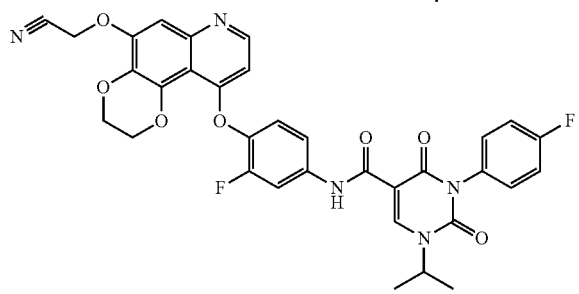
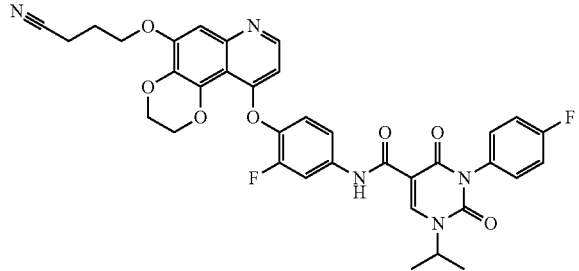
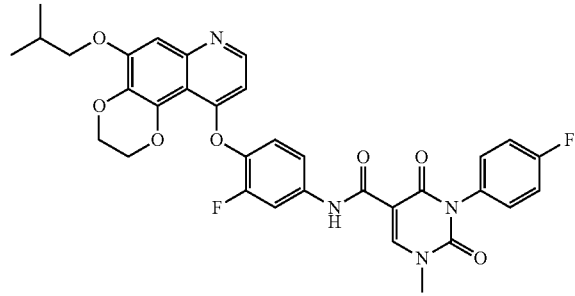
220
-continued
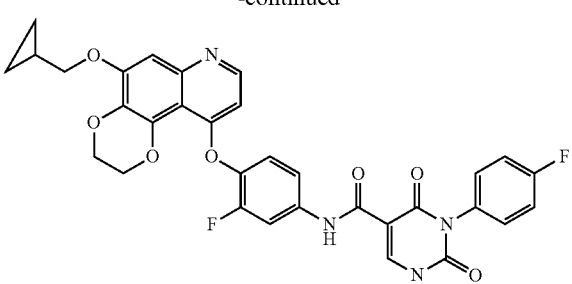
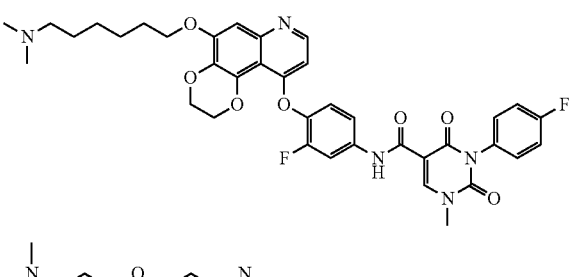
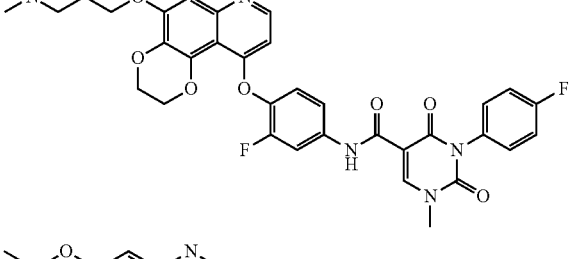
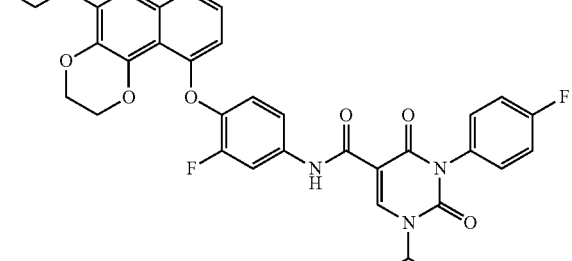
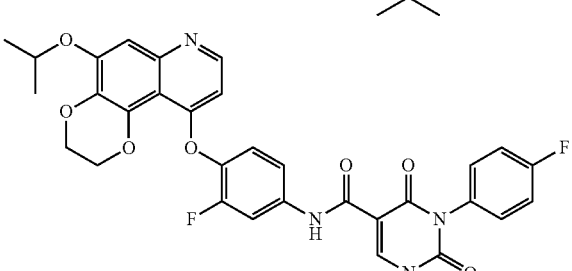
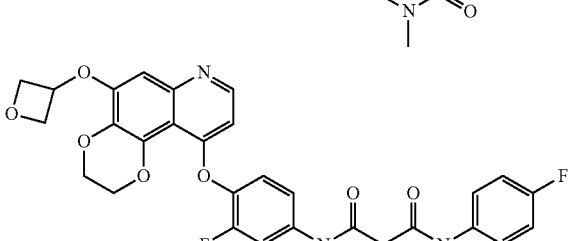
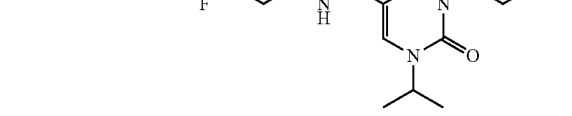

221
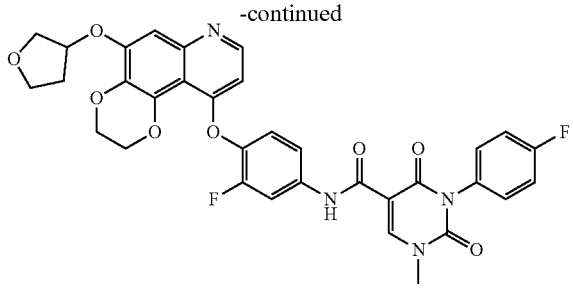
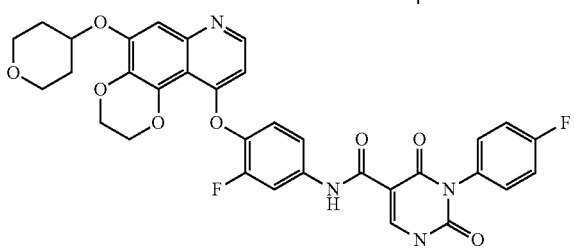
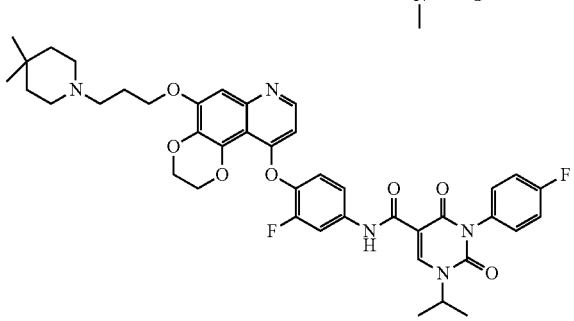
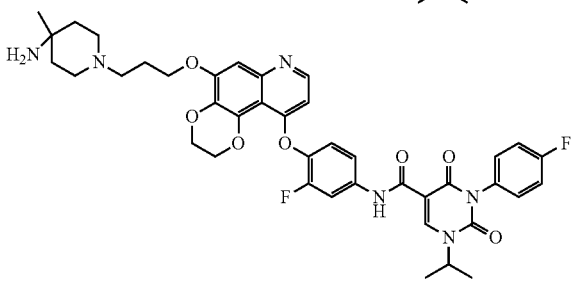
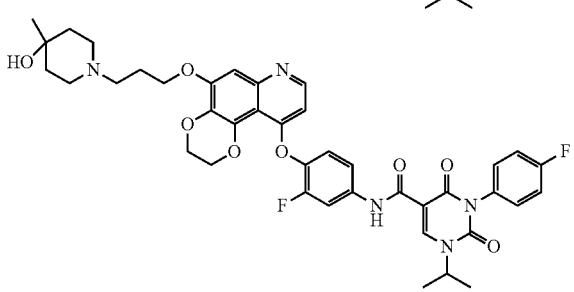
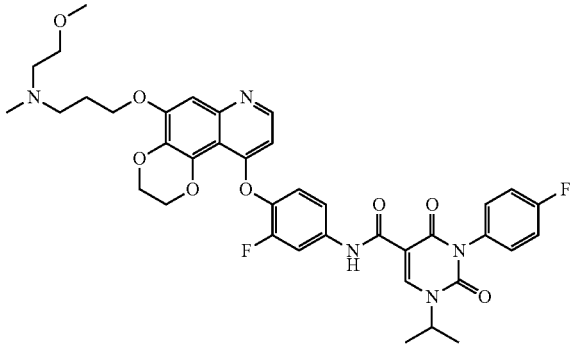
222
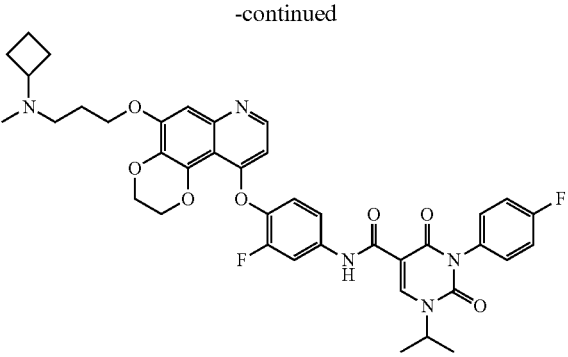
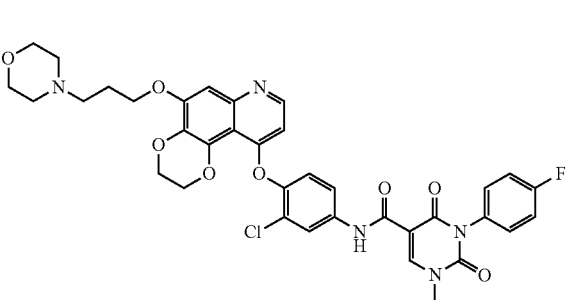
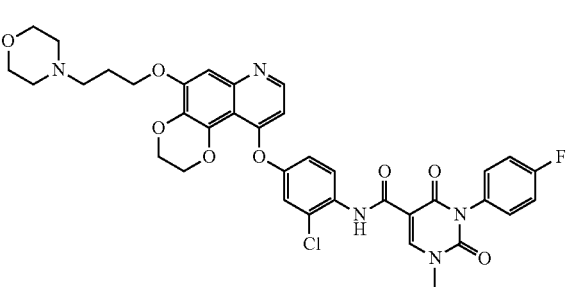
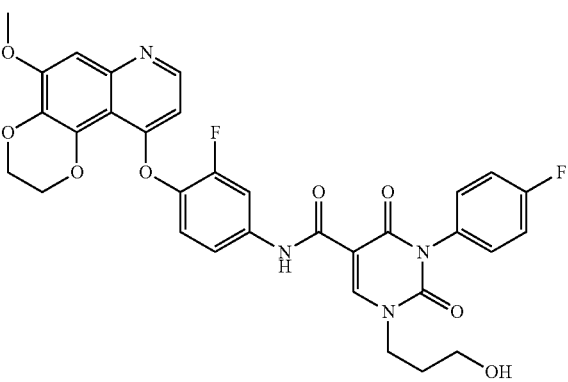
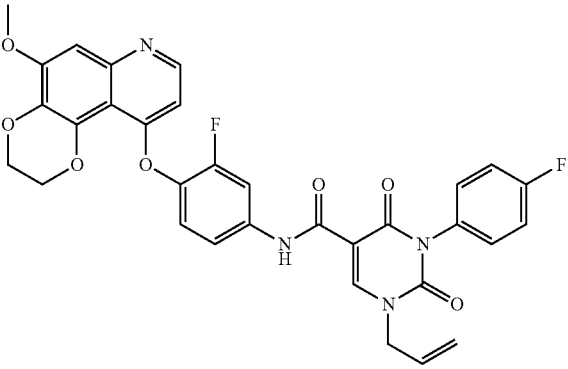

223
-continued
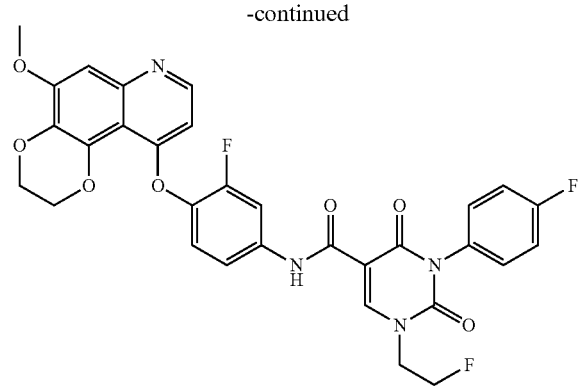
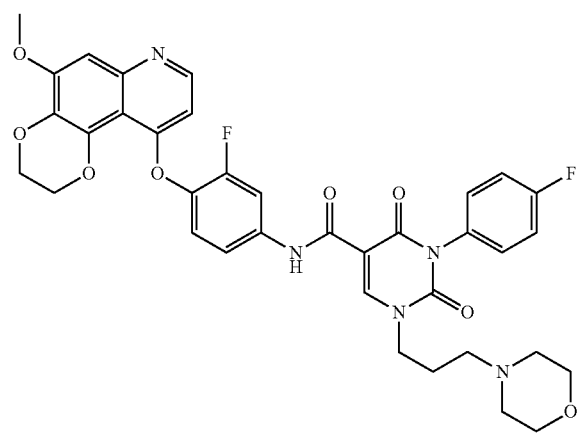
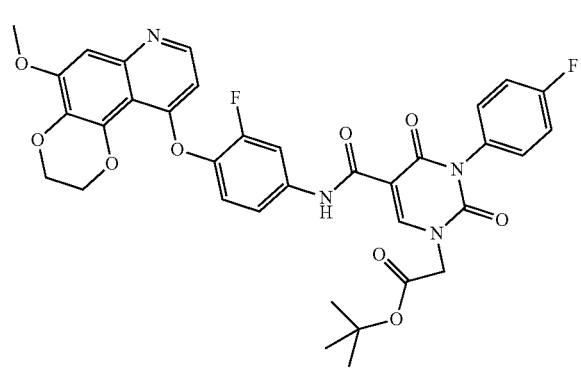
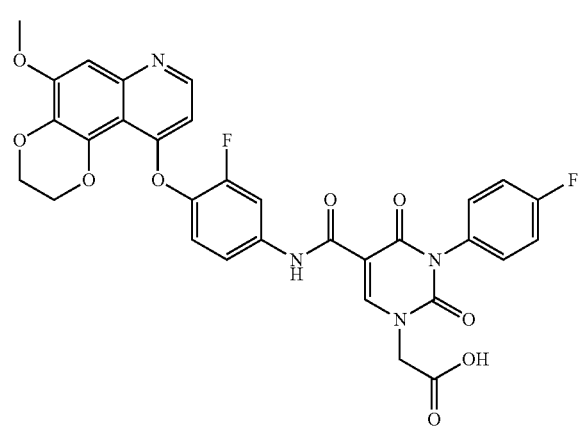
224
-continued
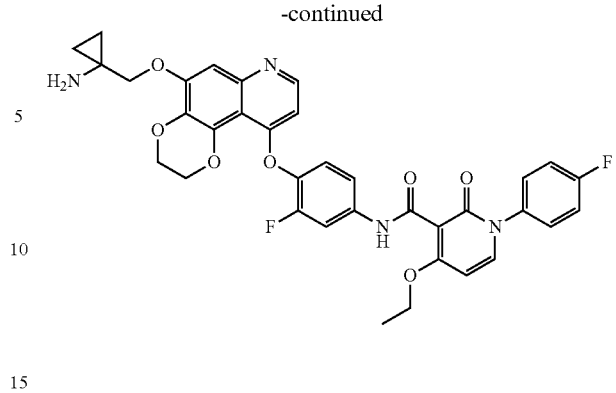
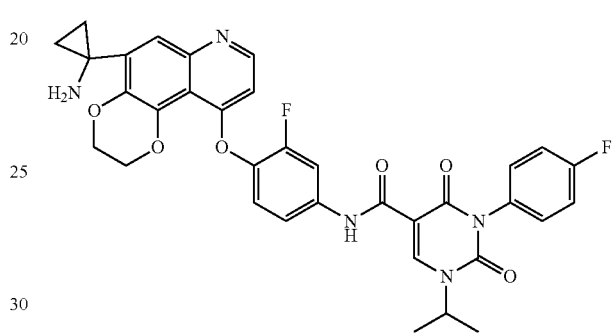
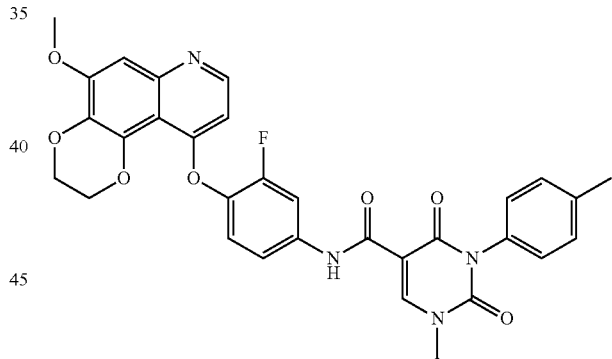
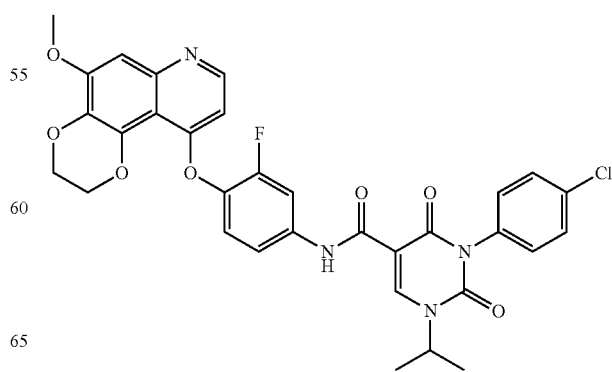

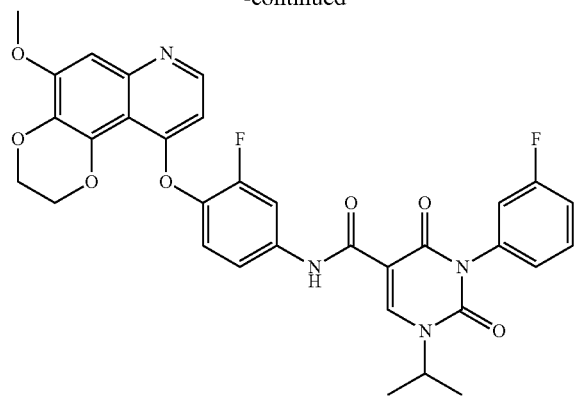
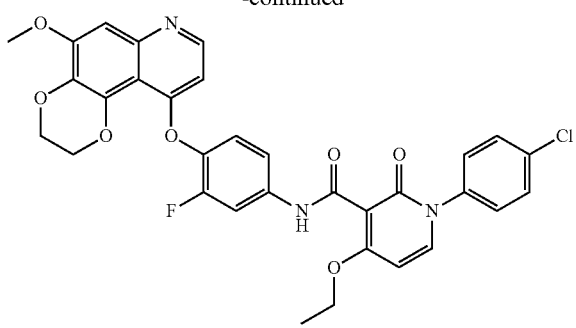
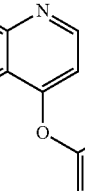
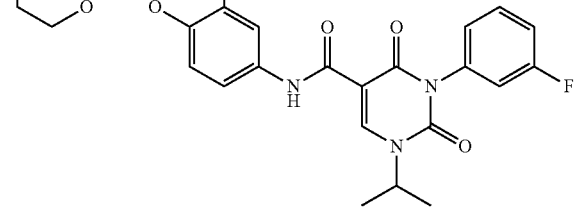
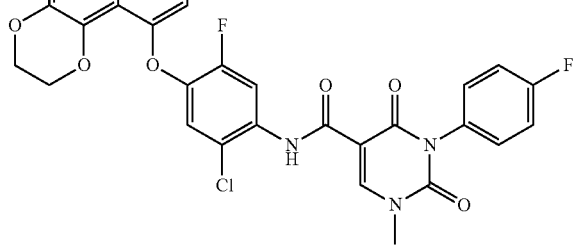
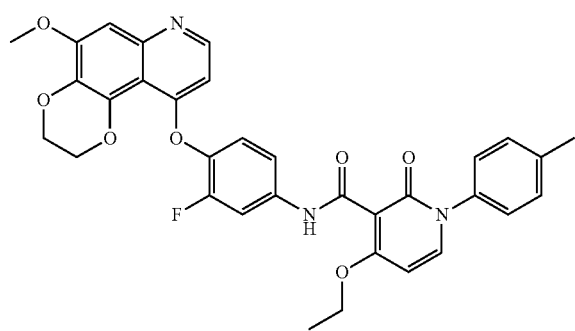
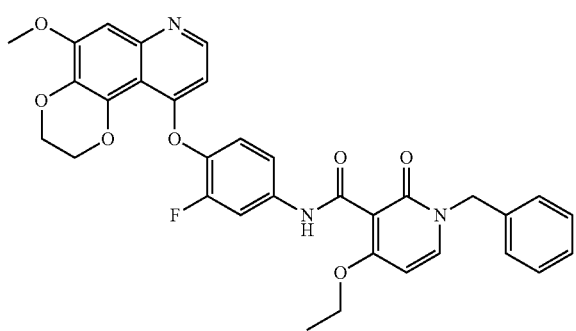

227
-continued
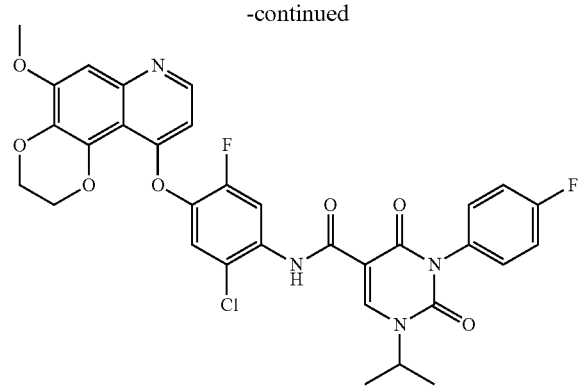
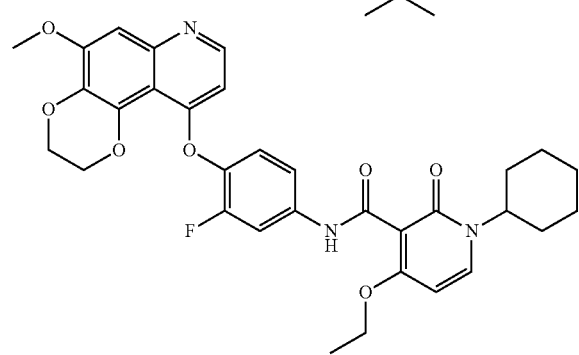
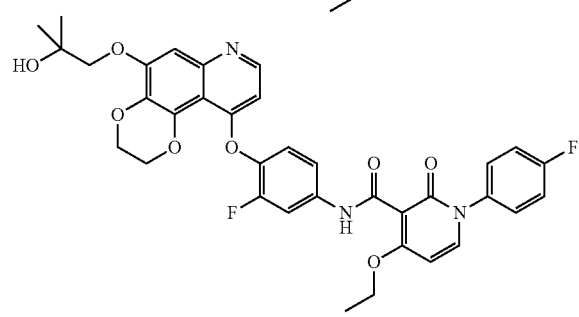
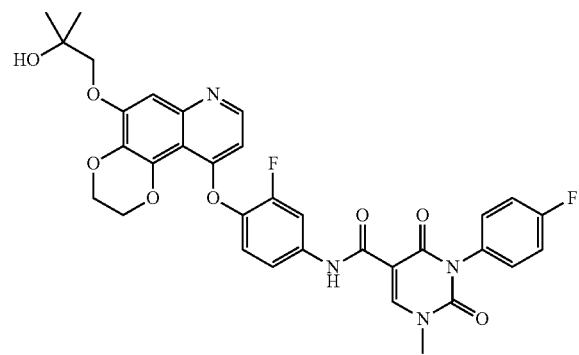
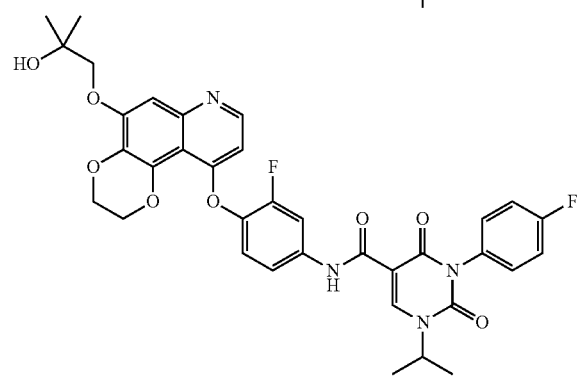
228
-continued
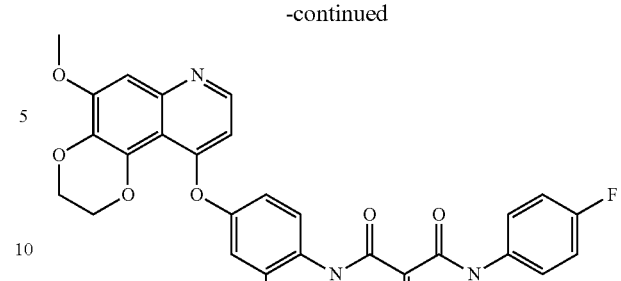
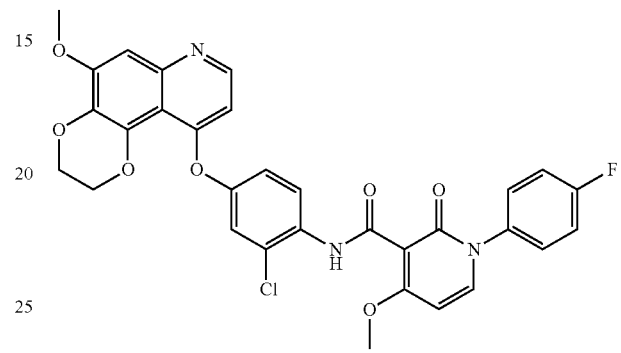
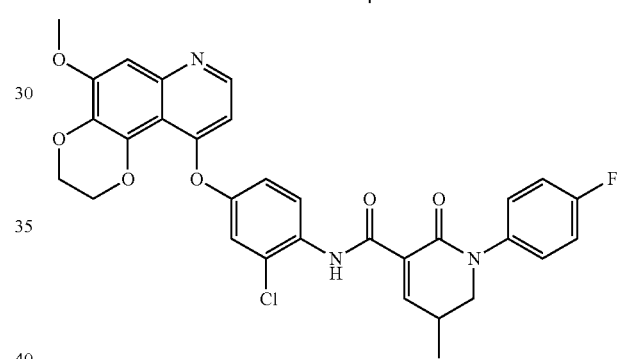
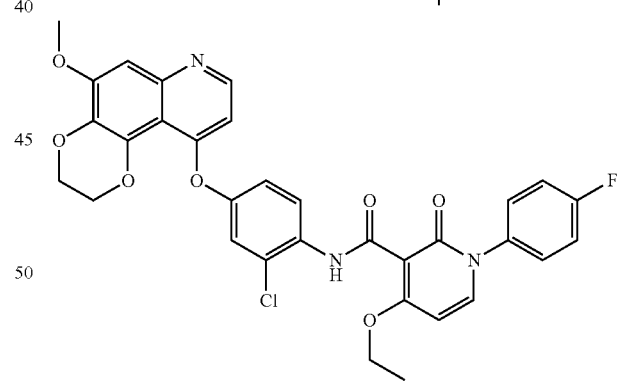
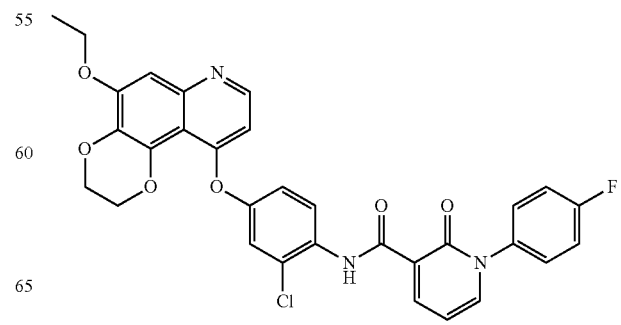

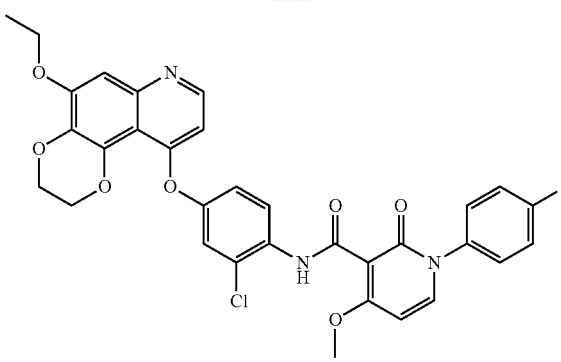
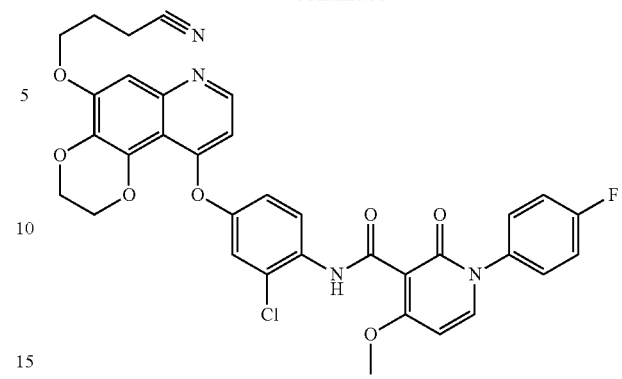
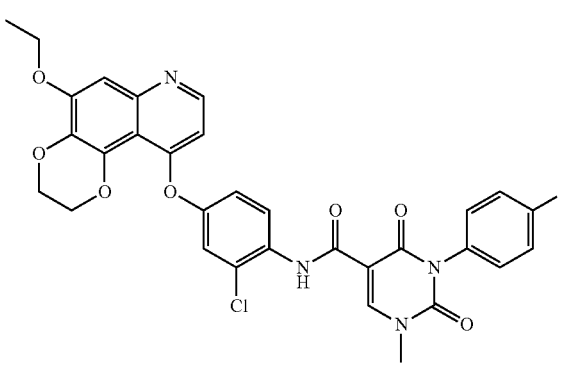
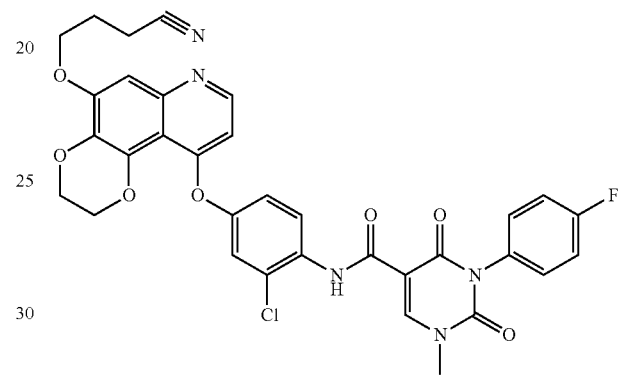
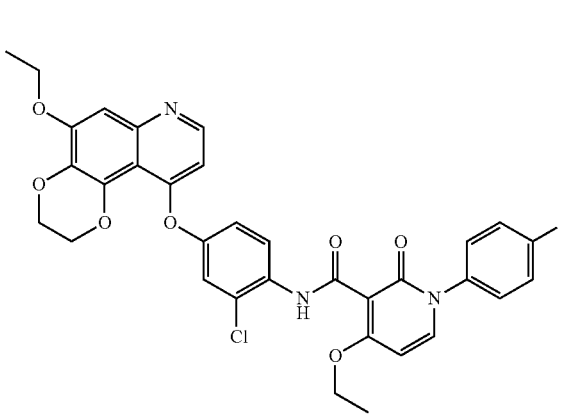
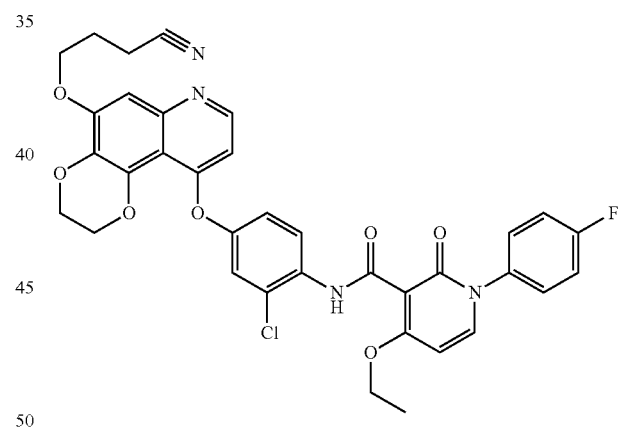
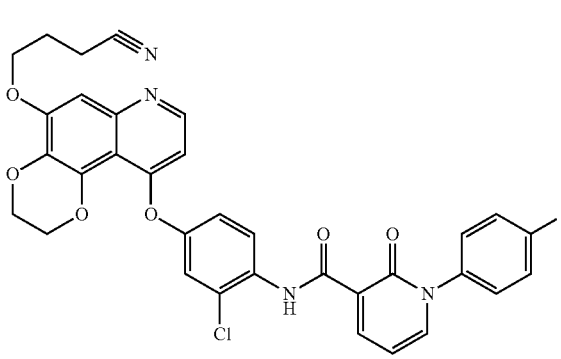
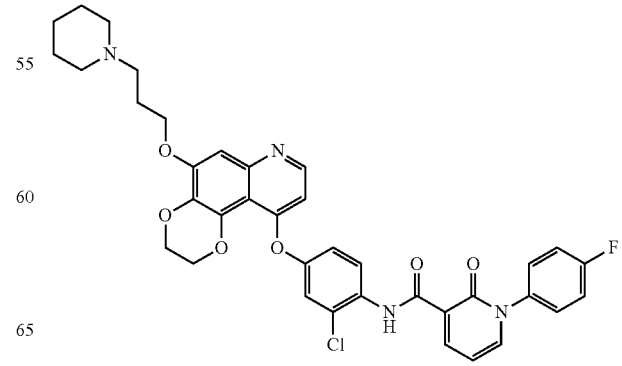

231
-continued
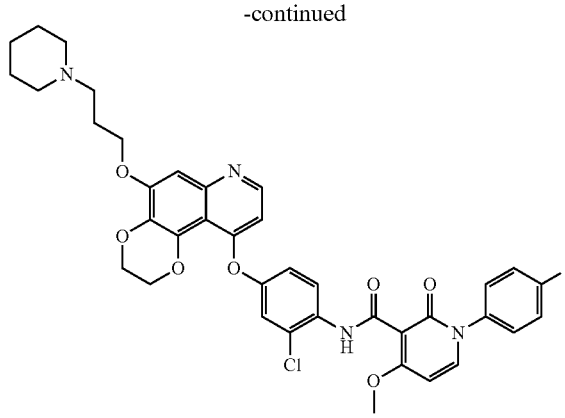
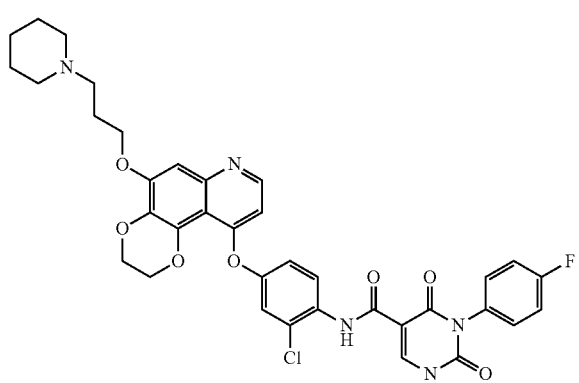
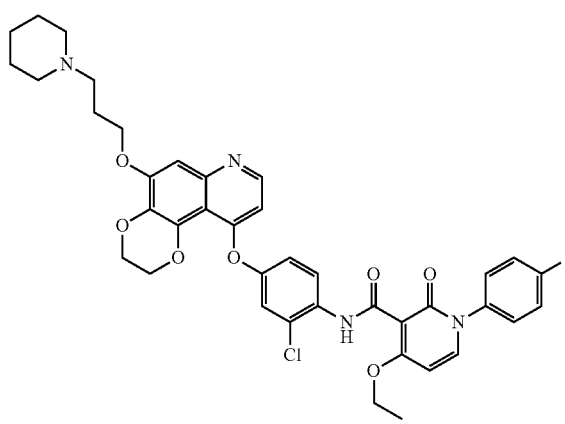
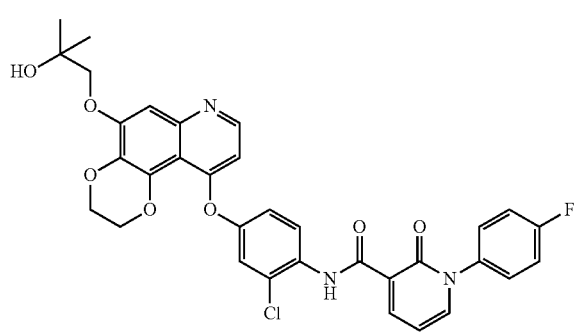
232
-continued
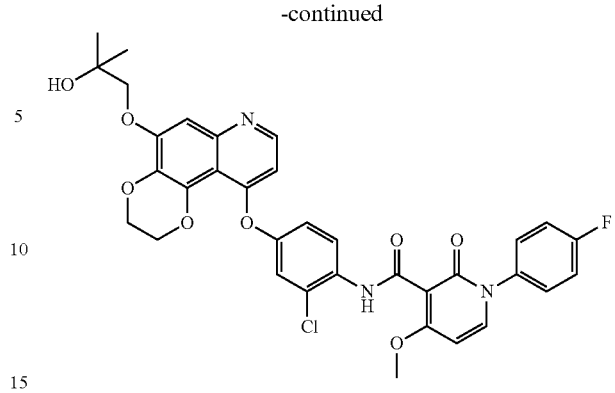
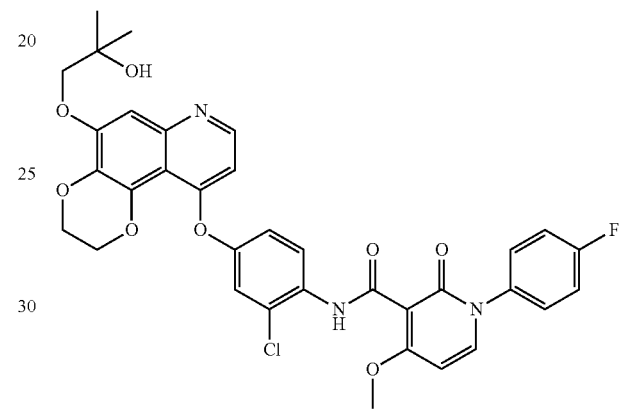
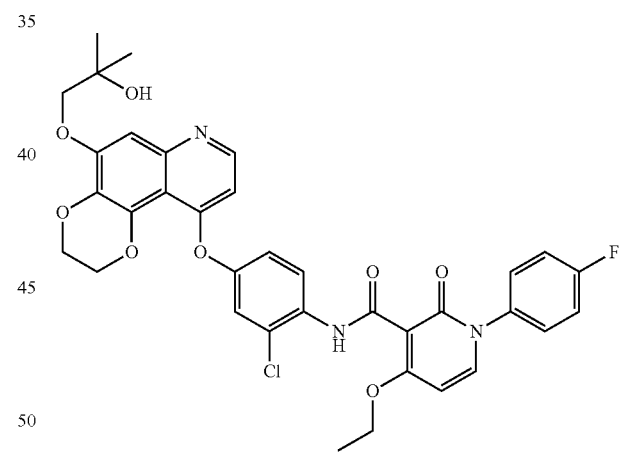
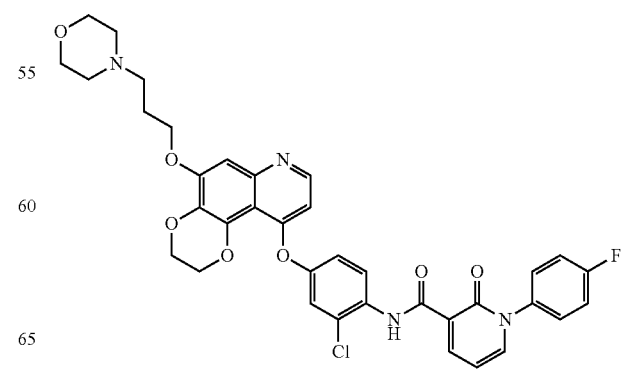

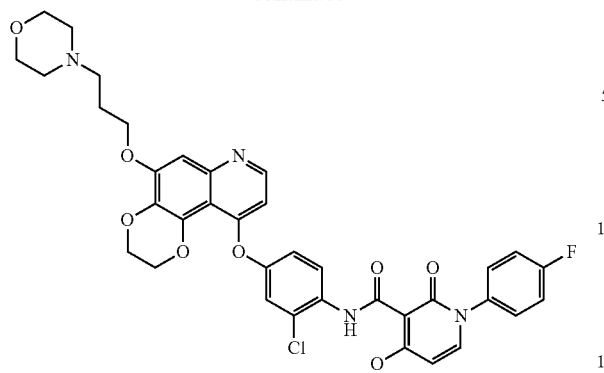
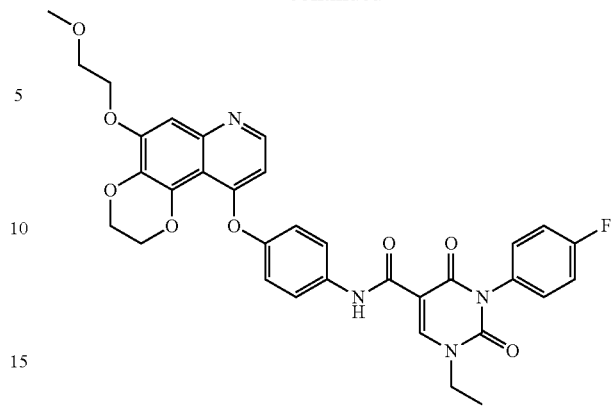
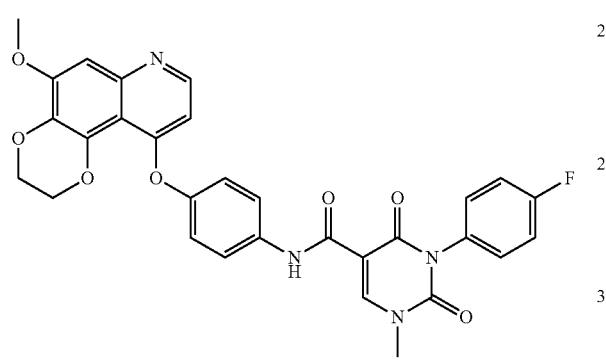
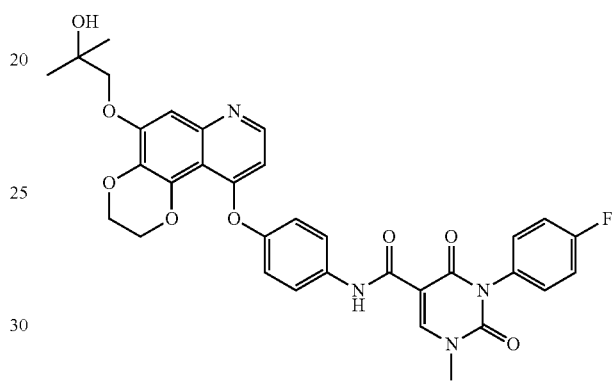
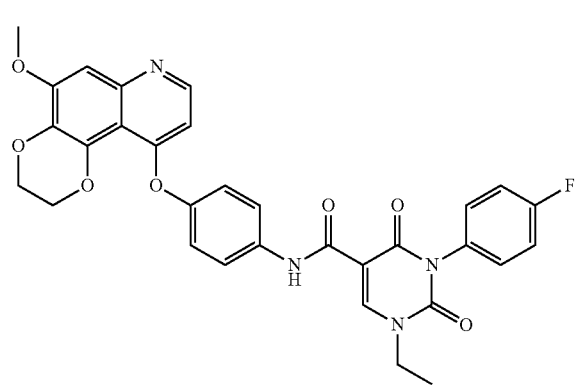
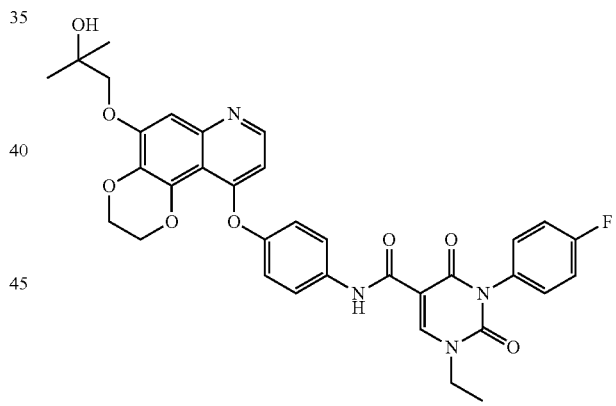
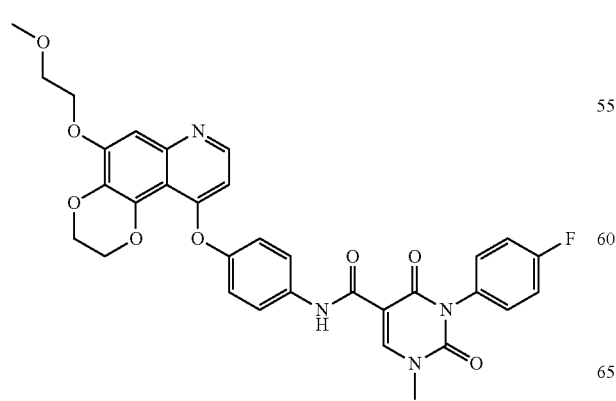
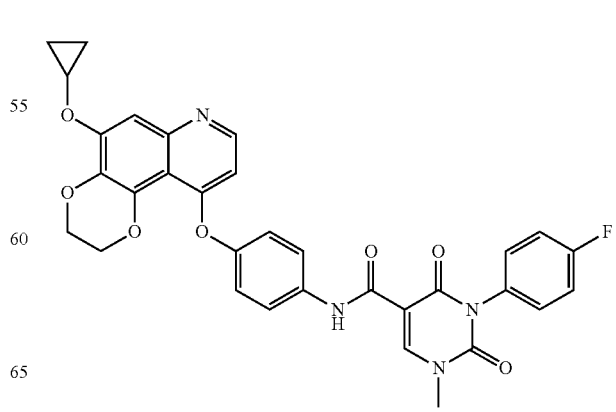

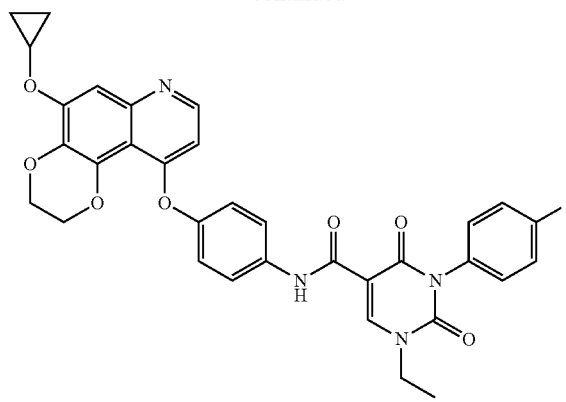
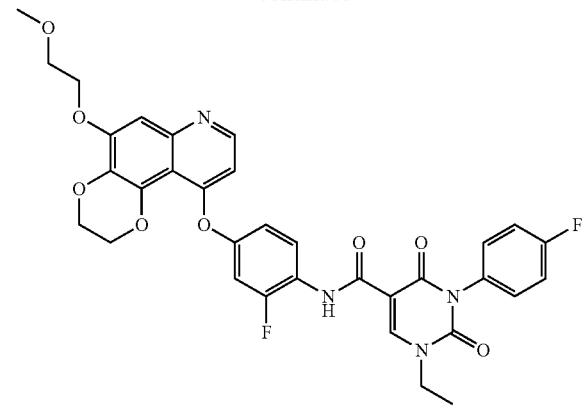
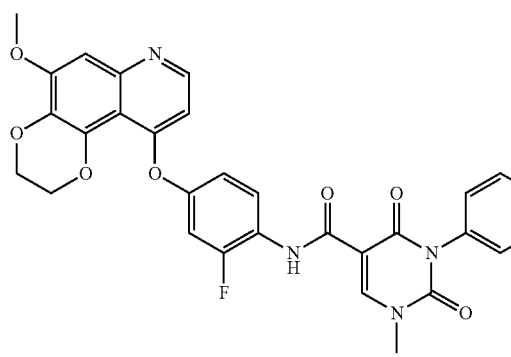
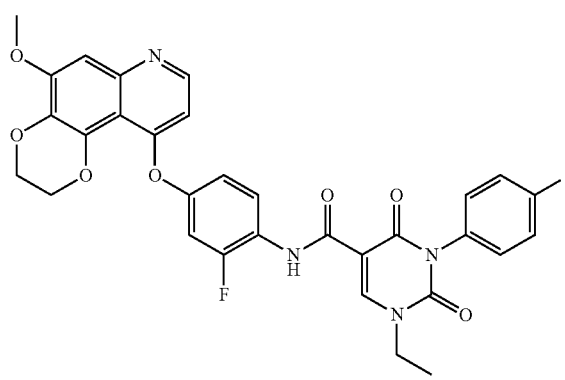
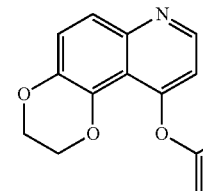
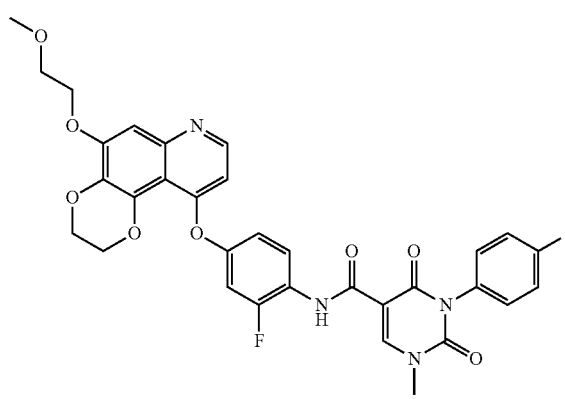
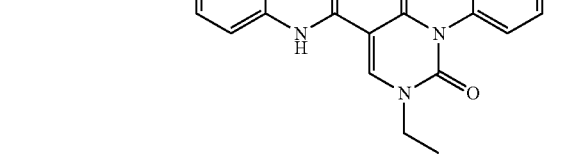

237
-continued
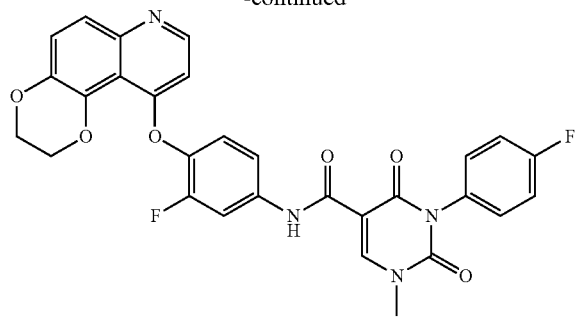
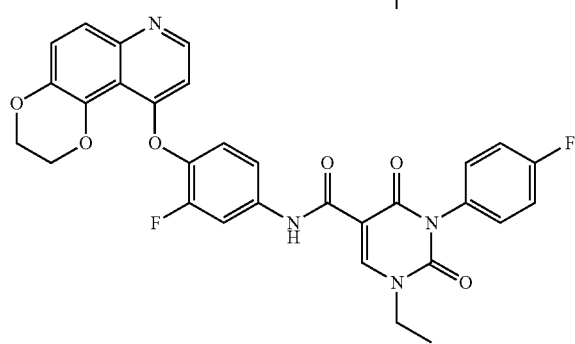
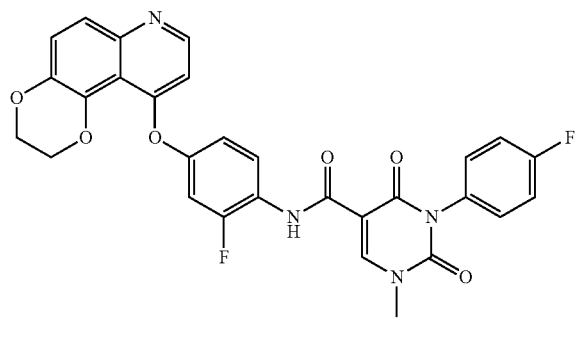
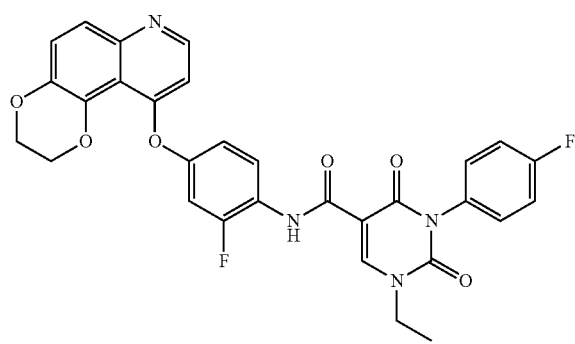
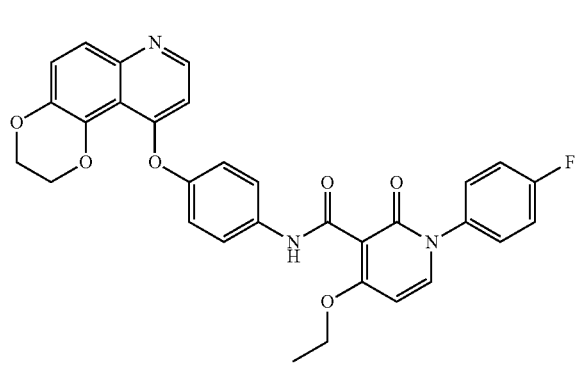
238
-continued
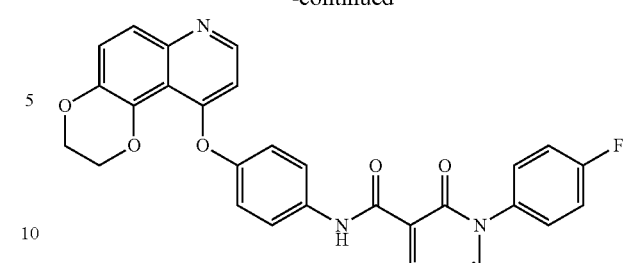
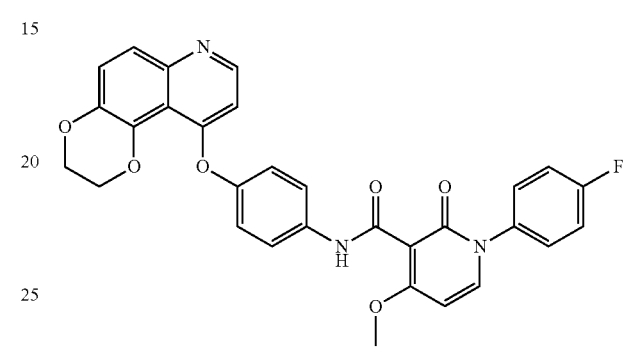
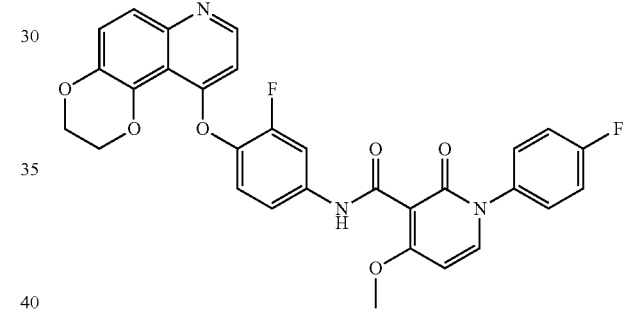
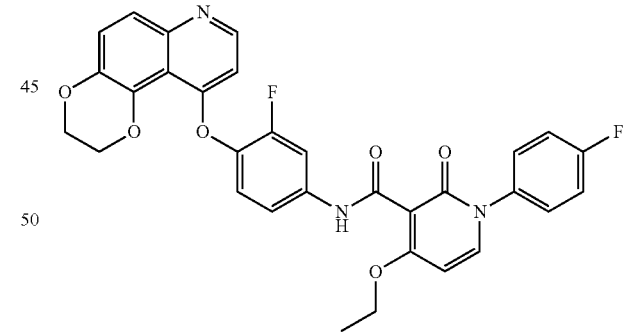
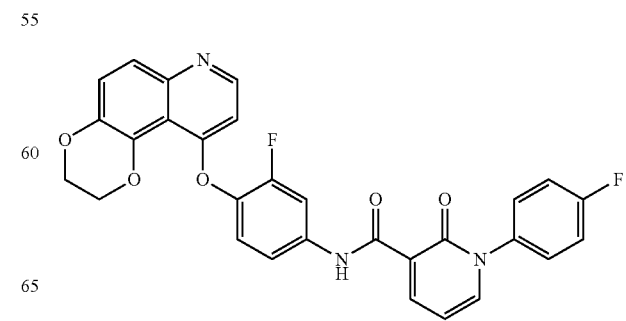

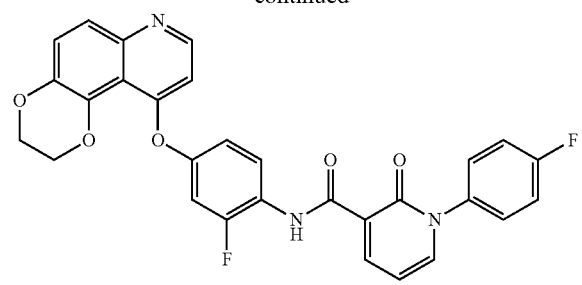
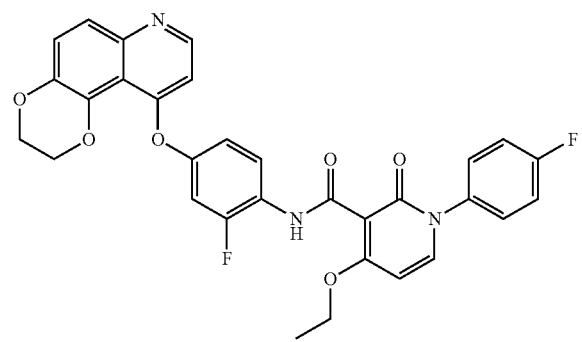
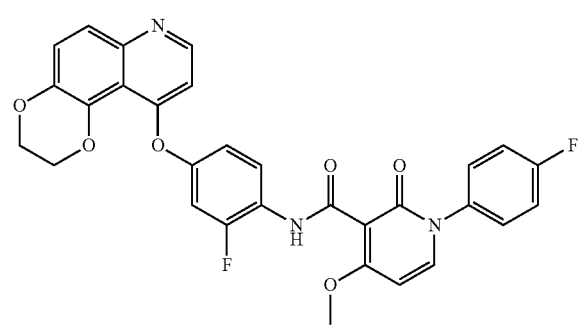
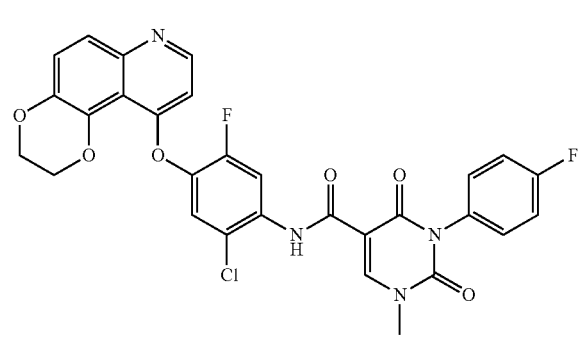
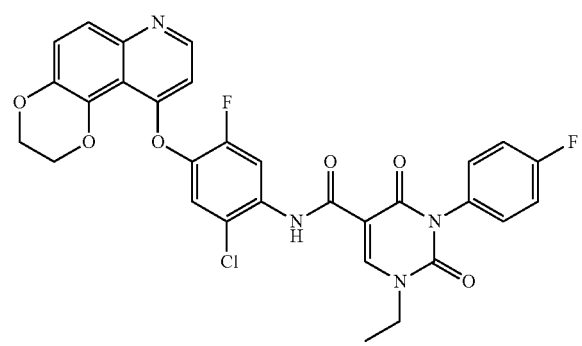
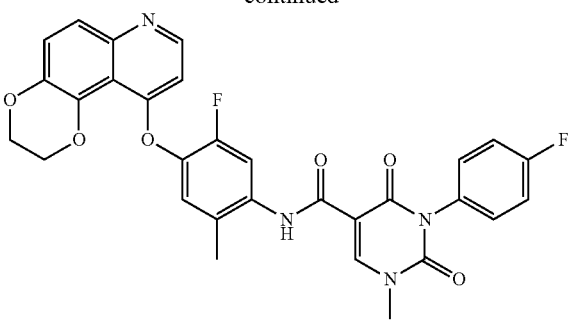
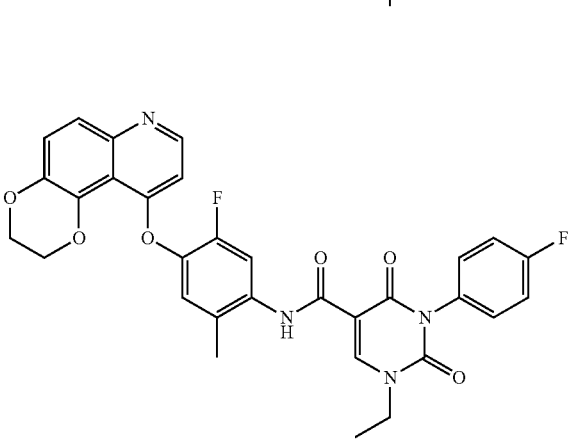
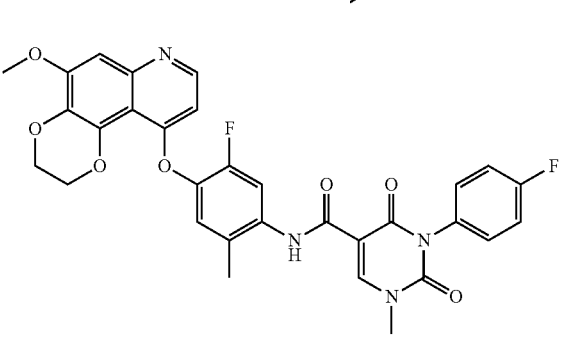
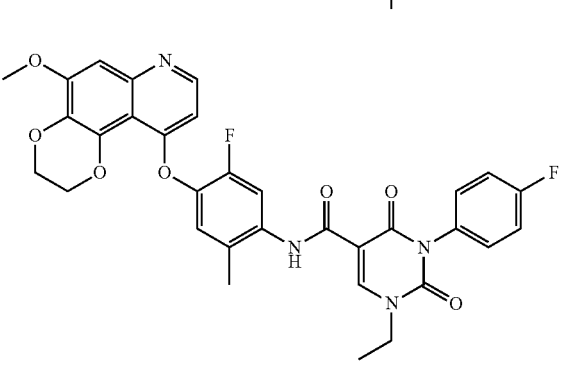
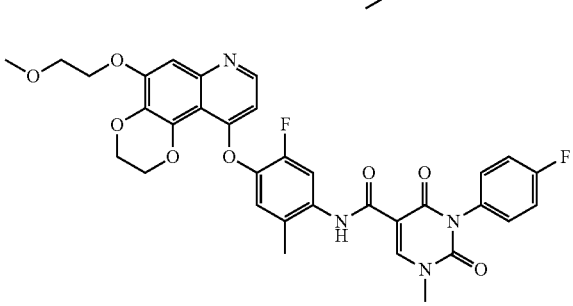

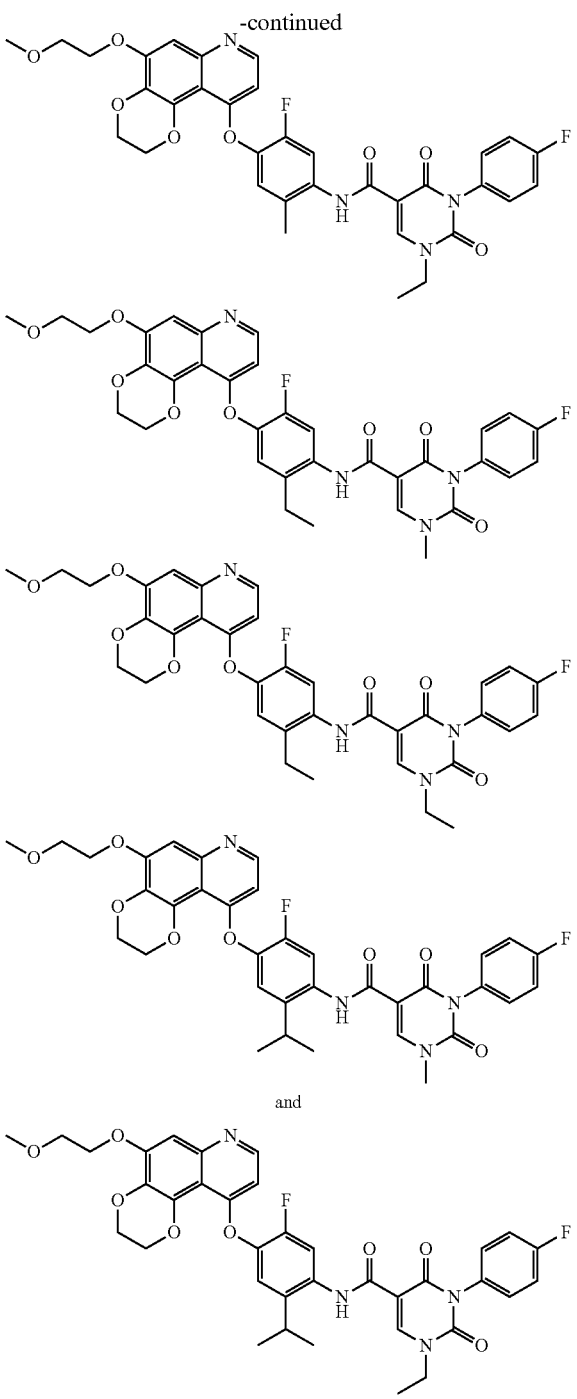

or a pharmaceutically acceptable salt, stereoisomer, or tautomer thereof.

12. A pharmaceutical composition comprising one or more pharmaceutically acceptable excipients and the compound according to claim 1, or a pharmaceutically acceptable salt, stereoisomer, or tautomer thereof.

13. A method for inhibiting tyrosine kinase activity in a subject, wherein the method comprises administering to the subject in need thereof a therapeutically effective amount of the compound according to claim 1, or a pharmaceutically acceptable salt, stereoisomer, or tautomer thereof; wherein the tyrosine kinase is selected from the group consisting of AXL, MER, mesenchymal-epithelial transition factor (c-MET), tropomyosin receptor kinase (TRK), and vascular endothelial growth factor receptor 2 (VEGFR2).

14. The method according to claim 13, wherein the subject has a disease related to tyrosine kinase selected from the group consisting of alopecia areata, atherosclerosis, bile duct cancer, biliary tract cancerous sarcoma, bladder cancer, bone marrow fibrosis, brain tumor, breast cancer, cervical cancer, colitis, colorectal cancer, Crohn' disease, dermatitis, endometrial cancer, esophageal cancer, fundus oculi disease, gastric cancer, gastrointestinal stromal tumor, glioblastoma, glioma, leukemia, liver cancer, liver fibrosis, lymphoma, melanoma, multiple myeloma, multiple sclerosis, nasopharyngeal cancer, non-small cell lung cancer, ovarian cancer, pancreatic cancer, prostate cancer, psoriasis, pulmonary fibrosis, rheumatoid arthritis, small cell lung cancer, systemic lupus erythematosus, thyroid cancer, vitiligo, and xerophthalmia.

15. The method according to claim 14, wherein the leukemia is acute myelocytic leukemia or chronic granulocytic leukemia.

16. The method according to claim 14, wherein the lymphoma is selected from the group consisting of B-cell lymphoma, non-Hodgkin's lymphoma, and T-cell lymphoma.

17. A process for preparing a compound of structural Formula (I) according to claim 1:

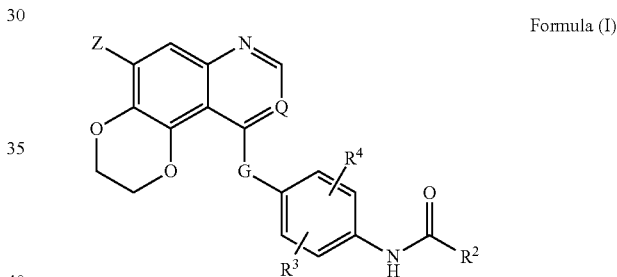

Formula (I)

wherein:
Z is H or OR$^1$;
R$^1$ is H, C$_1$-C$_{10}$ alkyl, (CH$_2$)$_n$R$^8$, or C$_3$-C$_8$ cycloalkyl;
  wherein the C$_1$-C$_{10}$ alkyl is optionally substituted with 1, 2, or 3 substituents independently selected from the group consisting of halogen, CN, CF$_3$, C$_1$-C$_3$ acyl, C(O)NH$_2$, NR$^a$R$^b$, OH, OC$_1$-C$_6$ alkyl, SC$_1$-C$_6$ alkyl, and C$_3$-C$_7$ cycloalkyl; and
  wherein the C$_3$-C$_8$ cycloalkyl is optionally substituted with 1, 2, or 3 substituents independently selected from the group consisting of halogen, CN, CF$_3$, C$_1$-C$_3$ acyl, C(O)NH$_2$, NR$^a$R$^b$, OH, OC$_1$-C$_6$ alkyl, =O, and SC$_1$-C$_6$ alkyl;
R$^8$ is 4- to 8-membered heteroalicyclyl;
  wherein the 4- to 8-membered heteroalicyclyl contains one or two ring heteroatoms or heteroatomic groups independently selected from the group consisting of N, NH, O, and S; and
  wherein the 4- to 8-membered heteroalicyclyl is optionally substituted with 1, 2, or 3 substituents independently selected from the group consisting of halogen, CN, C$_1$-C$_3$ alkyl, CF$_3$, C$_1$-C$_3$ acyl, NR$^a$R$^b$, OH, OC$_1$-C$_3$ alkyl, =O, and SC$_1$-C$_3$ alkyl;
each R$^a$ is independently H, C$_1$-C$_6$ alkyl, or C$_3$-C$_6$ cycloalkyl, wherein each C$_1$-C$_6$ alkyl is optionally and independently substituted with 1 substituent selected from the group consisting of $NH_2$, $NHC_1$-$C_3$ alkyl, $N(C_1$-$C_3$ alkyl$)_2$, $OC_1$-$C_3$ alkyl, and $SC_1$-$C_3$ alkyl;

each $R^b$ is independently H, $C_1$-$C_6$ alkyl, or $C_3$-$C_6$ cycloalkyl, wherein each $C_1$-$C_6$ alkyl is optionally and independently substituted with 1 substituent selected from the group consisting of $NH_2$, $NHC_1$-$C_3$ alkyl, $N(C_1$-$C_3$ alkyl$)_2$, $OC_1$-$C_3$ alkyl, and $SC_1$-$C_3$ alkyl;

Q is CH or N;

G is —NH—, —O—, or —S—;

$R^3$ is H, halogen, $C_1$-$C_3$ alkyl, $CF_3$, or $OC_1$-$C_3$ alkyl;

$R^4$ is H, halogen, $C_1$-$C_3$ alkyl, $CF_3$, or $OC_1$-$C_3$ alkyl;

$R^2$ is

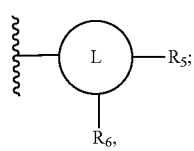

(i) ring L is unsaturated 5- or 6-membered heterocyclyl, aryl, or heteroaryl, wherein the 5- or 6-membered heterocyclyl or heteroaryl contains one, two, or three ring heteroatoms independently selected from the group consisting of N, O, and S; or (ii) ring L is

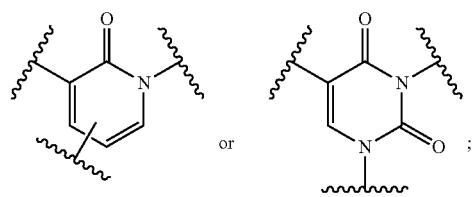

$R_5$ is H, $C_1$-$C_3$ alkyl, $C_4$-$C_6$ alkyl, or $OC_1$-$C_3$ alkyl, wherein the $C_1$-$C_3$ alkyl is substituted with 1, 2, or 3 substituents independently selected from the group consisting of halogen, alkenyl, C(O)OH, C(O)OC(CH$_3$)$_3$, OH, $OC_1$-$C_3$ alkyl, $C_3$-$C_6$ cycloalkyl, piperidinyl, 4-amino-4-methylpiperidinyl, 4-hydroxy-4-methylpiperidinyl, 4,4-dimethylpiperidinyl, piperazinyl, 4-methylpiperazinyl, morpholinyl, and pyrrolyl;

$R_6$ is $(CH_2)_tR_7$;

$R^7$ is $C_3$-$C_6$ cycloalkyl, aryl, or heteroaryl;

wherein the $C_3$-$C_6$ cycloalkyl is optionally substituted with 1 or more substituents independently selected from the group consisting of halogen, $C_1$-$C_3$ alkyl, $CF_3$, and $OC_1$-$C_3$ alkyl; and wherein the aryl or heteroaryl is optionally substituted with 1 or more substituents independently selected from the group consisting of halogen, $C_1$-$C_3$ alkyl, $CF_3$, and $OC_1$-$C_3$ alkyl;

n is 0, 1, 2, 3, 4, 5, 6, 7, 8, 9, or 10; and t is 0, 1, 2, or 3;

wherein the process comprises the following step:
reacting a compound represented by Formula (III):

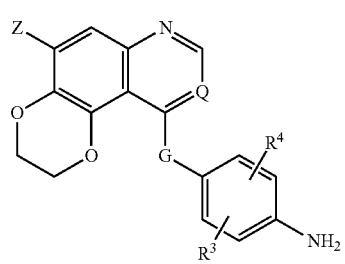

Formula (III)

wherein:

Z is H or $OR^1$;

$R^1$ is H, $C_1$-$C_{10}$ alkyl, $(CH_2)_nR^8$, or $C_3$-$C_8$ cycloalkyl;

wherein the $C_1$-$C_{10}$ alkyl is optionally substituted with 1, 2, or 3 substituents independently selected from the group consisting of halogen, CN, $CF_3$, $C_1$-$C_3$ acyl, $C(O)NH_2$, $NR^aR^b$, OH, $OC_1$-$C_6$ alkyl, $SC_1$-$C_6$ alkyl, and $C_3$-$C_7$ cycloalkyl; and wherein the $C_3$-$C_8$ cycloalkyl is optionally substituted with 1, 2, or 3 substituents independently selected from the group consisting of halogen, CN, $CF_3$, $C_1$-$C_3$ acyl, $C(O)NH_2$, $NR^aR^b$, OH, $OC_1$-$C_6$ alkyl, =O, and $SC_1$-$C_6$ alkyl;

$R^8$ is 4- to 8-membered heteroalicyclyl;

wherein the 4- to 8-membered heteroalicyclyl contains one or two ring heteroatoms or heteroatomic groups independently selected from the group consisting of N, NH, O, and S; and wherein the 4- to 8-membered heteroalicyclyl is optionally substituted with 1, 2, or 3 substituents independently selected from the group consisting of halogen, CN, $C_1$-$C_3$ alkyl, $CF_3$, $C_1$-$C_3$ acyl, $NR^aR^b$, OH, $OC_1$-$C_3$ alkyl, =O, and $SC_1$-$C_3$ alkyl;

each $R^a$ is independently H, $C_1$-$C_6$ alkyl, or $C_3$-$C_6$ cycloalkyl, wherein each $C_1$-$C_6$ alkyl is optionally and independently substituted with 1 substituent selected from the group consisting of $NH_2$, $NHC_1$-$C_3$ alkyl, $N(C_1$-$C_3$ alkyl$)_2$, $OC_1$-$C_3$ alkyl, and $SC_1$-$C_3$ alkyl;

each $R^b$ is independently H, $C_1$-$C_6$ alkyl, or $C_3$-$C_6$ cycloalkyl, wherein each $C_1$-$C_6$ alkyl is optionally and independently substituted with 1 substituent selected from the group consisting of $NH_2$, $NHC_1$-$C_3$ alkyl, $N(C_1$-$C_3$ alkyl$)_2$, $OC_1$-$C_3$ alkyl, and $SC_1$-$C_3$ alkyl;

Q is CH or N;

G is —NH—, —O—, or —S—;

$R^3$ is H, halogen, $C_1$-$C_3$ alkyl, $CF_3$, or $OC_1$-$C_3$ alkyl;

$R^4$ is H, halogen, $C_1$-$C_3$ alkyl, $CF_3$, or $OC_1$-$C_3$ alkyl; and n is 0, 1, 2, 3, 4, 5, 6, 7, 8, 9, or 10;

with a compound represented by Formula (II):

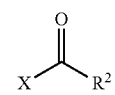

Formula (II)

wherein:
X is halogen or OH;
$R_2$ is

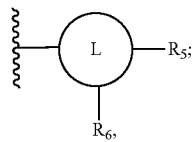

(i) ring L is unsaturated 5- or 6-membered heterocyclyl, aryl, or heteroaryl, wherein the 5- or 6-membered heterocyclyl or heteroaryl contains one, two, or three ring heteroatoms independently selected from the group consisting of N, O, and S; or
(ii) ring L is

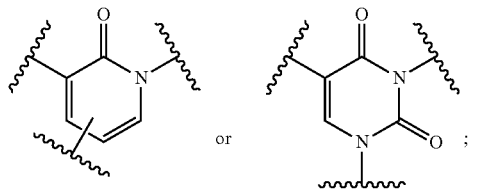

;

$R_5$ is H, $C_1$-$C_3$ alkyl, $C_4$-$C_6$ alkyl, or $OC_1$-$C_3$ alkyl, wherein the $C_1$-$C_3$ alkyl is substituted with 1, 2, or 3 substituents independently selected from the group consisting of halogen, alkenyl, C(O)OH, $C(O)OC(CH_3)_3$, OH, $OC_1$-$C_3$ alkyl, $C_3$-$C_6$ cycloalkyl, piperidinyl, 4-amino-4-methylpiperidinyl, 4-hydroxy-4-methylpiperidinyl, 4,4-dimethylpiperidinyl, piperazinyl, 4-methylpiperazinyl, morpholinyl, and pyrrolyl;

$R_6$ is $(CH_2)_tR^7$;

$R^7$ is $C_3$-$C_6$ cycloalkyl, aryl, or heteroaryl;

wherein the $C_3$-$C_6$ cycloalkyl is optionally substituted with 1 or more substituents independently selected from the group consisting of halogen, $C_1$-$C_3$ alkyl, $CF_3$, and $OC_1$-$C_3$ alkyl; and wherein the aryl or heteroaryl is optionally substituted with 1 or more substituents independently selected from the group consisting of halogen, $C_1$-$C_3$ alkyl, $CF_3$, and $OC_1$-$C_3$ alkyl; and t is 0, 1, 2, or 3;

to afford the compound of structural Formula (I) above.

\* \* \* \* \*